(12) United States Patent
Jumbe et al.

(10) Patent No.: US 11,240,579 B2
(45) Date of Patent: Feb. 1, 2022

(54) SENSOR SYSTEMS AND METHODS FOR CHARACTERIZING HEALTH CONDITIONS

(71) Applicant: LEVEL 42AI, Mountain View, CA (US)

(72) Inventors: Nelson L. Jumbe, Mountain View, CA (US); Andreas Schuh, Mountain View, CA (US); Peter Rexelius, Mountain View, CA (US); Michael Morimoto, Mountain View, CA (US); Dimosthenis Katsis, Mountain View, CA (US); Nikola Knezevic, Mountain View, CA (US); Steve Krawczyk, Mountain View, CA (US); Kevin Hammond, Mountain View, CA (US); Krzysztof Krawiec, Mountain View, CA (US); Gregory A. Kirkos, Mountain View, CA (US)

(73) Assignee: LEVEL 42 AI, Mountain View, CA (US)

(*) Notice: Subject to any disclaimer, the term of this patent is extended or adjusted under 35 U.S.C. 154(b) by 0 days.

(21) Appl. No.: 17/096,806

(22) Filed: Nov. 12, 2020

(65) Prior Publication Data

US 2021/0345939 A1 Nov. 11, 2021

Related U.S. Application Data

(60) Provisional application No. 63/022,362, filed on May 8, 2020, provisional application No. 63/022,336, filed
(Continued)

(51) Int. Cl.
*H04R 1/04* (2006.01)
*H04R 9/08* (2006.01)
(Continued)

(52) U.S. Cl.
CPC .............. *H04R 1/04* (2013.01); *A61B 5/0002* (2013.01); *A61B 5/0531* (2013.01); *A61B 5/277* (2021.01);
(Continued)

(58) Field of Classification Search
CPC . H04R 1/04; H04R 9/025; H04R 9/08; H04R 1/46; H04R 9/045; A61B 5/277;
(Continued)

(56) References Cited

U.S. PATENT DOCUMENTS 4,246,906 A * 1/1981 Winberg ................ G01K 13/20
600/549
4,792,145 A 12/1988 Eisenberg et al.
(Continued)

FOREIGN PATENT DOCUMENTS

CA 2610845 C 8/2015
CN 106419953 A 2/2017
(Continued)

OTHER PUBLICATIONS

Avisoft Bioacoustics, Condenser Ultrasound Microphone CM16/CMPA, webpage, http://www.avisoft.com/ultrasound-microphones/cm16-cmpa/.
(Continued)

*Primary Examiner* — Oyesola C Ojo
(74) *Attorney, Agent, or Firm* — BCF LLP

(57) ABSTRACT

A sensing system comprising a hand-held sensing device with a vibracoustic sensor module (VSM). The VSM comprises a voice coil component comprising a coil holder supporting wire windings; a magnet component comprising a magnet supported by a frame, a magnet gap configured to receive at least a portion of the voice coil component in a spaced and moveable manner; a connector connecting the voice coil component to the magnet component, the con-
(Continued)

nector being compliant and permitting relative movement of the voice coil component and the magnet component; a diaphragm configured to induce a movement of the voice coil component in the magnet gap responsive to incident acoustic waves; a housing for retaining the vibroacoustic sensor module having a handle end and a sensor end, the sensor end having an opening, the VSM positioned such that at least a portion of the diaphragm extends across the opening.

19 Claims, 105 Drawing Sheets
(48 of 105 Drawing Sheet(s) Filed in Color)

Related U.S. Application Data on May 8, 2020, provisional application No. 63/067,179, filed on Aug. 18, 2020, provisional application No. 63/075,056, filed on Sep. 4, 2020, provisional application No. 63/075,059, filed on Sep. 4, 2020.

(51) Int. Cl.
| | | |
|---|---|---|
| *H04R 9/02* | (2006.01) | |
| *H04R 9/04* | (2006.01) | |
| *H04R 1/46* | (2006.01) | |
| *A61B 5/00* | (2006.01) | |
| *A61B 5/318* | (2021.01) | |
| *A61B 8/08* | (2006.01) | |
| *G01P 15/08* | (2006.01) | |
| *G01P 1/00* | (2006.01) | |
| *G10L 25/66* | (2013.01) | |
| *A61B 7/04* | (2006.01) | |
| *A61B 5/0531* | (2021.01) | |
| *A61B 5/277* | (2021.01) | |

(52) U.S. Cl.
CPC .............. *A61B 5/318* (2021.01); *A61B 5/412* (2013.01); *A61B 5/7267* (2013.01); *A61B 7/04* (2013.01); *A61B 8/488* (2013.01); *G01P 1/00* (2013.01); *G01P 15/08* (2013.01); *G10L 25/66* (2013.01); *H04R 1/46* (2013.01); *H04R 9/025* (2013.01); *H04R 9/045* (2013.01); *H04R 9/08* (2013.01); *A61B 2560/0214* (2013.01); *A61B 2560/0252* (2013.01); *A61B 2560/0257* (2013.01); *A61B 2560/0431* (2013.01); *A61B 2560/0443* (2013.01); *A61B 2562/0204* (2013.01); *A61B 2562/0219* (2013.01)

(58) Field of Classification Search
CPC ......... A61B 5/0531; A61B 5/318; A61B 7/04; A61B 8/488; A61B 5/412; A61B 5/0002; A61B 5/7267; A61B 2560/0257; A61B 2560/0252; A61B 2560/0443; A61B 2560/0431; A61B 2560/0214; A61B 2562/0219; A61B 2562/0204; G01P 15/08; G01P 1/00; G10L 25/66
See application file for complete search history.

(56) References Cited

U.S. PATENT DOCUMENTS

| | | | |
|---|---|---|---|
| 6,048,319 A | 4/2000 | Hudgins et al. | |
| 6,478,744 B2* | 11/2002 | Mohler | A61B 7/00 |
| | | | 600/485 |
| 6,661,897 B2* | 12/2003 | Smith | A61B 7/04 |
| | | | 381/67 |
| 7,037,268 B1 | 5/2006 | Sleva et al. | |
| 7,066,894 B2 | 6/2006 | Halleck et al. | |
| 7,416,531 B2 | 8/2008 | Mohler | |
| 7,885,700 B2 | 2/2011 | Clark | |
| 8,024,974 B2* | 9/2011 | Bharti | H04R 1/46 |
| | | | 73/591 |
| 8,054,061 B2 | 11/2011 | Prance | |
| 8,264,246 B2 | 9/2012 | Mahalingham | |
| 8,264,247 B2 | 9/2012 | Prance | |
| 8,475,396 B2 | 7/2013 | Jones | |
| 8,790,264 B2 | 7/2014 | Sandler et al. | |
| 8,860,401 B2 | 10/2014 | Prance | |
| 8,923,956 B2 | 12/2014 | Clark | |
| 9,101,274 B2* | 8/2015 | Bakema | A61B 7/04 |
| 10,123,764 B2 | 11/2018 | Boyd | |
| 10,307,132 B2* | 6/2019 | Chung | A61L 2/10 |
| 10,485,449 B2 | 11/2019 | MacAuslan | |
| 10,542,961 B2 | 1/2020 | Barsimantov et al. | |
| 10,548,561 B2 | 2/2020 | Telfort et al. | |
| 10,595,731 B2 | 3/2020 | Gopalakrishnan et al. | |
| 10,758,142 B2 | 9/2020 | Moon et al. | |
| 2003/0128847 A1 | 7/2003 | Smith | |
| 2006/0153416 A1 | 7/2006 | Kaneda et al. | |
| 2009/0211838 A1* | 8/2009 | Bilan | A61B 7/04 |
| | | | 181/131 |
| 2011/0021928 A1 | 1/2011 | Giovangrandi | |
| 2011/0208060 A1 | 8/2011 | Haase et al. | |
| 2012/0209132 A1* | 8/2012 | Jones | G01S 5/18 |
| | | | 600/528 |
| 2014/0073864 A1 | 3/2014 | Engelbrecht et al. | |
| 2014/0303452 A1 | 10/2014 | Ghaffari | |
| 2015/0126883 A1 | 5/2015 | An et al. | |
| 2016/0030006 A1 | 2/2016 | Okuya et al. | |
| 2016/0089089 A1 | 3/2016 | Kakkar et al. | |
| 2016/0133151 A1 | 5/2016 | O'Dowd et al. | |
| 2016/0235621 A1* | 8/2016 | Choe | A61H 7/005 |
| 2016/0256111 A1* | 9/2016 | Cheng | A61B 5/7203 |
| 2018/0108440 A1* | 4/2018 | Stevens | G16H 50/20 |
| 2018/0206747 A1 | 7/2018 | Rinderknecht et al. | |
| 2018/0228468 A1 | 8/2018 | Adler et al. | |
| 2018/0279968 A1* | 10/2018 | Boyd | H04R 1/46 |
| 2018/0289354 A1 | 10/2018 | Cvijanovic et al. | |
| 2018/0303434 A1 | 10/2018 | Selvaraj | |
| 2019/0000413 A1 | 1/2019 | Adler et al. | |
| 2019/0053778 A1* | 2/2019 | Lin | A61B 5/25 |
| 2019/0080803 A1 | 3/2019 | Lotan et al. | |
| 2019/0099156 A1 | 4/2019 | Bocca et al. | |
| 2019/0110774 A1* | 4/2019 | Flynn | A61B 8/4411 |
| 2019/0150771 A1 | 5/2019 | Jeong et al. | |
| 2019/0159960 A1 | 5/2019 | Nakata et al. | |
| 2019/0223827 A1 | 7/2019 | Boyd | |
| 2019/0365263 A1 | 12/2019 | Raj et al. | |
| 2020/0138399 A1 | 5/2020 | Li et al. | |
| 2020/0205770 A1 | 7/2020 | Friedman et al. | |
| 2020/0237309 A1 | 7/2020 | Golda et al. | |

FOREIGN PATENT DOCUMENTS

| | | | |
|---|---|---|---|
| CN | 108514428 A | 9/2018 | |
| CN | 110916715 A | 3/2020 | |
| EP | 2462871 A1 | 6/2012 | |
| EP | 2976016 A4 | 12/2016 | |
| RU | 2700471 C9 | 4/2020 | |
| WO | 1988004911 A1 | 7/1988 | |
| WO | 2005037096 A1 | 4/2005 | |
| WO | WO-2005037096 A1 * | 4/2005 | ............... A61B 8/06 |
| WO | 2009079976 A3 | 11/2009 | |
| WO | 2017141165 A1 | 8/2017 | |
| WO | 2018075521 A9 | 8/2018 | |
| WO | 2019048960 A1 | 3/2019 | |
| WO | 2019048961 A1 | 3/2019 | |
| WO | 2020077002 A1 | 4/2020 | |

OTHER PUBLICATIONS

Roland, Rubix 24 USB Audio Interface, Webpage, https://www.roland.com/us/products/rubix24/.
Siglent, SDG1032X Arbitrary Waveform Generators, Webpage, https://siglentna.com/product/sdg1032x/.

(56) References Cited

OTHER PUBLICATIONS

Mackie, M48 Phantom Power Supply, Webpage, https://www.sweetwater.com/store/detail/M48PwrSupply-mackie-m48-phantom-power-supply.
TDK Invensense, ICS-4132 Bottom Port Digital Output Multi-Mode Microphone w/Ultrasonic Mode, Webpage, https://invensense.tdk.com/products/digital/ics-41352/.
Pro_Wave Electronics, 400ST/R160 Air Ultrasonic Ceramic Transducers, Webpage, https://www.mouser.com/new/pro-wave-electronics/pro-wave-400st-r160-transducers/.
Jordi Laguarta, COVID-19 Artificial Intelligence Diagnosis using only Cough Recordings, IEEE Open Journal of Engineering in Medicine and Biology, Sep. 29, 2020, Electronic ISSN: 2644-1276, Cambridge, MA.
Johannes J Struijk, Heart Sounds Obtained With Non-Contact Continuous-Wave Echo Doppler, Computing in Cardiology, Dec. 30, 2018, Aalborg University, Aalborg, Denmark, http://www.cinc.org/archives/2018/pdf/CinC2018-342.pdf.
Du Xuhao, Bowel sounds identification and migrating motor complex detection with low-cost piezoelectric acoustic sensing device, MDPI AG, Dec. 3, 2018, vol. 18 Issue: 12, pp. 4240, https://www.mdpi.com/1424-8220/18/12/4240.
Supreeya Swarup, Digital stethoscope: technology update, Medical Devices Evidence and Research, Dover Press, Jan. 4, 2018 ,vol. 2018:11 pp. 29-36, https://www.dovepress.com/digital-stethoscope-technology-update-peer-reviewed-article-MDER.
Richard Barnert, Modal Improved Condenser Microphone, AES E-Library, Nov. 1, 2001, https://www.aes.org/e-lib/browse.cfm?elib=9845.
Edward Walters, The pathophysiological basis and consequences of fever, Critical Care, Springer Science and Business Media LLC, vol. 20, Issue 1, https://ccforum.biomedcentral.com/articles/10.1186/s13054-016-1375-5.
Omer T. Inan, Ballistocardiography and seismocardiography: a review of recent advances, IEEE Journal of Biomedical and Health Informatics, IEEE, vol. 19, Issue 4, pp. 1414-1427, https://ieeexplore.ieee.org/document/6916998.
Sharon S. Evans, Fever and the thermal regulation of immunity: the immune system feels the heat, Nature Reviews Immunology, Springer Science and Business, vol. 15, Issue 6, pp. 335-349, https://www.nature.com/articles/nri3843.
Jure Kranjec, Novel methods for noncontact heart rate measurement: a feasibility study, IEEE Transactions on Instrumentation and Measurement, IEEE, vol. 53, Issue 4, pp. 838-847, https://ieeexplore.ieee.org/document/6654357.
Eugenijus Kaniusas, Transmission of body sounds—an overview, Ultrasound, Sage Publications, vol. 1, Issue 58, pp. 7-12, https://www.researchgate.net/publication/283259308_Transmission_of_body_sounds_an_overview.
Pro-Wave Electronics, Air ultrasonic ceramic transducers, Jan. 1, 2005, http://www.prowave.com.tw/english/products/ut/ep/40ep250.htm.
Prof. K.Barsauskas Ultrasound Institute Kaunas University, Absorption of ultrasonic waves in air, ISSN 1392-2114 ULTRAGARSAS, Nr.1(50). 2004., Jan. 1, 2004, https://pdfs.semanticscholar.org/c408/db1cbccdc558cdb76ad761bc149eae8504c7.pdf.
Chapter 4, The Acoustics of the Body, Course at University of Notre Dame, Physics in medicine—part 1 physics in the body—chapter 4—acoustics of the body, pp. 152-205, Jan. 1, 2003, https://www3.nd.edu/~nsl/Lectures/mphysics/Medical%20Physics/Part%201.%20Physics%20of%20the%20Body/Chapter%204.%20Acoustics%20of%20the%20Body/Chapter%204.%20Acoustics%20of%20the%20Body.pdf.
Alfred J. Bedard, Atmospheric infrasound, Physics Today, AIP Publishing, vol. 53, Issue 3, pp. 32-37, Mar. 1, 2000 , https://physicstoday.scitation.org/doi/10.1063/1.883019.
J.M. Randell, Resonant frequencies of standing humans, Ergonomics, Informa UK, vol. 40, Issue 9, pp. 879-886, Sep. 1, 1997, https://www.tandfonline.com/doi/abs/10.1080/001401397187711.
Orbbec 3D Tech Intl. Inc., Astra Embedded S, http://shop.orbbec3d.com/Astra-Embedded-S_p_52.html, Nov. 10, 2020.
Melexis, MLX90614 Family, Datasheet Single and Dual Zone Infra Red Thermometer in TO-39, Sep. 13, 2019.
Francesca Romana Parente, An Electronic System for the Contactless Reading of ECG Signals, Journal, Oct. 28, 2017, vol. 17, Issue 11, Sensors, Internet.
Olaf Bolke, Experimental Modal Analysis Based on Non-Contact Measurements With a Commercial Microphone Array, 26th Annual Congress on Sound and Vibration, Jul. 7-11, 2019, Semantic Scholar, 2019 Montreal Canada.
Johannes J Struijk, Heart Sounds Obtained With Non-Contact Continuous-Wave Echo Doppler, Computing in Cardiology, Dec. 30, 2018, Aalborg Denmark.
Jure Kranjec, Novel methods for noncontact heart rate measurement: a feasibility study, vol. 63, Issue 4, IEEE Explore Transactions on Intrumentation and Measurement, Apr. 2014, Internet.
KP Venkatesh, Capturing higher modes of vibration of micromachined resonators, Journal of Physics Conference Series, IOP Publlishing, vol. 181, pp. 012079, Sep. 1, 2009, Internet.
Akinori Ueno, Capacitive Sensing of Electrocardiographic Potential Through Cloth From the Dorsal Surface of the Body in a Supine Position: A Preliminary Study, Journal, IEEE Xplore Transactions on Biomedical Engineering, vol. 54, Issue 4, pp. 759-766, IEEE, Mar. 19, 2007.
Guido Giuliani, Self Mixing Laser Diode, Journal, Measurement Science & Technology, vol. 4, No. 1, Nov. 21, 2002, IOP Publishing.
Richard Barnert, Modal Improved Condenser Microphone, Audio Engineering Society, Convention Paper 5466 AES E-Library, AES Convention 111, Paper No. 5466, Nov. 1, 2001, New York, NY.
International Search Report and Written Opinion issued in co-pending International application No. PCT/IB2021/053919 dated Aug. 12, 2021.

\* cited by examiner

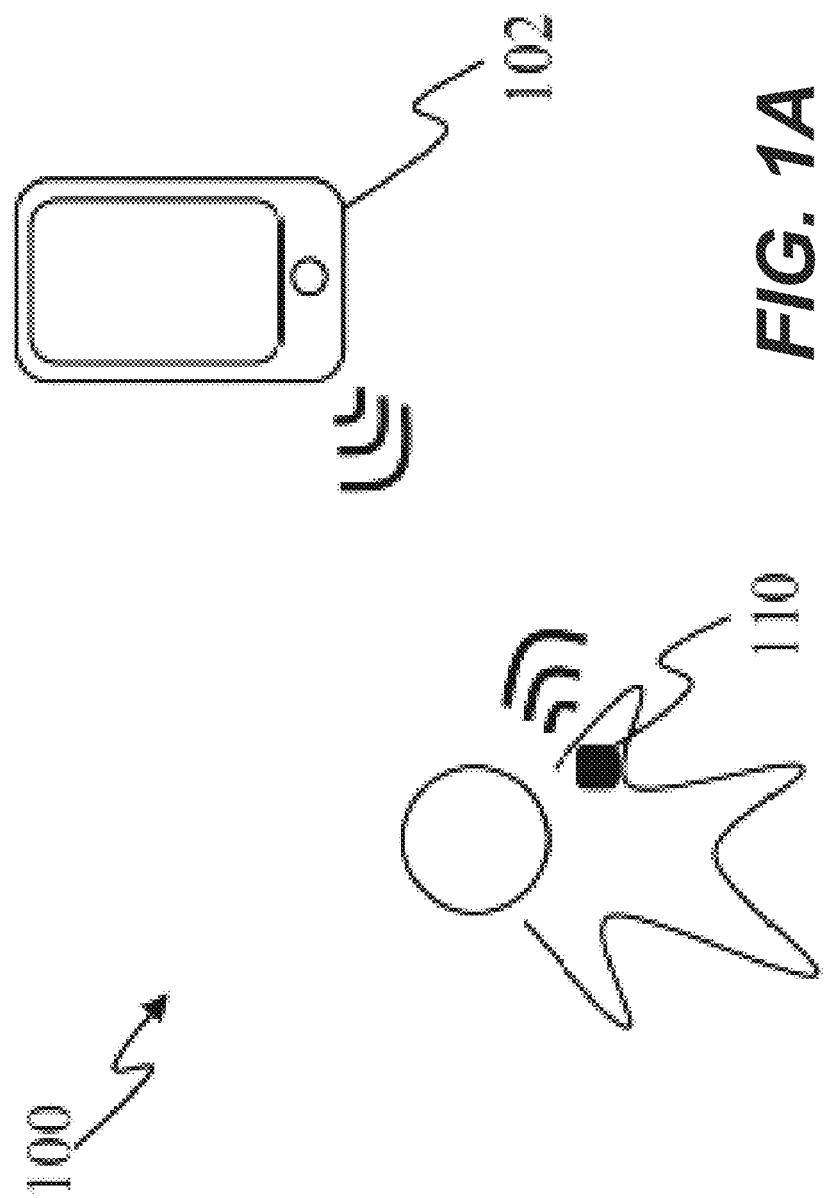

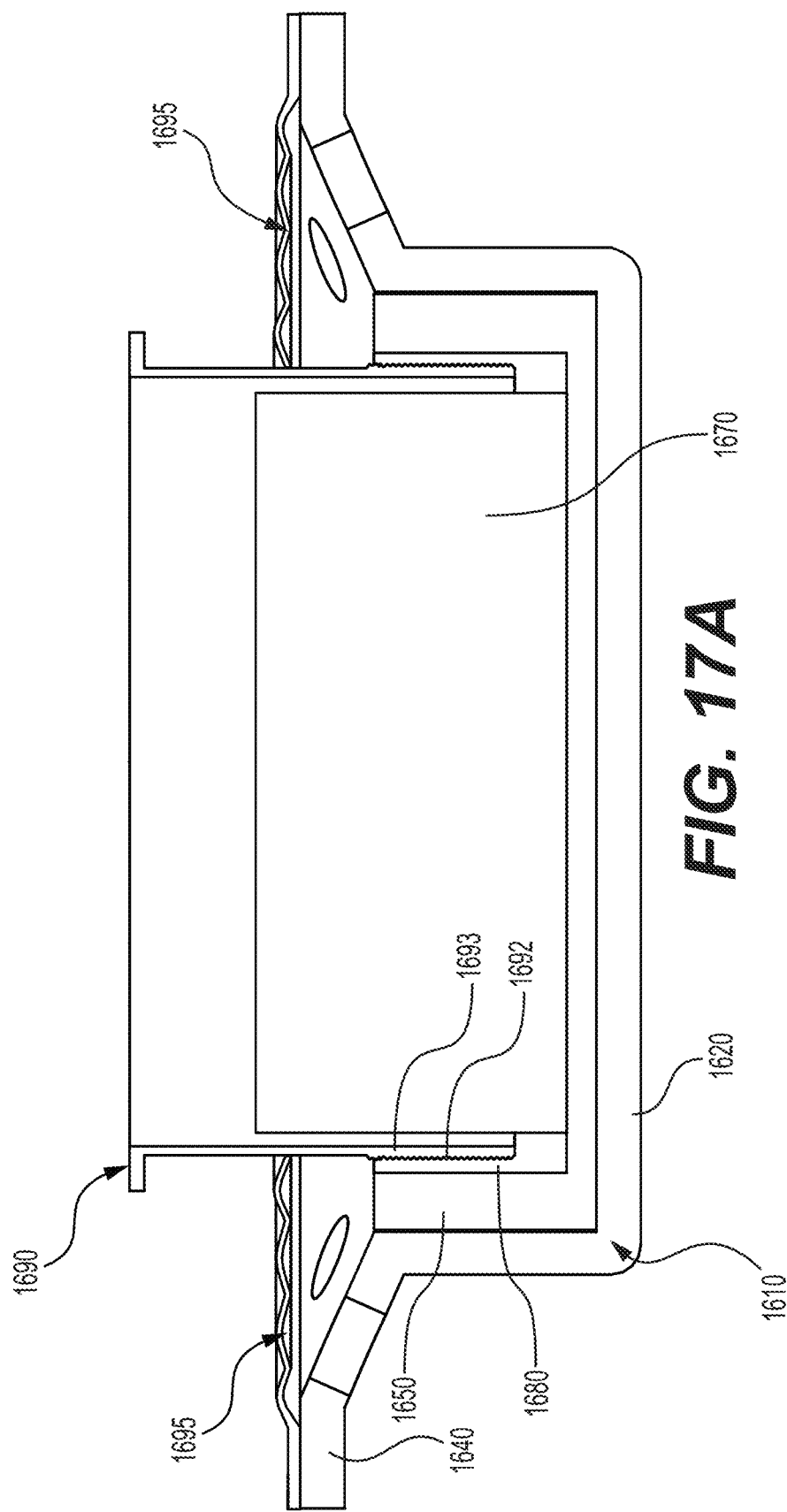

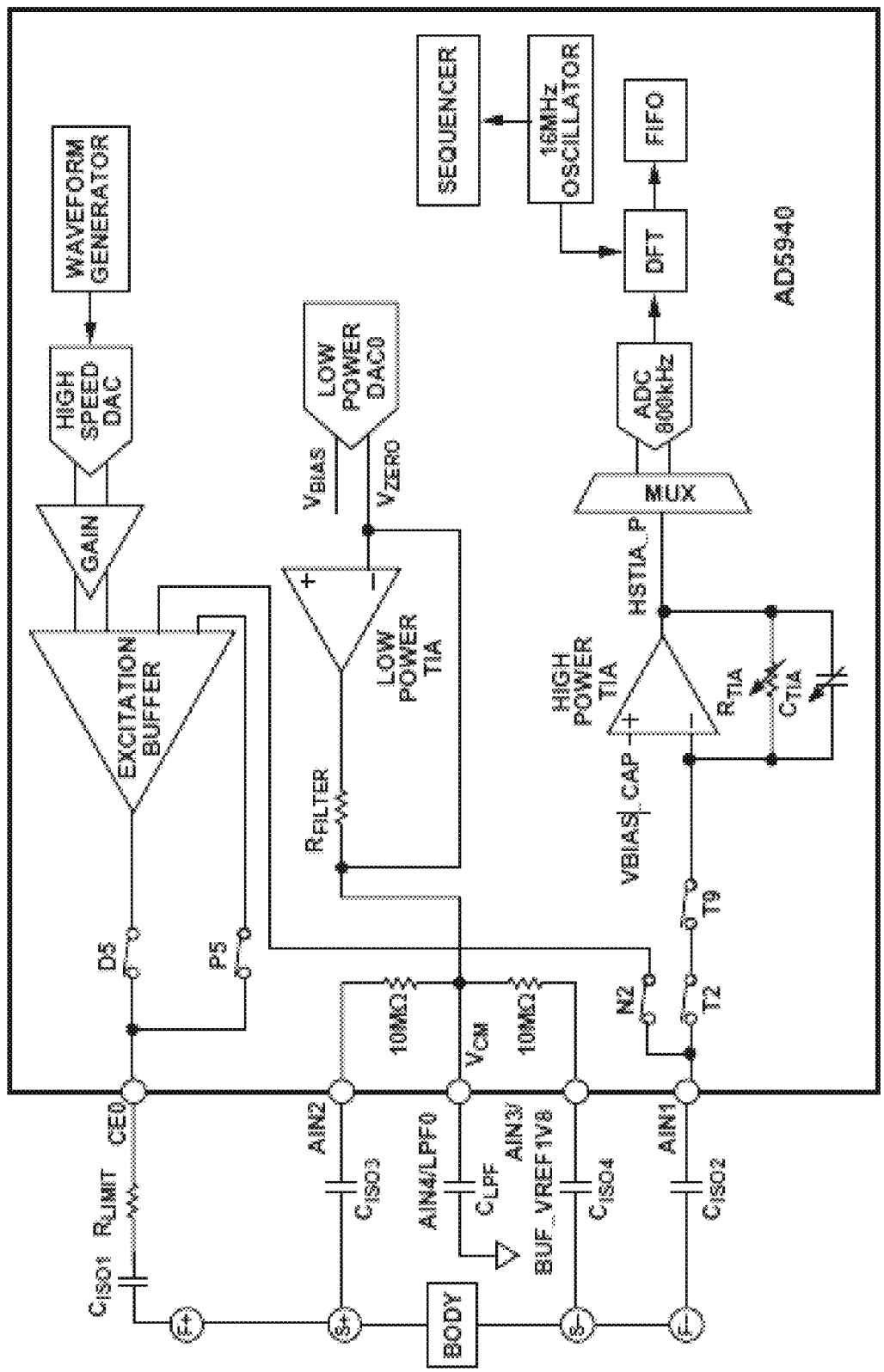
FIG. 22F *PRIOR ART*

SENSOR SYSTEMS AND METHODS FOR CHARACTERIZING HEALTH CONDITIONS

CROSS-REFERENCE

This application claims the benefit of U.S. Provisional Patent Application Ser. No. 63/022,362 filed May 8, 2020; U.S. Provisional Patent Application Ser. No. 63/022,336 filed May 8, 2020; No. 63/075,056 filed Sep. 4, 2020; Ser. No. 63/075,059 filed Sep. 4, 2020; and U.S. 63/067,179 filed Aug. 18, 2020. The contents of the aforementioned applications are incorporated by reference herein in their entirety.

TECHNICAL FIELD

This invention relates generally to the field of monitoring and diagnosis, such as for identifying a health condition or other physical condition of a subject using active and/or passive sensing techniques.

BACKGROUND

Traditionally, medical care practitioners utilize a suite of instruments to help assess biological characteristics of a patient, with each instrument specialized for a particular biometric or class of biometrics. However, the array of instruments required for a holistic and comprehensive assessment of a patient leads to challenges such as greater complexity, steeper learning curves for proper use, greater cost, and relative lack of portability and data interoperability.

Furthermore, some conventional instruments have limited functionality that contribute to an incomplete picture of patient health. For example, medical care practitioners have traditionally used tools such as stethoscopes to observe audible body sounds of a patient, such as those generated by the heart, lungs, and gastrointestinal system. However, conventional stethoscopes are unable to help a medical care practitioner observe certain cardiac, respiratory, and/or digestive related information encoded in various low frequency, low amplitude inaudible signals. Furthermore, it is not currently well-understood how to analyze such signals to assess patient health. Thus, using conventional technology, low frequency, low amplitude indicators of patient health are neither detected nor considered in conventional medical practice, leading to non-comprehensive diagnostic picture of a patient.

Furthermore, conventional stethoscopes require contact with the skin of the patient for adequate signal detection, and thereby have limited uses when, for various reasons such as contamination risk, modesty, or exigency, signal detection must occur through clothing.

Accordingly, there is a need for a new and improved sensor platform for characterizing one or more health and other physical conditions of a subject.

SUMMARY

Generally, in some variations, the present technology provides systems comprising a sensor platform. The sensor platform may include a sensing device such as a vibroacoustic sensor module including one or more sensors configured to detect a vibroacoustic signal, a signal processing system configured to extract, from the detected vibroacoustic signal, a vibroacoustic signal component originating from a subject, and at least one processor configured to characterize a bodily condition of the subject based at least in part on the extracted vibroacoustic signal component using, for example, a machine learning model. In some variations, the bodily condition of a subject may include a health condition of a subject. For example, the signal processing system may be configured to extract a biological vibroacoustic signal component originating from a living subject, and the at least one processor may be configured to characterize a health or other bodily condition of the subject based at least in part on the extracted vibroacoustic biological signal component. Additionally or alternatively, the bodily condition of a subject may include another suitable physical condition (e.g., structural condition) of a living or nonliving subject.

Additionally, in some variations, a method for characterizing a bodily condition may include detecting a periodic or aperiodic vibroacoustic signal with a vibroacoustic sensor module, the vibroacoustic sensor module comprising a plurality of sensors, extracting, from the detected vibroacoustic signal, a vibroacoustic signal component originating from a subject, and characterizing a bodily condition of the subject based at least in part on the extracted vibroacoustic signal component using a machine learning model. In some variations, the bodily condition of a subject may include a health condition of a subject. For example, the method may include extracting a biological vibroacoustic signal component from a vibroacoustic signal originating from a living subject, and characterizing a health condition of the subject based at least in part on the extracted biological vibroacoustic signal component using a machine learning model. Additionally or alternatively, the bodily condition of a subject may include another suitable physical condition (e.g., structural condition) of a living or nonliving subject.

Furthermore, in some variations, a vibroacoustic sensor module may include one or more sensors configured to detect a vibroacoustic signal, and one or more deflecting structures interfacing with one or more of the sensors, wherein the vibroacoustic sensor module has a bandwidth ranging from about 0.01 Hz to at least about 160 kHz, or from about 0.01 Hz to at least about 50 kHz Advantageously, according to certain variations, there are provided systems and methods for diagnosing or monitoring bodily conditions of subjects remotely in a non-invasive manner. Direct skin contact is not required and variants of the system and method can operate through clothing. In certain variations, systems and methods can operate at a distance of about 1 mm, 2 mm, 1 cm, 10 cm, 1 meter, 2 meter, 3 meter, 4 meter, 5 meter, 6 meter, 7 meter, 8 meter, 9 meter or 10 meter from the subject.

In certain variations, systems and methods may be well suited for screening for infectious bodily conditions, such as with a coronaviridae virus (e.g. Covid-19). Current Covid-19 screening approaches are either simple and fast but lack accuracy (e.g., temperature checks), or are accurate but neither simple nor fast (e.g., antibody screening). The gold standard for COVID-19 diagnosis is real-time reverse-transcriptase polymerase chain reaction (RT-qPCR), however, RT-PCR testing has been limited in certain situations to individuals with overt symptoms, and there are often significant delays between testing and result reporting—providing opportunity for unknown infectious spread. COVID-19 IgG antibody, or serology, testing can inform on past infections quickly and cheaply. However, antibodies can take days to weeks to develop, and the duration of their effectiveness remains unknown. Other screening approaches, such as those now being employed by many schools, daycares, hospitals, and other public spaces, rely on temperature scans for fever, and self-reported coughing and fatigue. However, these focus on non-specific symptoms that may not emerge for days after infection. Current screening approaches, therefore, are impractical, inconvenient, do not identify individuals at early infection stages, cannot discern COVID-19 or COVID-19-associated multisystem inflammatory syndrome in children (MIS-C), and do not consider common comorbidities, including influenza and pneumonia, respiratory failure, hypertension, diabetes, and cardiopulmonary dysfunction that exacerbates disease trajectory, and outcomes.

In the context of the present specification, unless expressly provided otherwise, a bodily condition may refer to, but is not limited to, one or more of a viral infection in a subject, a bacterial infection in a subject, a cognitive state of the subject, a reportable disease, fracture, tear, embolism, clot, swelling, occlusion, prolapse, hernia, dissection, infarct, stenosis, hematoma, edema. Contusion, osteopenia and presence of a foreign body in the subject such as an improvised explosive device (IED), surgically implanted improvised explosive device (SIIED), and/or body cavity bomb (BCB). Examples of viral infections include but are not limited to infections of coronaviridae (e.g. Covid-19, SARS). Reportable diseases are diseases considered to be of great public health importance. In the United States, local, state, and national agencies (for example, county and state health departments or the United States Centers for Disease Control and Prevention) require that these diseases be reported when they are diagnosed by doctors or laboratories. Diseases reportable to the CDC include: Anthrax, Arboviral diseases (diseases caused by viruses spread by mosquitoes, sandflies, ticks, etc.) such as West Nile virus, eastern and western equine encephalitis, Babesiosis, Botulism, Brucellosis, Campylobacteriosis, Chancroid, Chickenpox, *Chlamydia*, Cholera, Coccidioidomycosis, Cryptosporidiosis, Cyclosporiasis, Dengue virus infections, Diphtheria, Ebola, Ehrlichiosis, Foodborne disease outbreak, Giardiasis, Gonorrhea, *Haemophilus* influenza, invasive disease, Hantavirus pulmonary syndrome, Hemolytic uremic syndrome, post-diarrheal, Hepatitis A, Hepatitis B, Hepatitis C, HIV infection, Influenza-related infant deaths, Invasive pneumococcal disease, Lead-elevated blood level, Legionnaire disease (legionellosis), Leprosy, Leptospirosis, Listeriosis, Lyme disease, Malaria, Measles, Meningitis (meningococcal disease), Mumps, Novel influenza A virus infections, Pertussis, Pesticide-related illnesses and injuries, Plague, Poliomyelitis, Poliovirus infection, nonparalytic, Psittacosis, Q-fever, Rabies (human and animal cases), Rubella (including congenital syndrome), *Salmonella* paratyphi and *typhi* infections, *Salmonellosis*, Severe acute respiratory syndrome-associated coronavirus disease, Shiga toxin-producing *Escherichia coli* (STEC), Shigellosis, Smallpox, Syphilis, including congenital syphilis, Tetanus, Toxic shock syndrome (other than streptococcal), Trichinellosis, Tuberculosis, Tularemia, Typhoid fever, Vancomycin intermediate *Staphylococcus aureus* (VISA), Vancomycin resistant *Staphylococcus aureus* (VRSA), Vibriosis, Viral hemorrhagic fever (including Ebola virus, Lassa virus, among others), Waterborne disease outbreak, Yellow fever, Zika virus disease and infection (including congenital).

In the context of the present specification, unless expressly provided otherwise, by "remote screening" is meant that the subject does not have direct contact with at least sensor module components of the present system. Remote screening includes situations in which certain components of the system are spaced from the subject. There is no limitation on a distance of the spacing. Remote screening includes signal detection "over clothing" and/or "through clothing".

In the context of the present specification, unless expressly provided otherwise, by animal is meant an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Animals in the context of the present disclosure are understood to include vertebrates. The term vertebrate in this context is understood to comprise, for example fishes, amphibians, reptiles, birds, and mammals including humans. As used herein, the term "animal" may refer to a mammal and a non-mammal, such as a bird or fish. In the case of a mammal, it may be a human or non-human mammal. Non-human mammals include, but are not limited to, livestock animals and companion animals.

In the context of the present specification, unless expressly provided otherwise, a computer system may refer, but is not limited to, an "electronic device", an "operating system", a "communications system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

In the context of the present specification, vibroacoustic refers to vibrations or acoustical signals propagating through air, biological structures, solids, gases, liquids, or other fluids. This term also encompasses the term mechanoacoustics.

In the context of the present specification, the sensing device may be a sensoriactuator, which can be considered as a device configured to generate a sensor signal that is a function of its electrical response to an electrical input signal and its mechanical response.

Variations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

FIGS. 1A to 1D depict schematic illustrations of a sensor system for characterizing a bodily condition of a subject.

FIGS. 17A and 17B are cross-sectional views of the example vibroacoustic sensor modules of FIGS. 16A and 16B, respectively.

FIG. 22F depicts a wet electrode bioimpedance analysis application diagram.

FIG. 5I shows sensor data extracts (vibroacoustic only) of two Subject Cases and three Control Cases taken while the patients were in different positions and performing different actions (sitting, standing, supine, left lateral, cough and hand squeeze, speech) with the sensing device position on the right $2^{nd}$ a ICS location on their bodies.

DETAILED DESCRIPTION

Non-limiting examples of various aspects and variations of the invention are described herein and illustrated in the accompanying drawings.

1. Systems for Characterizing a Bodily Condition 1.a. Overview

Figure 1B:
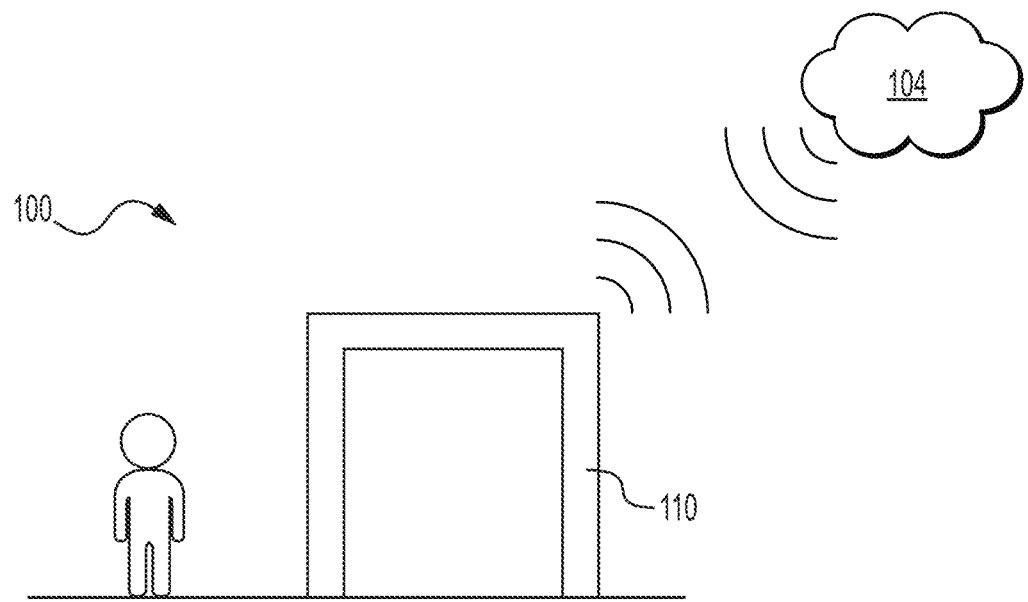

As shown in FIG. 1A, a system 100 for characterizing a bodily condition (e.g., health condition) may include one or more sensing devices 110 with one or more sensors configured to detect one or more biological parameters (e.g., vibroacoustic signals) of a subject.

In some variations, the one or more sensing devices 110 may be modular and include interchangeable subsystems adapted for modular experimentation, optimization, manufacture, rapid field configurability, etc. as part of a modular sensing platform. For example, the sensing device 110 may include a sensor module with one or more various sensor types, an electronics module, a housing, and/or other modular components that may be interchangeable for different applications and contexts. Such a modular sensing platform may provide an architecture well-suited for a modular suite of, for example, ambulatory wearable devices, remote screening devices and/or point-of-care solutions for healthcare, etc.

The one or more sensing devices 110 may have any suitable form factor for detecting biological parameters of the subject in a non-contact or contact manner. The sensing device 110 may be configured and positionable in any suitable manner relative to the subject to capture the suitable parameter(s).

For example, the sensing device 110 may include a handheld housing such that a user may hold and/or manipulate the sensing device 110 sufficiently near or on the subject to capture sensor data (FIG. 1A). The sensing device 110 may be configured to capture suitable parameters through clothing of the subject, or on direct contact with skin of the subject.

As another example, the sensing device 110 may include a wearable housing that may be applied to the subject (e.g., with an adhesive patch) (FIG. 1A) or coupled to clothing or other garments worn by the subject.

Figure 1C:
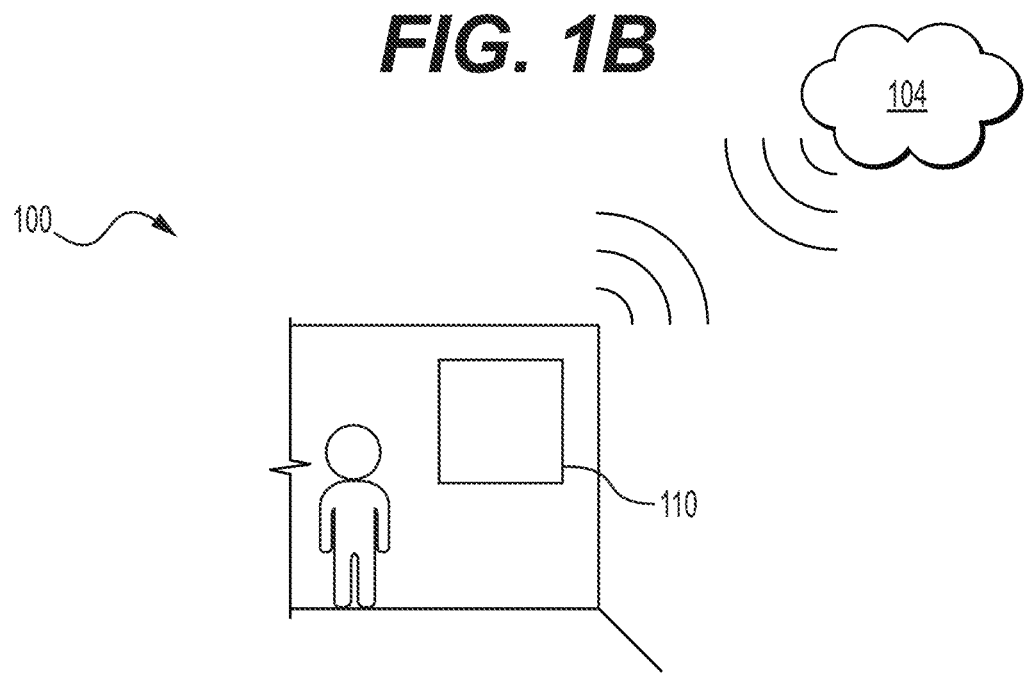

In some variations, the sensing device 110 is configured to capture data from the subject in a remote manner. In this respect, the sensing device 110 may be a standalone device (FIGS. 1B and 1C), arranged to be supported by a floor, wall, ceiling or other structural support, and configured to capture data from the subject in proximity to the sensing device 110.

In other variations, the sensing device 110 may be integrated in furniture as beds, bedding, mattresses, pillows, blankets, couches, chairs, vehicle seating, or devices such as scales, mirrors, panels, kiosks, doorways, signs and fitness equipment, etc.

Figure 1D:
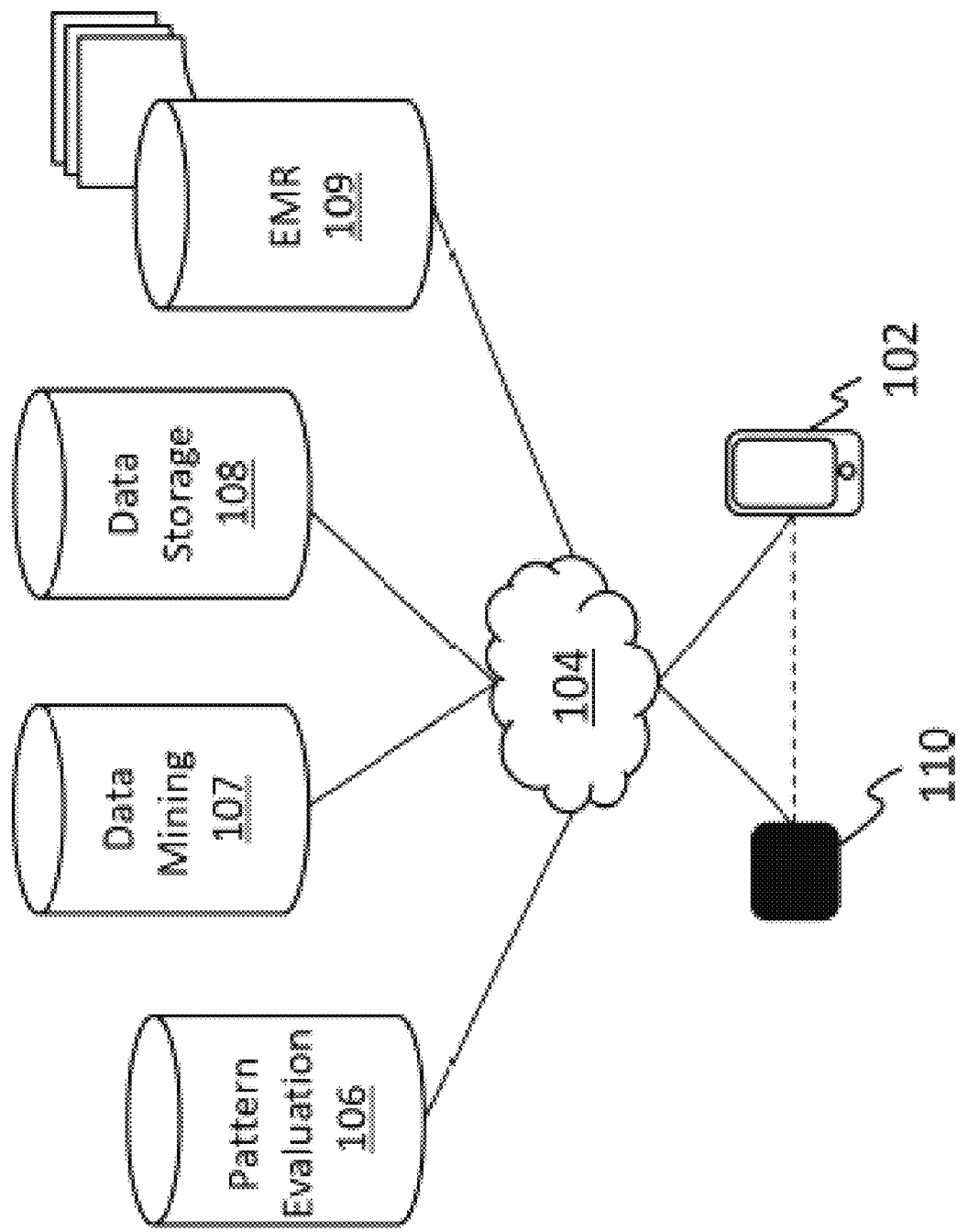

The sensing device 110 may be configured to communicate (e.g., wirelessly communicate) with one or more computing devices 102, such as a mobile computing device, smart watch, local data gateway, or computer for processing, analyzing, communication, and/or storage, etc. of sensor data and/or other suitable information. For example, as shown in FIG. 1D, the sensing device 110 may be configured to communicate over a network 104 with the computing device 102 and/or other suitable modules. The computing device 102 may additionally or alternatively collect data from other devices such as scales, fitness and sports equipment, blood pressure sensors, blood glucose sensors, and/or one or more suitable mobile applications that can provide supplementary environmental and social determinants of health contextual information.

Additionally or alternatively, the sensing device 110 may be configured to communicate directly with the computing device 102 and/or other devices without the network 104 (e.g., in pairwise fashion). In other variations, the sensing device 110 may be configured to communicate directly with the network 104.

In some variations, the sensing device 110 may be configured to communicate with suitable modules such as, for example, a pattern evaluation module 106 which may incorporate artificial intelligence (e.g., through application of one or more trained machine learning models) to characterize one or more bodily conditions of the subject based on sensor data. Parsed data may be stored locally on a computing device and/or on smartphone gateway (e.g., sensor data, results of analysis of sensor data, etc.) or may be stored in a suitable data storage module 108 such as a server or through cloud storage, and/or an electronic medical record 109 associated with the subject. Additionally, in some variations the machine learning model(s) used to analyze the sensor data may be continuously trained or updated using additional health history, sensor fusion, and/or environmental and/or social determinants of health context data overtime as further described below. For example, sensor data may be mined via a data mining module 107 for use in training and increasing the accuracy of predictive and/or prescriptive models across patient populations. A communication module may be provided for communicating data between the various modules of the system.

In some variations, one or more components of the system 100 for characterizing a bodily condition (e.g., health condition) may include various output interfaces such as for communicating information relating to the bodily condition (e.g., sensor data, analysis of sensor data, operational status, etc.). For example, as shown in FIGS. 1A-1H, the system 100 for characterizing a bodily condition may include the sensing device 110 (e.g., handheld device, wearable device, standalone device, etc.), and the computing device 102. The computing device 102 may be a stand alone device and separate from the sensing device (e.g. smartphone), or be incorporated with the sensing device 110. In some variations, the computing device 102 may be implemented as a network-on-chip (NoC) technology. In some variations, the computing device 102 and/or the sensing device may be implemented as a wearable device. The sensing device 110 may include a charging base 120 (FIG. 1H). Furthermore, one or more of the sensing device 110, the computing device 102, and the charging base 120 may include at least one output interface. For example, as shown in FIG. 1F, the sensing device 110 may include a display and/or one or more other suitable visual indicators such as a light indicator (e.g., LED indicator). As another example, the computing device 102 may include a haptic interface and/or audio output (e.g., speaker device). As another example, the charging base 120 may include a haptic interface and/or visual indicator such as a light indicator (e.g., LED indicator). However, it should also be understood that in some variations, any of the sensing device 110, the computing device 102, and/or the charging base 120 may include any suitable combination of interfaces, such as one or more of visual, audio, haptic, etc. One or more of the sensing device 110, the computing device 102, the network, and the charging base 120 may be configured to communicate information among each other (e.g., in a wireless manner, over a network, etc.) as described in further detail herein.

1.b. Vibroacoustic Sensor Platform

In some variations, the system 100 for characterizing a bodily condition is a vibroacoustic sensor platform configured to detect and process vibroacoustic signals, either alone or in combination with other sensor signals (not necessarily vibroacoustic signals), to diagnose or monitor a bodily condition of the subject.

In these variations, the system 100 includes a sensor module comprising one or more sensors configured to detect vibroacoustic signals as well as, optionally, signals which are not vibroacoustic signals, such as subject temperature, environmental conditions, etc. The detected signals by the sensor module is referred to generally herein as "sensor data". The sensor data may originate at least partially from the subject as well as from an environment of the subject. The sensor module may be embodied in a single sensing device 110 or in multiple sensing devices 110.

The system 100 may further comprise a signal processing system configured to extract from the detected sensor data a biological signal component originating from the subject. In some variations, the extracted biological signal component comprises a biological vibroacoustic signal component originating from the subject.

The system 100 may also comprise at least one processor configured to characterize or monitor a bodily condition of the subject based at least in part on the extracted biological signal component, such as the biological vibroacoustic signal component, using for example a machine learning model. It is to be understood that the bodily condition may be characterized on the sensor data, such as, one or more of: the vibroacoustic signal data, the extracted biological vibroacoustic signal component; signals which are not vibroacoustic signals; and biological signals extracted from the non-vibroacoustic signals originating from the subject.

The at least one processor may be embodied in one or more computing devices configured to perform processing, analysis, communication, and/or storage, etc. of sensor data from the sensor module.

The sensor module may be configured to detect a wide spectrum of vibroacoustic frequencies, which may provide useful indications of human health, animal health, and/or structural health separately and concurrently, including those that are not conventionally monitored or detected. More specifically, in certain variations, the sensor module is configured to detect vibroacoustic signals below and above the threshold of human audibility.

Figure 1E:
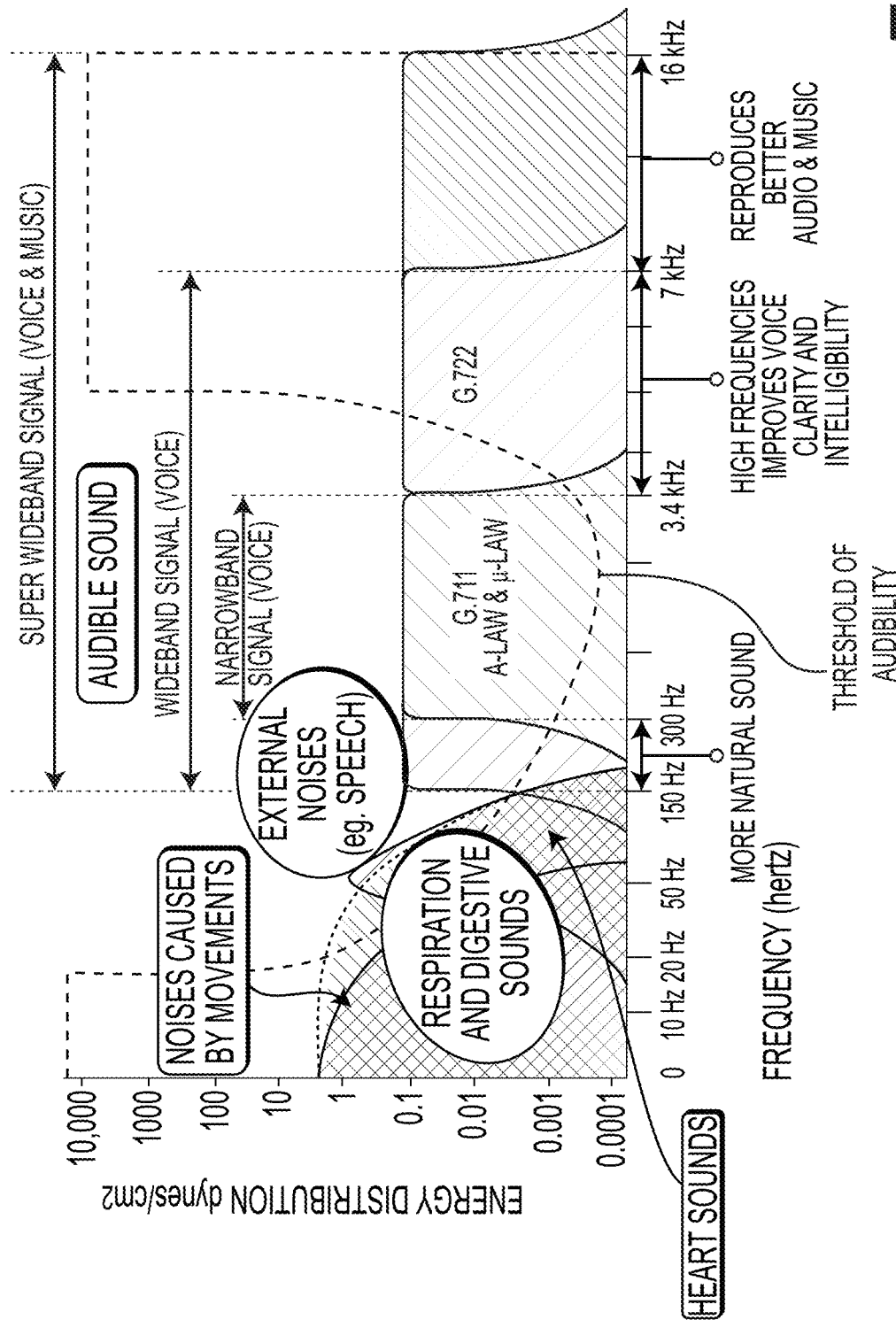
FIG. 1E illustrates various types of vibroacoustic data across a range of frequencies, energy distributions, and amplitudes in relation to the human ear's sensitivity across the range of frequencies.
Figure 1G:
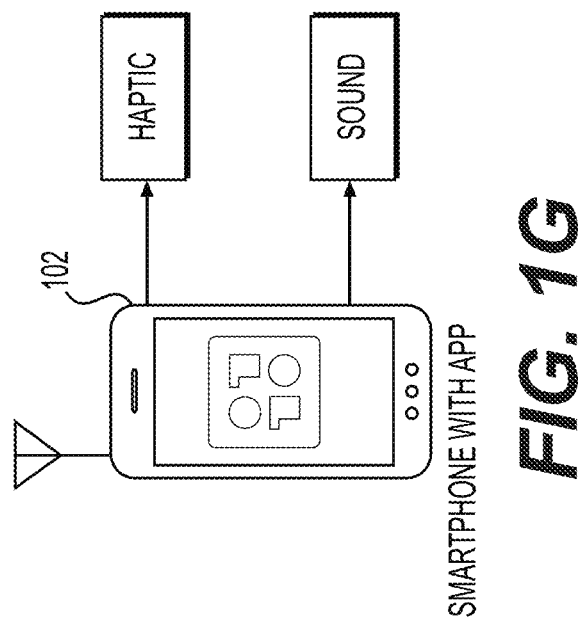
FIGS. 1F-1H depict schematic illustrations of various output interfaces of components of an example variation of a sensor system for characterizing a bodily condition of a subject.
Figure 1F:
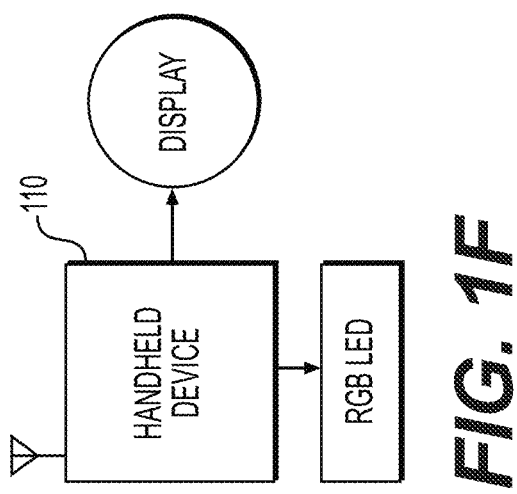
Figure 1H:
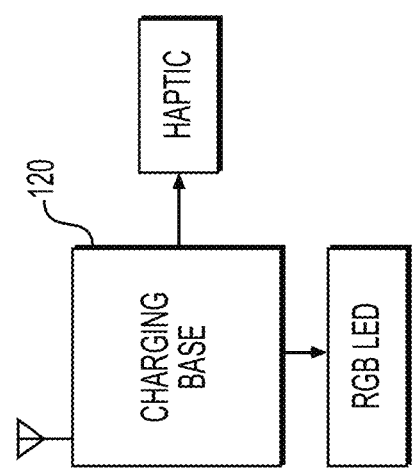

As shown in FIG. 1E, the threshold of human audibility decreases sharply as vibrational frequency falls below about 500 Hz. However, in a healthy subject at rest, most cardiac, respiratory, digestive, and movement-related information is inaudible to humans, as this information occurs at frequencies below those associated with speech. Thus, the majority of bodily vibrations are neither detected nor included in conventional diagnostic medical practices due to the low frequency band of these vibrations, and the limited bandwidth limits of conventional instruments (e.g., conventional stethoscopes). Variations of the system 100 described herein are capable of detecting, amplifying and analyzing a broad spectrum of infrasound, ultrasound, and far-ultrasound vibroacoustic frequencies, and are thus advantageous for a more comprehensive, holistic picture of subject health and condition.

Additional details of the system 100 and its components, sensing devices 110 and methods are described further below. Such systems 100, sensing devices 110 and methods are primarily described with respect to characterizing a bodily condition of a subject, which may be, for example, a human or other animal (e.g., for human healthcare and/or veterinary care). However, it should be understood that other applications of the systems 100, sensing devices 110 and methods may relate to characterization of non-living items, including but not limited to heating, ventilation, air conditioning (HVAC) systems, internal combustion engines, jet engines, turbines, bridges, aircraft wings, environmental infrasound, ballistics, drone and/or seacraft identification etc. For example, the systems 100, sensing devices 110, and methods may be applied to characterize structural health (e.g., characterizing structural integrity of bridges, buildings, aircraft, vehicles, etc.), environmental noise pollution, rotating motor engine performance optimization, surveillance etc.

1.c. Example Sensing Devices 1.c.i. Hand-Held Sensing Devices

Figure 2:
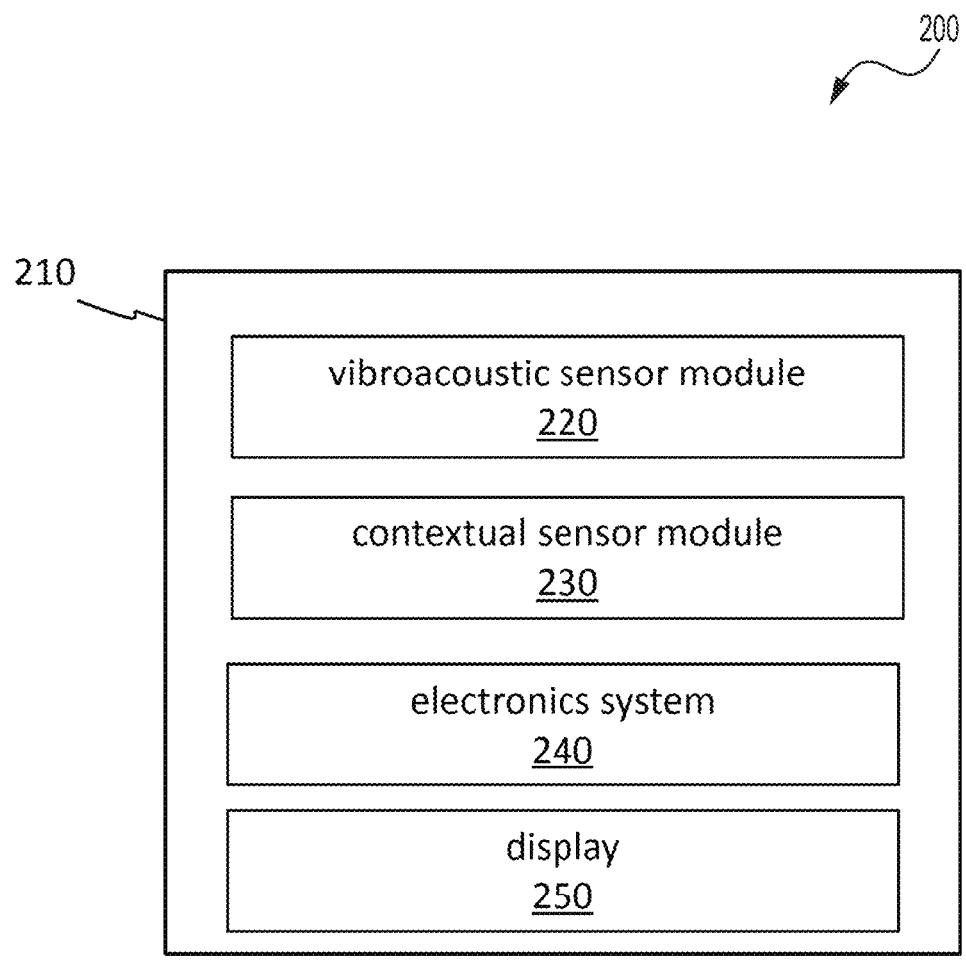
FIG. 2 depicts a schematic illustration of an example variation of a vibro-acoustic sensing device for characterizing a bodily condition of a subject.

In some variations, the system 100 may include, as shown schematically in FIG. 2, a sensing device 200 which is hand-held. The sensing device 200 includes a sensor module comprising: a vibroacoustic sensor module 220, and optionally a contextual sensor module 230; an electronics system 240 which may, for example, handle sensor data from the vibroacoustic sensor module 220 and/or the contextual sensor module 230. One or more of these components may be enclosed or otherwise at least partially arranged in a housing 210 of the sensing device 200, which may have any suitable form factor for different applications as further described below. In some variations, the housing 210 may include a display 250 for providing a user interface of the sensing device (e.g., for displaying information to a user, for permitting control of the sensing device, etc.). Certain other examples of the form factor of the sensing device 110 or 200 are illustrated in FIGS. 3A and 3B, 4A-4E, 4F-4G, 5A-5I, 27A-27B, 28A-28B, 29, 30, 31A-31E, 32A-32B, and 33A-33C.

Figure 3A:
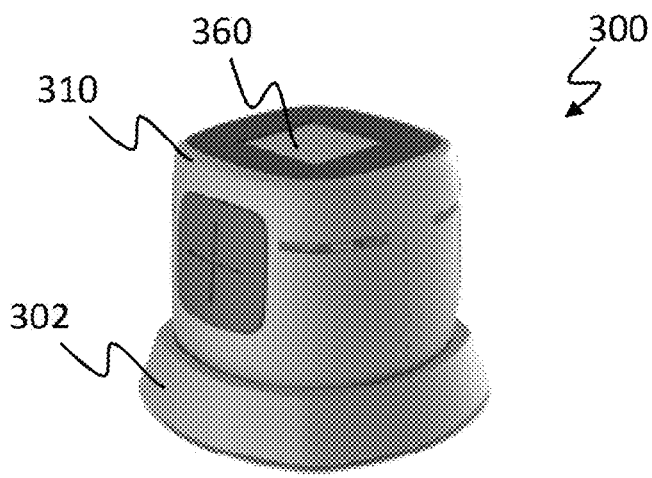
FIGS. 3A and 3B depict an assembled view and an exploded view, respectively, of an example variation of a sensing device for characterizing a bodily condition of a subject.
Figure 3B:
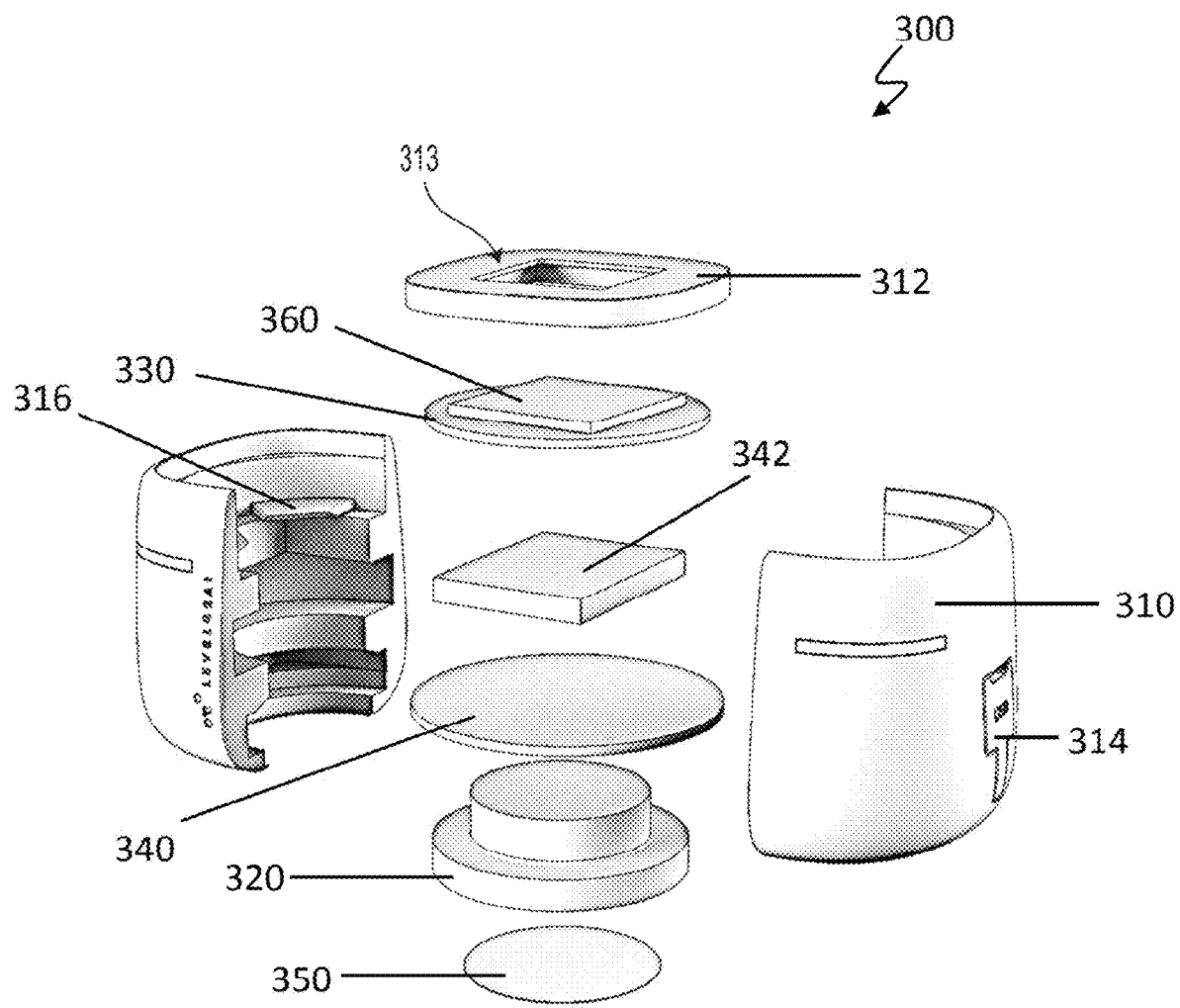

FIGS. 3A and 3B illustrate another example sensing device 300, which is a variation of the sensing device 110. As shown in FIG. 3A, the sensing device 300 may include a housing 310 within which various sensing device components may be arranged. The housing 310 shown in FIG. 3A is configured as a handheld housing 310 having a generally cuboid shape; however, it should be understood that other housing variations may have other shapes (e.g., spherical, ellipsoid, other prismatic shapes, etc.). Other exemplary sensing device form factors are described in further detail below.

In some variations, a base 302 may be coupled to the housing 310. The base 302 may, for example, provide a surface on which the housing 310 may rest and/or provide an indication of device orientation (e.g., indicate a primary direction along which the sensor module within the housing 310 is sensing). In some variations, the base 302 may function as a charging cradle, with the housing 310 separable from the base 302 when the sensing device 300 is in use.

As shown in the exploded view of FIG. 3B, the housing 310 may surround a vibroacoustic sensor module 320 that includes one or more sensors for collecting vibroacoustic signals, an optional contextual sensor module 330, and an electronics system 340 including components for processing the sensor data from the vibroacoustic sensor module 320 and optionally the contextual sensor module 330. In some variations, electronic components (within the vibroacoustic sensor module and/or in the electronics system 340, for example) may perform various signal processing functions to extract a biological vibroacoustic signal component from sensor data, and/or perform analysis via artificial intelligence (e.g., utilizing one or more machine learning models) to characterize a bodily condition based on the biological vibroacoustic signal component.

In some variations, the housing 310 may include one or more guides or compartments for receiving and positioning the various internal device components. For example, as shown in FIG. 3B, the housing 310 may include one or more internal projections 316 (e.g., shoulder, lip, or other guide) configured to restrain an adjacent device component such as the vibroacoustic sensor module 320 or electronics system 340. The restraint may be provided by an interference fit, one or more fasteners, and/or the like. Although FIG. 3B depicts the internal device components as generally axially aligned, it should be understood that in other variations, the components may be arranged in any suitable manner (e.g., orthogonal to one another, etc.).

The housing 310 may include one or more openings and/or other structures to facilitate communication with sensors. For example, the housing 310 may include a sensor opening adjacent to the vibroacoustic sensor module 320 to permit entry and propagation of vibroacoustic waves toward the vibroacoustic sensor(s) in the module and/or a membrane or other receiver that interfaces with the vibroacoustic sensor(s). Additionally or alternatively, in some variations the sensing device 300 may include an impedance matching diaphragm 350 arranged in series with the vibroacoustic sensor module 320 to improve sensitivity to a wide range of vibroacoustic frequencies. The diaphragm 350 may be dome shaped, for example, impedance matching may refer to the operating state in which the load impedance and the internal impedance of the excitation source match to each other (e.g., within a tolerated impedance difference), thereby leading to a maximum power output. A mismatch in the impedances may result in undesirably high attenuation and/or reflection of source signals away from the vibroacoustic sensor module. This problem may be addressed, for example, by developing impedance matching circuits using machine-fabricated tunable components leveraging a plurality of diaphragm cutout designs (also referred to as "apertures", examples of which are shown in FIG. 18) for an optimal dynamic range in the low infrasound domain. A combined diaphragm/transducer solution may include a suitable protective material (e.g., rubber, felt liner, light foam, etc.) around the diaphragm and fixture area to protect the interior of the transducer from water and particulate matter by sealing any gaps. Diaphragm may include a passive material (including but not limited to polymer, polyamide, polycarbonate, polypropylene, carbon fiber, fiber glass, etc.) fabricated as the structural layer with optimized dimensions for the physical system form factor. In order to obtain the tunable impedance matching system and structural layer(s), the gap between the diaphragm and voice coil may be tunable. The structural layer(s) may be spun and patterned to ensure the shape and optimal weight and subsequently bonded.

In some variations, the housing 310 may include a power connection port 314 enabling a connection of an auxiliary power source to the electronics system 340 and/or other powered components. Additionally or alternatively, the housing 310 may include a data connection port (not shown) that may provide a (wired option for uploading or downloading data or other information to and from the electronics system 340. In some variations, power and data may be communicated via the same port (e.g., via a USB connection).

Furthermore, in some variations the housing 310 may include a user interface, such as a display 360 which is visible through a screen or opening in a bezel 312 of a top cover 313 or other suitable portion of the housing 310. The display 360 may include an LED screen, LCD screen, or other suitable monitor screen. The display 360 may be configured to display information to a user (e.g., diagnostic information, sensor data, device status, etc.) such as on a graphical user interface (GUI), to permit control of the sensing device (e.g., power states, operational mode, etc.), and/or the like. In some variations, the display 360 may include a touchscreen to receive user input. In some variations, the vibroacoustic sensor or a dedicated microphone may be used to receive vocal user input. Additionally, or alternatively, user input may be provided to the sensing device 300 through one or more hardware user interface elements on or coupled to the housing (e.g., buttons, slides, switches, touch sensors, etc.). Additionally, or alternatively, information about the device and/or analysis may be communicated through other components (e.g., visual notifications with an array of LEDs, audible notifications with a speaker device, tactile notifications with a vibrational motor, etc.). For example, in some variations, acoustic data may be played back over one or more speaker devices (or communicated to a peripheral device for playback). Furthermore, in some variations, one or more device orientation and/or positional sensors (e.g., Inertial Measuring Unit (IMU), accelerometer, gyroscope, etc.) may be used for user input and function manipulation of the sensing device (e.g., shaking or rotating the sensing device may toggle between device settings, wake up or put the sensing device into a sleep or standby mode, etc.).

The housing 310 may be constructed in various suitable manners, such as injection molding, milling, 3D printing, etc. As shown in FIG. 3B, the housing 310 may include multiple connectable portions (e.g., two halves of a shelled housing) that join to form one or more internal volumes receiving internal device components. The connectable portions may be coupled together with mechanical interlocking features (e.g., pins and holes sized to engage in a friction fit), fasteners (e.g., screws, adhesive, etc.), and/or in any suitable manner. Alternatively, the housing 310 may be integrally formed as a single piece.

In some variations, some of the components of the sensing device 300 may be intended as reusable and/or upcycled, while other components may be disposable. For example, in some variations inexpensive components such as the housing 310 and/or subject-contacting components (e.g., impedance-matching diaphragm) may be replaced, while more expensive components such the electronic components of the sensing device 300 may be re-used. In some variations, components may be disinfected (e.g., with isopropyl alcohol) instead of being replaced and disposed of. In this respect, the disinfectable components may be made of a material suitable for disinfection such as by one or more of alcohol, hydrogen peroxide, steam, ethylene dioxide, gamma irradiation, ultraviolet light. In some variations, the sensing device 300 may include one or more sensors (e.g., proximity sensors, Hall effect sensors, contact sensors, etc.) that detect and authenticate the attachment and detachment of replaceable parts, so that the system 100 can intelligently monitor uses, sterile change events, duration of use between changes in sterile covers, battery levels, number of uses and/or other usage data, etc. Such data may, for example, be used to monitor a report on compliance with best practices and required protocols for maintaining cleanliness.

In some variations, the housing 310 may be configured to be attachable to another type of device such as a stethoscope. In this respect, retroactive attachability may be facilitated by windings for screw attachment or other fasteners.

Figure 4A:
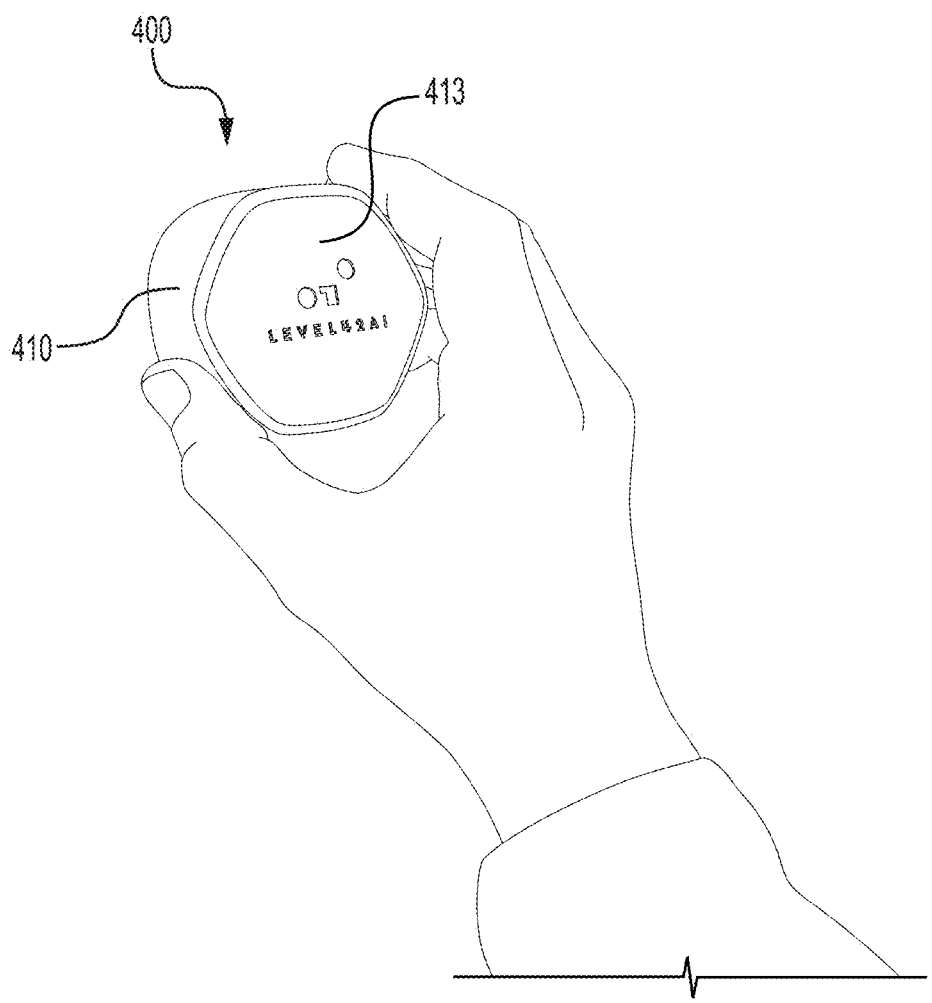
FIGS. 4A and 4B depict an assembled view and an exploded view, respectively, of another example variation of a sensing device for characterizing a bodily condition of a subject.
Figure 4B:
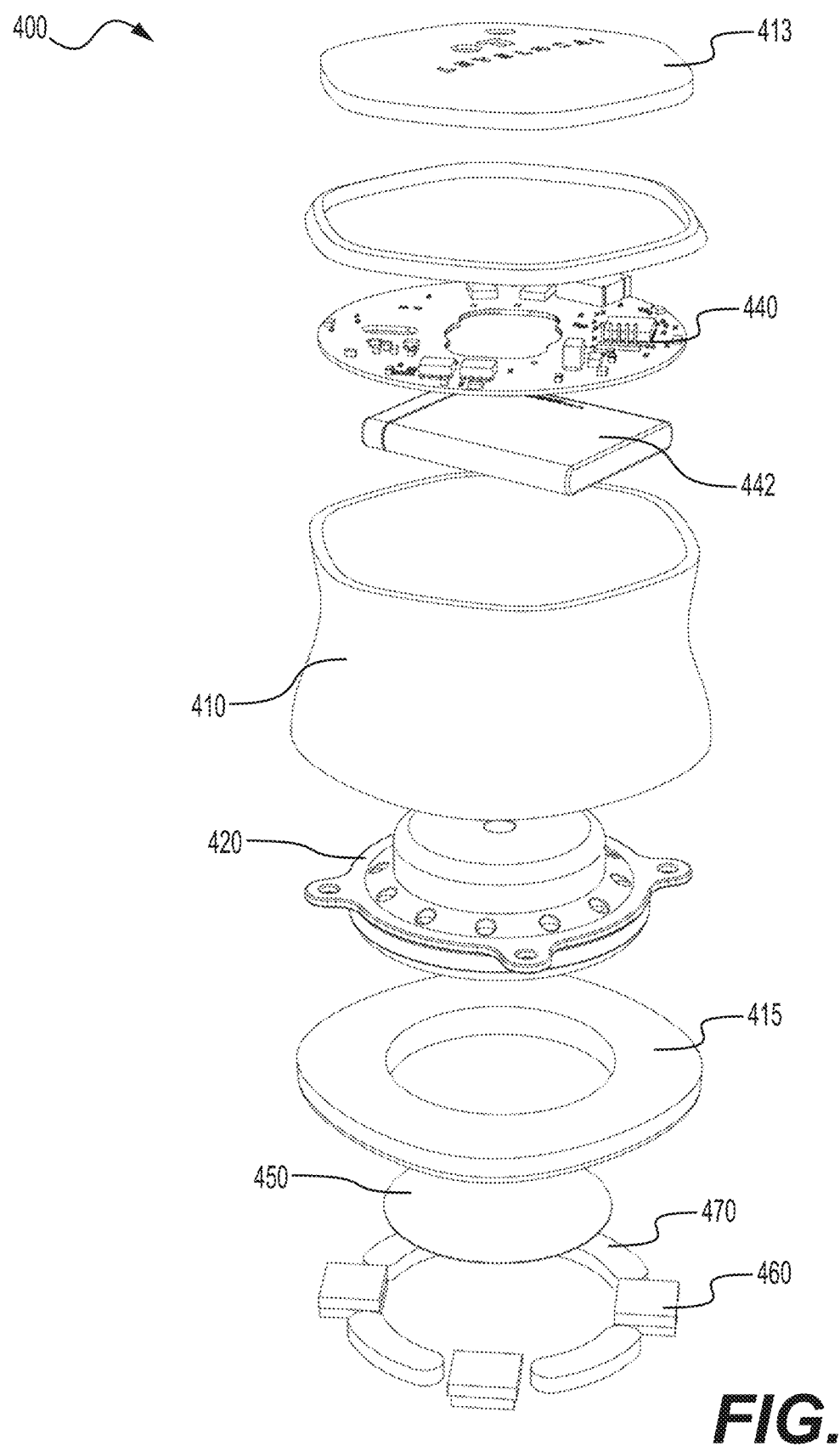
Figure 4C:
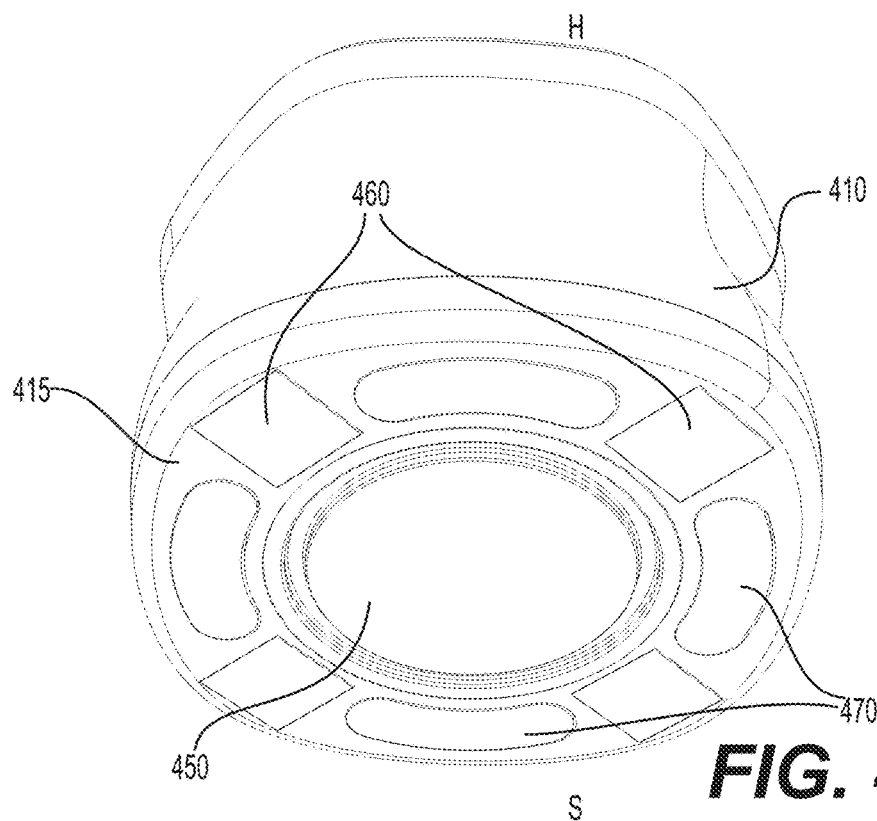
FIG. 4C depicts a perspective view from a sensor end of the sensing device of FIGS. 4A and 4B.
Figure 4D:
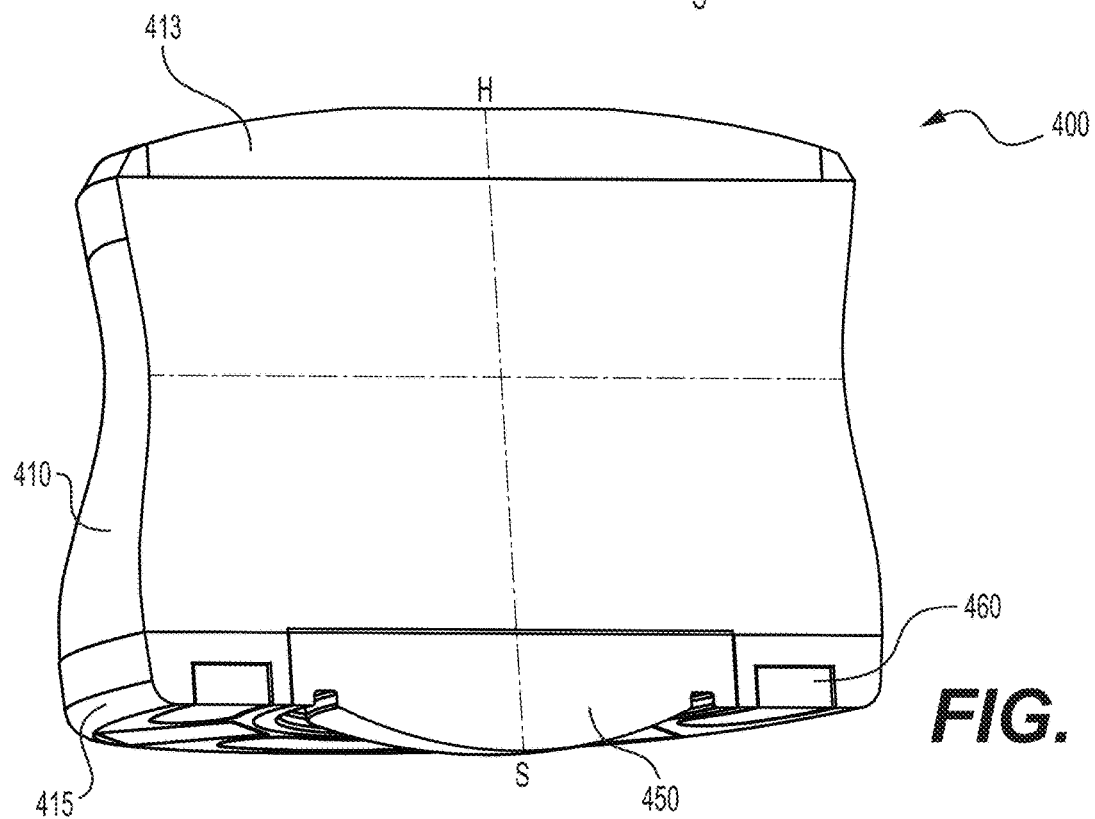
FIG. 4D depicts a cross-section through the sensing device of FIGS. 4A and 4B with some of the internal components omitted for clarity.
Figure 4E:
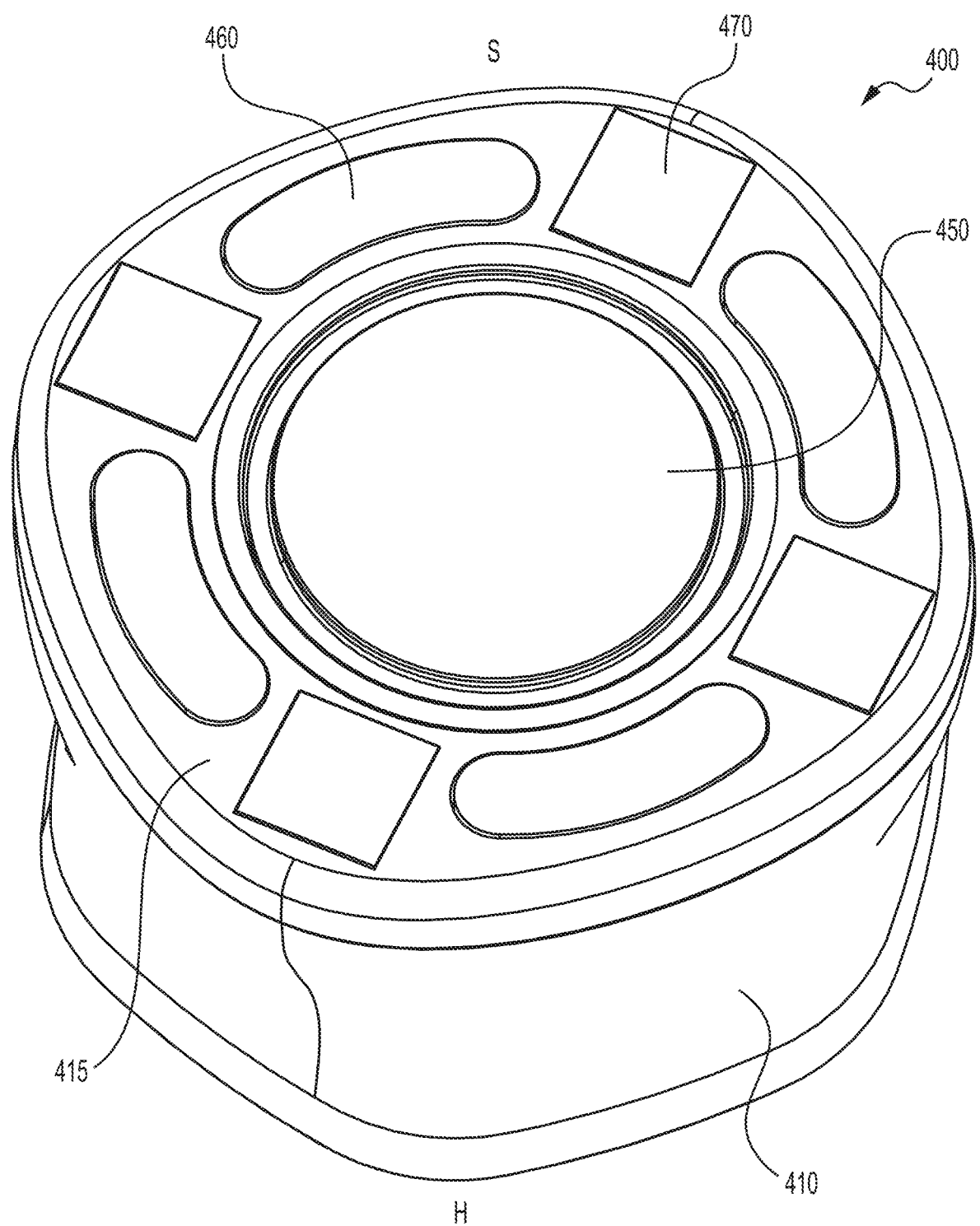
FIG. 4E depicts a perspective view from a handle end of the sensing device of FIGS. 4A and 4B.

FIGS. 4A-4E illustrate a sensing device 400, which is another example variation of the sensing device 110 of the system 100. The sensing device 400 is also modular and includes multiple components that can be assembled together. For example, the sensing device 400 includes a housing 410 connectable to a top cover 413 and a bottom cover 415. The sensing device 400 has a handle end H and a sensor end S. As before, the housing 410 may be couplable to a base (not shown), for charging and/or support. The housing 410 is configured to substantially surround one or more of the components including: a vibroacoustic sensor module 420, an electronics system 440, a power source 442, a diaphragm 450 (such as an impedance matching diaphragm 450), first and optionally second capacitive electrodes 460, 470 for electrocardiogram (ECG) measurements. In certain variations, the first capacitive electrodes 460 comprise Electric Potential Integrated Circuit (EPIC) electrodes 460. In certain variations, the second capacitive electrodes 470 comprise Driven Right Leg (DRL) electrodes 470. In certain other variations, the capacitive electrodes 460, 470 may be omitted (FIG. 4H). The diaphragm 450 is supported by the bottom cover 415 and extends from an opening in the bottom cover 415.

Figure 4F:
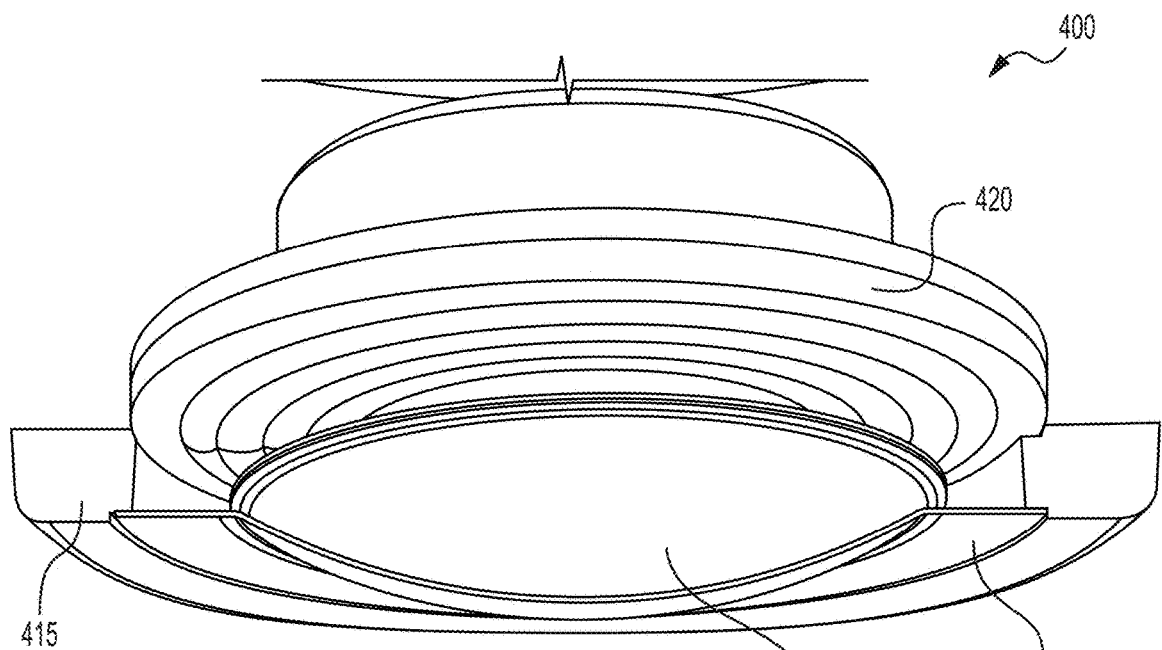
FIG. 4F depicts a close-up perspective view of the sensor end of the sensing device of FIGS. 4A and 4B with some of the housing cut-away for clarity.
Figure 4G:
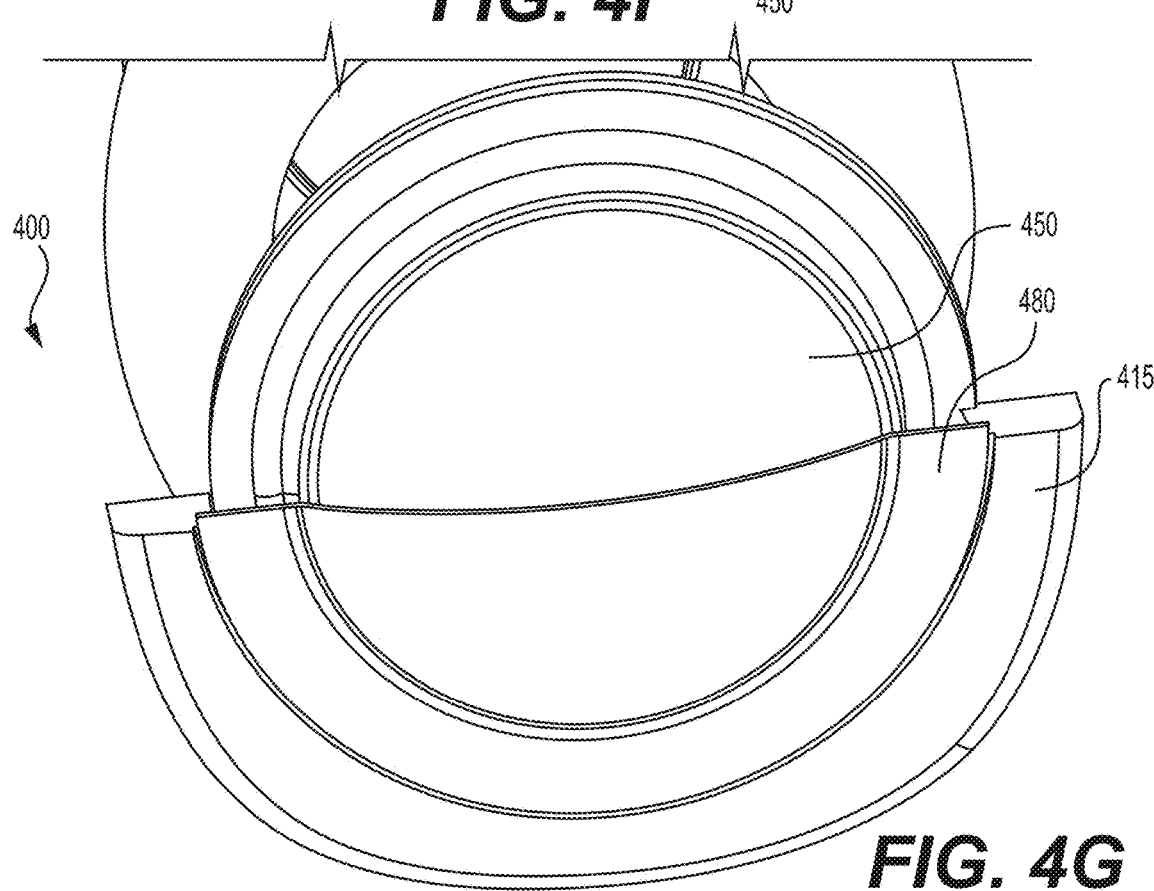
FIG. 4G depicts a close-up plan view of the sensor end of the sensing device of FIG. 4F.
Figure 4H:
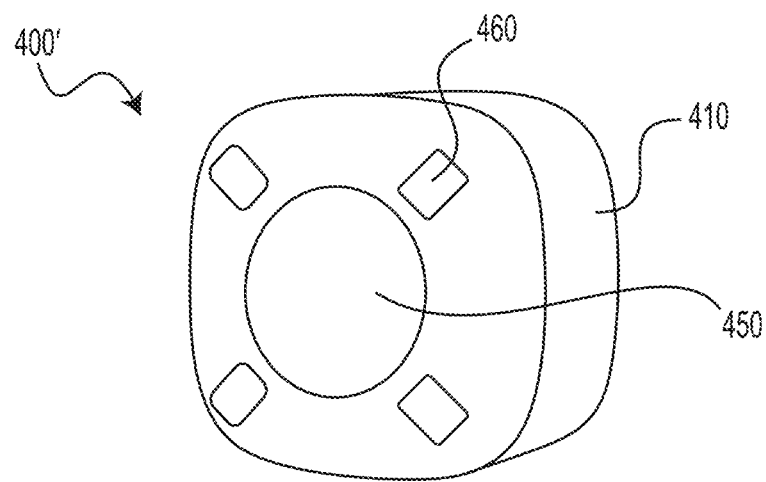
FIG. 4H depicts a perspective view of another example variation of a sensing device for characterizing a bodily condition of a subject.

As seen in FIGS. 4F and 4G, in certain variations, an outer cover 480 may also be provided to seal a connection between the bottom cover 415 and the diaphragm 450 for limiting or preventing foreign body ingress. The outer cover 480 may be made of rubber, or any other suitable material including material suitable for medical applications. The outer cover 480 may be connected to the bottom cover 415, such as by adhesive. In the variations of FIGS. 4F and 4G, the outer cover 480 stops short of a perimeter of the bottom cover 415. However, in certain other variations, the outer cover 480 extends entirely across the bottom cover 415, and may also extend upwards from the bottom cover 415 like a cap. This can allow the sensor end S of the sensing device 400 to be soaked in liquid, such as a disinfecting solution. Solution could be provided within a base like 302, for sterilization or cleaning. In certain variations, a gap between the diaphragm 450 and the bottom cover 415 to be covered can be anywhere between 0.001 mm and 20 mm; such as bout 2 mm, about 4 mm, about 6 mm, about 8 mm, or about 10 mm.

Figure 4I:
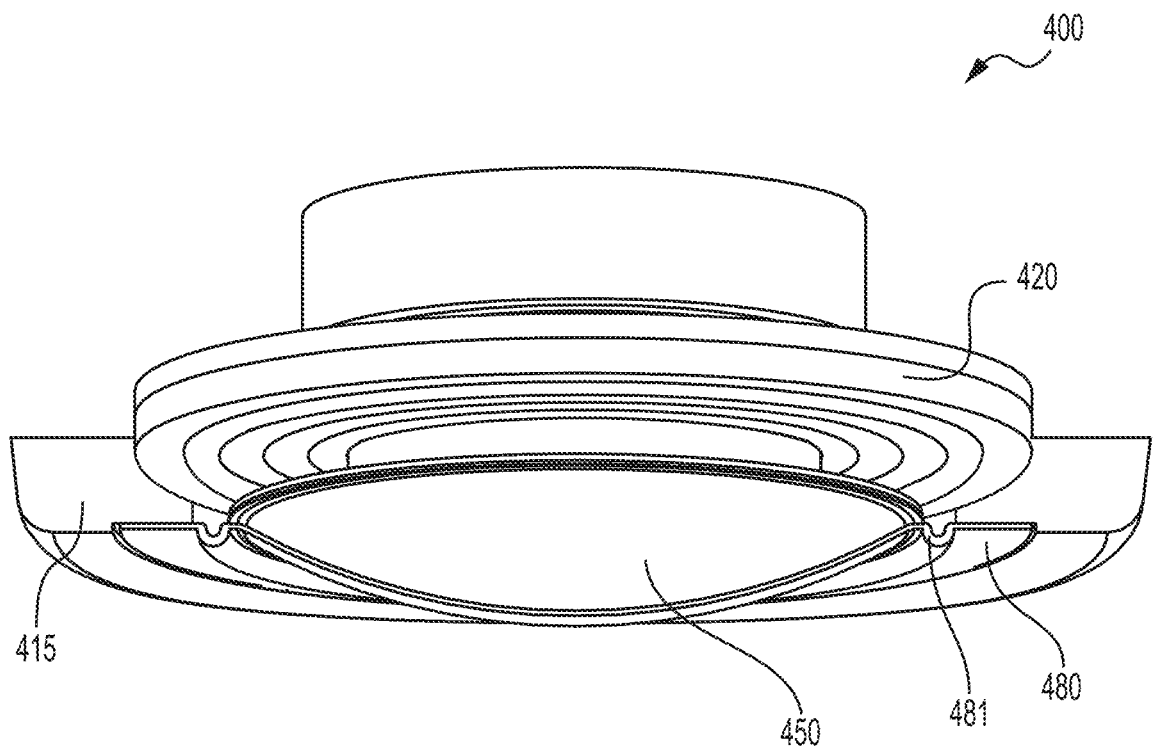
FIG. 4I depicts a close-up plan view of the sensor end of a variant sensing device to the one of FIG. 4G.

FIG. 4I depicts a variation of the outer cover 480 of the sensing device 400, in that a bend 481 is included in the outer cover 480 which can permit expansion of the outer cover 480 to account for movement of the diaphragm. The bend is positioned radially. In this variation, a gap between the diaphragm 450 and the bottom cover 415 is about 2 mm, and the bend 481 has a radius of about 2 mm. This may allow compliant and linear travel of the diaphragm for up to 4 mm out of plane. As a variation, the outer cover 480, including the bend 481 may extend all the way across the bottom and up the side of the device to be fluid resistant (not shown).

The sensing device 400 differs from the sensing device 300 in form factor, as well as the type of sensors included. More specifically, the sensing device 400 does not include the contextual sensor module 330. The sensing device 400 may include the EPIC electrodes 460 and DRL electrodes 470 for collecting ECG data. The EPIC and DRL electrodes 460, 470 will be described in further detail below with reference to FIGS. 19-22.

In certain variations, the sensing device 400 is sized and shaped to be handheld. Optimization of the size and shape of the sensing device 400 has a number of considerations including one or more of: a spacing of the EPIC electrodes 460 and the DRL electrodes 470 from one another and/or the vibroacoustic sensor module 420 to avoid interference, and a size of the diaphragm 450. Accordingly in one variation, four EPIC electrodes 460 and four DRL electrodes 470 are provided, spaced apart from one another and positioned around the diaphragm 450. The diaphragm 450 has a diameter of about 39 mm, and each EPIC electrode is about 10 mm long. It will be appreciated that the arrangement of the electrodes 460, 470 and their size may vary from that as illustrated. Sensing devices with alternative dimensions are within the scope of this present disclosure.

In certain variations, one or more of the DRL electrodes 470 may comprise a guard electrode. In fact, in certain variants, a function of the electrode 470 may be configurable as either a guard electrode or a DRL electrode depending on whether the use is skin contact or no direct skin contact. In certain other variants the bottom cover 415 is made of a conductive material and configured as a guard electrode.

FIG. 4H illustrates a sensing device 400' which is a variation of the sensing device 400 of FIGS. A-E, which differs only in that the EPIC electrodes 460 and Driven Right Leg (DRL) electrodes 470 for sensing ECG data have been omitted. The sensing device 400' is configured to detect only vibroacoustic signals.

1.c. ii. Example Sensors of the Vibrometer Sensor Modules

In certain variations, a vibroacoustic sensor module, such as the vibroacoustic sensor module 220, 320, 420, 2720, 2820, 2920, 3140 may include one or more sensors configured to detect a vibroacoustic signal. The vibroacoustic sensor module may also include one or more deflecting structures interfacing with a sensor component of the sensor. For example, the one or more sensors may be selected and/or arranged to interface with the one or more deflecting structures so as to measure various characteristics of the movement of the deflecting structure(s) (e.g., in response to vibroacoustic waves). Such movement, which is measurable by the one or more sensors, may be analyzed to assess bodily condition(s) of a subject. As further described below, in some variations, the one or more sensors may also be arranged on a flexible circuit board or other structure that is suitably flexible so as to not significantly interfere with the interfacing of the sensor(s) and deflecting structure(s), thereby avoiding reduction in sensitivity and/or bandwidth of the vibroacoustic sensor module. Exemplary variations of sensor arrangements and deflecting structures are described in further detail below.

In some variations, the vibroacoustic sensor module may have a bandwidth suitable for detecting vibroacoustic signals in the infrasound range, such as a bandwidth ranging from about 0.01 Hz to at least about 20 Hz. Furthermore, in some variations, the vibroacoustic sensor module may have wider bandwidths covering a wider spectrum of infrasound-to-ultrasound, such as a bandwidth ranging from about 0.01 Hz to at least 160 kHz. In some variations, the biological vibroacoustic signal component extracted from the detected vibroacoustic signal may have a bandwidth ranging from about 0.01 Hz to 0.1 Hz.

For example, in some variations the vibroacoustic sensor module may have an overall bandwidth ranging from about 0.01 Hz to at least about 50 kHz, from about 0.01 Hz to at least about 60 kHz, from about 0.01 Hz to at least about 70 kHz, from about 0.01 Hz to at least about 80 kHz, from about 0.01 Hz to at least about 90 kHz, from about 0.01 Hz to at least about 100 kHz, from about 0.01 Hz to at least about 110 kHz, from about 0.01 Hz to at least about 120 kHz, from about 0.01 Hz to at least about 130 kHz, from about 0.01 Hz to at least about 140 kHz, from about 0.01 Hz to at least about 150 kHz, from about 0.01 Hz to at least about 160 kHz, from about 0.01 Hz to more than about 150 kHz.

The vibroacoustic sensor module may, in some variations, include a single sensor that provides one or more of the abovementioned bandwidths of detected vibroacoustic signals.

In some other variations, the vibroacoustic sensor module may include a suite of multiple vibroacoustic sensors, each having a respective bandwidth forming a segment of the overall vibroacoustic sensor module bandwidth. At least some of these multiple sensors may have respective bandwidths that at least partially overlap. Accordingly, various sensor module bandwidths may be achieved based on a selection of particular sensors that collectively contribute to a particular vibroacoustic sensor module bandwidth. In other words, bandwidth extension and linearization approach (bandwidth predistortion) may utilize modular sensor fusion and response feedback information, such as to compensate for bandwidth limitations of any particular single sensor with overlapped combinations of sensors to cover a wider bandwidth with optimal performance.

For example, the vibroacoustic sensor module may include one or more sensors for measuring vibroacoustic signals. The one or more sensors may be selected from passive and active sensors for obtaining vibroacoustic data such as one or more of a microphone, a voice coil, accelerometer, pressure sensors, piezoelectric transducer elements, doppler sensors, etc. For example, the vibroacoustic sensor module may include a voice coil-based sensor. In another example, the vibroacoustic sensor module may include a voice coil-based sensor and an echo doppler based ultrasound sensor. The vibroacoustic sensor module may include one or more microphones such as a dynamic microphone, a large diaphragm condenser microphone, a small diaphragm condenser microphone, and/or a ribbon microphone. Additionally, or alternatively, the vibroacoustic sensor module may include a linear position transducer. Such sensors may be configured to detect and measure vibroacoustic signals by interfacing with a suitable deflecting structure that moves in response to a vibroacoustic signal. In some variations, the vibroacoustic sensor module may combine multiple microelectromechanical systems technologies cross-axis inertial sensors capable of detecting vibroacoustic signals ranging from about 20 Hz to about 20 kHz.

Additionally, or alternatively, the vibroacoustic sensor module may include a MEMS cross-axis inertial sensor fusion capable of detecting vibroacoustic signals ranging from about 1 Hz (or less) to a few kHz (e.g., between about 1 Hz and about 2 kHz). Even further, the vibroacoustic sensor module may additionally or alternatively include a MEMS cross-axis inertial sensor capable of detecting vibroacoustic signals ranging from about 0.01 Hz to several hundred Hz (e.g., between about 0.05 Hz and about 10 kHz). Additionally, or alternatively, other suitable vibroacoustic sensors may be included in the vibroacoustic sensor module, such as a voice coil transducer, piezoelectric transducer, etc. In some variations, transmission of vibroacoustic waves may occur through an intermediate medium such as air and/or across a deflecting structure.

Furthermore, a suite of multiple kinds of sensors in the vibroacoustic sensor module may be configured to more fully capture longitudinal and transverse vibrations, as well as environmental context and environmental disturbances (alone or in combination with the contextual sensor module described in further detail below). In some variations, environmental context signals may be useful for contextualizing the relevant vital physiology data collected. Additionally, or alternatively, in some variations, environmental disturbance data (e.g., ambient noise) may be used for noise cancellation from the relevant biological vibroacoustic signal component. Such noise cancellation may, for example, be performed as active noise cancellation on the device, or as a postprocessing step. In some variations, a deflecting structure in the vibroacoustic sensor module may generally have a nominal or resting configuration in which the deflecting structure is arranged in a plane, and the deflecting structure may deflect or flex in response to out-of-plane forces. In these variations, the deflecting structure may be configured to have low stiffness (or resistance) against out-of-plane movement with good compliance to skin movement, yet high stiffness or resistance against in-plane movement and low crosstalk between axes within the plane. Accordingly, a deflecting structure have high sensitivity to acoustic waves directed toward the deflecting structure (that is, acoustic waves having a vector component that is orthogonal to the deflecting structure) but be robust against noise contributed by other forces.

Furthermore, in some variations, a deflecting structure in the vibroacoustic sensor module may have relatively low mass on the movable portion of the deflecting structure to reduce inertia (and further improve sensitivity to out-of-plane forces). In some variations, the deflecting structure may be designed with low or no hysteresis, such that out-of-plane movement is highly linear.

Additionally, or alternatively, the deflecting structure may be designed to have low material fatigue over time, so as to be predictable and consistent over the long-term use of the sensing device.

The deflecting structure may, in some variations, include a more rigid material such as a rigid plastic, and may be formed through 3D printing, milling, injection molding, or in any suitable manner. For example, the deflecting structure may include a material including but not limited to polyamide, polycarbonate, polypropylene, carbon fiber, fiber glass, and/or other suitable material.

Flexure Arm-Type Vibroacoustic Sensor Modules

In some variations, the vibroacoustic sensor module may include one or more deflecting structures that include at least one flexure arm. For example, FIGS. 5A-5I depict an exemplary variation of a vibroacoustic sensor module 500 having multiple flexure arms. As shown in the cross-sectional views of FIGS. 5A and 5B, the vibroacoustic sensor module 500 may be arranged in a housing 510 of a vibroacoustic sensing device (e.g., which may be similar, for example, to the sensing device 300 shown in FIGS. 3A and 3B or the sensing device 400 shown in FIGS. 4A and 4B), such as restrained in a slot or other cavity of the housing 510. In some variations, the vibroacoustic sensor module 500 may include one or more flexure arms configured to deflect in a direction generally orthogonal to a sensing side (S) of the housing 510.

Figure 5A:
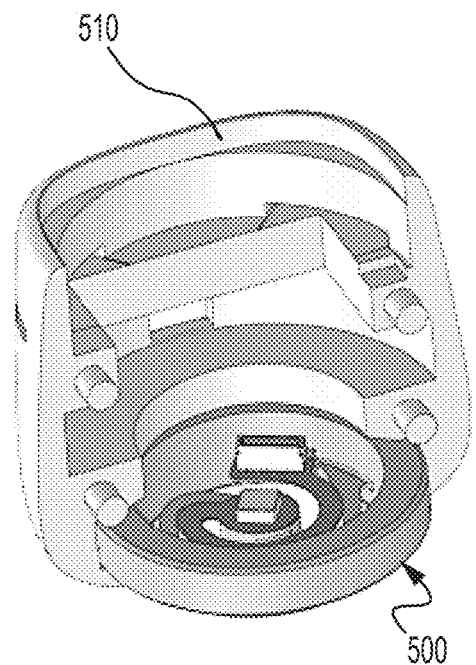
FIGS. 5A and 5B depict a perspective cross-sectional view and a cross-sectional view, respectively, of a portion of an example variation of a sensing device for characterizing a bodily condition of a subject.
Figure 5B:
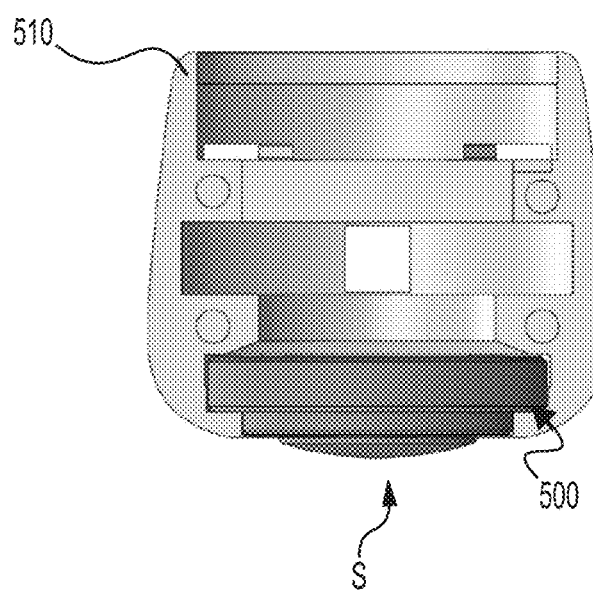
Figure 5C:
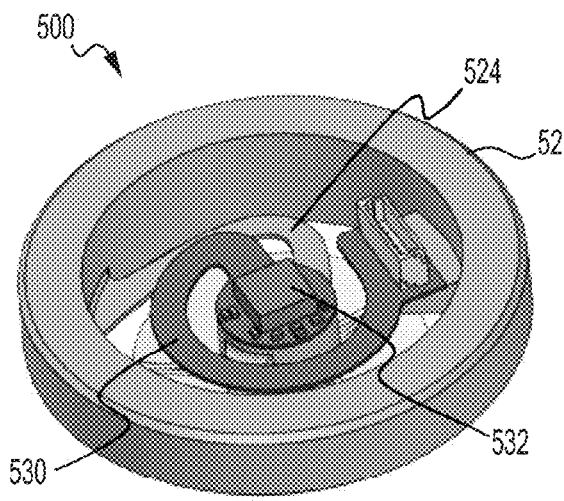
FIGS. 5C and 5D depict upper and lower perspective views, respectively, of an example variation of a vibroacoustic sensor module with flexure arms.
Figure 5D:
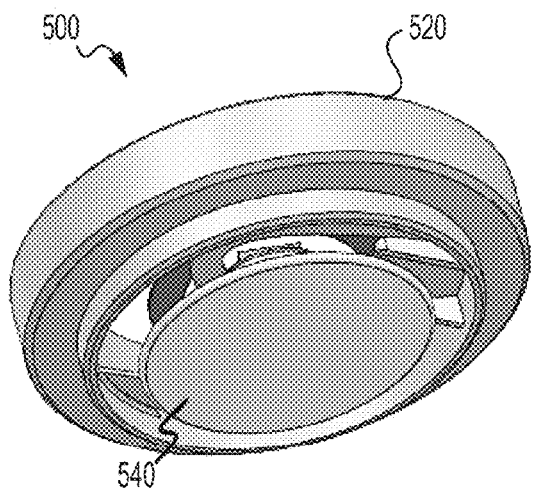
Figure 5E:
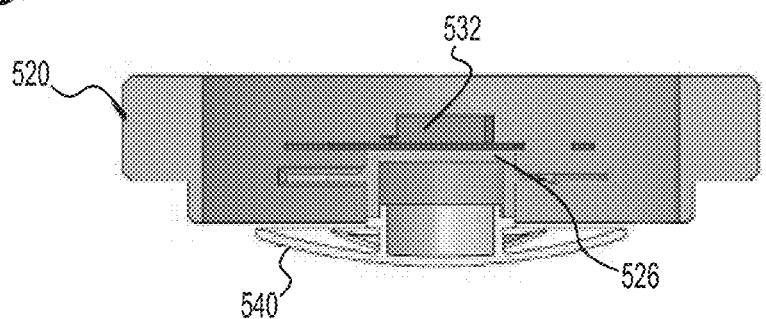
FIG. 5E depicts a cross-sectional view of the vibroacoustic sensor module depicted in FIGS. 5C and 5D.
Figure 5F:
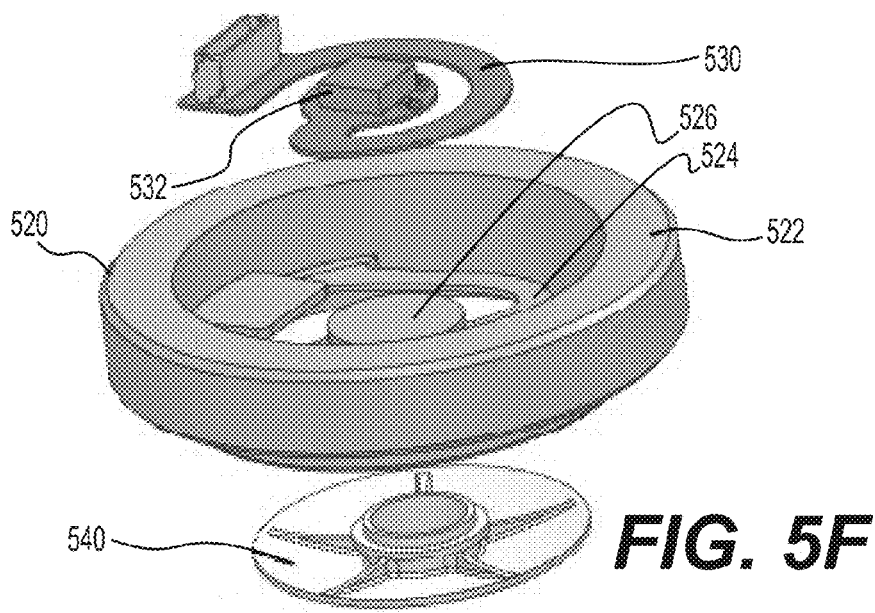
FIG. 5F depicts an exploded view of the vibroacoustic sensor module depicted in FIGS. 5C and 5D.

As shown in FIGS. 5C-5F, the vibroacoustic sensor module 500 may include a deflecting structure 520 and a flex circuit 530 including a cross-axis inertial sensor such as an accelerometer 532 (e.g., MEMS accelerometer). The deflecting structure 520 may include two or more flexure arms 524 supported at an outer end by a frame 520 and supported at an inner end by a central hub 526 functioning as a signal pickup. In some variations, the flexure arms may be radially distributed around the central hub 526. The flex circuit 530 may include at least one accelerometer 532 and may be attached at an inner end to the central hub 526, such that the accelerometer 532 moves with the central hub 526 in response to impinging vibroacoustic waves. In some variations, an impedance matching receiver 540 may also be coupled to the central hub 526 to enhance the sensitivity of the deflecting structure 420 to impinging vibroacoustic waves. As shown in FIG. 5E, the receiver 540 may be a dome-shaped diaphragm, for example. Thus, vibroacoustic waves may cause movement of the receiver 540 and deflecting structure 520 that is detected and measured by the accelerometer 532.

Figure 5G:
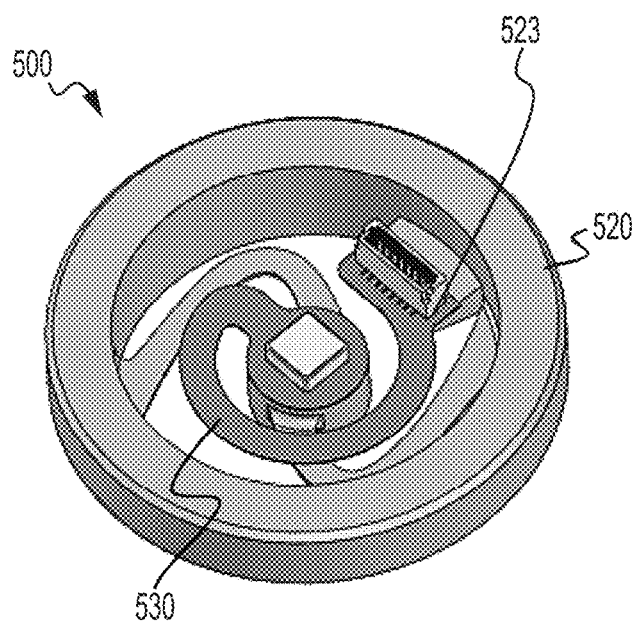
FIG. 5G depicts an upper perspective view of the example variation of a vibroacoustic sensor module with flexure arms shown in FIG. 5C.
Figure 5H:
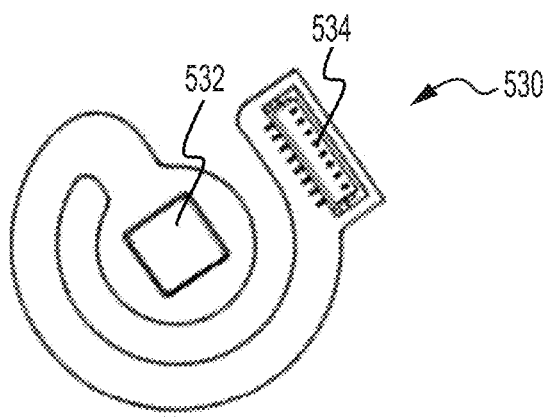
FIG. 5H depicts an example variation of a flex circuit in the vibroacoustic sensor module depicted in FIG. 5G.
Figure 5I:
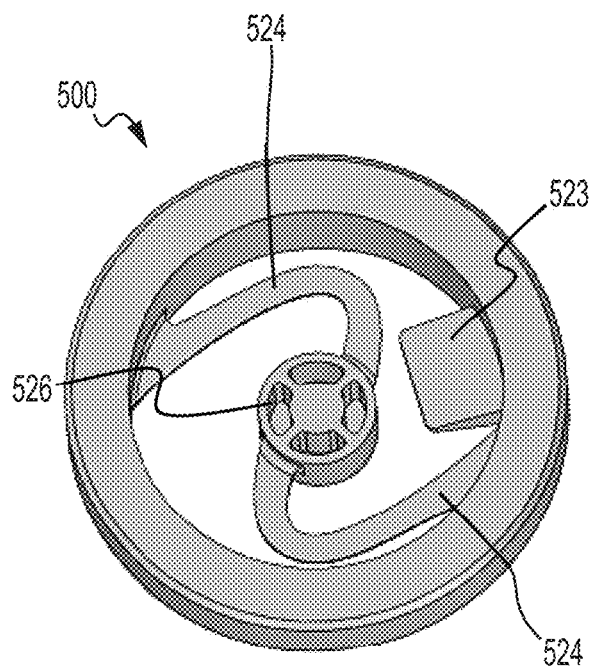
FIG. 5I depicts an example variation of a deflecting structure with flexure arms in the vibroacoustic sensor module depicted in FIG. 5G.

FIGS. 5G-5I illustrate additional details of the vibroacoustic sensor module 500. As shown in FIGS. 5G and 5I, the deflecting structure 520 may include two flexure arms 524 coupled to the central hub 526 generally within a plane. The flexure arms 524 may be radially distributed around the central hub 526, and in some variations radially equidistant or asymmetrically distant (as to be tuned to different resonance frequencies and thereby different frequency bands) from each other (i.e., the two flexure arms 524 may be arranged about 180 degrees apart around the central hub). The flexure arms 524 may be wavy (e.g., arched or sinusoidal), which helps optimize out-of-plane flexibility and in-plane rigidity. The cross-axis inertial sensor (on the flex circuit 530) may rest on a cantilever to allow effective coupling with minimal mechanical constraints from other parts of the system. A pre-buckled, out-of-plane, arc-shaped geometry allows the flexure arms 424 (e.g., serpentine interconnects) to assume traction free architectures that absorb tensile deformations in multiple modes. Finite element modeling (FEM) may highlight significant mechanical advantages of these noncoplanar interconnects, via out of plane linearity and compliance with stiffness to in-plane movement, compared with conventional planar serpentine layouts. Accordingly, out-of-plane forces (e.g., vibroacoustic waves) may urge the flexure arms 524 to deflect and the central hub to move out-of-plane, while the flexure arms 524 have low or no lateral in-plane movement. In some variations, as shown in FIG. 5I, the central hub may be at least partially cored out with one or more cutouts to reduce the hub's mass and inertia (which may, for example help improve its sensitivity to out-of-plane forces).

As described above, the flex circuit 530 may, like the flexure arms 524, be flexible and receptive to out-of-plane movement. The flex circuit 430 may provide the vibrometer sensor module with an overall lower agile stiffness that is advantageously more isotropic. In some variations, as shown in FIG. 5H, the flexible circuit board 530 may have a general spiral shape within a plane, winding outwards from an inner end to an outer end. As described above, the inner end of the flexible circuit board 530 may be coupled to the central hub 526 such that an accelerometer 532 on the inner end of the flexible circuit board 430 may move in tandem with the central hub 526 (e.g., in response to vibroacoustic waves). At its outer end, the flexible circuit board 530 may be configured to attach to a flex circuit anchor 523 (e.g., on or coupled to the frame of the deflecting member 520) shown in FIG. 5I. The outer end of the flexible circuit board 530 may also include a cable connector 534 electrically connected to conductive traces (not shown) that traverse the flexible circuit board 530 to and from the accelerometer 532, such that signals can be communicated to and from the accelerometer 532 via the cable connector 534 and conductive traces.

Figure 6A:
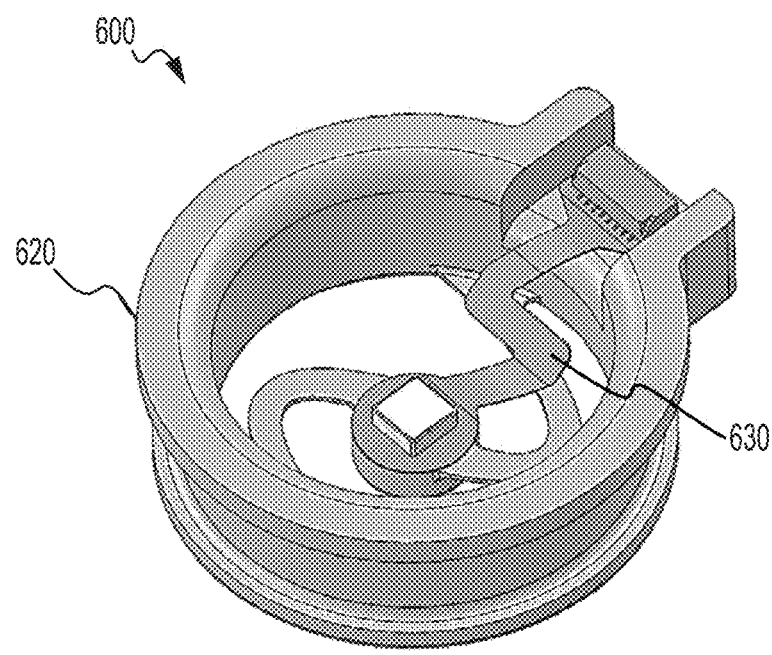
FIG. 6A depicts a schematic illustration of an example variation of a vibroacoustic sensor module with flexure arms.
Figure 6B:
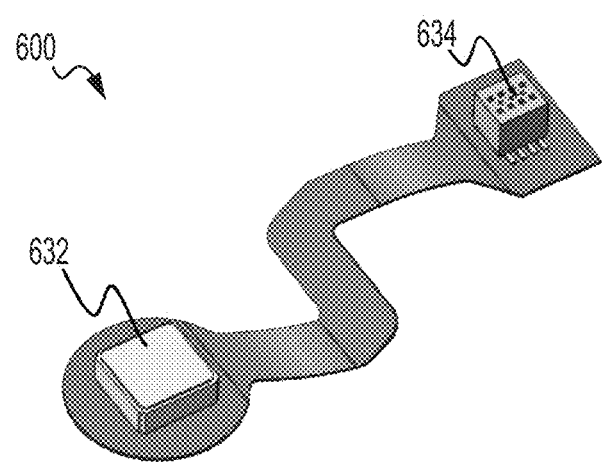
FIG. 6B depicts a schematic illustration of an example variation of a flex circuit in the vibroacoustic sensor module depicted in FIG. 6A.

However, the flexible circuit board 530 may have any suitable shape that may be sufficiently flexible and receptive to out-of-plane movement. For example, FIG. 6A depicts an exemplary variation of a vibroacoustic sensor module 600 that includes a deflecting structure 620 with two flexure arms meeting at a central hub and a flexible circuit board 630 coupled to the deflecting structure 620. Similar to flexible circuit board 530 described above with respect to FIGS. 5A-5I, the flexible circuit board 630 includes a cable connector 634 on an outer end of the flexible circuit board 630, and an accelerometer 632 on an inner end of the flexible circuit board 630, with conductive traces extending between the accelerometer 632 and the cable connector 634 for signal communication to and from the accelerometer 632. However, as shown in FIG. 6B, unlike the spiral-shaped flexible circuit board 530, the flexible circuit board 630 may have a generally zig-zag shape.

In some variations, the flexure arms may have a flexure thickness of less than about 1 mm to be sufficiently sensitive to vibroacoustic signals, yet sufficiently resilient. For example, flexure arms may be formed from an SLA type photopolymer with good stiffness and low internal damping.

Figure 7A:
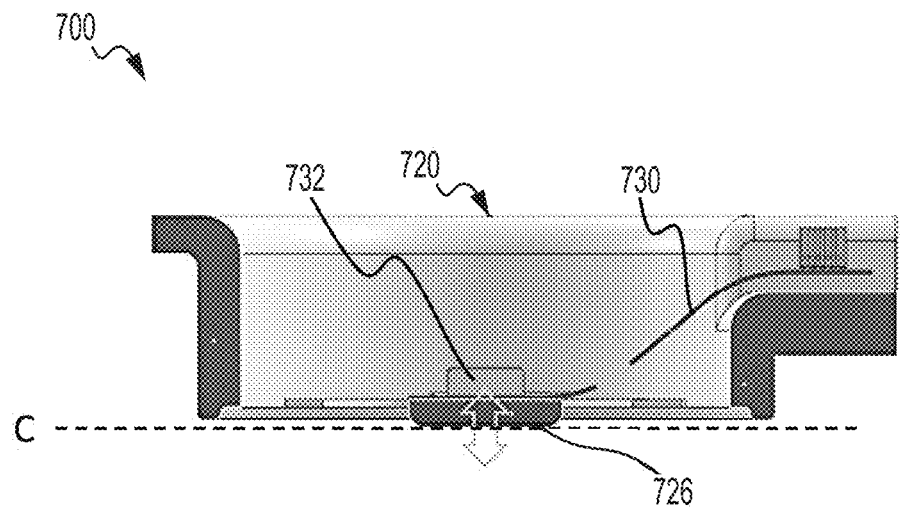
FIGS. 7A and 7B depict cross-sectional views of an example variation of a vibroacoustic sensor module with differing clearance distances between a deflecting structure and surface of a subject.

In some variations, the central hub of the deflecting structure (e.g., deflecting structures 520 and 620) may have varying thicknesses to provide for different amounts of clearance for the flexure arms. For example, FIG. 7A depicts a vibroacoustic sensor module 700 including a deflecting structure 720 and a flexible circuit board 730. Similar to that described above, the deflecting structure 720 may include a central hub 726 that is configured to move in a transverse direction as indicated by the arrow, as flexure arms move in an out-of-plane manner.

Figure 7B:
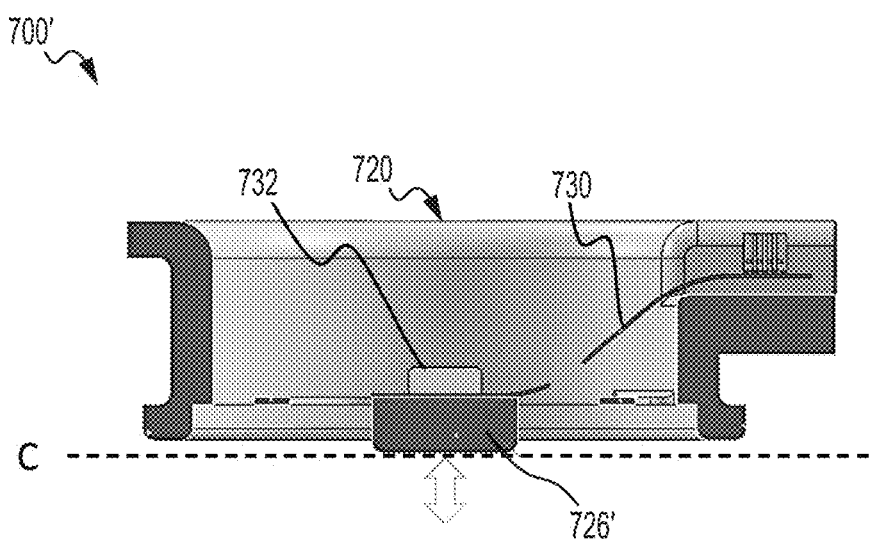

FIG. 7B depicts a similar vibroacoustic sensor module 700' that is similar to vibroacoustic sensor module 700, except that the vibroacoustic sensing module 700' has a thicker central hub 726' that extends farther from the rest of the deflecting structure. The central hubs 726 and 726' may be placed against a contact surface (C) (e.g., a subject's skin) when the sensing device is in use, but the thicker central hub 726' provides for a greater distance between the flexure arms of the deflecting structure 720 and the contact surface (C) than central hub 726 does.

Figure 8A:
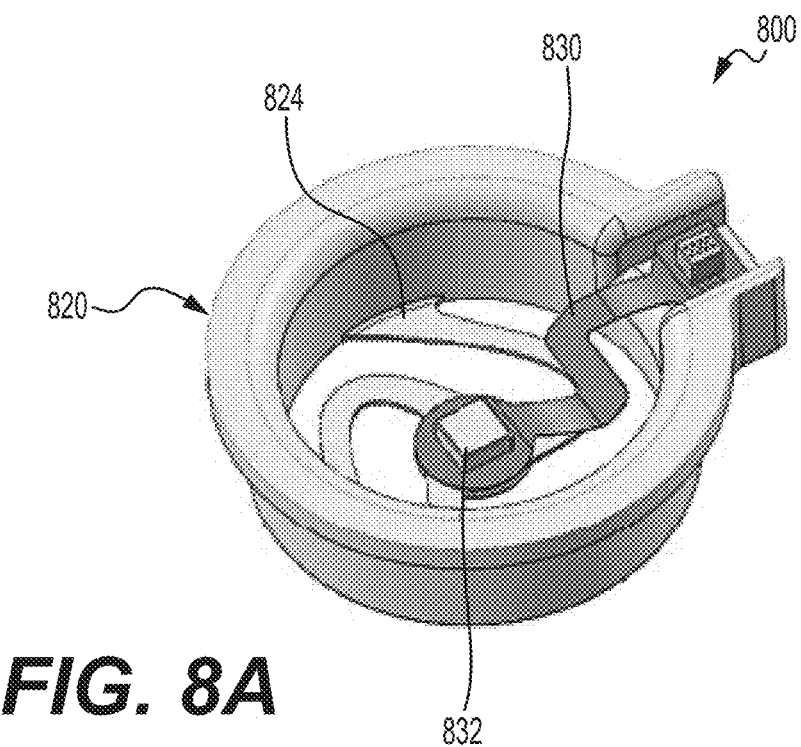
FIGS. 8A and 8B depict perspective and plan views, respectively, of a schematic illustration of an example variation of a vibroacoustic sensor module with flexure arms.
Figure 8B:
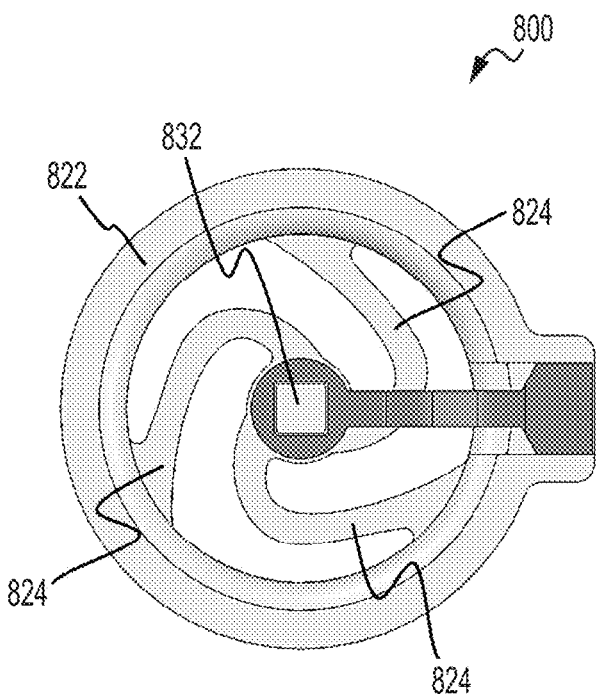

Although FIGS. 5A-5I depict an exemplary variation of a deflecting structure 520 having two flexure arms, it should be understood that other variations of deflecting structures may include other suitable numbers of flexure arms. The flexure arms may be radially distributed around a central hub, and in some variations may be equally radially or asymmetrically distributed around the central hub so as to be tuned to different resonance frequencies and thereby different frequency bands. For example, FIGS. 8A and 8B depict a vibroacoustic sensor module 800 including a deflecting structure 820 having three flexure arms 824. The three flexure arms may be wavy (e.g., arched or sinusoidal) and equally radially arranged around a central hub of the deflecting structure (i.e., the three flexure arms may be arranged about 120 degrees apart around the central hub). The vibroacoustic sensor module 800 may further include a flexible circuit board 830. While the flexible circuit board 830 is shown in FIGS. 8A and 8B as having a zig-zag shaped similar to the flexible circuit board 620 shown in FIG. 6B, in other variations the flexible circuit board 830 may be spiral shaped similar to that shown in FIG. 5H, or other suitable shapes.

Furthermore, the flex circuit may be unnecessary if the sensor(s) can be powered through induction or piezoelectrical phenomena and the sensor can communicate data back to the electronic systems through induction, radio frequencies, magnetic flux changes, or optical communication.

Furthermore, in some variations the deflecting structure may have four or more flexure arms. For example, in some variations, the deflecting structure may include four flexure arms in line with the sensor mass edges (e.g., based on FEM for design optimization). In yet other variations, the deflecting structure may include five, six, or more than six flexure arms. In addition to such a mechanical deflecting structure design, higher-performance flexible dielectric nanocomposite materials may be incorporated into the deflecting structure, including but not limited to any combination of graphene, reduced graphene oxide/titanium dioxide (rGO/TiO2) nanocomposites, polyvinyl alcohol modified polyvinylidene fluoride-graphene oxide, Polyvinyl fluoride (PVF) or —(CH2CHF)n-, and/or poly(vinylidene fluoride) or Polyvinylidene fluoride or polyvinylidene difluoride (PVDF) incorporated with reduced graphene oxide (rGO) and poly(vinyl alcohol)-modified rGO (rGO-PVA). Nanocomposites may have inherently unique properties and convenience to fabricate into different morphological nanostructures, such as by spraying and doping of substrates as atomically thin single layers to nanoribbons. In yet other variations, the deflecting structure may include five, six, or more than six flexure arms.

Figure 9A:
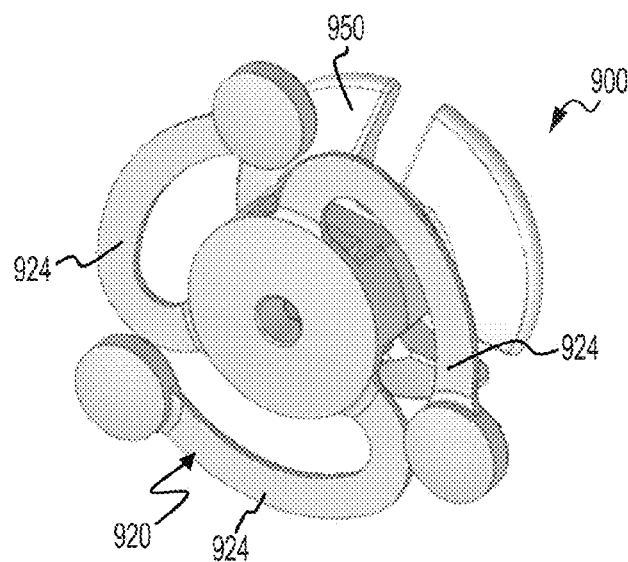
FIGS. 9A and 9B depict upper perspective and lower perspective views, respectively, of an example variation of a vibroacoustic sensor module including flexure arms.
Figure 9B:
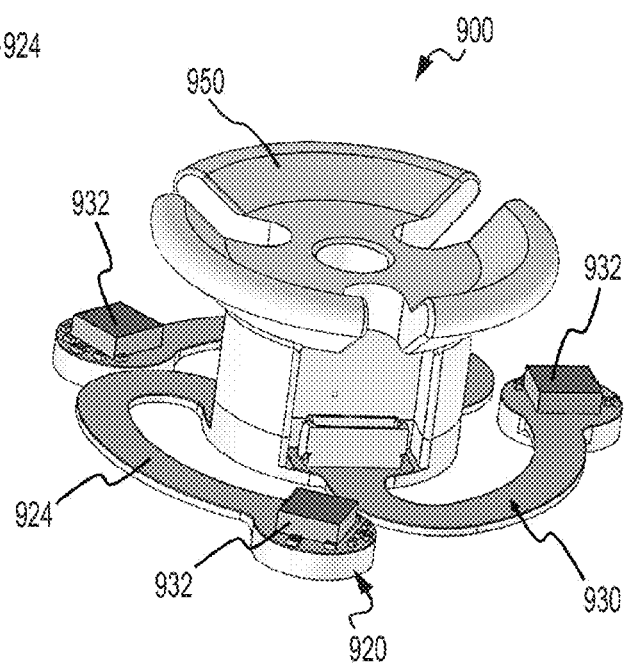
Figure 9C:
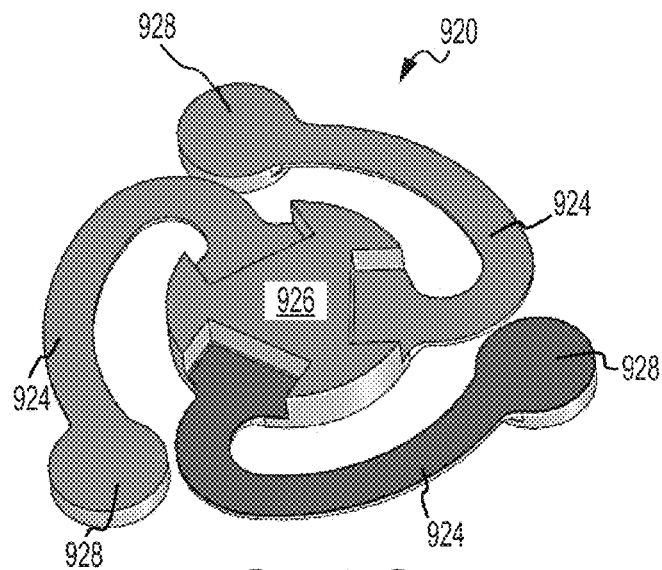
FIG. 9C depicts a schematic illustration of an example variation of a deflecting structure with flexure arms in the vibroacoustic sensor module depicted in FIGS. 9A and 9B.
Figure 9D:
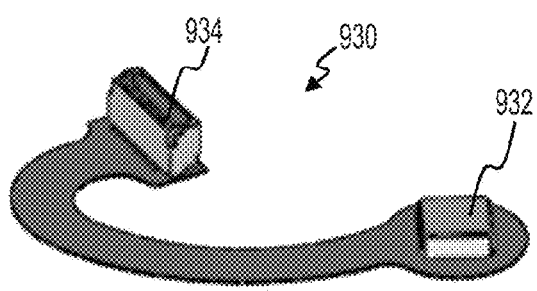
FIG. 9D depicts a schematic illustration of an example variation of a flex circuit in the vibroacoustic sensor module depicted in FIGS. 9A and 9B.

While the above description primarily describes deflecting structures in which an accelerometer is coupled to a central hub that connects two or more flexure arms, in some variations the deflecting structure may include multiple accelerometers, with each accelerometer coupled to a respective flexure arm. For example, as shown in FIGS. 9A-9C, an exemplary variation of a vibroacoustic sensor module 900 may include a deflecting structure 920 having multiple flexure arms 924 arranged radially around a central hub 926, and accelerometers 932 located on the outer or distal ends of the flexure arms 924. In some variations, the deflecting structure 920 may include a handle portion 950 may be handheld (and/or be used to secure to another portion of the sensing device). The flexure arms 924 may be wavy (e.g., sinusoidal or arched) and/or equally radially arranged around the central hub 926, similar to that described above. In this variation, as shown in FIG. 9D, a flexible circuit board 930 may be coupled to each flexure arm 924 and shaped in a similar manner as its respective flexure arm 924. Furthermore, in some variations, the vibroacoustic sensor module 900 may include a receiver (e.g., dome-shaped diaphragm) coupled to the central hub 926 of the deflecting structure. Similar to the vibroacoustic sensor modules described above, the central hub 926 may move out-of-plane in response to vibroacoustic signals, which may result in a set of corresponding out-of-plane movements of the accelerometer mounts 928 effected by the flexure arms 924 that are detectable by the accelerometers 932 on the outer ends of the flexure arms 924.

Although the vibroacoustic sensor module 900 is shown in FIGS. 9A and 9B as including a deflecting structure with three flexure arms, it should be understood that the deflecting structure may include more than three (e.g., four, five, six, or more than six) flexure arms arranged around the central hub, each flexure arm having a respective accelerometer arranged thereon.

Membrane-Type Vibroacoustic Sensor Modules

Figure 10A:
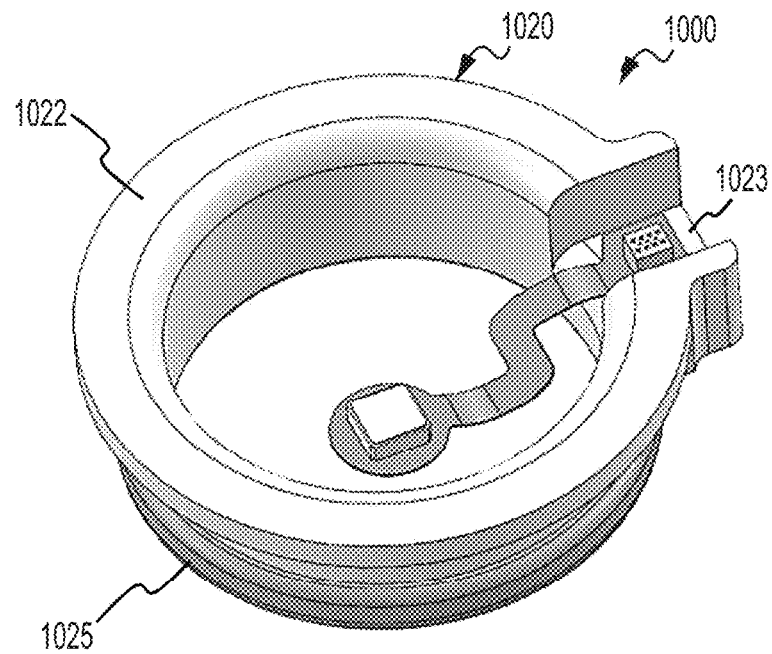
FIGS. 10A and 10B depict perspective and cross-sectional views, respectively, of an example variation of a vibroacoustic sensor module including a membrane and at least one cross-axis inertial sensor (e.g., accelerometer).
Figure 10B:
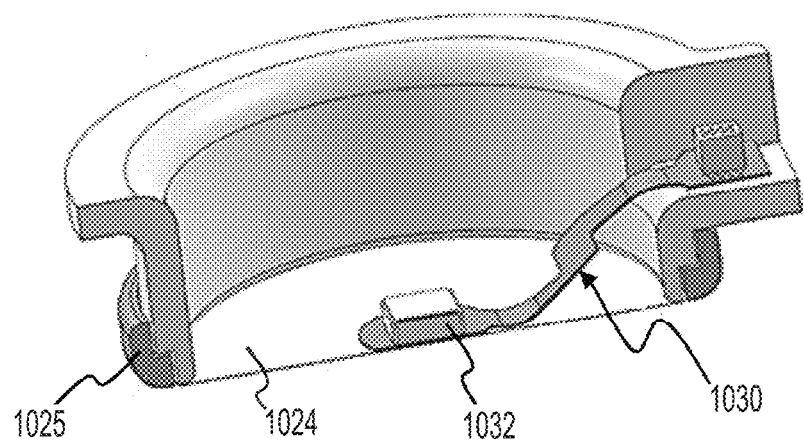

In some variations, the deflecting structure may include a membrane, and one or more sensors may be arranged to interface with the membrane to detect the membrane's out-of-plane movement in response to vibroacoustic signals. For example, as shown in FIGS. 10A and 10B, a vibroacoustic sensor module 1000 may include a deflecting structure 1020 having a membrane 1024 extending across a frame 1022, and an accelerometer 1032 coupled to a central region of the membrane 1024 via a flexible circuit board 1030. The membrane may comprise a thin sheet or diaphragm of flexible material that is taut over the frame 1022, such as an elastomeric material (e.g., latex, nitrile, etc.). In some variations, the membrane may be coupled to the frame 1022 with one or more suitable fasteners, such as a clamp ring 1025 that radially compresses and secures the membrane 1024 to the frame 1022, other suitable fasteners (e.g., epoxy) or in any other suitable manner. In some variations, FEM design optimization models suggest an optimal membrane thickness range of 10 to 5000 micrometers and diameter between about 2.5 millimeters and about 75 millimeters. One goal of the membrane is to enable collection of high data fidelity while providing a comfortable, non-irritating data harvest interface. The membrane material may be configured to deform naturally with low amplitude movements of the body. For example, in some variations, the membrane design may incorporate deformable, non-coplanar interconnects, a strain-isolation layer at the base, a soft-encapsulation overlayer and/or a hollow air-pocket configuration. Together, these features may provide low-modulus, elastic mechanics for ultrasensitive signal pickup.

Similar to the flexure arm-based variations of vibroacoustic sensor modules described above, the vibroacoustic sensor module 1000 may include a flexible circuit board 1030 that is flexible and receptive to out-of-plane forces. For example, FIGS. 10A and 10B depict a flexible circuit board 1030 that has a zig-zag shape similar to that shown in FIG. 6B, but it should be understood that the flexible circuit 1030 may alternatively have a spiral shape (such as that shown in FIG. 5H) or any suitable shape. The flexible circuit board 1030 may have an inner end having an accelerometer 1032 and an outer end having a cable connector 1034, with conductive traces extending between the accelerometer 1032 and the cable connector for signal communication to and from the accelerometer 1032. In some variations, at least the inner end the flexible circuit board 1030 may be coupled to the membrane with epoxy or any other suitable fastener or in any suitable manner. Accordingly, movement of the membrane 1024 may be tracked and measured by the accelerometer 1032, and corresponding vibroacoustic sensor signals from the accelerometer 1032 may be analyzed such as for detecting one or more bodily conditions of a subject.

Figure 11A:
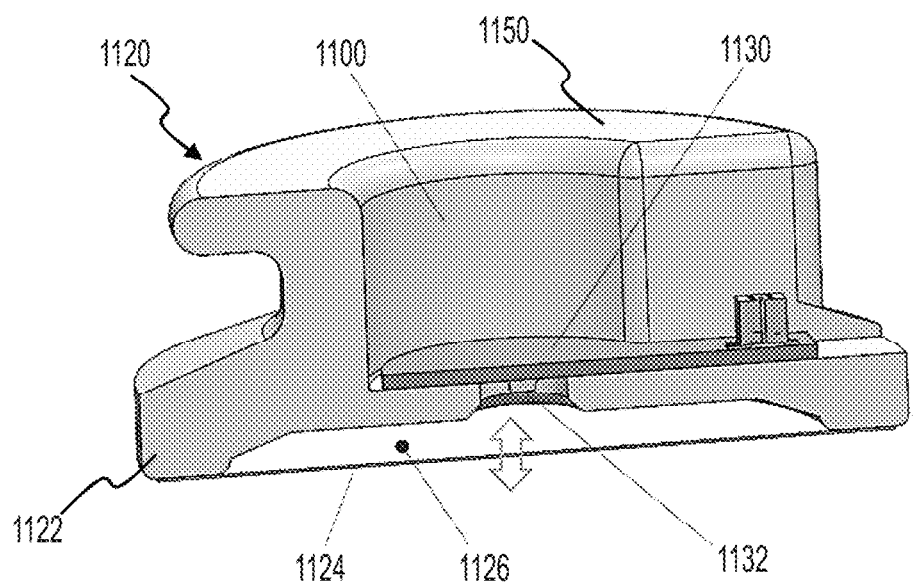
FIGS. 11A and 11B depict cross-sectional and cross-sectional exploded views, respectively, of an example variation of a vibroacoustic sensor module including a membrane and at least one cross-axis inertial sensor (e.g., pressure sensor).
Figure 11B:
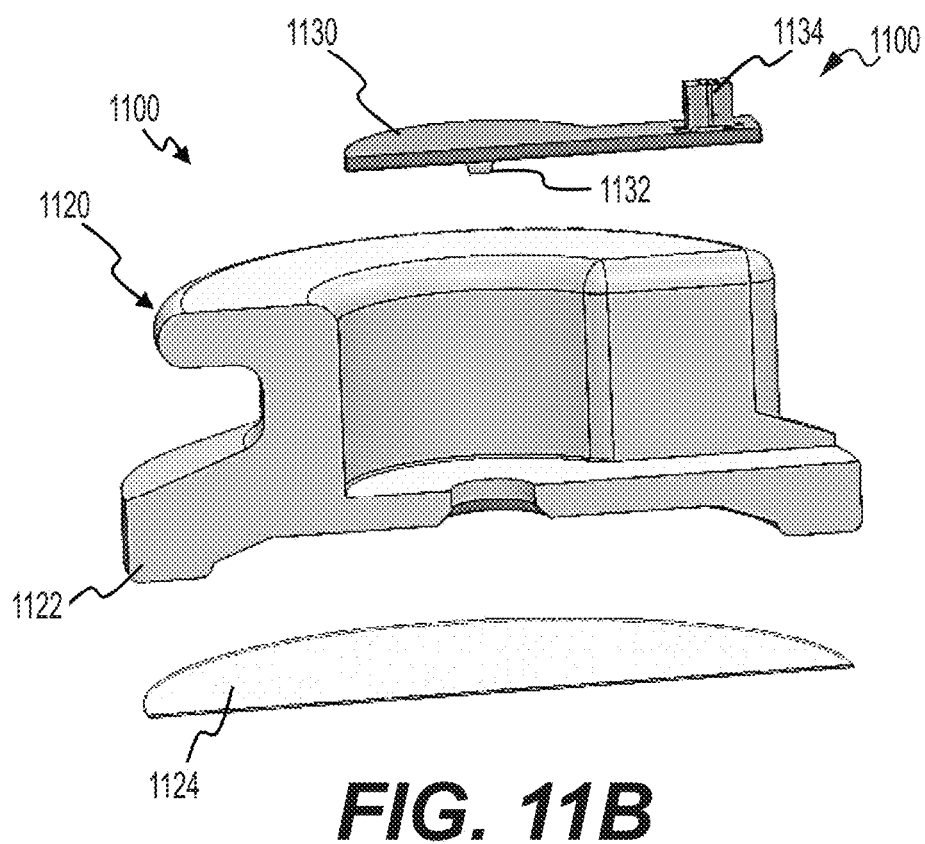

Additionally or alternatively, in some variations, a vibroacoustic sensor module may include a membrane-based deflecting structure that interfaces with or interacts with one or more sensors across a cavity. For example, as shown in FIGS. 11A and 11B, a vibroacoustic sensor module 1100 may include a deflecting structure 1120 having a cavity 1126 that is sealed by a membrane 1124 extending across a frame 1122. In some variations, the deflecting structure 1120 may include a handle portion 1150 may be handheld (and/or be used to secure to another portion of the sensing device).

Figure 11C:
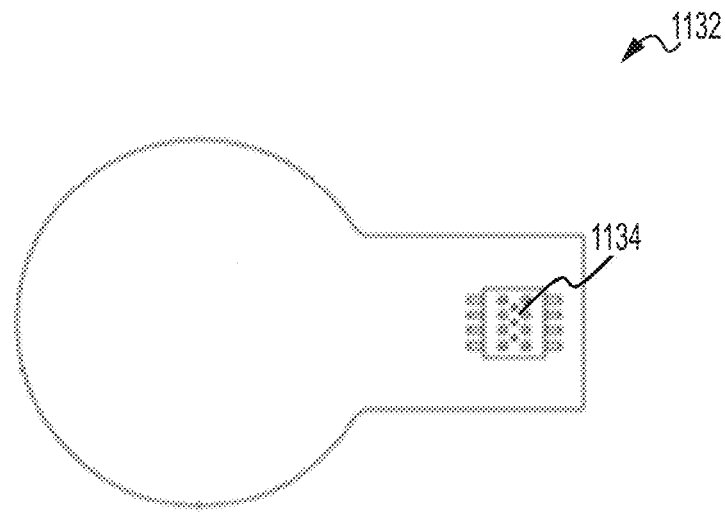
FIGS. 11C-11E depict top, side, and bottom views of an example variation of a circuit board with a pressure sensor in the vibroacoustic sensor module depicted in FIGS. 11A and 11B.
Figure 11D:
Figure 11E:
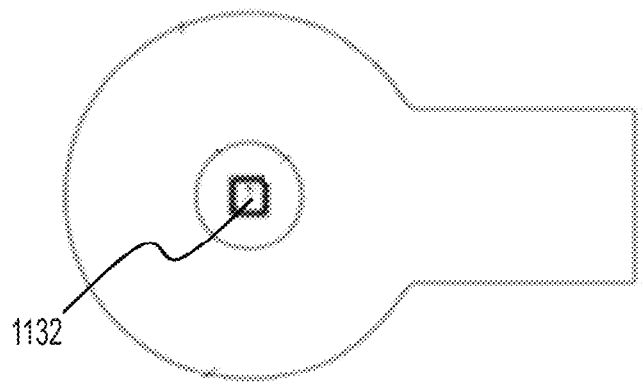

The membrane 1124 may be constructed and attached in a manner similar to that described above with respect to FIGS. 10A and 10B. Furthermore, FIGS. 11C-11E depict an exemplary rigid circuit board 1130 including one or more sensors 1132 and a cable connector 1134. Signals to and from the sensor(s) 1032 may be communicated via conductive traces extending between the sensor(s) 1132 and a cable connector 1134. As shown in FIGS. 11A and 11B, the rigid circuit board 1130 may be positioned in the vibroacoustic sensor module 1100 such that the one or more sensors 1132 are located within or adjacent the cavity (or otherwise arranged in fluid communication with the cavity, such as through an opening). For example, as shown in FIG. 11A, a sensor 1132 may be located opposite the membrane 1124. In such arrangements, deflection of the membrane 1124 in response to vibroacoustic waves may cause changes within the cavity that are detectable and measurable by the one or more cross-axis inertial sensors 1132. For example, in some variations the one or more sensors 1132 may include a pressure sensor (e.g., MEMS pressure sensor) that detects pressure variations in the cavity induced by the deflection of the membrane 1124. For example, the pressure sensor may be read at a high rate (e.g., more than about 500 Hz) and the pressure data may be used to construct a low frequency signal waveform (e.g., between about 0.01 Hz to about 1 kHz; or about 0.01 Hz to about 0.5 kHz). As another example, in some variations the one or more sensors 1132 may include a microphone (e.g., MEMS microphone) that detects vibroacoustic waves traversing the cavity and induced by deflection of the membrane 1124. The microphone may be configured to sense a different bandwidth, such as between about 5 Hz to about 2 kHz-10 kHz.

Furthermore, in some variations, the one or more sensors 1132 may include both a pressure sensor and a microphone, and/or any other suitable sensors (e.g., voice coil transducer, piezoelectric transducer, etc.).

Figure 12A:
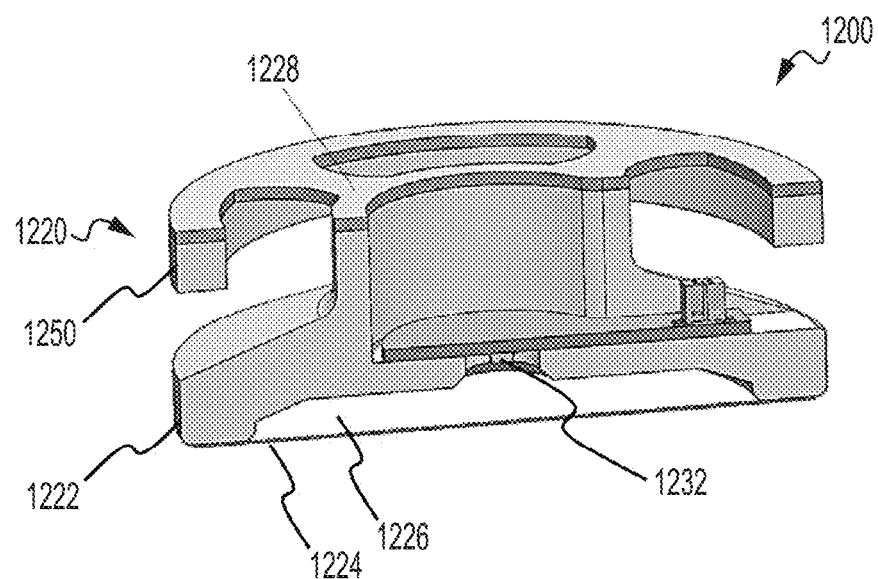
FIGS. 12A and 12B depict cross-sectional and cross-sectional exploded views, respectively, of an example variation of a vibroacoustic sensor module including a dampening feature.
Figure 12B:
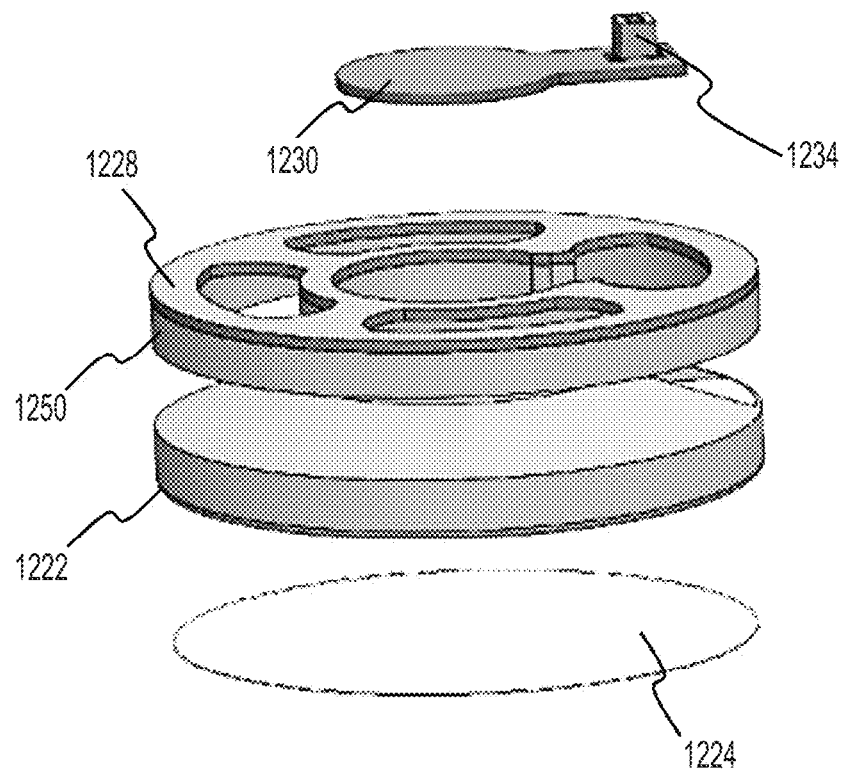

In some variations, a vibroacoustic sensor module may include a dampening feature to help isolate the sensing components from hand movements that may introduce noise and/or error into the acquired vibroacoustic signals. For example, FIGS. 12A and 12B depict a variation of a vibroacoustic sensor module 1200 that is similar to that described above with reference to FIGS. 10A and 10B, in that the vibroacoustic sensor module 1200 may include a deflecting structure 1220 having a cavity 1226 that is sealed by a membrane 1224 extending across a frame 1222. The deflecting structure 1220 may include an annular handle portion 1250 that is indirectly coupled to the central frame 1212 via a flexible layer 1228 and/or other suitable flexible structures that help isolate the sensing components (e.g., sensor(s) 1232, membrane 1224, etc.) from hand pressure and other movement variations. The flexible layer 1228 may, for example, include a dampening material such as foam or an elastomeric material, and/or include dampening structures such as radial ribs that help dampen and/or decouple movements from the handle 1250 from the rest of the deflecting structure. The dampening could also be implemented in other "active" ways with one or more controlled mechanisms or materials, such as actuators (e.g., micro- and or servo motors), piezoelectric or electrosensitive polymers, etc.

Combination-Type Vibroacoustic Sensor Modules

Figure 13A:
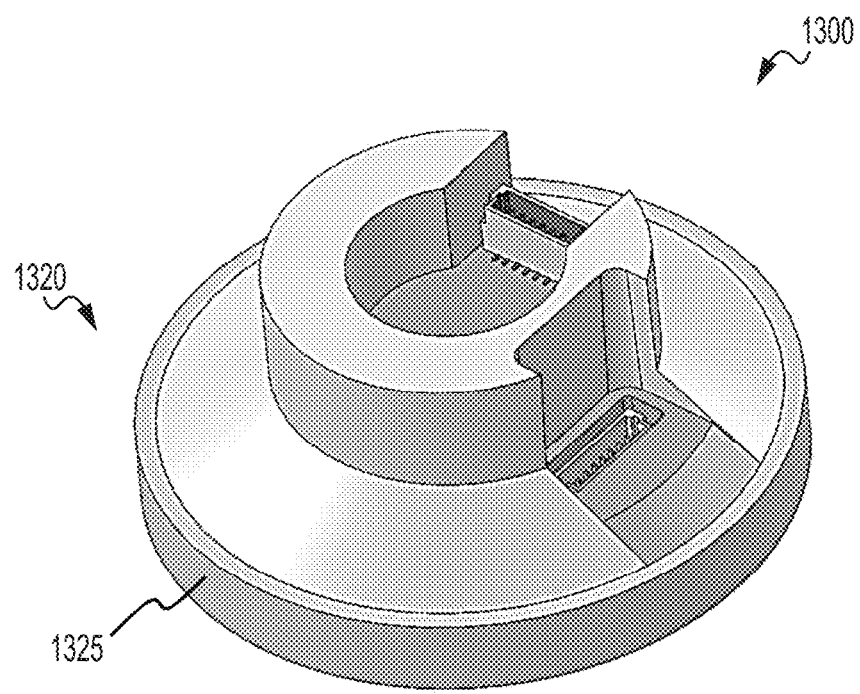
FIGS. 13A, 13B, and 13C depict perspective, cross-sectional, and exploded views, respectively, of an example variation of a vibroacoustic sensor module including an accelerometer and a microphone.
Figure 13B:
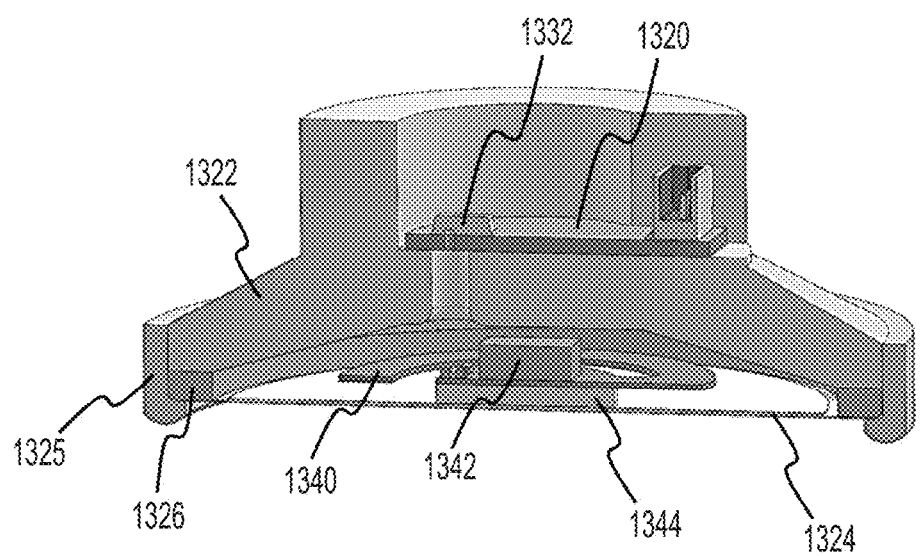
Figure 13C:
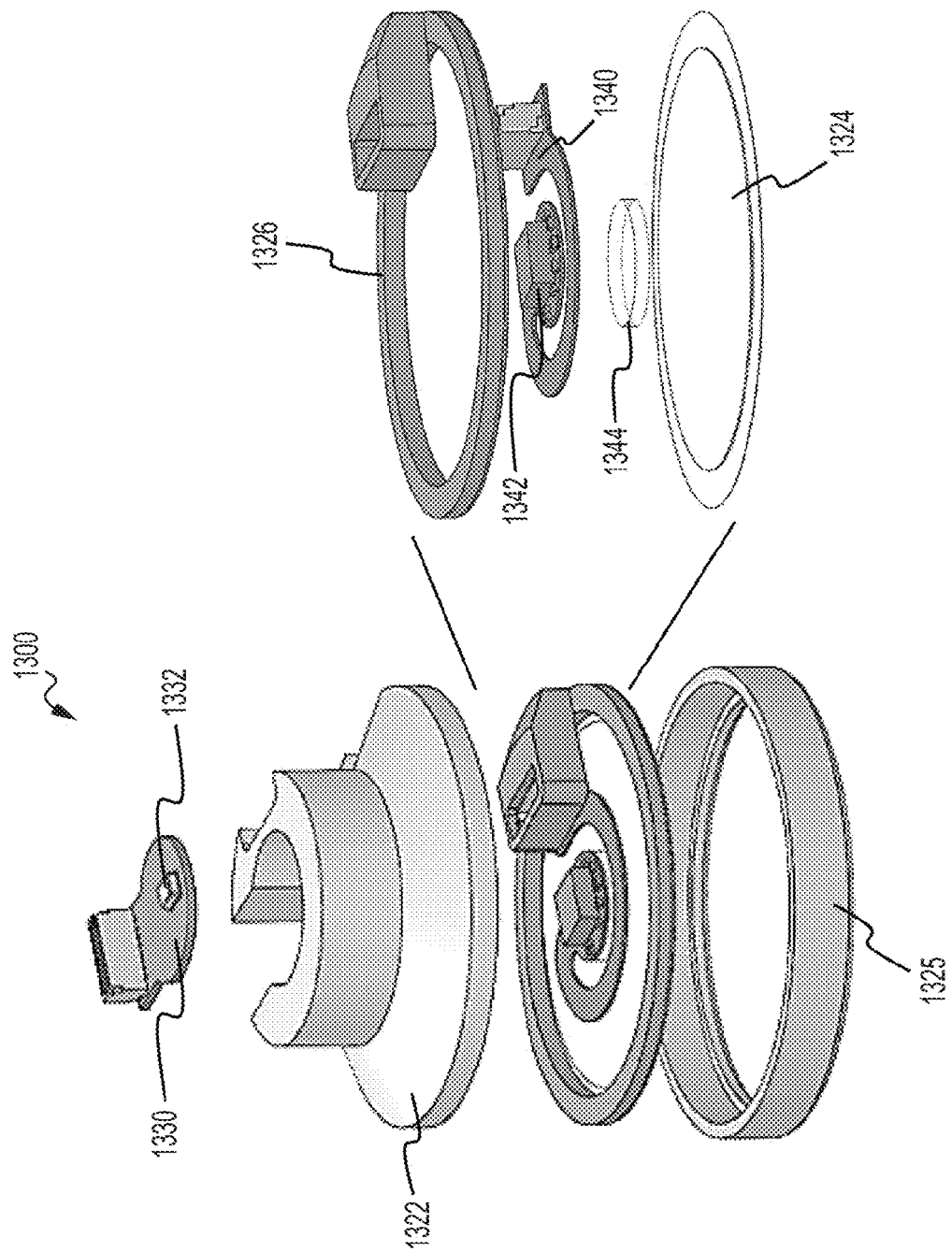

Furthermore, in some variations, a vibroacoustic sensor module may combine aspects of any of the above-described variations, such as to integrate multiple sensors for detecting vibroacoustic sensors in the same sensor module. For example, as shown in FIGS. 13A-13C, an exemplary variation of a vibroacoustic sensor module 1300 may include a variety of components enabling integration of an accelerometer and a microphone for a broader sensing bandwidth. For example, the vibroacoustic sensor module 1300 may include a deflecting structure 1320 including a membrane 1324 that interacts with both an accelerometer 1342 coupled to the membrane 1324 via a rigid or semi-rigid coupling disc 1344. The membrane 1324 may be tensioned over and attached to a support ring 1326, and the support ring 1326 may be attached to the frame 1322. Furthermore, the coupling disc 1324 may, for example, be coupled to the membrane 1324 with epoxy or another suitable kind of fastener, and simultaneously coupled to a portion of a flexible circuit board 1340 that includes the accelerometer 1342. Similar to that described above with respect to flexure arm-type sensor modules, movement of the membrane 1324 may be detected and measured by the attached accelerometer 1342 and translated into a vibroacoustic signal.

Furthermore, similar to that described above with membrane-type sensor modules, the membrane 1324 may extend over a cavity, and interface with a microphone sensor 1332 via the cavity. For example, the vibroacoustic sensor module 1300 may include a rigid circuit board 1330 having a microphone sensor 1332 configured to detect vibroacoustic signals transmitted across the membrane 1324 and the cavity. Additionally, or alternatively, the rigid circuit board 1330 may include a pressure sensor and/or other suitable sensor (e.g., voice coil transducer, piezoelectric transducer, etc.).

Figure 14:
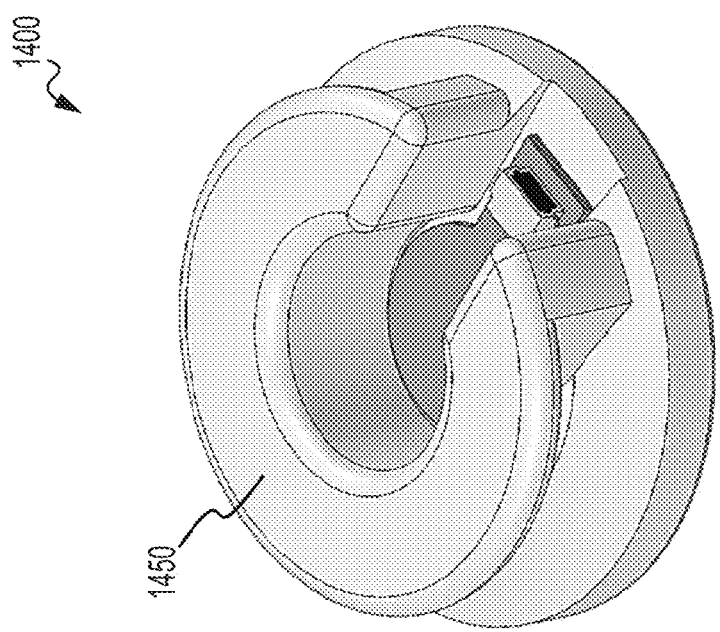
FIG. 14 depicts an example variation of a vibroacoustic sensor module including a handle portion.

In some variations, a combined-type sensor module may include a handle portion for enabling manual manipulation of the sensor module. For example, as shown in FIG. 14, a vibroacoustic sensor module 1400 may include an accelerometer and a microphone for detecting and measuring vibroacoustic waves, and may be similar to the vibroacoustic sensor module 1400, except that the vibroacoustic sensor module 1400 may include a handle portion 1450 having a flange-like gripping feature. However, other variations may include a handle portion having any suitable shape.

Figure 15:
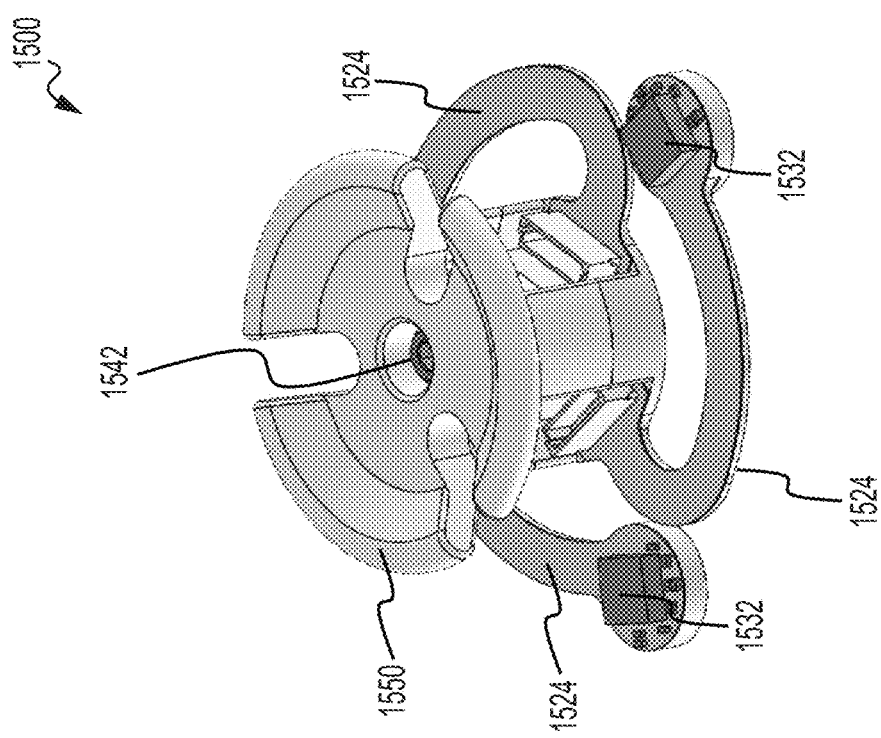
FIG. 15 depicts an example variation of a vibroacoustic sensor module including flexure arms and a plurality of cross-axis inertial sensors (e.g., accelerometer, pressure sensor).

In some variations, a vibroacoustic sensor module may include a variety of components enabling integration of an accelerometer and a pressure sensor. For example, as shown in FIG. 15, an exemplary variation of a vibroacoustic sensor module 1500 may include one or more accelerometers 1532 arranged on respective flexure arms 1524 (e.g., similar to the vibroacoustic sensor module 900 described above with reference to FIGS. 9A-9D), and a membrane whose deflection is measurable with a pressure sensor 1532 (e.g., similar to that described above with respect to FIGS. 11A and 11B.

Furthermore, it should be understood that other variations of vibrometer sensor modules may include combinations of different aspects of the above-described variations, such as to accommodate different kinds sensors capable of providing vibroacoustic signals (e.g., for various bandwidths or frequency ranges) and/or for use in different sensing device form factors and applications, etc.

Voice Coil Transducer

Figure 16A:
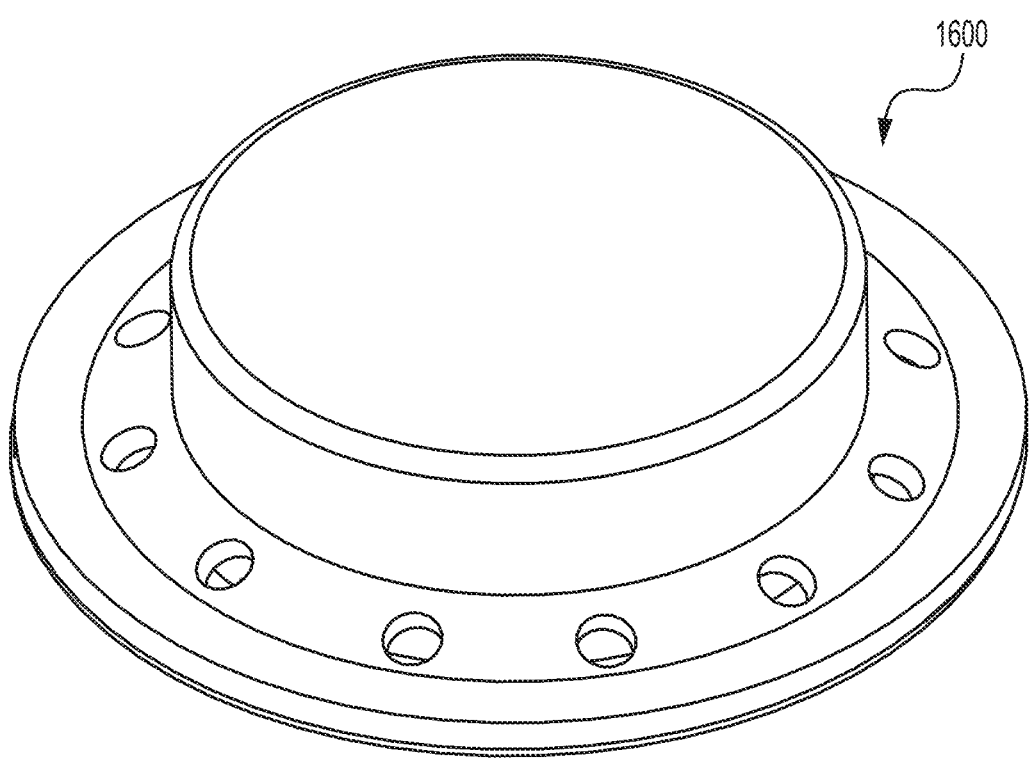
FIG. 16A depicts an assembled view of an example variation of a vibroacoustic sensor module including a voice coil having one or more spider layers.
Figure 16B:
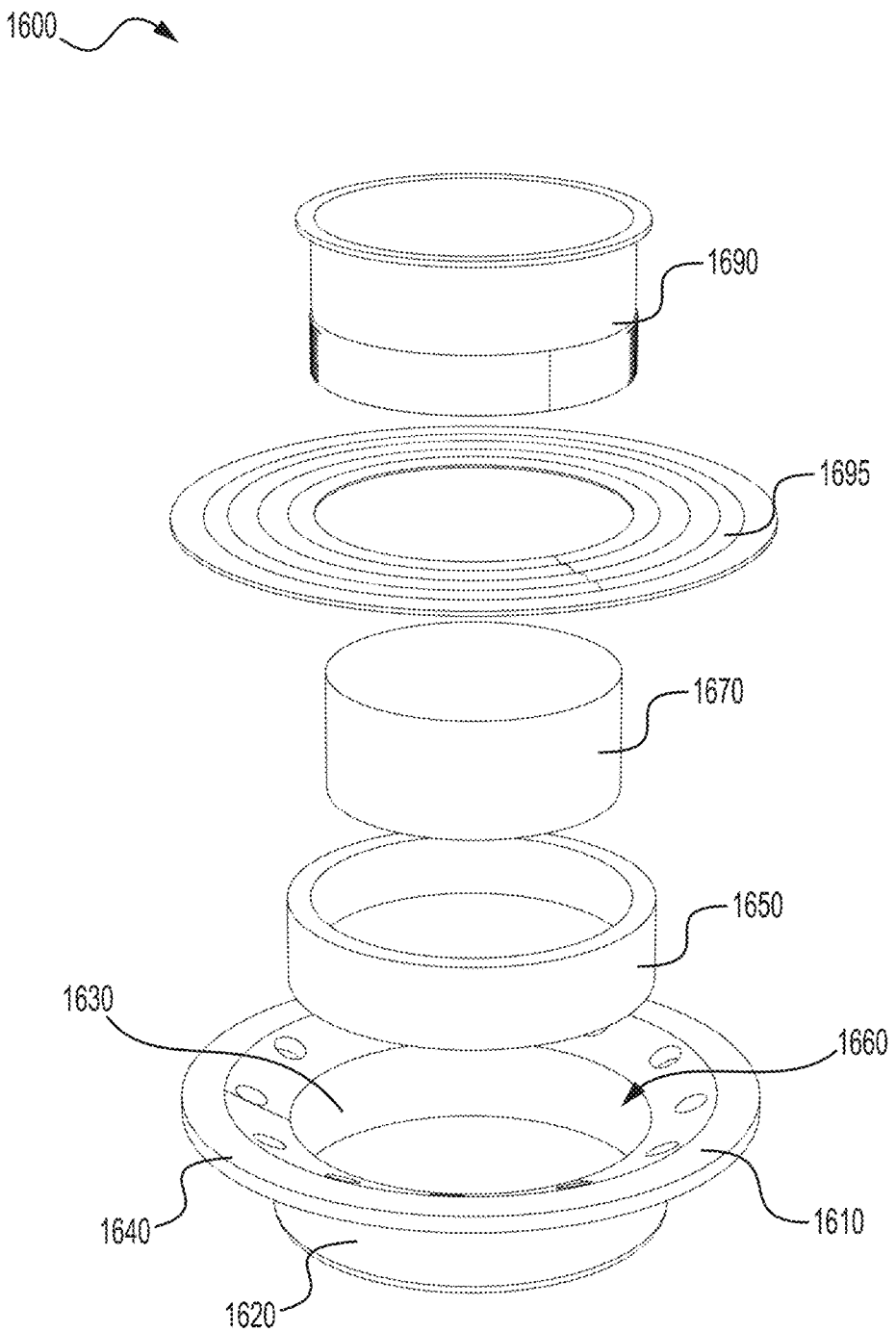
FIG. 16B is an exploded view of a vibroacoustic sensor module, such as the vibroacoustic sensor module of FIG. 16A, and having a single layer spider.
Figure 16C:
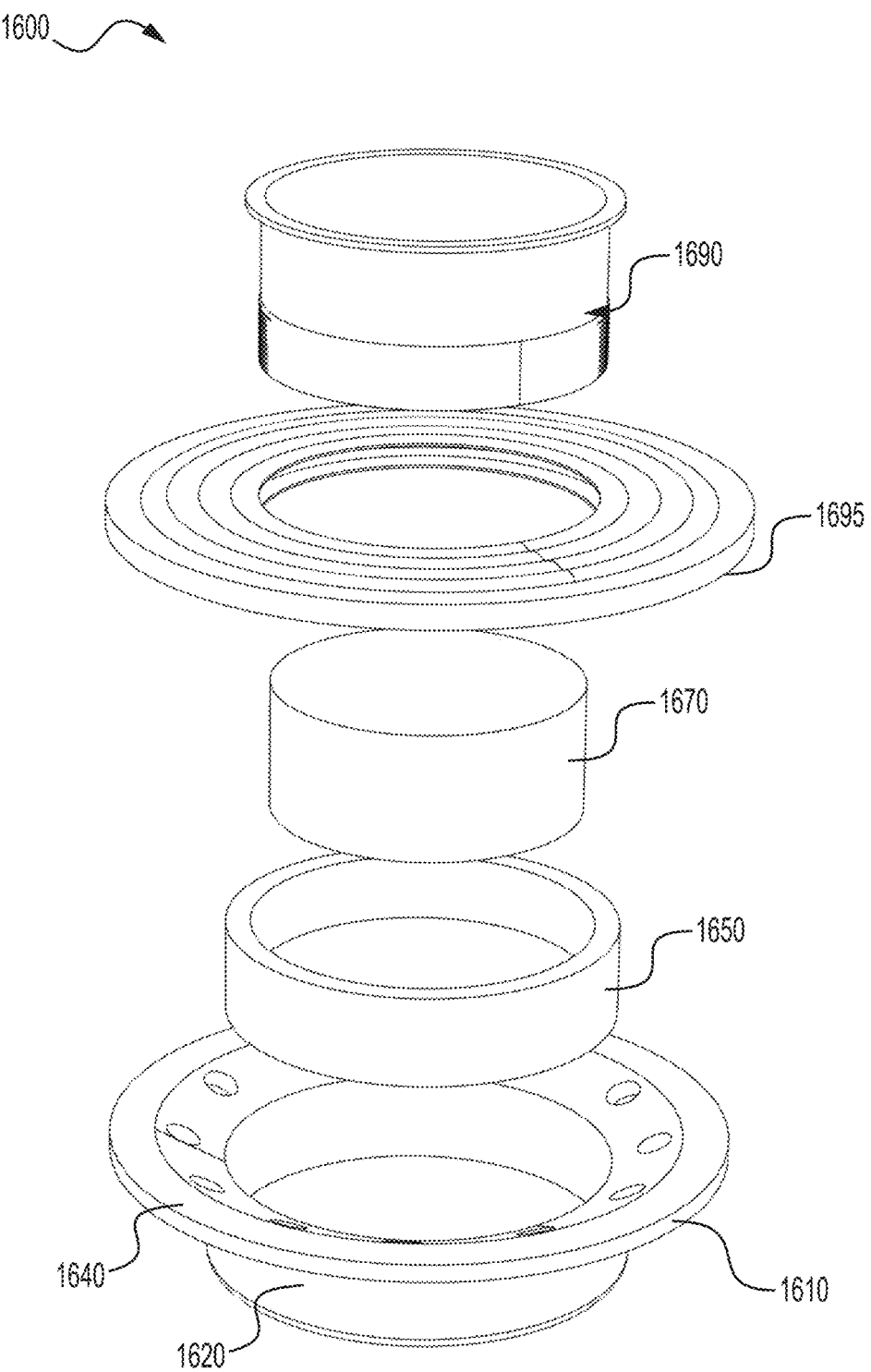
FIG. 16C is an exploded view of a vibroacoustic sensor module, such as the vibroacoustic sensor module of FIG. 16A, and having a double layer spider.

As described above, in some variations, the vibroacoustic sensor module may include a voice coil transducer alone or in combination with any of the above-described sensors and/or other suitable sensors. For example, FIGS. 16A-16C depict an exemplary variation of the voice coil transducer 1600. The voice coil transducer 1600 comprises a frame 1610 (also referred to as a surround pot) having a cylindrical body portion 1620 with a bore 1630, and a flange 1640 extending radially outwardly from the cylindrical body portion 1620. The frame 1610 may be made of steel. An iron core 1650 such as soft iron or other magnetic material is attached to the cylindrical body portion 1620 and lines the bore 1630 of the cylindrical body portion 1620. As can be seen, the iron core 1650 extends around the bore 1630 of the cylindrical body portion 1620 as well as across an end 1660 of the cylindrical body portion 1620. The iron core 1650 has an open end. A magnet 1670 is positioned in the bore 1630 and is surrounded by, and spaced from, the iron core 1650 to define a magnet gap 1680. A voice coil 1690, comprising one or more layers of wire windings 1692 supported by a coil holder 1693, is suspended and centered in relation to the magnet gap 1680 by one or more spiders 1695. The wire windings 1692 may be made of a conductive material such as copper or aluminum. A periphery of the spider is attached to the frame 1610, and a center portion is attached to the voice coil 1690. The voice coil 1690 at least partially extends into the magnet gap 1680 through the open end of the iron core 1650. The one or more spiders 1695 allow for relative movement between the voice coil 1690 and the magnet 1670 whilst minimizing or avoiding torsion and in-plane movements. A diaphragm (not shown in FIG. 16) is provided which may be attached to the voice coil transducer 1600. The diaphragm may be equated to the diaphragm 450. In steady state, when no pressure is being applied to the diaphragm, the voice coil 1690 may be positioned such that it is not fully received in the magnet gap (off-center in respect to optimal placement within the magnet gap). In use, the voice coil 1690 can be pushed into the magnet gap to center it when pressure is applied to the diaphragm under normal use.

A dust cap 1697 may be provided over the open end to prevent foreign object access. The voice coil transducer 1600 of FIGS. 16A-C may be incorporated into any of the sensing devices described herein, such as the sensing device 400 of FIGS. 4A-4F. The attachment of the diaphragm to a portion of the voice coil transducer 1600 (such as the cylindrical body portion 1620) may be by any suitable attachment means such as by adhesive. Alternatively, the diaphragm and the voice coil 1690 may be made as a single piece. In any of these variations, an outer cover (not shown) may be provided on top of the diaphragm to seal any openings between the diaphragm and the housing 1610. The outer cover may be made of an elastomeric material such as rubber.

In use, the sensing device 400 or the sensing device 300 can be used to detect acoustic signals of the subject by either coupling the diaphragm 450 or outer cover of the sensing device 400 to skin or clothing of the subject, or by positioning the subject and the sensing device 400 proximate to one another. Movements induced in the acoustic waves will cause the diaphragm 450 to move, in turn inducing movement of the voice coil 1690 within the magnet gap, resulting in an induced electrical signal.

In certain variations of the voice coil transducer, the configuration of the transducer is arranged to pick up more orthogonal signals than in-plane signals, thereby improving sensitivity. For example, the one or more spiders are designed to have out-of-plane compliance and be stiff in-plane. The same is true of the diaphragm whose material and stiffness properties can be selected to improve out-of-plane compliance. The diaphragm may have a convex configuration (e.g. dome shaped) to further help in rejecting non-orthogonal signals by deflecting them away. Furthermore, signal processing may further derive any non-orthogonal signals e.g. by using a 3 axis accelerometer. This either to further reject non-orthogonal signals or even to particularly allow non-orthogonal signals through the sensor to derive the angle of origin of the incoming acoustic wave.

It will be appreciated that different uses of the sensing device may require different sensitivities and face different noise/signal ratios challenges. For example, higher sensitivity and increased signal/noise ratio will be required for clothing contact uses compared to direct skin contact uses. Similarly, higher sensitivity and increased signal/noise ratio will be required for non-contact uses compared to contact uses.

Therefore, in order to provide sensing devices having sensitivities and signal/noise ratios suitable for different form factors (e.g. contact or non-contact uses), developers have discovered that modulation of certain variables can optimize the voice coil transducer for the specific intended use: magnet strength, magnet volume, voice coil height, wire thickness, number of windings, number of winding layers, winding material (e.g. copper vs aluminum), and spider configuration. This is further explained in Example 6.

In certain variations, the voice coil 1690 is configured to have an impedance of more than about 10 Ohms, more than about 20 Ohms, more than about 30 Ohms, more than about 40 Ohms, more than about 50 Ohms, more than about 60 Ohms, more than about 70 Ohms, more than about 80 Ohms, more than about 90 Ohms, more than about 100 Ohms, more than about 110 Ohms, more than about 120 Ohms, more than about 130 Ohms, more than about 150 Ohms, or about 150 Ohms. This is higher than a conventional heavy magnet voice coil transducer which has an impedance of about 4-8 Ohms. This is achieved by modulating one or more of the number of windings, wire diameter, and winding layers in the voice coil. Many permutations of these parameters are possible, and have been tested by the developers, as set out in Example 6. In one such variation, the voice coil comprises fine wire and was configured to have an impedance of about 150 Ohms, and associated lowered power requirement, by increasing the wire windings.

Developers also discovered that adaptation of the configuration of the spider 1695 contributed to increasing sensitivity and signal/noise ratio increases. More specifically, it was determined via experiment and simulation that making the spider more compliant such as by incorporating apertures in the spider 1695, increased sensitivity. Apertures also allow for free air flow. These are described in further detail below in relation to FIGS. 17 and 18.

The use of voice-coil based transducers for present uses is unintuitive, such as but not limited to contact with a body and/or the capture of sound below the audible threshold. Voice coils are commonly used in audio speaker systems and are optimized for the translation of electrical energy to acoustical energy. To achieve useful sound pressure levels, these audio speaker voice coils must be capable of handling high power in the range of 10 to 500 watts. The design considerations employed for this make them inappropriate for microphony or general sensing applications. Since electrical power can be described by the equation $P=IV=V^2/R$, low resistance voice coils allow for high power handling at relatively low voltages, that are compatible with the power semiconductors typically used in audio amplifiers. In fact, most manufacturers of audio equipment note the ability of their amplifiers to drive low impedance speaker loads as advantages. While a high turn number, high impedance coil would be more efficient in terms of force generated for a unit current, the voltage required to drive such a current would require bulky insulation that would interfere with thermal management. While ferrofluid cooling is a possible solution, the viscosity of such fluids reduce sensitivity. Of course, when high power amplifiers are available, that is not an issue. Therefore, low impedance speakers, such as 8- and 4-Ohm models are relatively common. These are characterized by heavy voice coils and magnet structures built to accommodate the heavy windings that these coils comprise. Noise may also be a factor: temperature induced thermal noise increases with higher impedance of a conductor/resistor.

Moreover, in order to maintain reasonable efficiency at low frequencies of around 20 Hz, woofers and subwoofers typically use very heavy cones, so voice coil mass is not a critical issue. Contrary, tweeters need light voice coils to enable reasonable efficiency in air-diaphragm impedance matching using small diaphragms with higher frequency bandwidth, and are therefore very inefficient when operating at low frequencies. Tweeters typically have very light and delicate diaphragms as well, thus are not suitable for direct contact microphony.

Crossover circuitry is also usually necessary in order to achieve wide frequency response of audio speakers operating between 20 Hz and 20 kHz due to the need of two-way and three-way transducer speaker designs.

However, conventional microphones typically operate under totally different conditions, where low sound pressure levels need to be picked up with a minimum of noise. To such end, they are typically constructed with low weight diaphragms and the best microphones typically need external power sources as they operate as variable capacitors rather than as true voice coil/magnetic gap transducers. Again, just like tweeters, the delicate diaphragms of sensitive microphone designs are not suitable for direct contact microphony due to their fragility. Owing to their method of operation, they also suffer from low dynamic range and high natural resonance frequencies.

Therefore, the discovery that an adapted voice coil transducer can be used as a biosignal microphone was a surprising development by the Developers. In certain variations of the present technology, it was discovered that by adapting the configurations of at least the voice coil and the spider of a traditional heavy magnet structure audio speaker, it was possible to achieve a microphone with a higher sensitivity, broader frequency range detection capabilities, dynamic and tunable frequency range, and high signal to noise characteristics. In certain variations, a single voice coil transducer of the current technology can provide a microphonic frequency response of less than about 1 Hz to over about 150 kHz or about 0.01 Hz to about 160 kHz Furthermore, the use of such a vibroacoustic sensor module also enabled the size of the vibroacoustic sensor module to be kept to a practical minimum for hand-held applications. These combinations of changes allowed for relatively higher voltage generation by the voice coil in response to vibroacoustic signals than would be possible using typical audio speaker voice coils. Consequently, the sensing of these voltages can be accomplished with low-noise J-FET based amplifiers, for example, to achieve the desired combination of frequency response, dynamic range, spurious signal rejection and signal to noise ratio.

Figure 16D:
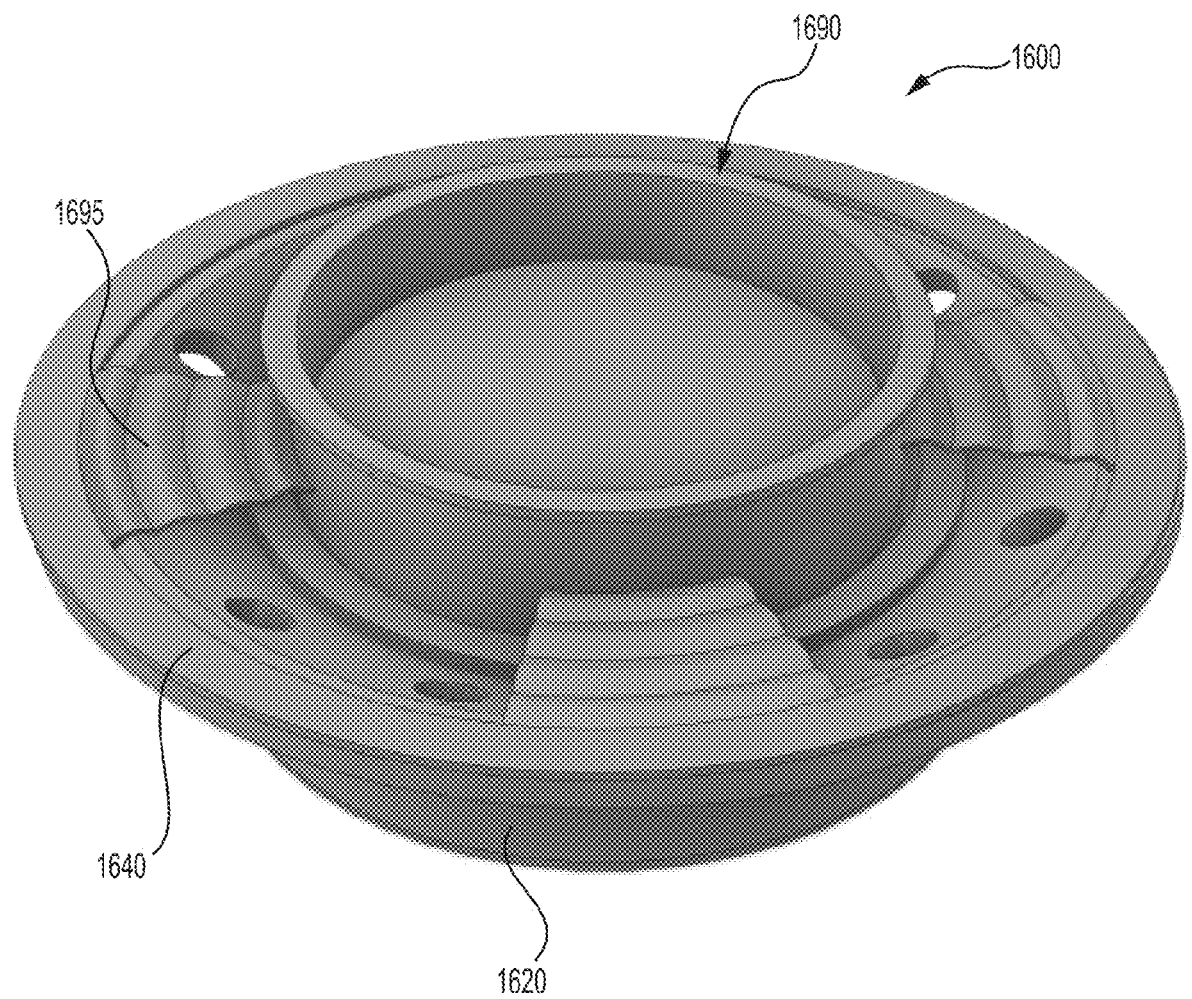
FIG. 16D is a perspective view of the example vibroacoustic sensor module of FIG. 16A with an outer housing omitted for clarity.
Figure 16E:
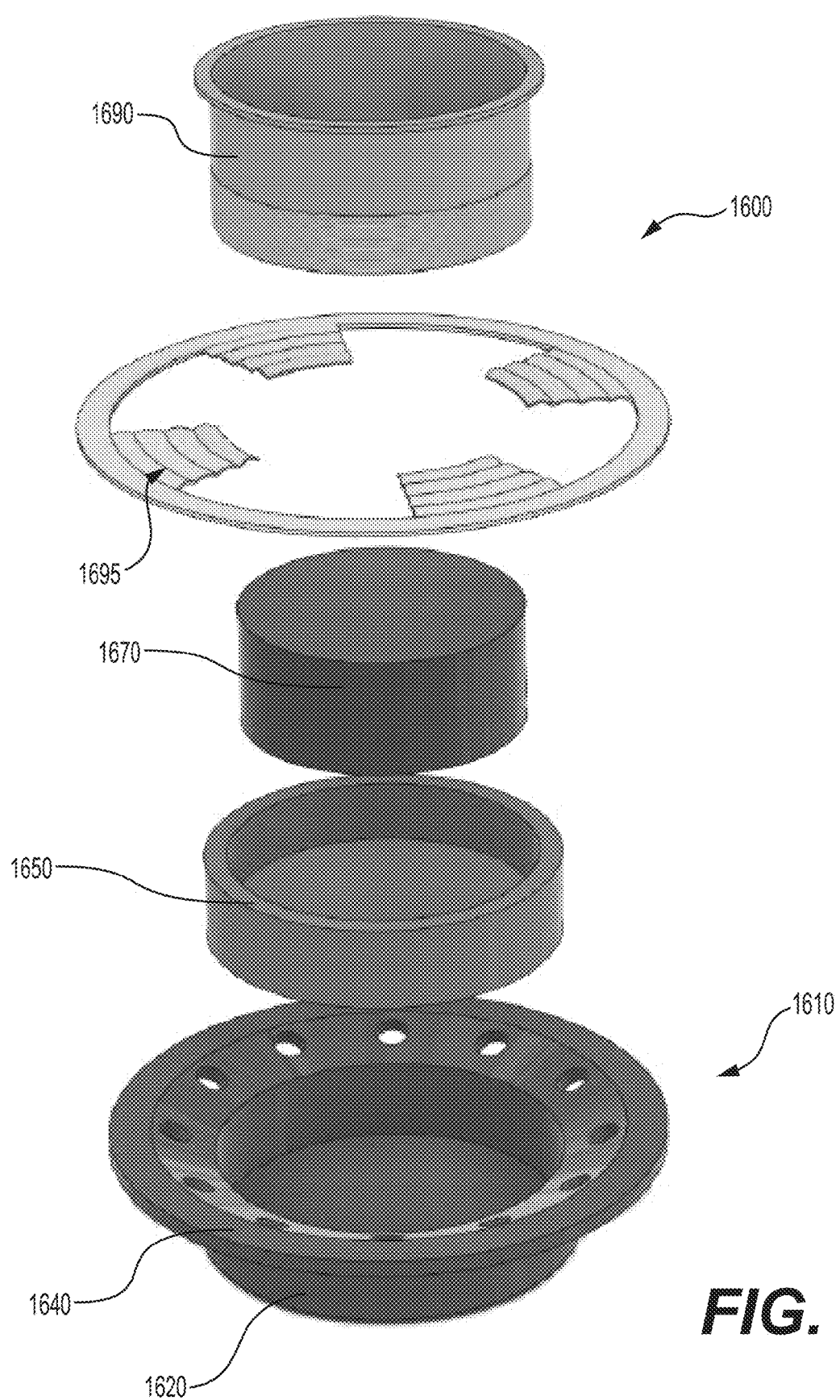
FIG. 16E is an exploded view of the vibroacoustic sensor module of FIG. 16D.

In certain variations of the present technology, the voice coil transducer 1600 comprises a single layer of spider 1695 (FIG. 16C). In certain other variations of the present technology, the voice coil transducer 1600 comprises a double layer of the spider 1695 (FIG. 16D). Multiple spider 1695 layers comprising three, four or five layers, without limitation, are also possible.

Figure 17B:
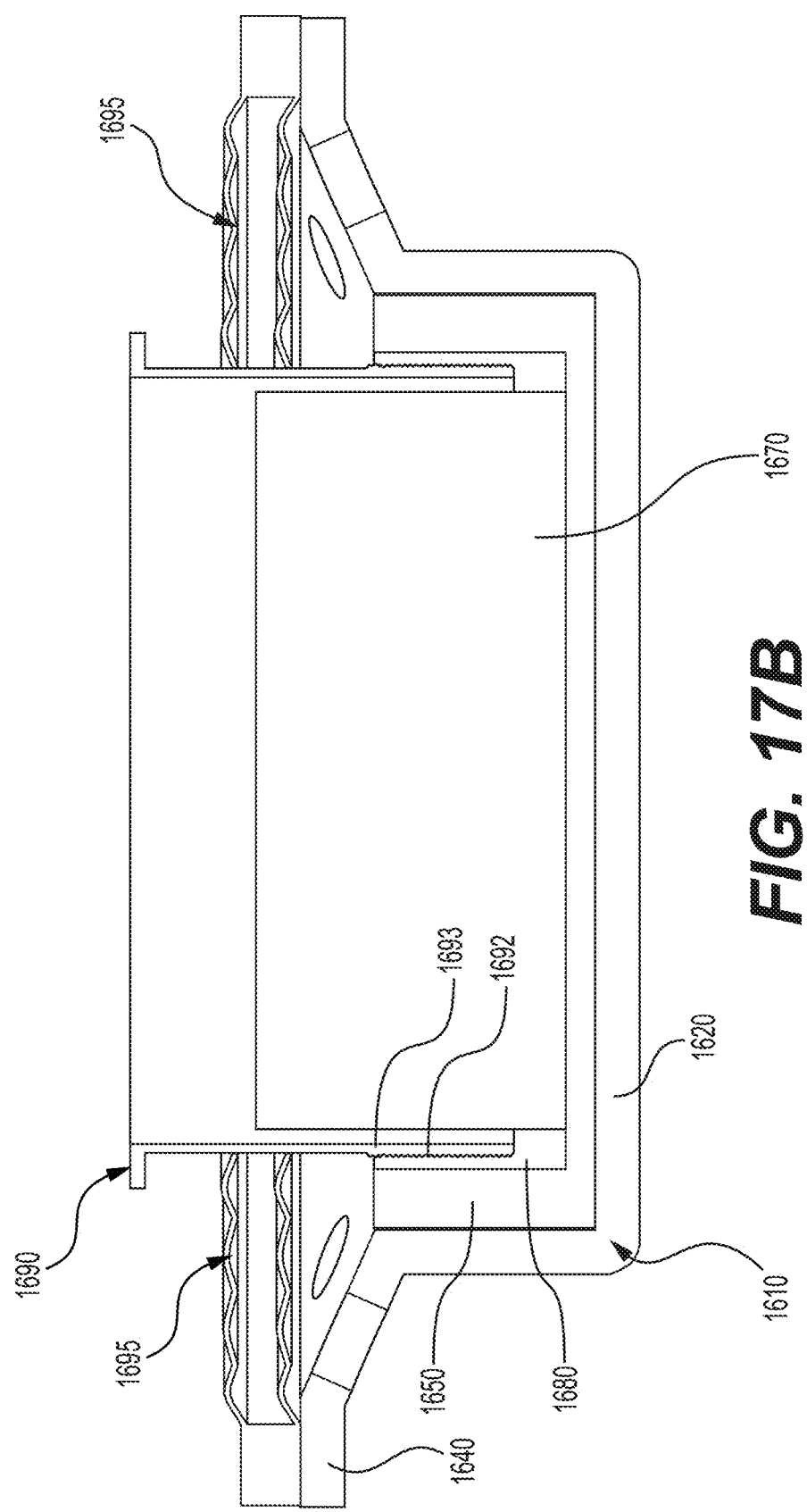
Figures 18A, 18B, 18C, 18D:
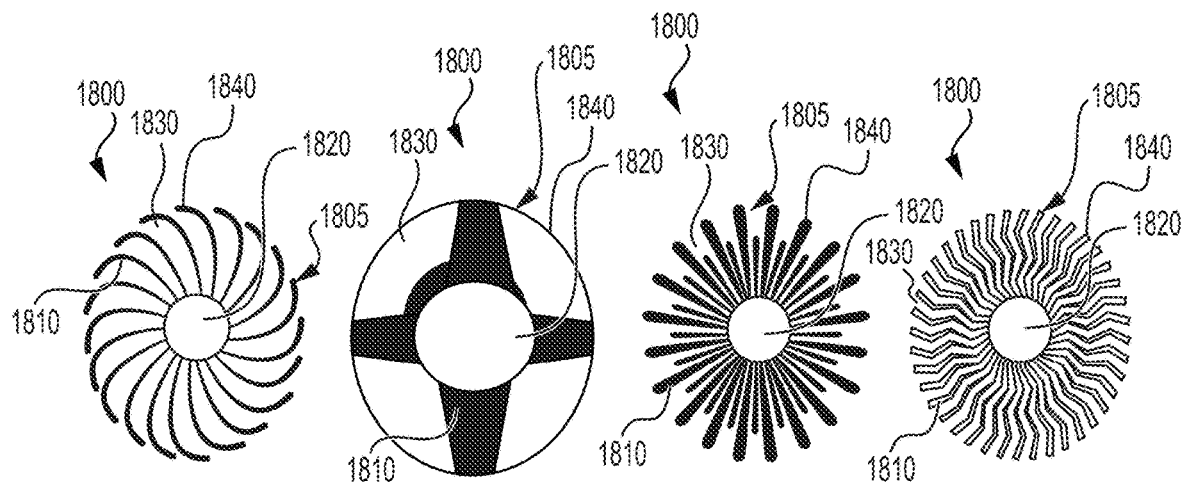
FIGS. 18A-18AB are example spiders for use with variants of the vibroacoustic sensor modules of any of FIGS. 16A-E, and 17A-B.
Figures 18E, 18F, 18G, 18H:
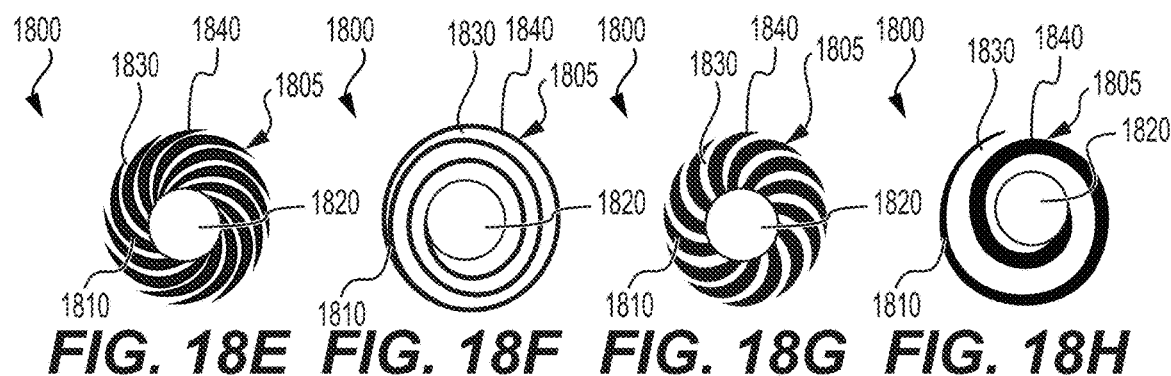
Figures 18I, 18J, 18K, 18L:
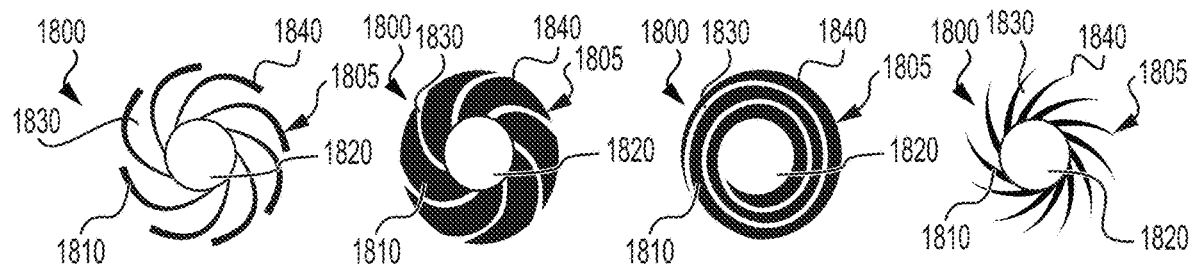
Figures 18M, 18N, 18O, 18P:
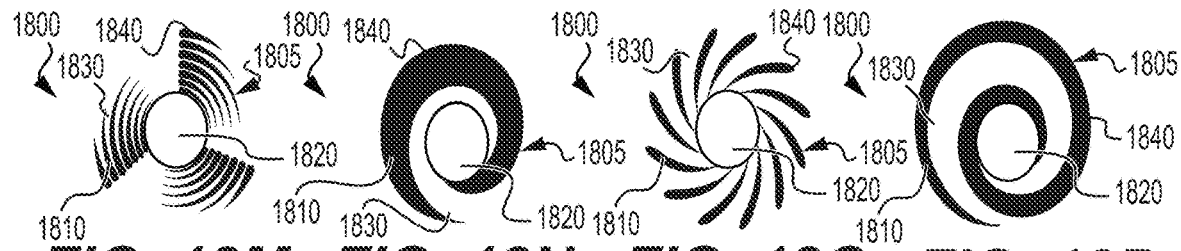
Figures 18Q, 18R, 18S, 18T:
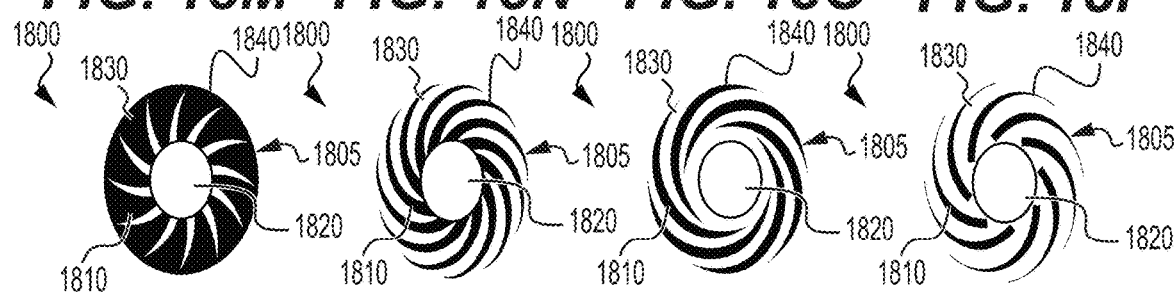
Figures 18U, 18V, 18W, 18X:
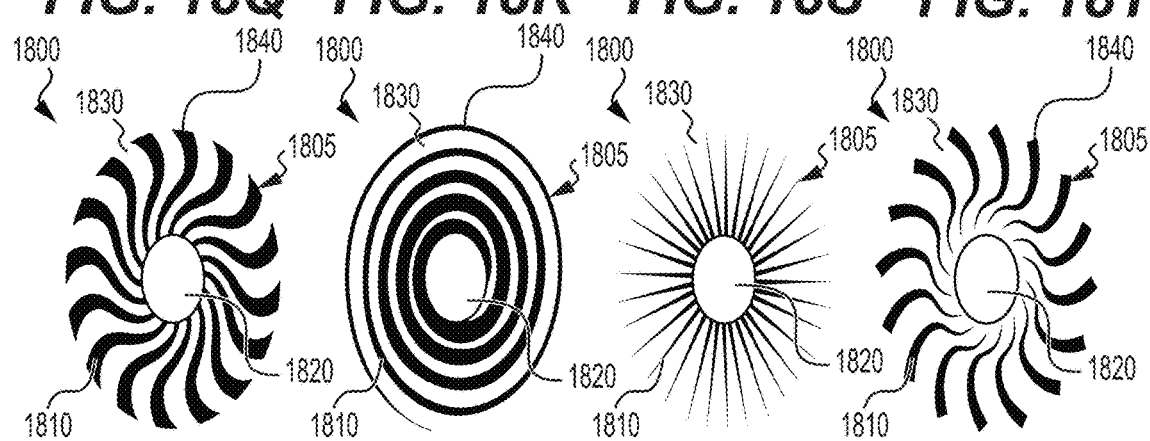
Figures 18A, 18Y, 18Z:
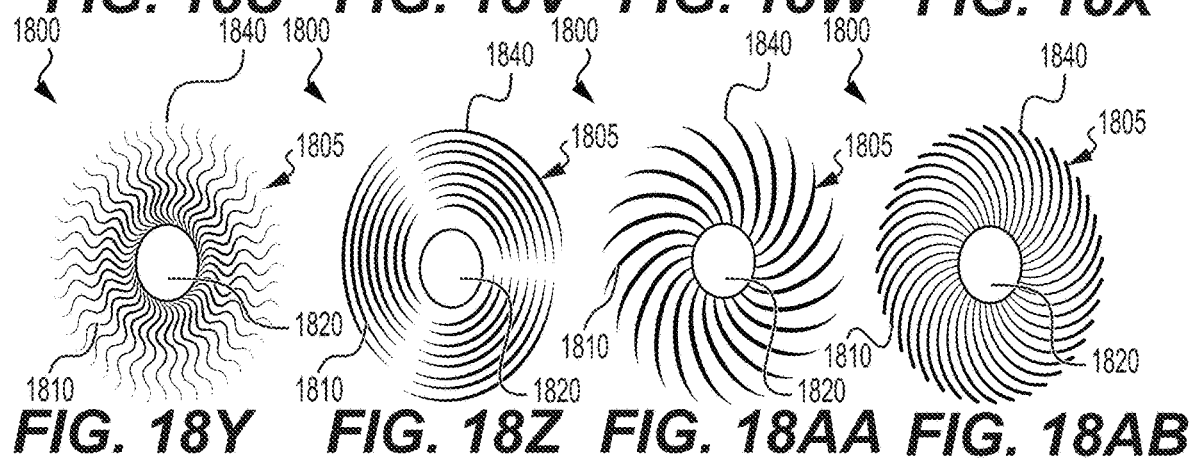

Certain configurations of the spider 1695 are illustrated in FIGS. 17 and 18A-18AB. As can be seen, instead of a one-piece corrugated continuous configuration as is known in conventional spiders of conventional voice coils, in certain variations of the current technology, the spider 1695 has a discontinuous surface. The spider 1695 may comprise at least two deflecting structures 1700 which are spaced from one another, permitting air flow therebetween. In certain configurations, the deflecting structures 1700 comprises two or more arms 1710 extending radially, and spaced from one another, from a central portion 1720 of the spider 1695. In the variation illustrated in FIGS. 17 A and B, and 18B the deflecting structure 1700 comprises four arms 1719 extending radially from the central portion 1720. The four arms 1710 increase in width as they extend outwardly. Each of the arms 1710 has a corrugated configuration. An aperture 1730 between each of the arms 1710 is larger than an area of each deflecting arm.

FIGS. 18A-AB show other variants of a spider 1800 for a voice coil transducer, such as the voice coil transducer 1600. The spider comprises a deflecting structure 1800 comprising one or more arms 1810 extending from a central portion 1820 and defining apertures 1830 therebetween. The one or more arms 1810 may be straight or curved. The one or more arms 1810 may have a width which varies along its length, or which is constant along its length. The one or more arms 1810 may be configured to extend from the central portion 1820 in a spiral manner to a perimeter 1840 of the spider 1800. A solid ring may be provided at the perimeter 1840 of the spider 1800. This has been omitted from FIGS. 18A-AB for clarity, but can be seen in FIG. 16E. In certain variations, there may be provided a single arm 1810 configured to extend as a spiral from the central portion 1820 of the spider 1800 to the perimeter 1840 of the spider 1800. In these cases, turns of the spiral arms 1810 define the apertures 1830. The spider 1800 may be defined as comprising a segmented form including portions that are solid (the arm(s) 1810) and portions which are the aperture(s) 1830 defined therebetween. The arms 1810 may be the same or different (e.g. FIG. 18C). In variants where more than one layer of the spider 1800 is provided in the voice coil transducer, the spiders 1800 of each layer may be the same or different.

The configuration chosen for a given use of the sensing device will depend on the amount of compliance required for that given use. For example, a voice coil configuration of low compliance may be chosen for contact applications than non-contact applications. For contact applications, spider may be coupled to the voice coil in such a way as to off-set the voice coil from the magnet gap when there is no pressure applied to the diaphragm, and when the expected pressure is applied to the diaphragm, the voice coil will be pushed into the magnet gap for optimum positioning and acoustic signal detection.

In certain variations, a compliance of the diaphragm may range from about 0.4 to 3.2 mm/N. The compliance range may be described as low, medium and high, as follows:

0.4 mm/N: low compliance→fs around 80-100 Hz;
1.3 mm/N: medium compliance→fs around 130 Hz;
3.2 mm/N: high compliance→fs around 170 Hz.

In some variations, two or more voice coil sensors may be included in the sensing device (e.g., in the vibroacoustic sensor module) which may enable triangulation of faint body sounds detected by the voice coil sensors, and/or to better enable cancellation and/or filtering of noise such as environmental disturbances. Sensor fusion data of two or more voice coil sensors can be used to produce low resolution sound intensity images.

In some variations, the voice coil transducer may be optimized for vibroacoustic detection, such as by using non-conventional voice coil materials and/or winding techniques. For example, in some variations, the voice coil material may include aluminum instead of conventional copper. Although aluminum has a lower specific conductance, overall sensitivity of the voice coil transducer may be improved with the use of aluminum due to the lower mass of aluminum. Additionally, or alternatively, the voice coil may include more than two layers or levels of winding (e.g., three, four, five, or more layers or levels), in order to improve sensitivity. In certain variants, the wire windings may comprise silver, gold or alloys for desired properties. Any suitable material may be used for the wire windings for the desired function. In certain other variants, the windings may be printed, using for example conductive inks onto the diaphragm.

Advantageously, certain variants of the present technology can be used as a standalone stethoscope or addition to a traditional acoustic stethoscope or appendage to a smartphone or phonocardiogram device to detect infrasound-to-ultrasound vibroacoustic signals from the subject. The sensing device may have any suitable form factor for contact or contactless vibroacoustic detection. The vibroacoustic sensor module of certain variants of the present technology has advantages over conventional acoustic and electrical stethoscopes which are used to detect acoustic signals relating to the subject.

Firstly, the present technology can be deployed for contactless applications such as remote monitoring. On the other hand, traditional acoustic stethoscopes require contact with the skin of the subject for adequate sound detection.

Secondly, acoustic signals can be detected over a broad range and with good signal to noise ratios. Conversely, traditional acoustic stethoscopes have poor sound volume and clarity as they convert the movement of the stethoscope diaphragm into air pressure, which is directly transferred via tubing to the listener's ears by inefficient acoustic energy transfer. The listener therefore hears the direct vibration of the diaphragm via air tubes.

The current technology also has advantages over conventional electrical stethoscope transducers, which tend to be one of two types: (1) microphones mounted behind the stethoscope diaphragm, or (2) piezo-electric sensors mounted on, or physically connected to, the diaphragm.

Microphones mounted behind the stethoscope diaphragm pick up the sound pressure created by the stethoscope diaphragm, and convert it to electrical signals. The microphone itself has a diaphragm, and thus the acoustic transmission path comprises or consists of a stethoscope diaphragm, the air inside the stethoscope housing, and finally the microphone's diaphragm. The existence of two diaphragms, and the intervening air path, can result in excess ambient noise pickup by the microphone, as well as inefficient acoustic energy transfer. This inefficient acoustic energy transfer is a prevalent problem in the below-described electrical stethoscopes. Existing electronic stethoscopes use additional technologies to counteract this fundamentally inferior sensing technique, such as adaptive noise canceling and various mechanical isolation mountings for the microphone. However, these merely compensate for the inherent inadequacies of the acoustic-to-electrical transducers.

Piezo-electric sensors operate on a somewhat different principle than merely sensing diaphragm sound pressure. Piezo-electric sensors produce electrical energy by deformation of a crystal substance. In one case, the diaphragm motion deforms a piezoelectric sensor crystal mechanically coupled to the diaphragm, resulting in an electrical signal. The problem with this sensor is that the conversion mechanism can produce signal distortion compared with sensing the pure motion of the diaphragm. The resulting sound is thus somewhat different in tone, and distorted compared with an acoustic stethoscope.

Capacitive acoustic sensors are in common use in high-performance microphones and hydrophones. A capacitive microphone utilizes the variable capacitance produced by a vibrating capacitive plate to perform acoustic-to-electrical conversion. A capacitive microphone placed behind a stethoscope diaphragm would suffer from the same ambient noise and energy transfer problems that occur with any other microphone mounted behind a stethoscope diaphragm.

Acoustic-to-electrical transducers operate on a capacitance-to-electrical conversion principle detecting diaphragm movement directly, converting the diaphragm movement to an electrical signal which is a measure of the diaphragm motion. Further amplification or processing of the electrical signal facilitates the production of an amplified sound with characteristics very closely resembling the acoustic stethoscope sound, but with increased amplification, while maintaining low distortion.

This is a significant improvement over the more indirect diaphragm sound sensing produced by the microphonic or piezoelectric approaches described above. Since the diaphragm motion is sensed directly, the sensor is less sensitive to outside noise, and the signal is a more accurate measure of the diaphragm movement. With an acoustic stethoscope, diaphragm movement produces the acoustic pressure waves sensed by the listener's ears. With an acoustic-to-electrical sensor, that same diaphragm movement produces the electrical signal in a direct manner. The signal is used to drive an acoustic output transducer such as earphones or headphones, to set up the same acoustic pressure waves impinging on the listener's ears.

While acoustic-to-electrical transducers overcome many of the inherent problems faced by earlier stethoscope designs, it adds considerable white noise to the signal. White noise is a sound that contains every frequency within the range of human hearing (generally from 20 Hz to 20 kHz) in equal amounts. Most people perceive this sound as having more high-frequency content than low, but this is not the case. This perception occurs because each successive octave has twice as many frequencies as the one preceding it. For example, from 100 Hz to 200 Hz, there are one hundred discrete frequencies. In the next octave (from 200 Hz to 400 Hz), there are two hundred frequencies.

As a result, the listener has difficulty discerning the human body sound from the white noise. For sounds of the body with higher intensities (i.e., louder sounds) the listener can hear the body sounds well, but lower-intensity sounds disappear into the background white noise. This is not the case in certain variations of the present technology.

Echo Sensor-Based Vibroacoustic Modules

Variants of the system 10 or the sensing device 110 may include one or more echo sensor based vibroacoustic modules, such as but not limited to one or more of: echo sensors based on Continuous Wave Doppler (CWD), Pulsed Wave Doppler (PWD), and Time-of-Flight.

Continuous Wave Doppler (CWD): A continuous ultrasound signal is emitted by a source oscillator, reflected of a subject and back into a receiver. Vibrations on the subject change the frequency/phase of the emitted Ultrasound signal which allows to retrieve the original vibration signal. This offers maximum sampling frequency of the subject under investigation.

Pulsed Wave Doppler (PWD): Short ultrasound bursts are sent, and receiver waits for response. This technique can resolve subject vibrations like the CWD, but due to the burst interval introduces a sampling frequency of the subject. The Nyquist frequency of the corresponding sampling frequency is (pulses per second)/2. Hence with one pulse every Millisecond the maximum resolved subject vibration frequency is 500 Hz. However, the PWD can resolve vibrations at a specific depth, or distance from the emitter/sensor. This is achieved by taking the time-of-flight information of the pulse into account and reject signals that outside the desired distance. Hence, the PWD can reject signals outside the target distance; signals that either are created by other sources or the emitted pulse that has traveled beyond the subject and reflected of a wall.

Time-of-Flight: A simpler version compared to the PWD is a pulsed Ultrasound signal where only the time-of-flight is considered.

Advantageously, these echo-based modules can permit measurement of vibrations (such as vibroacoustic signals from the subject), as well as distance or velocity. The echo-based modules are non-contact, non-invasive and not harmful to the subject. Vibroacoustic signals can be detected from a distance of about 1 cm to about 10 meters, in certain variations. A detection distance may be about 10 meters, about 9 meters, about 8 meters, about 7 meters, about 6 meters, about 5 meters, about 4 meters, about 3 meters, about 2 meters or about 1 meter. Signal detection can be performed through clothing or other apparel of the subject. Furthermore, signal detection over a broad spectrum can be obtained.

The echo based acoustic systems broadly comprise an emitter component and a receiver component and are active systems which rely on the receiver component detecting a signal from the subject responsive to an emitted signal by the emitter incident on the subject. Therefore, in certain variations, emission signals within the ultrasound range are used, preferably above 25 kHz to keep some headroom to the end of the audible spectrum (as it is not desirable to use emission signals within the audible range). On the higher end, the maximum may be around 100 kHz due to ultrasonic signal absorption in air and ADC sampling rates. At 50 kHz the acoustic absorption in air is about 1-2 dB/m, at 100 kHz about 2-5 dB/m, at 500 kHz about 40-60 dB/m and at 1 Mhz about 150-200 dB/m. Technological challenges at higher frequencies involve the ability to capture the signal in sufficient quality, such as the availability of fast Analog-to-Digital converters.

The number of emitter components and receiver components in the echo sensor module is not limited. Different combinations may be used as will be explained in further detail with reference to FIGS. 33D-H. For example, there may be provided a single emitter component and a single receiver component; or two emitter components and a single receiver component; or single emitter component and two receiver components; or two emitter components and two receiver components.

The emitter component can be any type of emitter configured to emit an ultrasound signal. Emitters should possibly be as unidirectional as possible. One example is the Pro-Wave Electronics 400ET/R250 Air Ultrasonic Ceramic Transducer.

The receiver component can be of any receiver type configured to detect the emitted ultrasound signal from the subject. In certain variations, the receiver component can be a microphone capable of capturing the ultrasound signal with sufficient signal-to-noise ratio. This could include any type of microphone such as condenser, dynamic or MEMS microphones. In certain variations, Ultrasound capable MEMS microphones are preferred due to compactness. In other variations, the receiver component is a specialized Ultrasound receiver that is tuned to that frequency. In certain variations, the receiver component is as unidirectional as possible. Examples of receiver components include the Pro-Wave Electronics 400ST/R100 Transducer; the Pro-Wave Electronics 400ST/R160 Transducer; or Invensense ICS-41352.

1.c.iii. Examples of Other Sensors

According to certain variations, the system 100 may include sensor modules, other than the vibroacoustic sensor modules described above. The one or more other sensor modules may be incorporated within a housing of the sensing device, or may be separate and connected thereto.

Bioelectric-Based Sensor Module

In certain variations of the system 10, such as the sensing device 400, there is also provided a bioelectric-based sensor module. In certain variations, the bioelectric-based sensor module is configured to detect electrical impulses on the skin of the subject. These may be representative of electrical impulses in the nerves of the heart tissue of the subject. The bio-electric based sensor module can therefore function as an ECG module, and is therefore referred to herein as an ECG sensor module. The ECG sensor module may indicate bodily conditions, such as: trauma to the nervous tissue network of the heart; damage to the heart tissue such as from a prior heart attack or infection, severe nutritional imbalances, stress from excessive physiological or psychological pressure.

For example, as illustrated in FIG. 4B, in certain variations, the sensing device 400 of the sensing module comprises capacitive sensor electrodes such as the Electrical Potential Integrated Circuit (EPIC) electrodes 460 and the Driven right Leg (DRL) electrodes 470.

Figure 19:
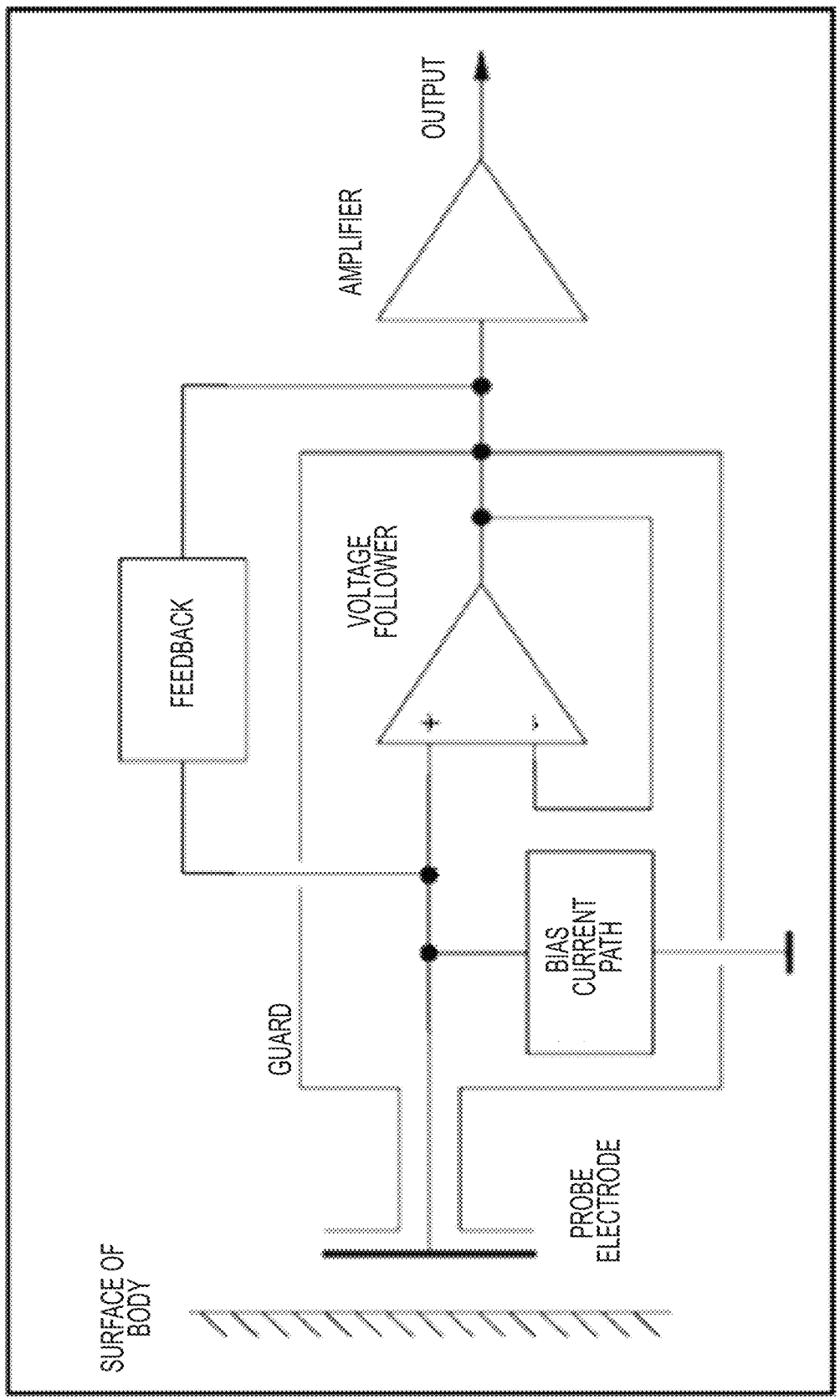
FIG. 19 depicts an example circuit of an ECG sensor module of example variations of the sensing device.

FIG. 19 illustrates the basic circuit of the ECG sensor module. The operation can be described as follows.

The dipole is the elemental unit of cardiac activity. Each dipole consists of a positive (+) and negative (−) charge generated by the action of ion channels. As activation spreads, the sources sum together and act as a continuous layer of sources. Stated simply, an electric dipole consists of two particles with charges equal in magnitude and opposite in sign separated by a short distance. In the heart, the charged particles are ions such as sodium ($Na^+$), potassium ($K^+$), calcium ($Ca^{2+}$), phosphates ($PO_4^{3-}$), and proteins. The separation is the distance across the cardiac cell membrane. Because they are too large to pass through the small cell membrane channels, the negatively charged particles remain in the cell, whereas the positive ions move back and forth through specific channels and "ion pumps" to create polarization and depolarization across the membrane.

If enough dipoles are present together, they create a measurable voltage. Resting cardiac cells within the heart are normally at −70 mV. This means that at rest, there is naturally a charge imbalance present in the heart. This imbalance, called polarization of the cell, attracts positive ions toward the interior of the cell. When a cardiac cell is activated by an outside stimulus, channels in the cell membrane activate, and the excess positive ions outside of the cell rush into the cell. This process, called depolarization, makes the cell less negatively charged and is associated with "activation" of the cardiac cell. When millions of these cells activate together, the heart contracts and pumps blood to the rest of the body. The combined activation of these cells generates enough voltage to be measured on the surface of the skin by an electrocardiogram (ECG). The resulting intracardiac electrogram (EGM) extends beyond the area of the dipole signal by a factor of five, reducing resolution and acuity.

Variations of the ECG sensor module of the present technology comprise one or more bio-electric sensors to measure electrical fields and electrical impulses.

For close coupling (Cext>>Cin) this is usually defined by Equation 1:

$$C_{ext} = \frac{\varepsilon_0 \varepsilon_r a}{d}$$

where:
a=the equivalent shared electrode/target area
d=the distance between target and sensor
$\varepsilon_0$=the permittivity of free space
$\varepsilon_r$=the relative permittivity of the dielectric in which the sensor is operating For remote coupling (Cext>>Cin) we have the limiting case (self-capacitance) shown in Equation 2:

$$C_{ext} = 8\varepsilon_0 \varepsilon_r r$$

where r is the diameter of the sensor plate.

Analysis of the circuit shows us that we have a classic single-pole transfer function as shown in Equation 3:

$$\frac{V_o(t)}{V_{in}(t)} = \frac{Z_{in}}{Z_{in} + Z_{ext}}$$

The corner frequency (Fc1) can be expressed in Equation 4:

$$Fc1 = \frac{1}{2\pi(C_{ext} + C_{in})R_{in}}$$

The input capacitance for the ECG sensor module can be driven as low as $10^{-17}$ F with the input resistance being boosted to values up to around $10^{15}\Omega$, thus keeping the interaction with the target field to an absolute minimum and ensuring that all currents are small displacement currents only. Bootstrapping techniques control the values for $C_{in}$ and $R_{in}$ to give effective values, allowing us to control both the gain plateau and the corner frequency (Fc1 moves to Fc2). The response of the ECG sensor module was optimized via staging design and positive feedback loops.

Figure 20:
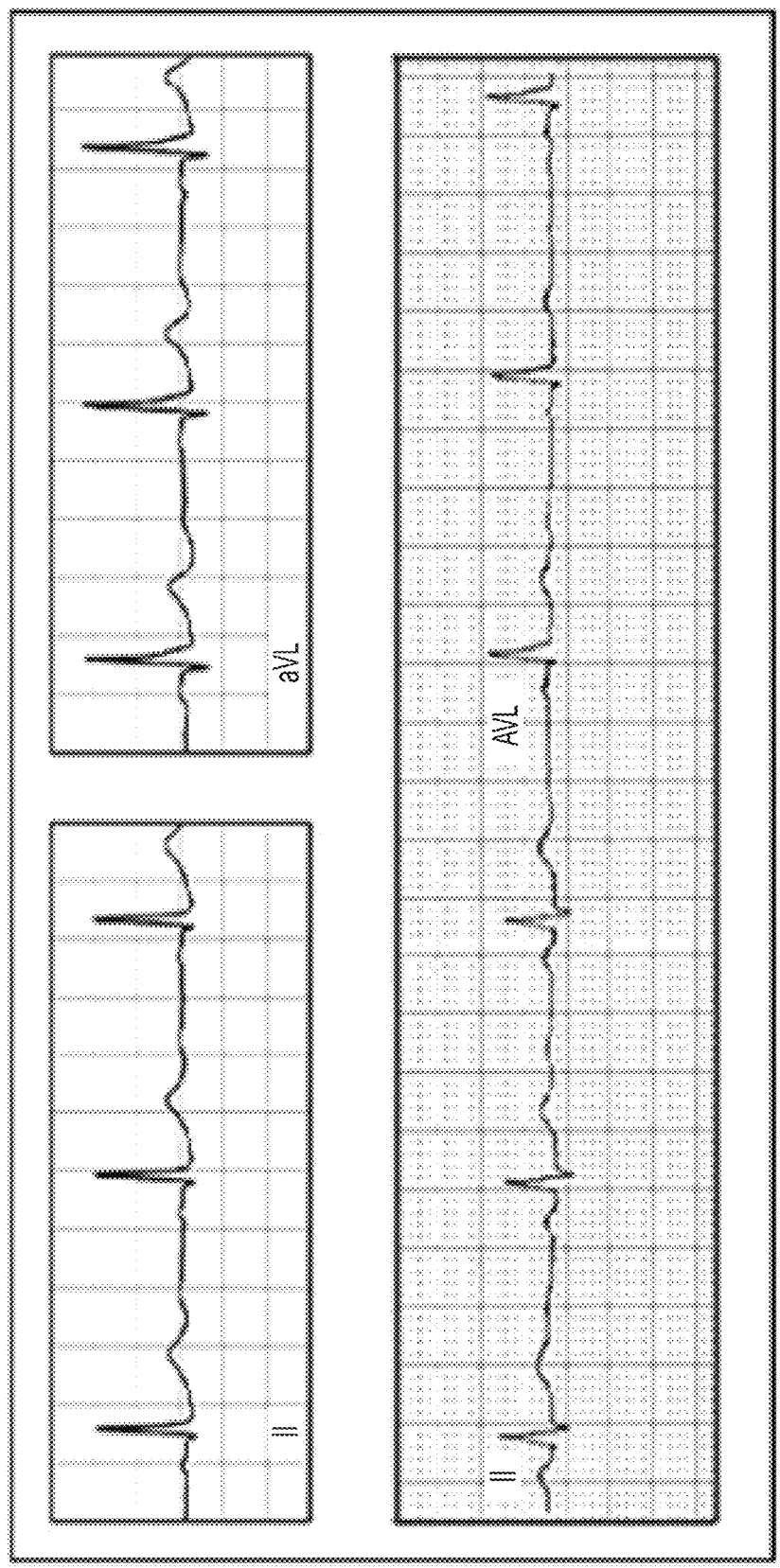
FIG. 20 shows a comparison between results obtained an example variation of the ECG sensor module of the present technology and traditional wet electrodes for leads II and a VL.

The ECG sensor module can be used, as a replacement technology for traditional wet-electrode ECG pads, because it requires neither gels nor other contact-enhancing substances. When the ECG sensor module is placed on (or in close proximity to) the patient, an ECG signal can be recovered. The sensor is capable of both simple "monitoring" ECG as well as making more exacting clinical screening and pre-diagnostic measurements. In applications for infectious bodily condition diagnosis, such as for Covid-19, the ECG sensor module can be used as a replacement for the traditional twelve-lead ECG, in which electrodes are placed on the limbs and torso to achieve a clearer picture of how the patient's heart is working. The ECG sensor module four-lead array of electric potential sensors can be used to recreate each and all the 12-lead ECG traces required with resolution as good as or better than that achieved using traditional systems. FIG. 20 shows a comparison between the results using variations of the ECG sensor module and using traditional wet electrodes for leads II and a VL. The top figure illustrates the control and the lower figure is the experimental.

Referring now to the DRL electrodes and their operation, with reference to FIGS. 4B-E, FIGS. 21 and 22.

Figure 21:
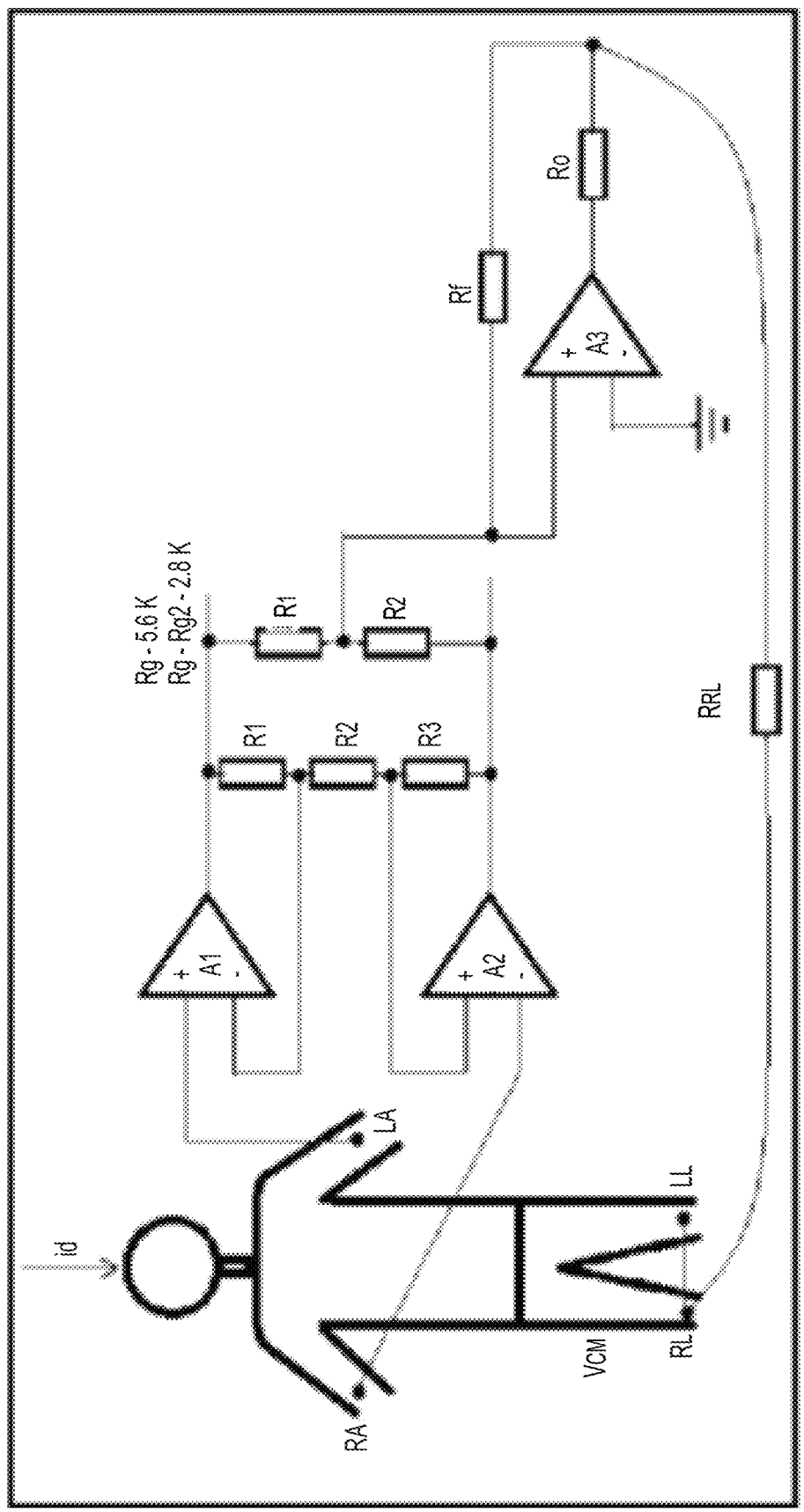
FIG. 21 depicts an example circuit of Driven Right Leg sensor used during ECG procedures of the prior art.

Driven Right Leg (DRL) is a technology within conventional ECG systems for attempting to reduce the noise that is picked up by ECG sensors. DRL is a differential electronic technique for improving spurious signal rejection and signal to noise ratio in the acquisition of bioelectric signals. Typically, this technique is used during ECG procedures and involves the application of at least one electrode, in contact with the skin, to the lower leg of a subject, as shown in FIG. 21. However, the existing technique cannot be used through clothing, and is not practical for use in an ambulating patient as it typically requires a patient to be sitting or lying down, at least for skin contact electrode placement. Therefore, Developers have developed the current ECG sensor module which, in certain variations, does not require attachment to the leg of the subject, whilst improving spurious signal rejection and improving signal to noise ratio. In certain variations, the ECG sensor module comprises at least one EPIC sensor and at least one DRL sensor.

Figure 22A:
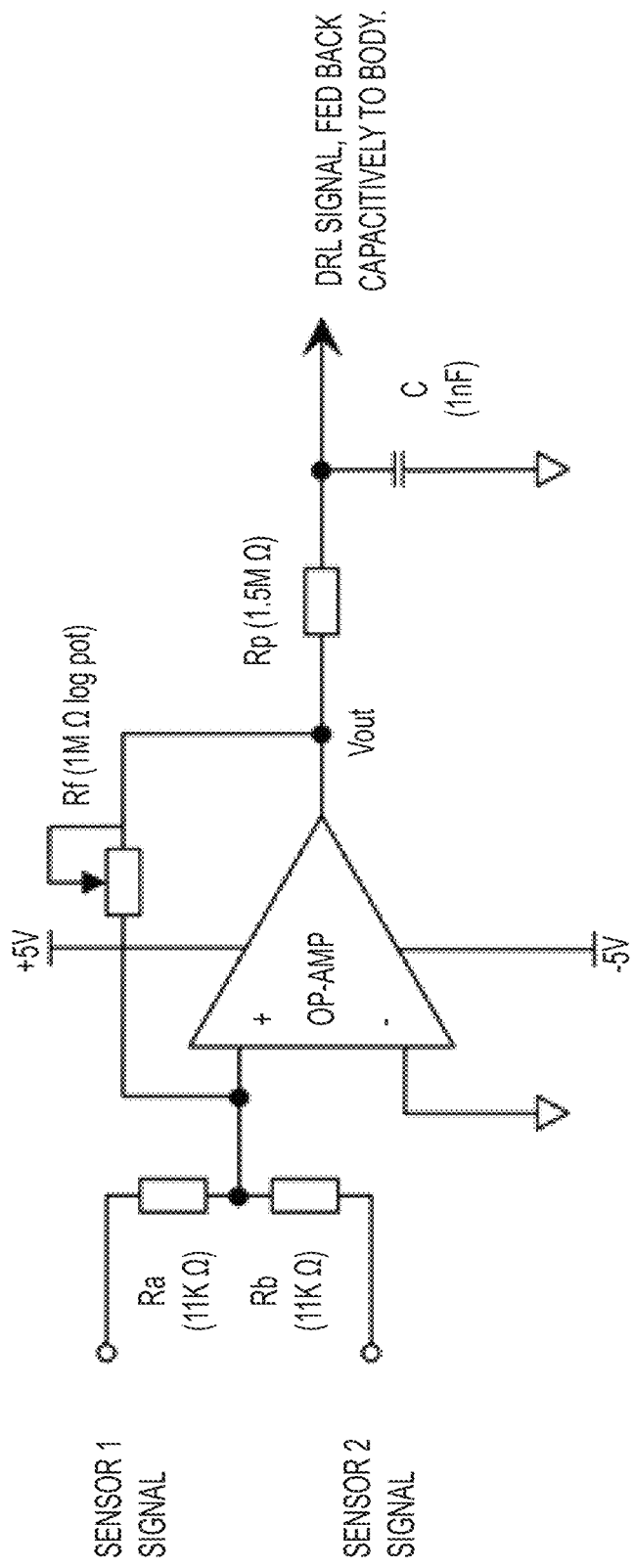
FIG. 22A depicts a prototype circuit diagram for a Driven Right Leg (DRL) sensor for use in an example variation of a sensing device.
Figure 22B:
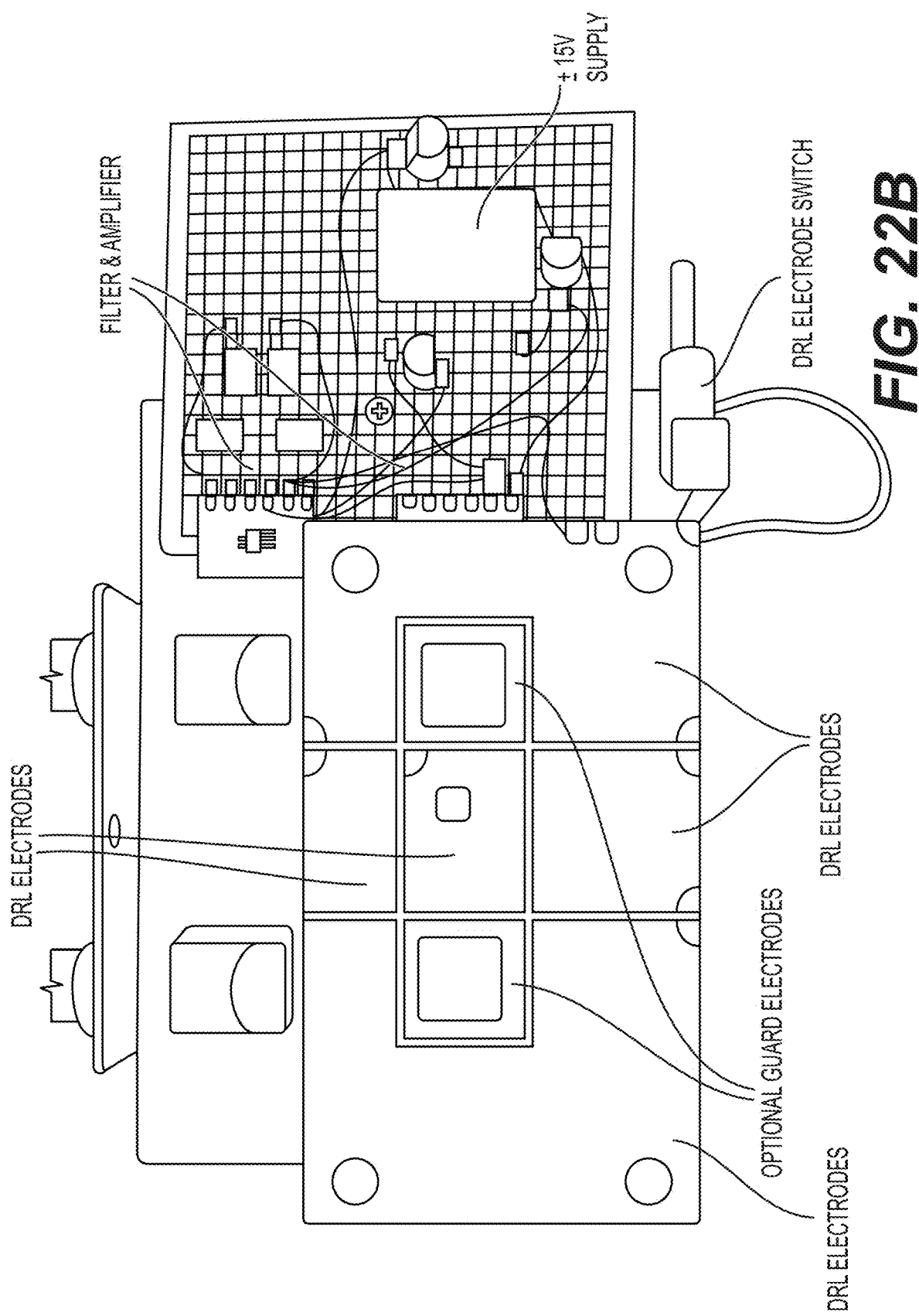
FIG. 22B depicts an experimental set up involving five DRL electrodes spaced between and around two EPIC electrodes, with optional guard electrodes, for use in an example variation of a sensing device.

According to certain variations of the current technology, a prototype circuit diagram for the at least one DRL sensor is shown in FIG. 22A. FIG. 22B shows an experimental set up involving five DRL electrodes spaced between and around two EPIC electrodes, with optional guard electrodes. The guard electrodes provide grounding which is important when there is direct contact to skin. They provide a reference of the signal to system ground when in direct contact with skin; otherwise the ECG signal would not be detected or be very noisy. The guard electrodes, as a 3D structure, can also function as a Faraday cage to provide EMI shielding. When there is no direct contact with skin (such as with through clothed uses), that is where the DRL comes in to provide that reference through capacitive coupling and an active feedback signal. Then, the guard electrodes lose their grounding purpose but still offer EMI shielding. It can allow the switching from DRL to non-DRL functionalities. In the experimental set-up, the two EPIC electrodes were spaced approximately 46 mm apart. The DRL sensor between the two EPIC sensors was approximately 21 mm wide. Each DRL sensor surrounding each EPIC sensor had an outer dimension of 15 mm squared.

Figure 22C:
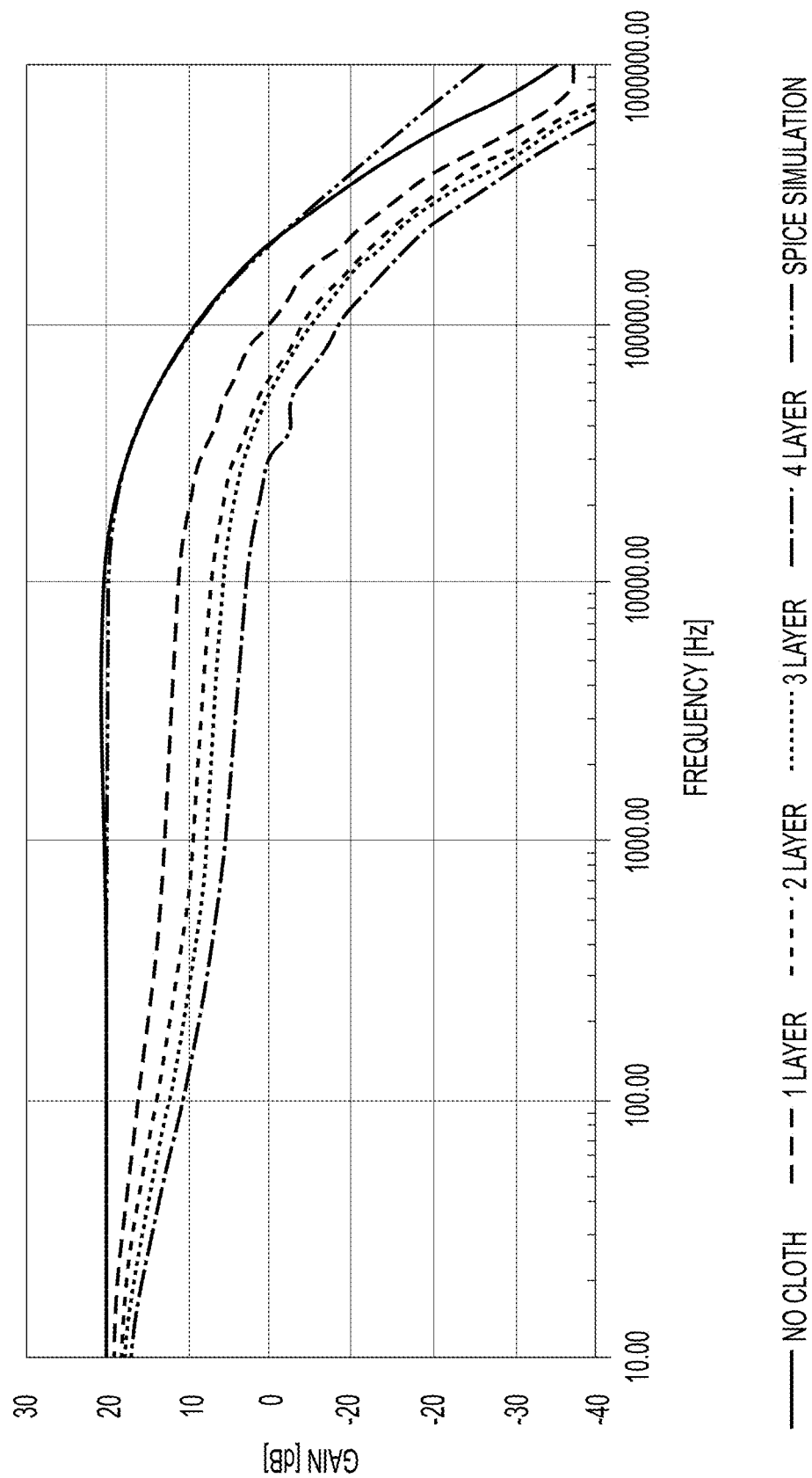
FIGS. 22C and 22D show experimental results of a gain and phase response of the DRL feedback circuit of FIG. 22E compared to simulation using various numbers of 0.58 mm cloth separators.
Figure 22D:
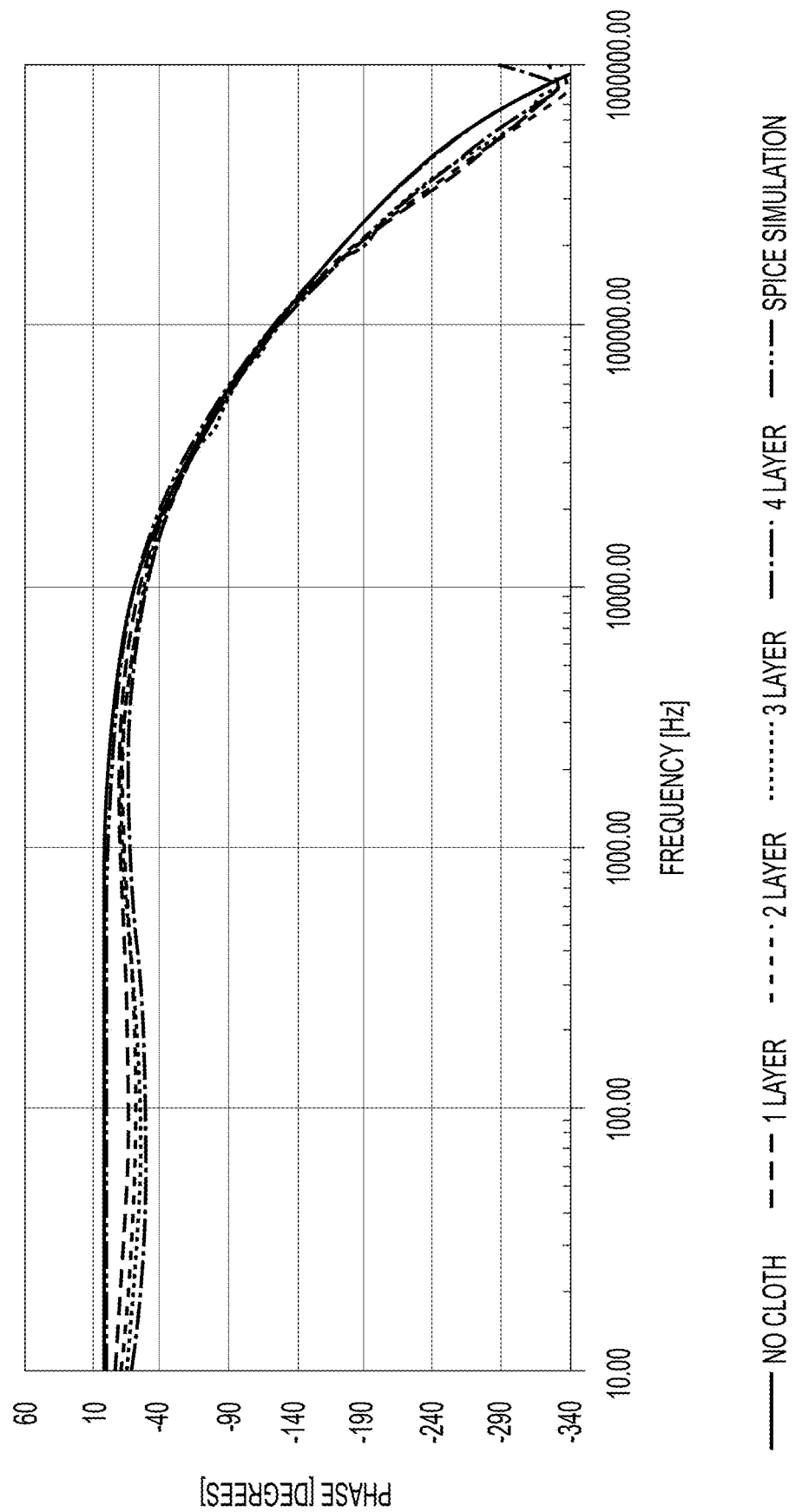
Figure 22E:
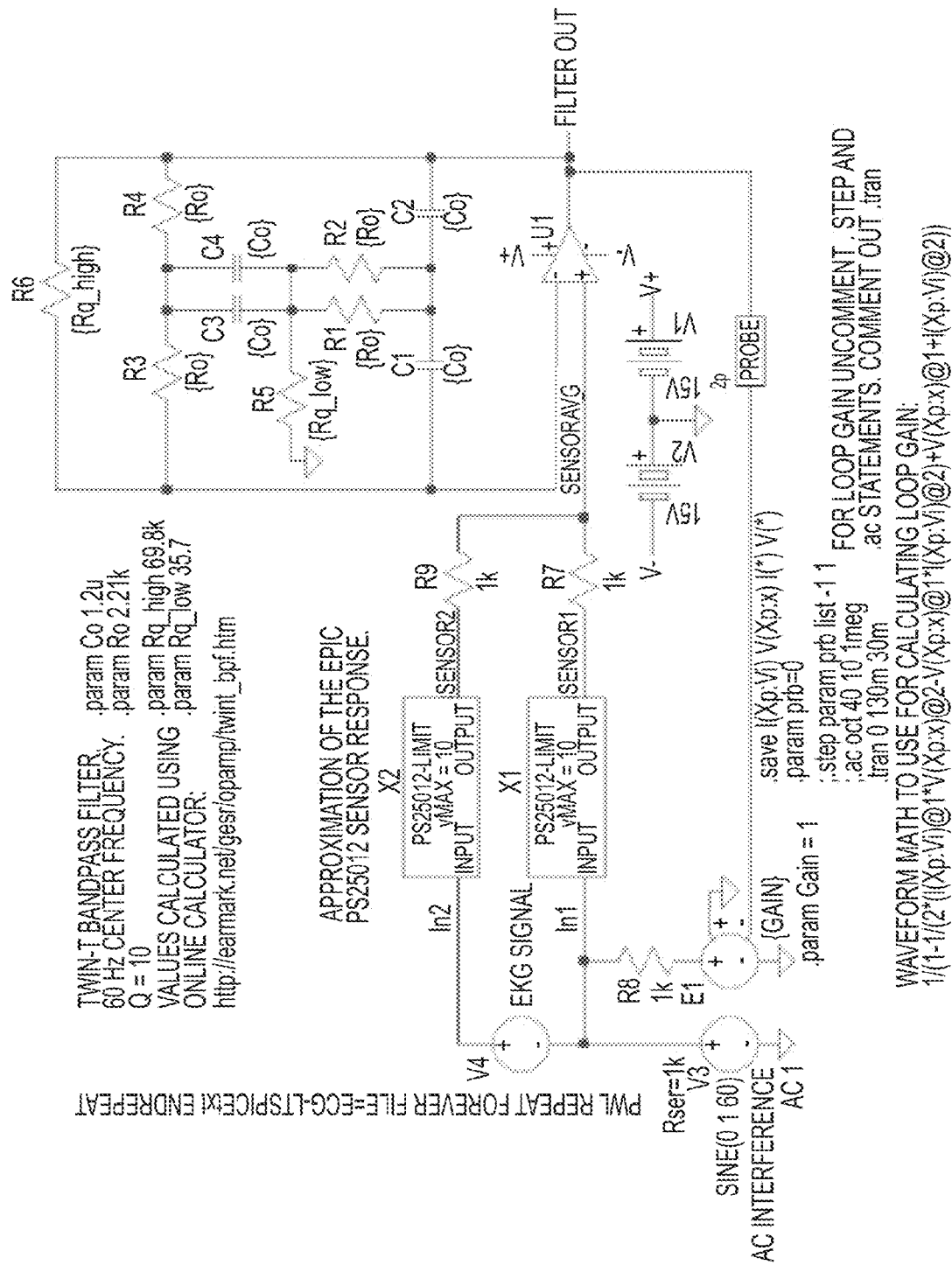
FIG. 22E depicts an example variation of a DRL feedback circuit of a Driven Right Leg sensor of the present technology.

The gain and phase response of the full circuit model of the DRL feedback circuit shown in FIG. 22E was compared to the SPICE ("Simulation Program with Integrated Circuit Emphasis") simulation using various numbers of 0.58 mm cloth separators and the results are shown in FIGS. 22C and 22D, showing satisfactory results with four layers of cloth between the sensor and skin even at 200 kHz. The DRL feedback circuit incorporates a twin-T filter, the bioelectric sensor model, 60 Hz noise source and a simulated ECG signal.

Without being bound to any theory, the EPIC capacitive sensors generally require some ground reference to be able to pick up the body electrical signals without being dominated by noise. Such noise is often dominated by the 50/60 Hz powerline interference. In contact EPIC use, meaning the ECG sensor setup has direct contact with the skin, this issue is less relevant as electrically conductive grounding electrodes can supply the necessary signal reference to the body. However, when trying to use the EPIC sensor in a non-contact setup the missing conductive path to the body introduces challenges. This can be solved by using a DRL feedback to the body, either through a direct conductive or non-contact capacitive electrode. Since the focus of the EPIC technology is on capacitive (non-galvanic) measurements of body electrical signals, it makes most sense to feed back the DRL signal capacitively as well. This allows the integration of DRL electrodes directly on the stethoscope nearby the EPIC sensors with the ability to measure electrical signals through clothing or other obstacles, and without any conductive path to the skin.

The DRL works by feeding back an amplified signal of the sum or in any other suitable combination (i.e. weighted sum, difference, sum of only a subset of sensors, etc.) of two or more EPIC sensor signals. Amplification needs proper tuning to cancel the noise picked up by the EPIC sensors but can be implemented as an automatic algorithm. Also, there can be a number of combinations on which and how many EPIC sensor signals are combined to create a DRL signal for each of the available DRL electrodes. This process can as well be automated.

In certain variations, advantageously, the EPIC and the DLR electrodes required for performing an ECG may be spaced within 5 cm or less of each other. Furthermore, in certain variations, advantageously, the relative disposition of the electrodes provides for increase in spurious signal rejection and higher signal to noise in the signal compared to where the DRL electrodes are disposed further away from each other as they typically are in existing ECG tests.

Bioimpedance-Based Sensor Modules

Bioimpedance-based sensor modules can be used to detect skin potentials. Electrodermal activity (EDA) is a marker of sympathetic network activity. Electrodermal activity is generated by the sweat glands and overlying epidermis and mediated by supraspinal sites that include the orbitofrontal cortex, posterior hypothalamus, dorsal thalamus, and ventrolateral reticular formation. This response, which occurs spontaneously and can be evoked by stimuli such as respiration, cough, loud sounds, startle, mental stress, and electrical stimuli, is referred to as the sympathetic skin response or the peripheral autonomic surface potential. EDA is composed of two components: (1) the phasic component of the skin conductance response (SCR), which is observed after activation of sudomotor fibers, and (2) the skin conductance level (SCL) which corresponds to the baseline of the skin conductance specific to a given subject. The SCR is the component used as a strong marker of the sympathetic network. It ranges from 0.05 to 1.5 Hz. The EDA active recording electrode is placed on the palmar or plantar surface and the indifferent electrode on the volar surface. With low pass filter settings of 0.1-2 Hz and high pass filter setting of 1-5 kHz, the latency in the upper extremity ranges between 1.3 and 1.5 seconds and in the lower extremity between 1.8 and 2.1 seconds.

While ECG and related techniques measure bioelectric signals that originate within a subject, bioimpedance measurements, such as galvanic skin response, interrogate the subject's resistance or response to an applied electromotive force. Measurement of galvanic skin response traditionally was a DC measurement requiring Silver/Silver Chloride electrodes. A general term for DC and AC measurement is electrodermal activity (EDA), and bioimpedance for AC-only measurements. An advantage of AC measurement over DC is that dry electrodes may be used. In certain variations of the present system 10, non-contact electrodes are possible, as only an alternating potential needs to be applied to the body to induce an alternating current in the body.

The problem of electrode impedance is dealt with by employing a four-wire measurement topology that mostly removes the effect of electrode impedance on measurements. Two drive electrodes force a signal through the body and two sense electrodes measure the differential voltage. The impedance is calculated using Ohm's law: Impedance=sense voltage drive current. The capacitors block DC current from flowing. $R_{ACCESSX}$ represent wire & electrode resistances in traditional contact measurements. $R_{LIMIT}$ is a safety current limit, to stay within safety requirements in case of hardware or software failure.

The typical wet electrode bioimpedance analysis application diagram is shown in FIG. 22F.

Figure 22G:
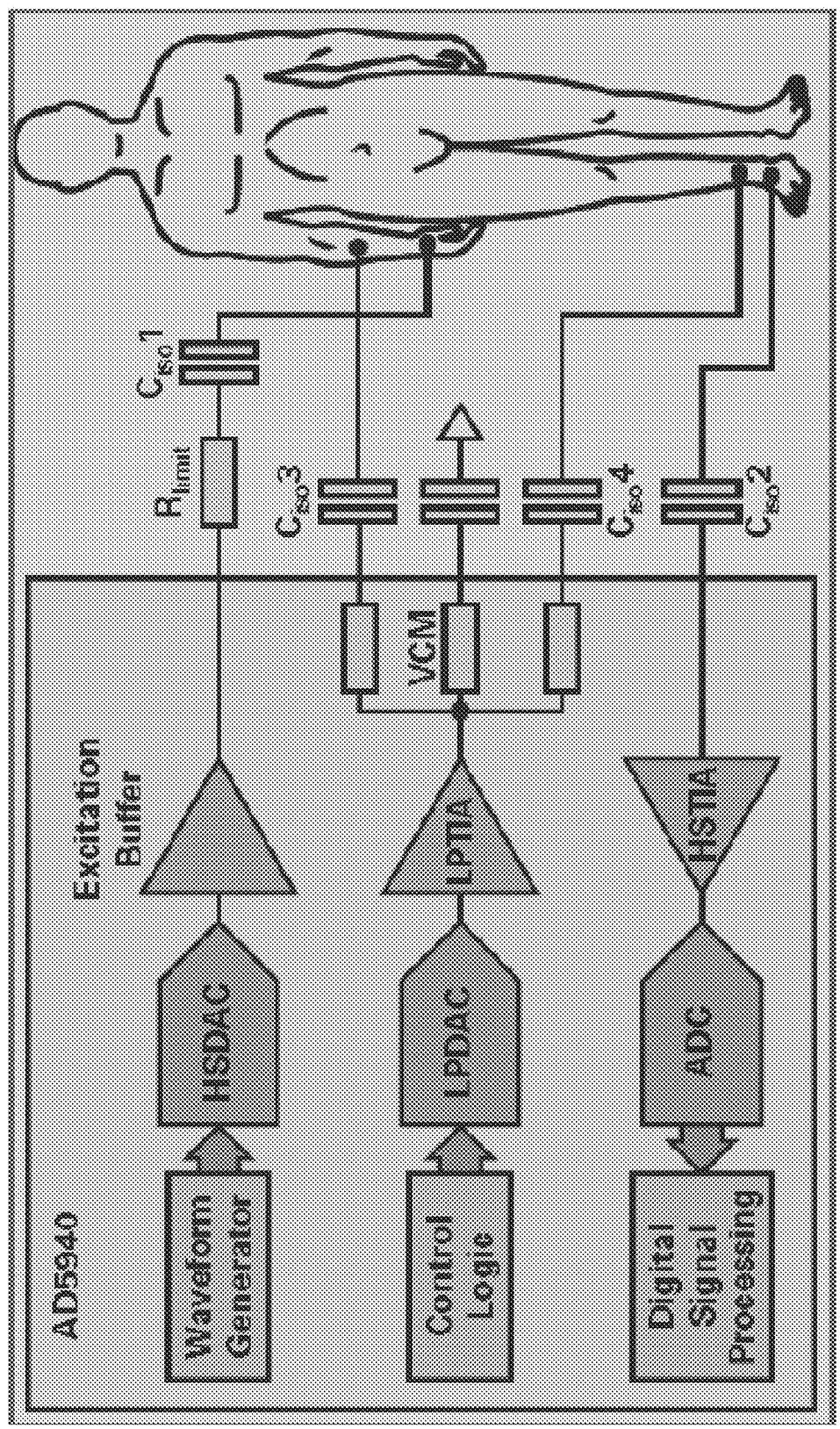
FIG. 22G depicts a system diagram of an example sensor for bioimpedance.

One example sensor for bioimpedance is the AD5940 (Analog Devices, Inc., Norwood, Mass.) (FIG. 22G). The chip can perform AC measurements from sub-Hz up to 200 kHz. However, the application notes for this device do not enable the use of dry, or non-contact electrodes, or, of measurements through clothing.

Figure 22H:
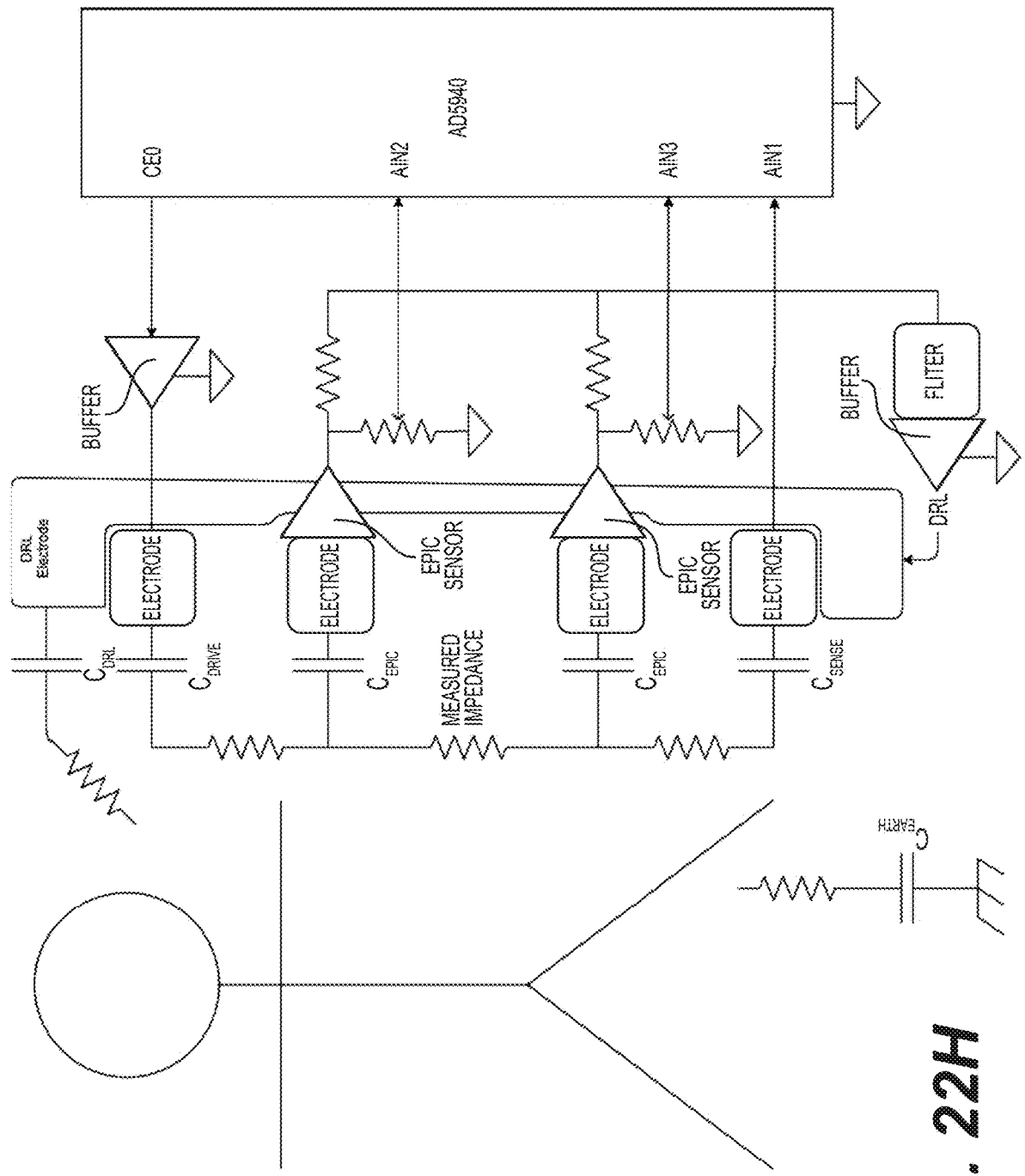
FIG. 22H depicts a circuit diagram of an example Electric Potential Integrated Circuit (EPIC) sensor.

Here we disclose devices, methods and systems for the measurement of electrodermal activity (EDA) and body impedance analysis (BIA) using Electric Potential Integrated Circuit (EPIC) sensors (such as those from Plessey Semiconductors Ltd., Roborough, Plymouth Devon), that allow non-contact, at a distance and through-clothing measurements. Certain EPIC sensors used within present systems and devices may include one or more as described in: U.S. Pat. Nos. 8,923,956; 8,860,401; 8,264,246; 8,264,247; 8,054,061; 7,885,700; the contents of which are herein incorporated by reference. A schematic diagram is shown in FIG. 22H.

In certain variations, there is provided the AD5940 functions as described, with the contact sense electrodes replaced by EPIC sensors. A DRL electrode may also be included, as with ECG, to prevent or minimize the sensors from saturating in a 50/60 Hz environment. Capacitive coupling to the DRL electrode and coupling to earth can affect the measurements: keeping the sense electrodes separated from the DRL electrode will minimize this error source. To couple enough bioimpedance drive current to the body through a small capacitance, the AD5940's output is amplified. The EPIC sensors, with a gain of 10, have their outputs padded down, to prevent overloading the AD5940's inputs. The DRL filter and amplifier is the same one described herein.

In some instances, a non-contact DRL electrode can be used. In other instances, a transconductance amplifier, such as a LM13700 OTA, Texas Instruments, Inc., Dallas, Tex., can be used to mitigate variances in drive electrode capacitance.

Example of Bioimpedance Analysis Using EPIC Sensors

Figure 22I:
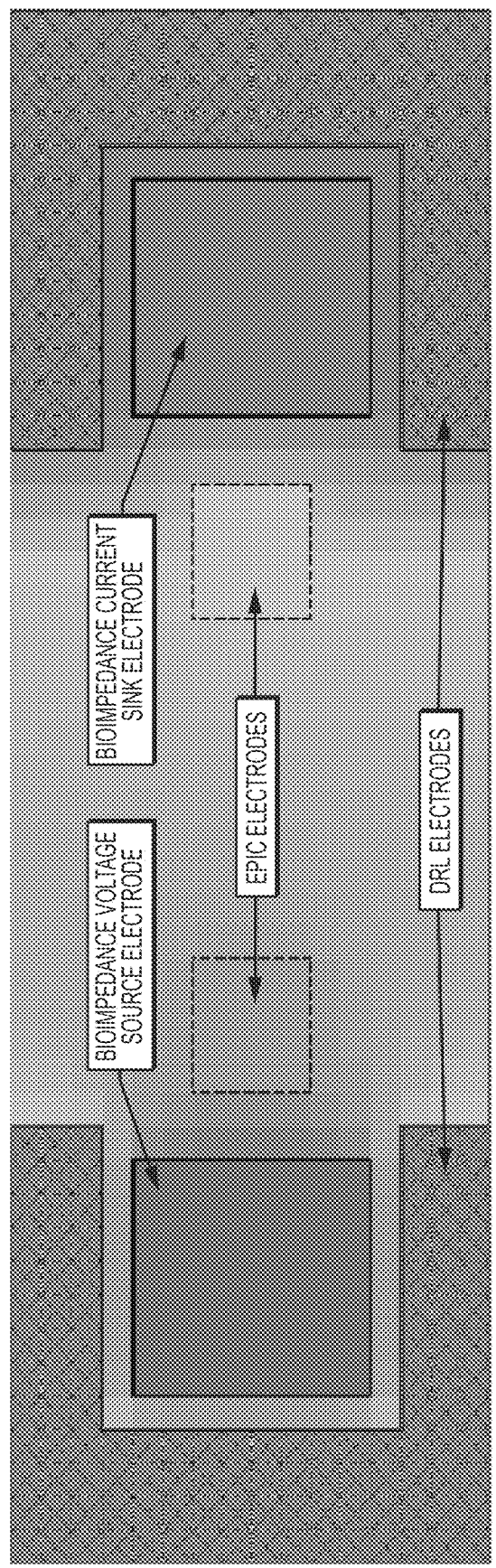
FIGS. 22I and 22J are heat maps of two simulations of EPIC sensors in direct skin contact for incorporation in an example variation of the sensing device.
Figure 22J:
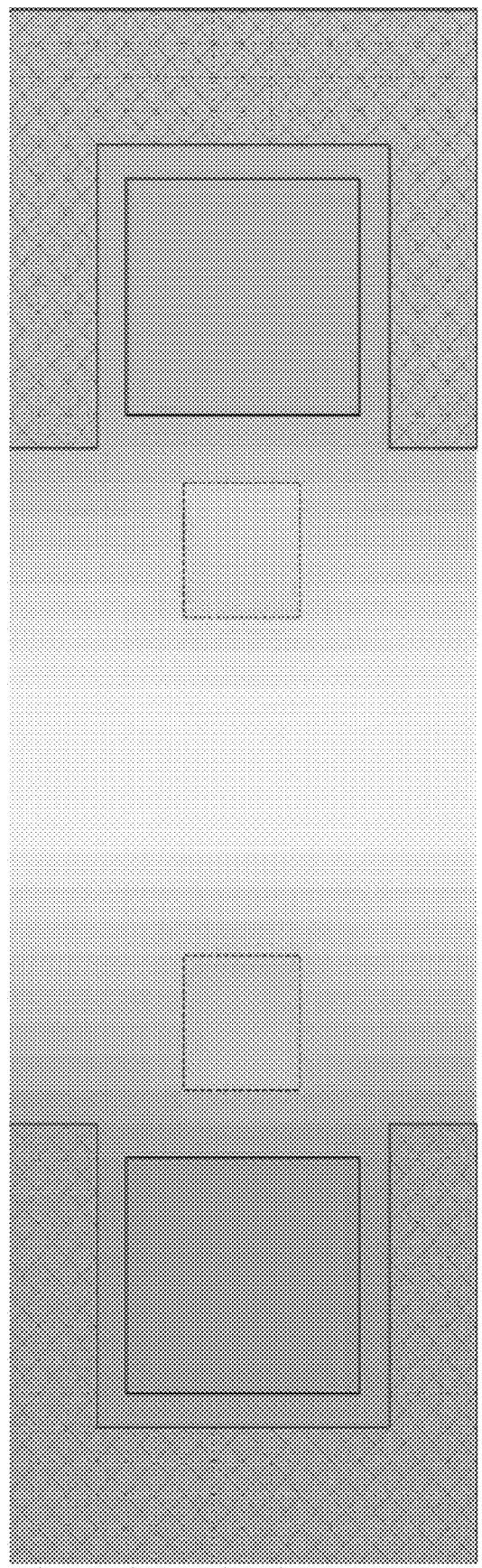

The AD5940's drive electrodes were in direct skin contact. Simulations of the electrodes were run and a heat map display generated. FIGS. 22I and J show heat map results of two simulations. The highest voltage (red) is at the bioimpedance drive electrode. The lowest voltage (green) is zero volts at the bioimpedance current-sensing input electrode. The voltage difference between the EPIC sensors was extracted in the simulation. In these figures, the difference between active and floating DRL electrodes is shown. Grounding the DRL electrodes significantly reduces the sensed voltage. Therefore, for initial experiments, these electrodes were left floating.

Figure 22K:
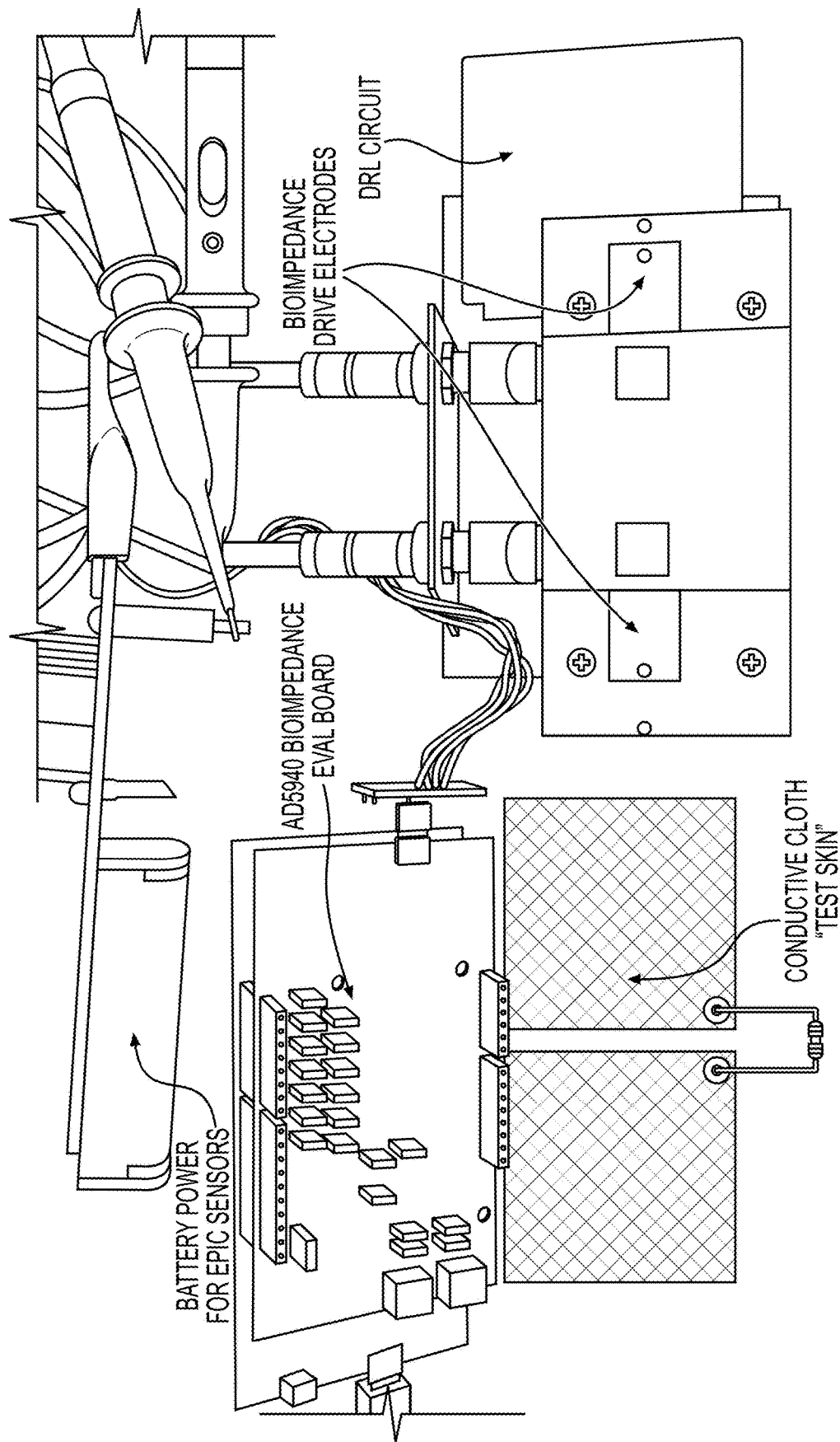
FIG. 22K depicts an experimental set up of an example variation of a sensing device for testing bioimpedance sensors in which a pair of conductive cloth pieces are connected by a resistor to create repeatable "skin" resistance.

FIG. 22K shows the test configuration, consisting of an AD5940 Eval board, a pair of EPIC sensors, a DRL circuit, and a (floating) battery supply for the sensors. Electrodes were fabricated from a 0.8 mm thick PCB with Copper milled out between the electrodes and openings milled for the EPIC sensors. Various test arrangements were created to ascertain system performance. In FIG. 22K, a pair of conductive cloth squares are connected by a resistor to create repeatable "skin" resistance.

Figure 22L:
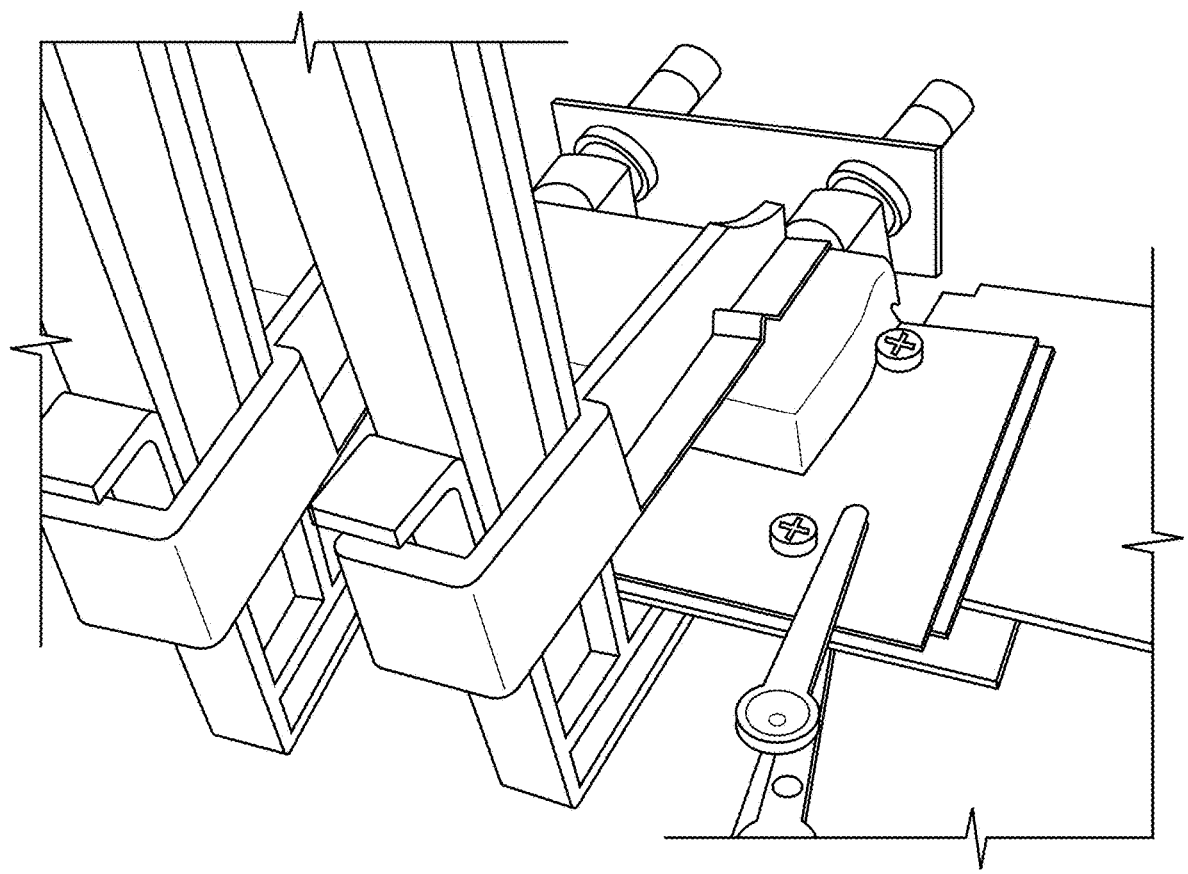
FIGS. 22L and 22M show alternative "skin" surrogate testing configurations".
Figure 22M:
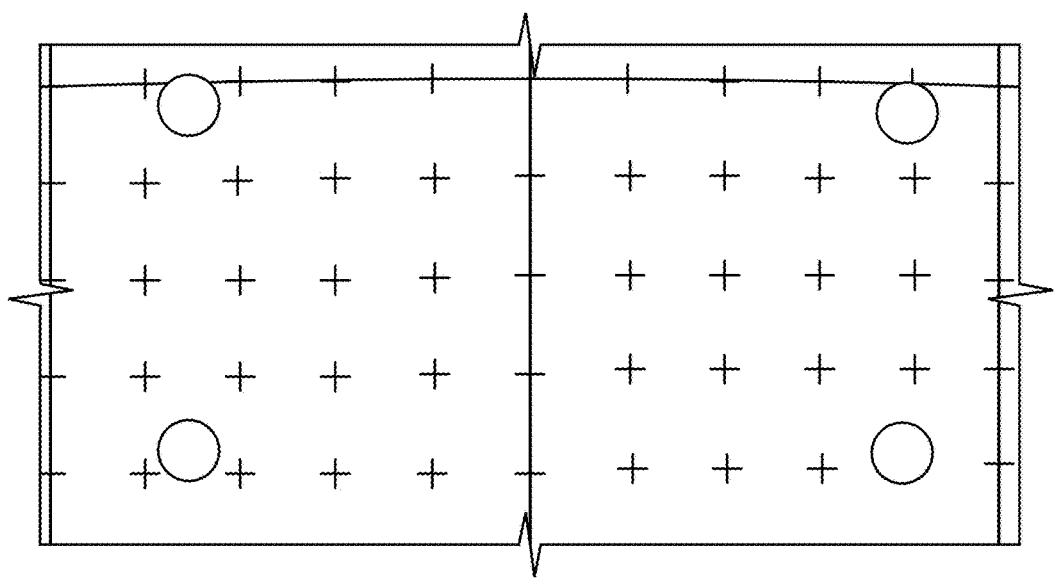

An alternative "skin", shown in FIG. 22L and FIG. 22M, uses conductive paper (Eisco Labs PH0918DFM). The paper is used as a teaching aid for visualizing electric fields: current is sent through the paper and voltages are measured along its surface. Progressive layers of Kapton tape were placed on the paper over the EPIC sensor areas. These layers were used to compare measurements with various spacing to the sensors. FIG. 22L shows the test configuration used for conductive paper and mesh "skins": the skin was clamped firmly against the sensors through compliant foam. The paper was clamped directly to the driven electrodes.

Two Changes were Made to the System as the Result of Early Measurements:

The EPIC sensors were the PS25014A5 model, with a low frequency cutoff of 30 Hz (not a limitation for bioimpedance). The DRL electrodes were connected to the bioimpedance drive electrodes. This increased contact area, improving measurement consistency.

Figure 22N:
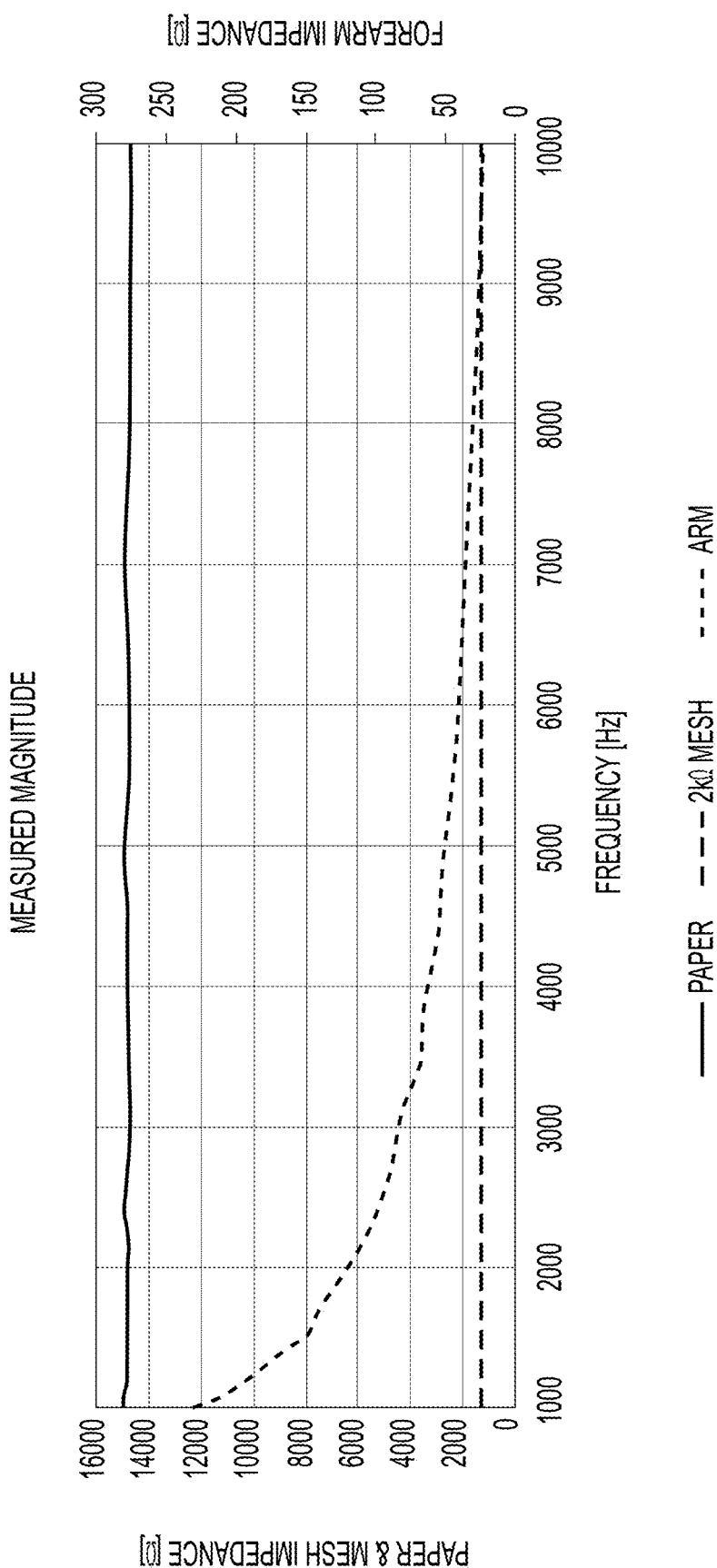
FIG. 22N shows impedance versus frequency scans obtained using two different skin surrogates and an arm and FIG. 22O shows phase versus frequency scans obtained using two different skin surrogates versus and an arm.
Figure 22O:
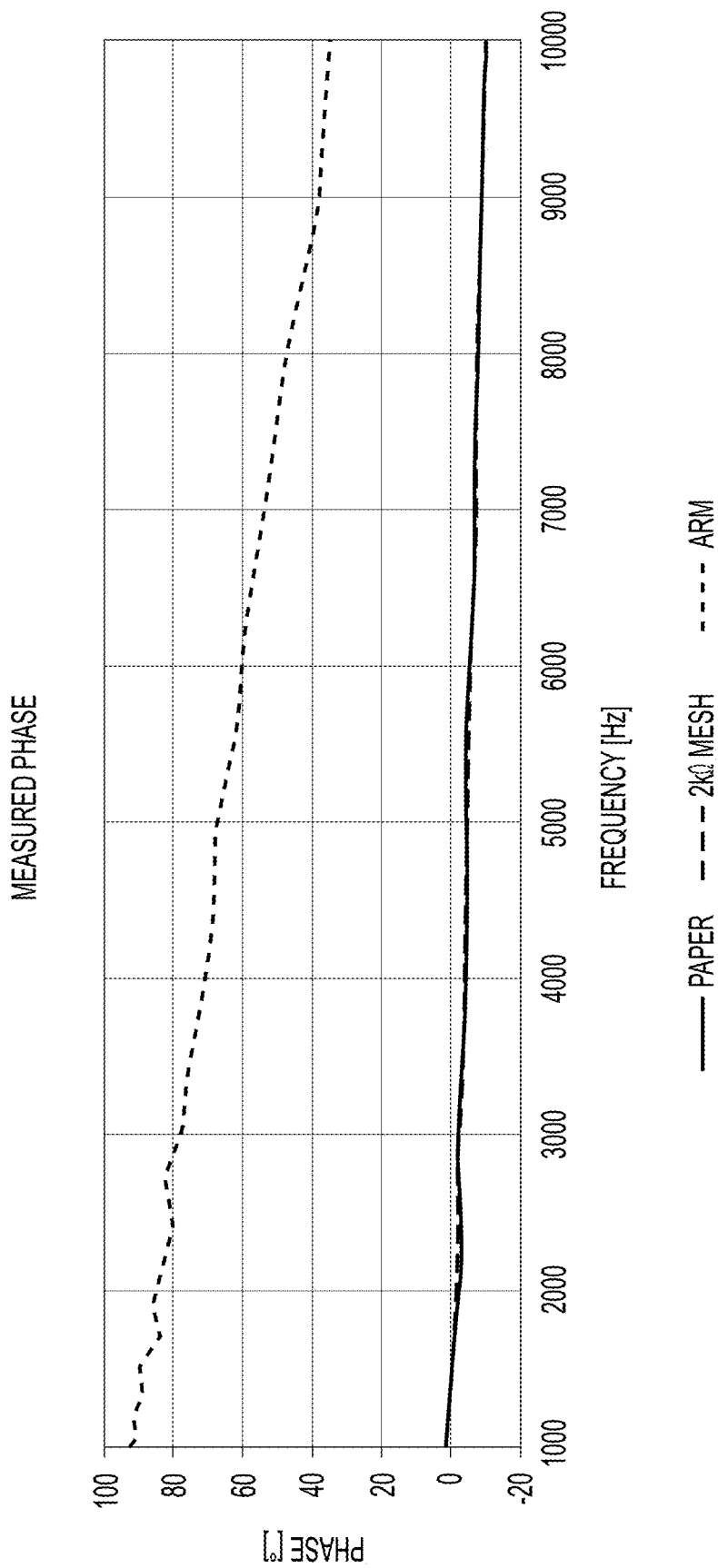

FIGS. 22N and 22O show impedance frequency scans of three "skins":
1. Conductive paper
2. Conductive mesh
3. Forearm The paper has the highest resistance, around 15 kΩ, the mesh at 1340Ω, and the forearm much lower, in the range 220-30Ω.

The phase plot shown in FIG. 22O shows that the real "skin"—the forearm, has a large reactive component. Forearm impedance is lower than expected. This may be attributable to the large areas for the drive electrodes. The measured impedance of the 2 kΩ mesh is low by about 20%. This reflects a lower gain of the EPIC sensors than expected.

Figure 22P:
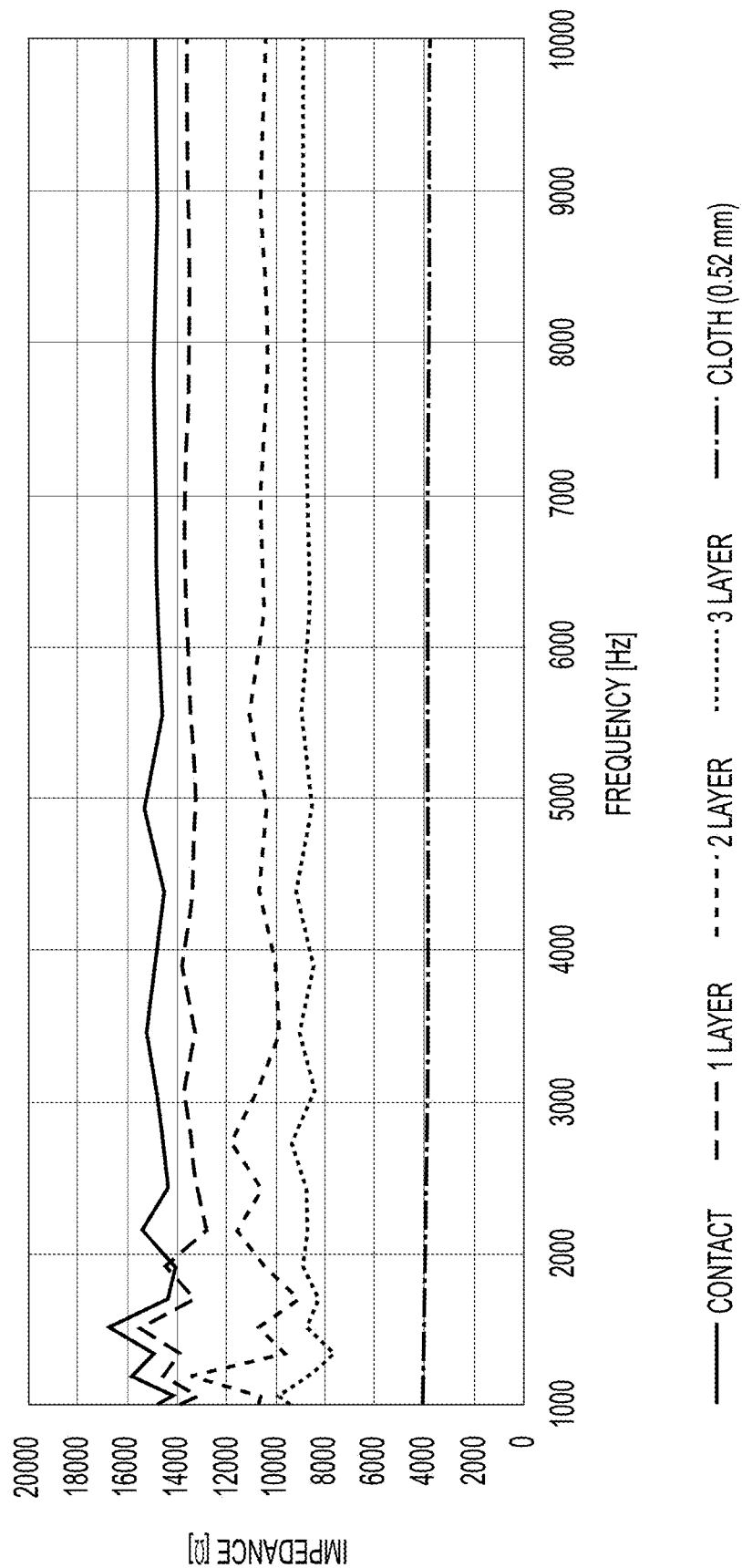
FIG. 22P shows impedance versus frequency response for various layers of conductive paper skin surrogate, direct contact and cloth.

The effects of spacing between the skin and electrodes were tested using conductive paper (these tests were run prior to discovering how low the forearm impedance was). The results are shown in FIG. 22P. The larger the spacing, the lower the apparent impedance. This is the result of the EPIC sensor measuring lower signal levels with increased spacing.

After consistent measurements were achieved with the synthetic "skins", testing with a forearm showed that typical impedances are much lower. Typical body fat bioimpedance measurements are made with widely spaced electrodes, which results in higher impedances. Signal levels are lower with lower impedances, but repeatable measurements with lower levels are to be reasonably expected.

Even without the DRL signal, the AD5940 seemed unperturbed by 60 Hz pickup. Between measurements, the EPIC sensors showed high levels of 60 Hz pickup. When the measurements started, however, 60 Hz noise level dropped dramatically. This may be due to the drive electrodes presenting a low impedance when active. The measurement method used by the AD5940 is also tolerant of 60 Hz interference.

We have developed a software-defined multi-modal sensor fusion and data fusion platform for improved data capture and low power/weak biosignals from diverse sensing modalities modeled after how the brain, five senses, and central and autonomic nervous systems are intertwined. This means using vibroacoustic sensors, electric potential sensors, volatile organic compound e-nose's, heat and light sensors, and cameras in the same ways that humans use their nose, eyes, ears and touch to understand their surroundings intuitively. Our goal was to develop a sensory modular platform, whereby the entire signal chain from electromechanical initiation at cell/tissue level through to mechanoacoustic transduction and vibroacoustic biosignal data (various audible and inaudible sounds from the human body) can be used to assess health. For example, a cough can signal many things by its length, intensity, frequency, etc. We have successfully developed methods for automated recognition of respiratory diseases such as COVID-19, pneumonia, asthma, cystic fibrosis, and chronic obstructive pulmonary disease (COPD). Additionally, vibroacoustic features such as articulation rate, effort, and auditory roughness can give clues to health of an individual, as can the pronunciations of vowel sounds and other speech patterns.

Contextual Sensor Module

Little is known about what happens in real life, how lifestyle and daily context impacts vital signs, how quality of life is impacted by disease and medical conditions and to what degree therapeutic and care recommendations are actually adhered to. Developers have determined that putting health data and care into context of daily life, can in certain variations, add key insights to get richer and personalized interpretation of biosignals, vital signs, and wellbeing. In some variations, the system 100 may further include one or more sensors providing environmental and/or other contextual data (e.g., social determinants of health). This may be used to calibrate and/or better interpret the vibroacoustic data acquired with the vibroacoustic sensor module, or any of the other sensor modules. Such data (e.g., environmental and/or social determinants of health) may, for example, help contextualize data for more accurate machine learning and/or AI data analysis. For example, as shown in FIG. 3B, in some variations, the sensing device 300 may include a contextual sensor module 330. Like the vibroacoustic sensor module 320, the contextual sensor module 330 may be interchangeable and modular, such as for use in a variety of different sensing device form factors including an integrated handheld sensing device as shown in FIG. 3B. The contextual sensor module 330 may be in communication with one or more processors (e.g., in the electronics system 340) such that sensor data from the contextual sensor module 330 may be taken into account when analyzing vibroacoustic data and/or other suitable data.

The contextual sensor module 330 may include one or more suitable sensors such as environmental sensors to measure one or more ambient characteristics and/or one or more characteristics of the sensing device relative to the environment. For example, the contextual sensor module 330 may include an ambient light sensor, an ambient humidity sensor, an ambient pressure sensor, an ambient temperature sensor, an air quality sensor (e.g., detection of volatile organic compounds (VOCs)), altitude sensor (e.g., relative pressure sensor), GPS, and/or other suitable sensor(s) to characterize the environment in which the sensing device is operating. Additionally, or alternatively, the contextual sensor module 330 may include an inertial measurement unit (IMU), individual gyroscope and/or accelerometer, and/or other suitable sensor(s) to characterize the sensing device relative to the environment.

Acoustocardiography (ACG) Sensor Module

In some variations, the system 100 may further include one or more sensor modules for detecting vibrations of the heart as the blood moves through the various chambers, valves, and large vessels, using an acoustic cardiography sensor module. The ACG sensor module can record these vibrations at four locations of the heart and provides a "graph signature." While the opening and closing of the heart valves contributes to the graph, so does the contraction and strength of the heart muscle. As a result, a dynamic picture is presented of the heart in motion. If the heart is efficient and without stress, the graph is smooth and clear. If the heart is inefficient, there are definite patterns associated each type of contributing dysfunction. The ACG is not the same as an ECG, which is a common diagnostic test. The electrocardiograph (ECG) records the electrical impulses as it moves through the nerves of the heart tissue as they appear on the skin. The ECG primarily indicates if the nervous tissue network of the heart is affected by any trauma, damage (for example from a prior heart attack or infection), severe nutritional imbalances, stress from excessive pressure. Only the effect on the nervous system is detected. It will not tell how well the muscle or valves are functioning, etc. In addition, the ECG is primarily used to diagnose a disease. The ACG not only looks at electrical function but also looks at heart muscle function, which serves as a window of the metabolism of the entire nervous system and the muscles. Using the heart allows a "real-time" look at the nerves and muscles working together. As a result of this interface, unique and objective insights into health of the heart and the entire person can better be seen.

Passive Acoustocerebrography (ACG) Sensor Module

In some variations, the system 100 may further include one or more passive acoustocerebrography sensor modules for detecting blood circulation in brain tissue. This blood circulation is influenced by blood circulating in the brain's vascular system. With each heartbeat, blood circulates in the skull, following a recurring pattern according to the oscillation produced. This oscillation's effect, in turn, depends on the brain's size, form, structure and its vascular system. Thus, every heartbeat stimulates minuscule motion in the brain tissue as well as cerebrospinal fluid and therefore produces small changes in intracranial pressure. These changes can be monitored and measured in the skull. The one or more passive acoustocerebrography sensor modules may include passive sensors like accelerometers to identify these signals correctly. Sometimes highly sensitive microphones can be used.

Active Acoustocerebrography (ACG) Sensor Module

In some variations, the system 100 may further include one or more active acoustocerebrography sensor modules. Active ACG sensor modules can be used to detect a multi-frequency ultrasonic signal for classifying adverse changes at the cellular or molecular level. In addition to all of the advantages that passive ACG sensor modules provide, the active ACG sensor module can also conduct a spectral analysis of the acoustic signals received. These spectrum analyses not only display changes in the brain's vascular system, but also those in its cellular and molecular structures. The active ACG sensor module can also be used to perform a Transcranial Doppler test, and optionally in color. These ultrasonic procedures can measure blood flow velocity within the brain's blood vessels. They can diagnose embolisms, stenoses and vascular constrictions, for example, in the aftermath of a subarachnoid hemorrhage.

Ballistocardiography (BCG) Sensor Module

In some variations, the system 100 may further include one or more ballistocardiograph sensor modules (BCG) for detecting ballistic forces generated by the heart. The downward movement of blood through the descending aorta produces an upward recoil, moving the body upward with each heartbeat. As different parts of the aorta expand and contract, the body continues to move downward and upward in a repeating pattern. Ballistocardiography is a technique for producing a graphical representation of repetitive motions of the human body arising from the sudden ejection of blood into the great vessels with each heart beat. It is a vital sign in the 1-20 Hz frequency range which is caused by the mechanical movement of the heart and can be recorded by noninvasive methods from the surface of the body. Main heart malfunctions can be identified by observing and analyzing the BCG signal. BCG can also be monitored using a camera-based system in a non-contact manner. One example of the use of a BCG is a ballistocardiographic scale, which measures the recoil of the person's body who is on the scale. A BCG scale is able to show a person's heart rate as well as their weight.

Electromyography (EMG) Sensor Module

In some variations, the system 100 may further include one or more Electromyography (EMG) sensor modules for detecting electrical activity produced by skeletal muscles. The EMG sensor module may include an electromyograph to produce a record called an electromyogram. An electromyograph detects the electric potential generated by muscle cells when these cells are electrically or neurologically activated. The signals can be analyzed to detect medical abnormalities, activation level, or recruitment order, or to analyze the biomechanics of human or animal movement. EMG can also be used in gesture recognition.

Electrooculography (EOG) Sensor Module

In some variations, the system 100 may further include one or more electrooculography (EOG) sensor modules for measuring the corneo-retinal standing potential that exists between the front and the back of the human eye. The resulting signal is called the electrooculogram. Primary applications are in ophthalmological diagnosis and in recording eye movements. Unlike the electroretinogram, the EOG does not measure response to individual visual stimuli. To measure eye movement, pairs of electrodes are typically placed either above and below the eye or to the left and right of the eye. If the eye moves from center position toward one of the two electrodes, this electrode "sees" the positive side of the retina and the opposite electrode "sees" the negative side of the retina. Consequently, a potential difference occurs between the electrodes. Assuming that the resting potential is constant, the recorded potential is a measure of the eye's position.

Electroolfactography (EOG) Sensor Module

In some variations, the system 100 may further include one or more Electro-olfactography or electroolfactography (EOG) sensor modules for detecting a sense of smell of the subject. The EOG sensor module can detect changing electrical potentials of the olfactory epithelium, in a way similar to how other forms of electrography (such as ECG, EEG, and EMG) measure and record other bioelectric activity. Electro-olfactography is closely related to electroantennography, the electrography of insect antennae olfaction.

Electroencephalography (EEG) Sensor Module

In some variations, the system 100 may further include one or more electroencephalography (EEG) sensor modules for electrophysiological detection of electrical activity of the brain. It is typically noninvasive, with the electrodes placed along the scalp, although invasive electrodes are sometimes used, as in electrocorticography. EEG measures voltage fluctuations resulting from ionic current within the neurons of the brain. Clinically, EEG refers to the recording of the brain's spontaneous electrical activity over a period of time, as recorded from multiple electrodes placed on the scalp. Diagnostic applications generally focus either on event-related potentials or on the spectral content of EEG. The former investigates potential fluctuations time locked to an event, such as 'stimulus onset' or 'button press'. The latter analyses the type of neural oscillations (popularly called "brain waves") that can be observed in EEG signals in the frequency domain. EEG can be used to diagnose epilepsy, which causes abnormalities in EEG readings. It can also used to diagnose sleep disorders, depth of anesthesia, coma, encephalopathies, and brain death. EEG, as well as magnetic resonance imaging (MRI) and computed tomography (CT) can be used to diagnose tumors, stroke and other focal brain disorders. Advantageously, EEG is a mobile technique available and offers millisecond-range temporal resolution which is not possible with CT, PET or MRI. Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are time-locked to more complex processing of stimuli.

Ultra-Wideband (UWB) Sensor Module

In some variations, the system 100 may further include one or more ultra-wideband sensor modules (also known as UWB, ultra-wide band and ultraband). UWB is a radio technology that can use a very low energy level for short-range, high-bandwidth communications over a large portion of the radio spectrum. UWB has traditional applications in non-cooperative radar imaging. Most recent applications target sensor data collection, precision locating and tracking applications. A significant difference between conventional radio transmissions and UWB is that conventional systems transmit information by varying the power level, frequency, and/or phase of a sinusoidal wave. UWB transmissions transmit information by generating radio energy at specific time intervals and occupying a large bandwidth, thus enabling pulse-position or time modulation. The information can also be modulated on UWB signals (pulses) by encoding the polarity of the pulse, its amplitude and/or by using orthogonal pulses. UWB pulses can be sent sporadically at relatively low pulse rates to support time or position modulation, but can also be sent at rates up to the inverse of the UWB pulse bandwidth. Pulse-UWB systems have been demonstrated at channel pulse rates in excess of 1.3 gigapulses per second using a continuous stream of UWB pulses (Continuous Pulse UWB or C-UWB), supporting forward error correction encoded data rates in excess of 675 Mbit/s.

A valuable aspect of UWB technology is the ability for a UWB radio system to determine the "time of flight" of the transmission at various frequencies. This helps overcome multipath propagation, as at least some of the frequencies have a line-of-sight trajectory. With a cooperative symmetric two-way metering technique, distances can be measured to high resolution and accuracy by compensating for local clock drift and stochastic inaccuracy.

Another feature of pulse-based UWB is that the pulses are very short (less than 60 cm for a 500 MHz-wide pulse, and less than 23 cm for a 1.3 GHz-bandwidth pulse)—so most signal reflections do not overlap the original pulse, and there is no multipath fading of narrowband signals. However, there is still multipath propagation and inter-pulse interference to fast-pulse systems, which must be mitigated by coding techniques.

Ultra-wideband is also used in "see-through-the-wall" precision radar-imaging technology, precision locating and tracking (using distance measurements between radios), and precision time-of-arrival-based localization approaches. It is efficient, with a spatial capacity of approximately 1013 bit/s/m$^2$. UWB radar has been proposed as the active sensor component in an Automatic Target Recognition application, designed to detect humans or objects that have fallen onto subway tracks.

Ultra-wideband pulse Doppler radars can also be used to monitor vital signs of the human body, such as heart rate and respiration signals as well as human gait analysis and fall detection. Advantageously, UWB has less power consumption and a high-resolution range profile compared to continuous-wave radar systems. However, its low signal-to-noise ratio has made it vulnerable to errors.

In the USA, ultra-wideband refers to radio technology with a bandwidth exceeding the lesser of 500 MHz or 20% of the arithmetic center frequency, according to the U.S. Federal Communications Commission (FCC). A Feb. 14, 2002 FCC Report and Order authorized the unlicensed use of UWB in the frequency range from 3.1 to 10.6 GHz. The FCC power spectral density emission limit for UWB transmitters is −41.3 dBm/MHz. This limit also applies to unintentional emitters in the UWB band (the "Part 15" limit). However, the emission limit for UWB emitters may be significantly lower (as low as −75 dBm/MHz) in other segments of the spectrum. Deliberations in the International Telecommunication Union Radiocommunication Sector (ITU-R) resulted in a Report and Recommendation on UWB in November 2005. UK regulator Ofcom announced a similar decision on 9 Aug. 2007. More than four dozen devices have been certified under the FCC UWB rules, the vast majority of which are radar, imaging or locating systems.

There has been concern over interference between narrowband and UWB signals that share the same spectrum. Earlier, the only radio technology that used pulses were spark-gap transmitters, which international treaties banned because they interfere with medium-wave receivers. UWB, however, uses lower power. The subject was extensively covered in the proceedings that led to the adoption of the FCC rules in the U.S. and in the meetings relating to UWB of the ITU-R leading to its Report and Recommendations on UWB technology. Commonly used electrical appliances emit impulsive noise (for example, hair dryers) and proponents successfully argued that the noise floor would not be raised excessively by wider deployment of low power wideband transmitters.

Seismocardiography (SCG) Sensor Module

In some variations, the system 100 may further include one or more seismocardiography (SCG) sensor modules for non-invasive measurement of cardiac vibrations transmitted to the chest wall by the heart during its movement. SCG was first introduced around the mid 20th century. Some promising clinical applications were suggested. These include the observation of changes in the SCG signal due to ischemia and the use of SCG in cardiac stress monitoring. The origin of SCG can be traced back to the 19th century when scientists reported observing a heartbeat while standing on a scale. Although SCG in general has not been deployed in the clinical environment, some promising applications have been suggested. For instance, SCG has been proposed to be of value in assessing the timing of different events in the cardiac cycle. Using these events, assessing, for example, myocardial contractility might be possible. SCG has also been proposed to be capable of providing enough information to compute heart rate variability estimates. A more complex application of cardiac cycle timings and SCG waveform amplitudes is the computing of respiratory information from the SCG.

Volatile Organic Compounds (VOC) Sensor Module

In some variations, the system 100 may further include one or more volatile organic compounds (VOC) sensor modules for detecting VOC or semi-VOCs in exhaled breath of the subject. The potential of exhaled breath analysis is huge, with applications in many fields including, but not limited to, the diagnosis and monitoring of disease. Certain VOCs are linked to biological processes in the human body. For instance, dimethylsulfide is exhaled as a result of fetor *hepaticus* and acetone is excreted via the lungs during ketoacidosis in diabetes. Typically, VOC Excretion or Semi-VOC excretion can be measured using plasmon surface resonance, mass spectroscopy, enzymatic based, semiconductor based or imprinted polymer-based detectors.

Vocal Tone Inflection (VTI) Sensor Module

In some variations, the system 100 may further include one or more vocal tone inflection (VTI) sensor modules. VTI analysis can be indicative of an array of mental and physical conditions that make the subject slur words, elongate sounds, or speak in a more nasal tone. They may even make the subject's voice creak or jitter so briefly that it's not detectable to the human ear. Furthermore, vocal tone changes can also be indicative of upper or lower respiratory conditions, as well as cardiovascular conditions. Developers have found that VTI analysis can be used for early diagnosis of certain respiratory conditions from a Covid-19 infection (see Examples 7 and 8).

Capacitive Sensor Module

In some variations, the system 100 may further include one or more capacitive/Non-contact sensor modules. Such sensor modules may include non-contact electrodes. These electrodes were developed since the absence of impedance adaptation substances could make the skin-electrode contact instable over time. This difficulty was addressed by avoiding physical contact with the scalp through non-conductive materials (i.e., a small dielectric between the skin and the electrode itself): despite the extraordinary increase of electrode impedance (>200 MOhm), in this way it will be quantifiable and stable over time.

A particular type of dry electrode, is known as a capacitive or insulated electrode. These electrodes require no ohmic contact with the body since it acts as a simple capacitor placed in series with the skin, so that the signal is capacitively coupled. The received signal can be connected to an operational amplifier and then to standard instrumentation.

The use of a dielectric material in good contact to the skin results in a fairly large coupling capacitance, ranging from 300 pF to several nano-farads. As a result, a system with reduced noise and appropriate frequency response is readily achievable using standard high-impedance FET (field-effect transistor) amplifiers.

While wet and dry electrodes require physical contact with the skin to function, capacitive electrodes can be used without contact, through an insulating layer such as hair, clothing or air. These contactless electrodes have been described generally as simple capacitive electrodes, but in reality there is also a small resistive element, since the insulation also has a non-negligible resistance.

The capacitive sensor modules can be used to measure heart signals, such as heart rate, in subjects via either direct skin contact or through one and two layers of clothing with no dielectric gel and no grounding electrode, and to monitor respiratory rate. High impedance electric potential sensors can also be used to measure breathing and heart signals.

Capacitive Plates Sensor Module

In some variations, the system 100 may further include one or more capacitive plate sensor modules. Surprisingly, Developers discovered that the resistive properties of the human body may also be interrogated using the changes in dielectric properties of the human body that come with difference in hydration, electrolyte, and perspiration levels. In this variation, the sensing device may comprise two parallel capacitive plates which are positionable on either side of the body or body part to be interrogated. A specific time varying potential is applied to the plates, and the instantaneous current required to maintain the specific potential is measured and used as input into the machine learning system to correlate the physiological states to the data. As the dielectric properties of the body or body part changes with resistance, the changes are reflected in the current required to maintain the potential profile. In certain variations, a target bodily condition can be screened using such a capacitive plate and permitting interrogation of the subject standing on the capacitive plate.

Machine Vision Sensor Module

In some variations, the system 100 may further include one or more machine vision sensor modules comprising one or more optical sensors such as cameras for capturing the motion of the subject, or parts of the subject, as they stand or move (e.g. walking, running, playing a sport, balancing etc.). In this manner, physiological states that affect kinesthetic movements such as balance and gait patterns, tremors, swaying or favoring a body part can be detected and correlated with the other data obtained from the other sensors in the apparatus such as center of mass positioning. Machine vision allows skin motion amplification to accurately measure physiological parameters such as blood pressure, heart rate, and respiratory rate. For example, heart/breath rate, heart/breath rate variability, and lengths of heart/breath beats can be estimated from measurements of subtle head motions caused in reaction to blood being pumped into the head, from hemoglobin information via observed skin color, and from periodicities observed in the light reflected from skin close to the arteries or facial regions. Aspects of pulmonary health can be assessed from movement patterns of chest, nostrils and ribs.

A wide range of motion analysis systems allow movement to be captured in a variety of settings, which can broadly be categorized into direct (devices affixed to the body, e.g. accelerometry) and indirect (vision-based, e.g. video or optoelectronic) techniques. Direct methods allow kinematic information to be captured in diverse environments. For example, inertial sensors have been used as tools to provide insight into the execution of various movements (walking gait, discus, dressage and swimming). Sensor drift, which influences the accuracy of inertial sensor data, can be reduced during processing; however, this is yet to be fully resolved and capture periods remain limited. Additionally, it has been recognized that motion analysis systems for biomechanical applications should fulfil the following criteria: they should be capable of collecting accurate kinematic information, ideally in a timely manner, without encumbering the performer or influencing their natural movement. As such, indirect techniques can be distinguished as more appropriate in many settings compared with direct methods, as data are captured remotely from the participant imparting minimal interference to their movement. Indirect methods were also the only possible approach for biomechanical analyses previously conducted during sports competition. Over the past few decades, the indirect, vision-based methods available to biomechanists have dramatically progressed towards more accurate, automated systems. However, there is yet to be a tool developed which entirely satisfies the aforementioned important attributes of motion analysis systems. Thus, these analyses may be used in coaching and physical therapy in dancing, running, tennis, golf, archery, shooting biomechanics and other sporting and physical activities. Other uses include ergonomic training for occupations that subject persons to the dangers of repetitive stress disorders and other physical stressors related to motion and posture. The data can also be used in the design of furniture, self-training, tools, and equipment design.

The machine vision module may include one or more digital camera sensors for imaging one or more of pupil dilation, scleral erythrema, changes in skin color, flushing, and/or erratic movements of a subject, for example. Other optical sensors may be used that operate with coherent light, or use a time of flight operation. In certain variants, the machine vision module comprises a 3D camera such Astra Embedded S by Orrbec.

Thermal Sensor Module

In some variations, the system 100 may further include one or more thermal sensor modules including an infrared sensor, a thermometer, or the like. The thermal sensor module may be incorporated with the sensing device or be separate thereto. The thermal sensor may be used to perform temperature measurements of one or more of a lacrimal lake and/or an exterior of tear ducts of the subject. In some variations, the thermal sensor module may comprise a thermopile on a gimbal, such as but not limited to a thermopile comprising an integrated infrared thermometer, 3V, single sensor (not array), gradient compensated, medical +−0.2 to +−0.3 degree kelvin/Centigrade, 5 degree viewing angle (Field of view—FOV)

Strain Gage Sensor Module

In some variations, the system may comprise strain gauge sensors that may be used to measure the subject's weight. In other variations these sensors may be used to acquire seismocardiograms or ballistocardiograms. These sensors, without limitations, may be resistive or piezo-electric strain gauges.

Sensor Module Combinations

Any combination of the abovementioned sensor modules can be used in variants of the present system 100. The sensor module combinations may be housed within a single device or multiple devices. A relative positioning of the sensor module combinations is selected to ensure that data is captured from the subject along the most appropriate plane. In certain variants, two sensor modules are positioned orthogonally to one another to capture data from the subject along different planes. For example, the sensor module combination may include: the capacitive plate sensor module positioned substantially horizontally and configured for the subject to stand on, and a vibroacoustic sensor module positioned substantially and configured to capture vibroacoustic signals from the subject.

Sensor Data

In typical applications, each modular system described above implemented individually would require the attachment of "markers" or "beacons" to the subject to allow for accurate signal chain tracking and surface motion amplification. By using sensor fusion, the current technology provides for methods to track limb and body motion without the need to attach a separate displacement sensor or beacon to the subject.

In certain variations, the sensor modules used with the system 100 may each capture data as catenated raw amplitude sequences or as combined short-time Fourier transform spectra. In certain variations, the data from the sensor modules is captured from the subject in less than 15 seconds per subject, and preferably in less than 10 seconds per subject.

1.d. Electronics System

In some variations, the sensing device may further include an electronics system. In the variation illustrated in FIG. 3B, the sensing device 300 includes the electronics system 340 including various electronics components for supporting operation of the sensing device 300. In the variation illustrated in FIG. 4B, the sensing device 400 includes the electronics system 440 including various electronics components for supporting operation of the sensing device 400. For example, at least a portion of the electronics system 340, 440 may include a circuit board arranged in the housing 310, 410 of the vibrometer sensing device 300, 400 in a modular fashion. The electronics system 340, 440 may be configured to perform signal conditioning, data analysis, power management, communication, and/or other suitable functionalities of the device. The electronics system 340, 440 may be in communication with other components of the sensing device such as the vibroacoustic sensor module 320, 420 contextual sensor module 330, 430, power source 342, 442 (e.g., battery), and/or display 330. Accordingly, the electronics system 340, 440 may, in some variations, function as a microcontroller unit module for the sensing device 300, 400.

Figure 23:
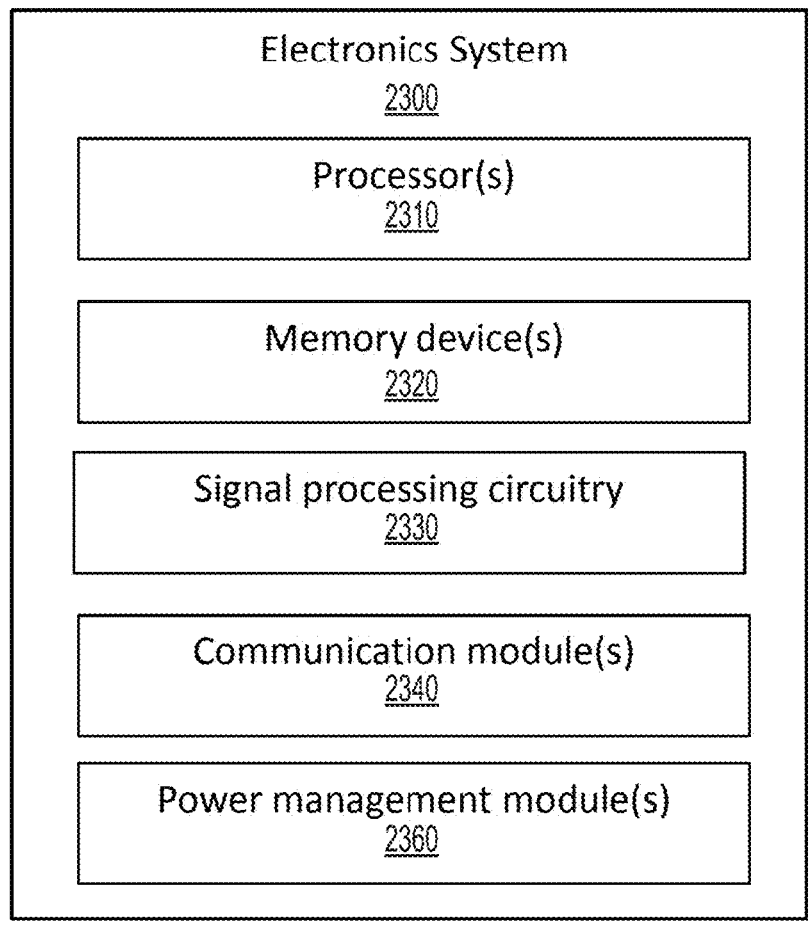
FIG. 23 is a schematic illustration of an example variation of an electronics system in a sensing device.

In some variations as shown in FIG. 23, an electronics system 2300 of a sensing device may include at least one processor 2310, at least one memory device 2320, suitable signal processing circuitry 2330, at least one communication module 2340, and/or at least one power management module 2360. One or more of these components or modules may be arranged one or more electronic circuit boards (e.g., PCB) which in turn may be mounted within a housing of the sensing device. In some variations, the electronics system may also include a microphone and/or speaker for enabling further functionality such as voice or data recording (e.g., permitting recitation of medical notes for an electronic health record, etc.).

The processor 2310 (e.g., CPU) and/or memory device 2320 (which can include one or more computer-readable storage mediums) may cooperate to provide a controller for operating the system. For example, the processor 2310 may be configured to set and/or adjust sampling frequency for any of the various sensors in the vibroacoustic sensor module 320, 420 and/or the contextual sensor module 330, 430. As another example, the processor 2310 may receive sensor data (e.g., before and/or or after sensor signal conditions) and the sensor data may be stored in one or more memory devices 2320. In some variations, some or all of the data stored on the memory device 2320 may be encrypted using a suitable encryption protocol (e.g., for HIPAA-compliant security). In some variations, the processor 2310 and memory device 2320 may be implemented on a single chip, while in other variations they may be implemented on separate chips.

The communication module 2340 may be configured to communicate sensor data, analysis data, and/or other information to an external computing device. Additionally, or alternatively, the communication module 2340 may communicate with external sources for microcontroller programming and software updates. The external computing device may be, for example, a mobile computing device (e.g., mobile telephone, tablet, smart watch), laptop, desktop, medical equipment, or other suitable computing device. The external computing device may be executing an application for presenting sensor data (and/or the results of analysis thereof) through a user interface to a user.

Additionally, or alternatively, the communication module 2340 may be configured to communicate data to one or more networked devices, such as a hub paired with the system 100, a server, a cloud network, etc. In some variations, the communication module 2340 may be configured to communicate information in an encrypted manner. While in some variations the communication module 2340 may be separate from the processor(s) as a separate device, in variations at least a portion of the communication module may be integrated with the processor 2340 (e.g., the processor may include encryption hardware, such as advanced encryption standard (AES) hardware accelerator (e.g., 128/256-bit key) or HASH (e.g., SHA-256)). Additional aspects of the communication scheme are described in further detail below with respect to the signal processing system.

The communication module 2340 may communicate via a wired connection (e.g., including a physical connection such as a cable with a suitable connection interface such as USB, mini-USB, etc.) and/or a wireless network (e.g., through NFC, Bluetooth, WiFi, RFID, or any type of digital network that is not connected by cables). For example, devices may directly communicate with each other in pairwise connection (1:1 relationship), or in a hub-spoke or broadcasting connection ("one to many" or 1:m relationship). As another example, the devices may communicate with each other through mesh networking connections (e.g., "many to many", or m:m relationships), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks (e.g., 3G, 4G, 5G) and/or use a mix of cellular, WiFi, and satellite communication.

In some variations, the communication module 2340 (e.g., used as input and function manipulation, and/or tactile feedback) may include multiple data communication streams or channels to help ensure broad spectrum data transfer (e.g., Opus 20 kHz with minimal delay codec). Such multiple data communication streams are an improvement over typical wireless data transmission codecs. For example, most wireless data transmission codecs (e.g., G.711) use a bandpass filter to only encode the optimal range of human speech, 300 Hz to 3,400 Hz (this is commonly referred to as a narrowband codec). As another example, some wireless data transmission codecs (e.g., G.722) encodes the range from 300 Hz to 7,000 Hz (this is commonly referred to as a wideband codec). However, most of the energy is concentrated below 1,000 Hz and there is virtually no audible sound above 5,000 Hz, while there is a measurable amount of energy above the 3,400 Hz cutoff of most codecs. The data throughput requirements for both G.711 and G.722 are the same because the modulation used in G.722 is a modified version of the PCM called Adaptive Differential Pulse Code Modulation (ADPCM). When this kind of complexity is added to a codec and process power remains constant, this will add latency. As such, G.711 will introduce latency well below just one millisecond but G.722 could introduce tens of milliseconds of delay—which is an unacceptably long delay in vibroacoustics.

The power management module 2360 may be configured to manage power from one or more power sources and distribute power to the processor, communication module, sensors, and/or any other electrical components as appropriate. For example, the power source may include one or more batteries (e.g., lithium ion battery) arranged in the housing of the sensing device as described above. In some variations, the power source may be rechargeable such as through wireless charging methods (e.g., inductive charging, RF coupling, etc.) or by harnessing kinetic and/or thermal energy such as that generated through motion (e.g., when the user walks while wearing the garment, including harvesting thermal energy from the body or by using energy gathering, amplifying, and storing cells that collect light and convert it to electrical signals, and/or cells that convert temperature or temperature gradients directly to electricity). In some variations, the power management module 2360 may be connected to the power source through a suitable charge controller.

In some variations, the power management module 2300 may include electronic components to convert the power to predetermined voltage outputs suitable for the other components (e.g., processor and/or memory devices, signal processing system, etc.) in the sensing device. For example, the power management module 2300 may include buck-boost converters to output 3.3 V and 5 V, and an on-board universal serial bus (e.g., USB-C) that can be used to charge the module and/or power source with an external charger (e.g., mobile charger, power outlet, etc.).

1.d. Signal Processing System

Various analog and digital processes may condition sensor data for extracting useful signal from noise and communicate suitable data to one or more external host devices (e.g., computing device such as mobile device, one or more storage devices, medical equipment, etc.). At least a portion of the signal processing chain may occur on-board a circuit board in one or more sensor modules (e.g., flexible or rigid circuit board in the vibroacoustic sensor module, the contextual sensor module, and/or any other sensor module). Additionally or alternatively, at least a portion of the signal processing system may occur outside of the sensor modules (e.g., electronics system 340, 440 or microcontroller unit module).

In some variations, a signal processing chain for handling data, such as the vibroacoustic sensor data, ECG data, the contextual data, thermal data, optical data, etc. may be configured to provide an output signal with low noise (high signal-to-noise ratio (SNR), provide sufficient amplification to allow proper digitization of the analog signal, and function in a manner that keeps the overall signal fidelity sufficiently high. The signal processing chain may also be configured to (i) overcome signal attenuation and loss of strength of a signal as it propagates over a medium or a plurality of media, and/or (ii) to move digitized data sufficiently quickly through the various components of the sensing device to as to avoid significant signal and/or data loss. In some variations, the signal processing chain may include a programmable gain stage to adjust gain in real-time during operation of the sensing device in order to optimize signal range for analog-to-digital converters. The frequency and bandwidth requirements of the signal processing chain may vary depending specific applications, but in some variations the signal processing chain may have a sufficient bandwidth to sample frequencies up to about 160 kHz or up to about 320 kHz, and have a low frequency response of about 0.1 Hz or lower.

High-precision signal control may be important in biofield and other vibroacoustic active and passive sensing to minimize signal and/or data loss. However, the difficulty to obtain model parameters is one of the main obstacles to obtain high-precision tracking control of biofield signals using a model-dependent method. The vibroacoustic system with uncertain parameters can defend against signal and/or data loss by having high precision of the system output information. In some variations, an adaptive output feedback control scheme may be implemented with an inline servo system with uncertain parameters and unmeasurable states instantiated with controller and parameter adaptation algorithms to guarantee that the biofield signal tracking error is uniformly bounded. This method may be combined with a traditional proportional-integral-derivative (PID) control method with optimal parameters (e.g., obtained using a genetic algorithm), a sliding mode control based on exponential reaching law, and/or adaptive control methods and adaptive backstepping sliding mode control, to achieve higher tracking accuracy. The vibroacoustic system also may have better anti-interference ability with respect to signal load change.

Vibroacoustic signal control, which may be termed active vibro-acoustic control, can be achieved in some variations with multiple servo motors, actuators and sensors and fully-coupled feedforward or feedback controllers. For example, in some variations, feedback may be achieved using multiple miniature cross-axis inertial sensors (e.g., accelerometers) together with either collocated force actuators or piezoceramic actuators placed under each sensor. Collocated actuator/sensor pairs and decentralized (local) feedback may be optimized over the bandwidth of interest to ensure stability of multiple local feedback loops. For example, the control system may include an array of actuator/sensor pairs (e.g., n×n array of such actuator/sensor pairs, such as 4×4 or greater), which may be connected together with $n^2$ local feedback control loops. Using force actuators, significant frequency-averaged reductions up to 1 kHz in both the kinetic energy (e.g., 20-100 dB) and transmitted sound power (e.g., 10-60 dB) can be obtained with an appropriate feedback gain in each loop.

Figure 24:
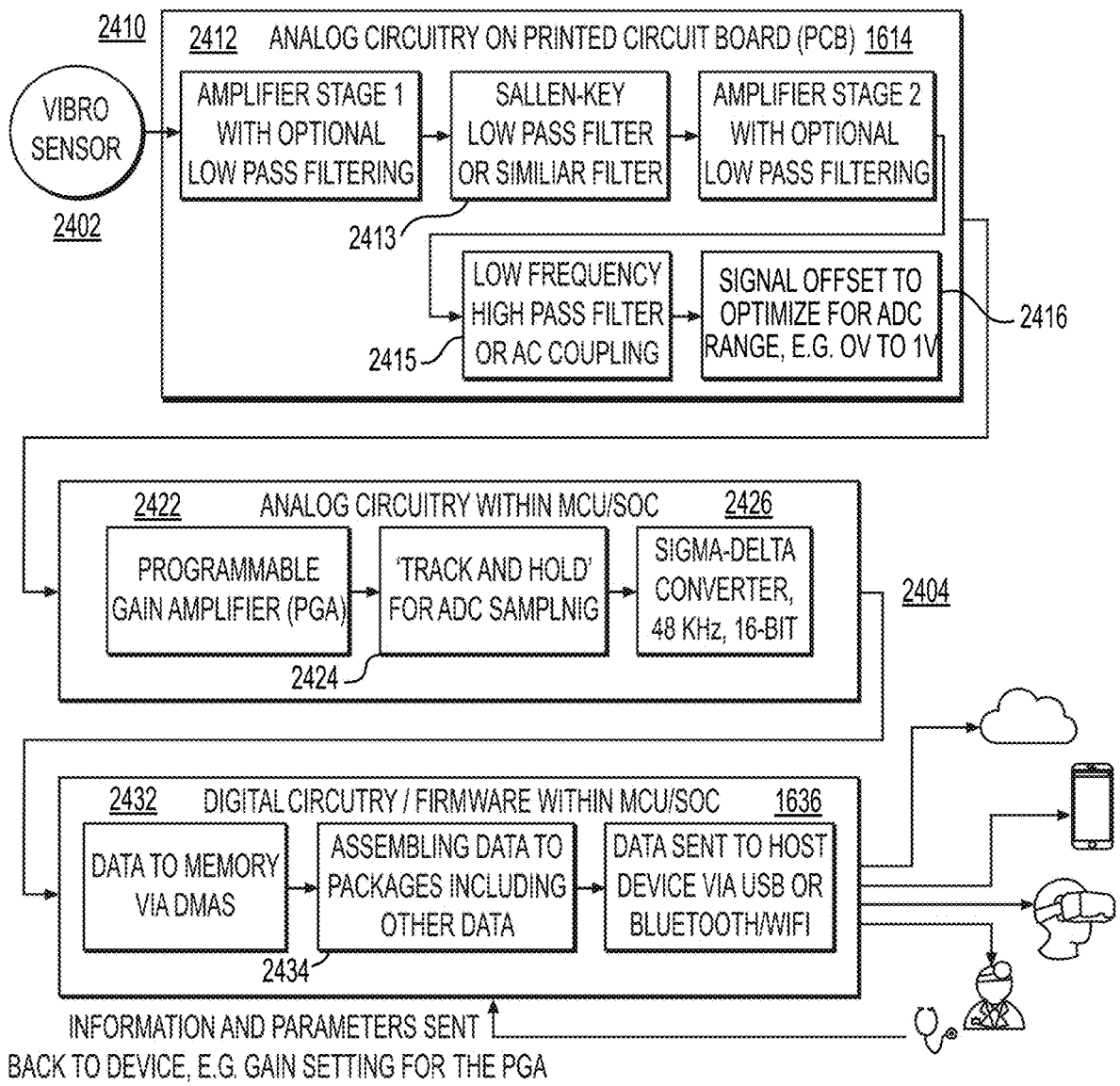
FIG. 24 is a schematic illustration of an example variation of a signal processing chain for conditioning vibroacoustic signals from a sensing device.

FIG. 24 depicts an exemplary signal processing chain for manipulating vibroacoustic sensor data from one or more sensors 2402 in the vibroacoustic sensor module. As shown in FIG. 24, a first set 2410 of analog signal processing steps may be performed by analog circuitry on one or more printed circuit boards (PCB), a second set 2420 of analog signal processing steps may be performed by analog circuitry within a microcontroller unit module, and a third set 2430 of digital signal processing steps may be performed by digital circuitry within the microcontroller unit module. However, it should be understood that these steps may be performed by analog and/or digital components located in any suitable location on or in the sensing device (e.g., electronics system).

The analog portion of the signal chain 2410, 2420 may be optimized for low noise and high SNR signal acquisition of vibroacoustic sensor signals. In addition to low noise components, the PCB itself may be designed and optimized for low noise operation. For example, the PCB may include multiple layers (e.g., 4 layers), including an entire layer dedicated as a ground plane, preventing ground loops, offering low resistance ground and acting as a shield between signal lines on the remaining layers. In some variations, as further described below, the signal chain may include low pass filtering of at least second to fourth order to help prevent aliasing.

The raw signals from the sensor 2402 may, in some variations, typically range from 100 V to 1 mV, but can be up to 10 mV for high SNR sensors in the sensing device. A first stage amplifier 2412 is of particular low noise input optimization and may have a gain of between about 50 and about 200, depending on the specific sensor. The first stage 2412 may also include a first order low pass filter with cutoff frequency at about 15 kHz-20 kHz. The signal may then be fed to an active filter stage 2413 of first order or second order with cutoff frequency at about 15 kHz-20 kHz. In some variations, this active filter stage may be a second order filter realized with a Sallen-Key Topology. The signal from the first stage may be fed to a second stage amplifier 2414, which may, in some variations, have a gain of between about 1 and about 10-100 with another low pass filter with cutoff at about 0.01 Hz to about 120 kHz (e.g., from about 0.01 Hz to at least about 50 kHz, from about 0.01 Hz to at least about 60 kHz, from about 0.01 Hz to at least about 70 kHz, from about 0.01 Hz to at least about 80 kHz, from about 0.01 Hz to at least about 90 kHz, from about 0.01 Hz to at least about 100 kHz, from about 0.01 Hz to at least about 110 kHz, from about 0.01 Hz to at least about 120 kHz, from about 0.01 Hz to at least about 130 kHz, from about 0.01 Hz to at least about 140 kHz, from about 0.01 Hz to at least about 150 kHz, from about 0.01 Hz to at least about 160 kHz, from about 0.01 Hz to more than about 160 kHz). In some variations, the signal may additionally be fed through another low frequency, high pass filter or AC coupling (1615) with cutoff at about 0.01 Hz.

The above-described filters (in 2412, 2413, 2414, 2415) may combine to form a second to fourth order filter with an overall cutoff frequency of between about 10 kHz and about 20 kHz, which serves as an antialiasing filter for the Sigma-Delta ADC downstream in the signal processing chain. At 20 kHz, the attenuation of the second order filter is about −15 dB, which can easily be compensated for in the digital domain. In some variations, the internal ADC sampling rate is about 3 MHz, so sufficient attenuation is needed at the Nyquist frequency of 1.5 MHz. The second order filter achieves greater than −100 dB at this frequency.

The signal from the second stage amplifier and low pass filter (2414) may be raised by an offset voltage (2416) between about 0.5 V and about 5 V in certain variations. In certain variations, the offset voltage may be between 0.5 V and about 2 V, or about 1 V and about 2 V. The offset may depend on the actual configured ADC range (e.g., the offset may be about 0.5 V at an ADC range of 0 V to 1 V). This offset may, for example, accommodate an ADC that only supports positive voltages for conversion. This stage also may incorporate an AC coupling capacitor with a cutoff frequency of about 0.01 Hz to 0.1 Hz (e.g., about 0.05 Hz), which may facilitate low frequency response and/or blocking DC offsets.

Figure 25A:
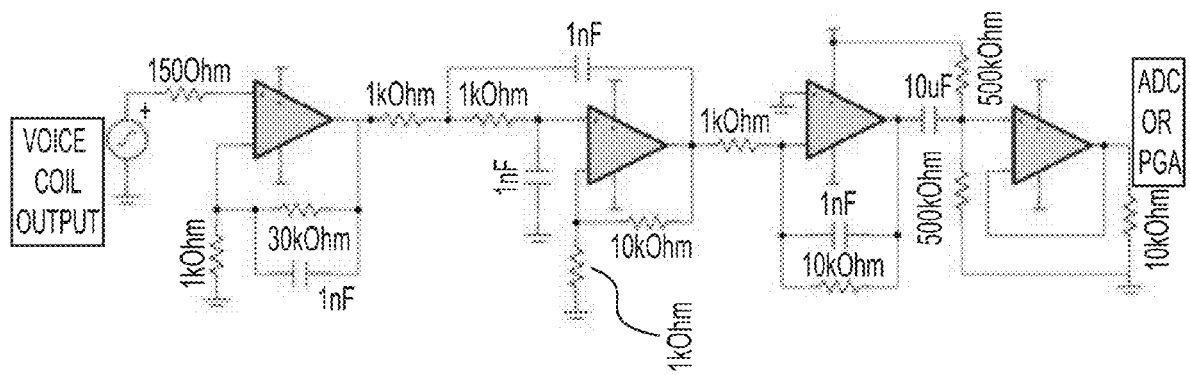
FIG. 25A illustrates an example signal processing circuitry in an analog portion of the signal processing chain of FIG. 24.
Figure 25B:
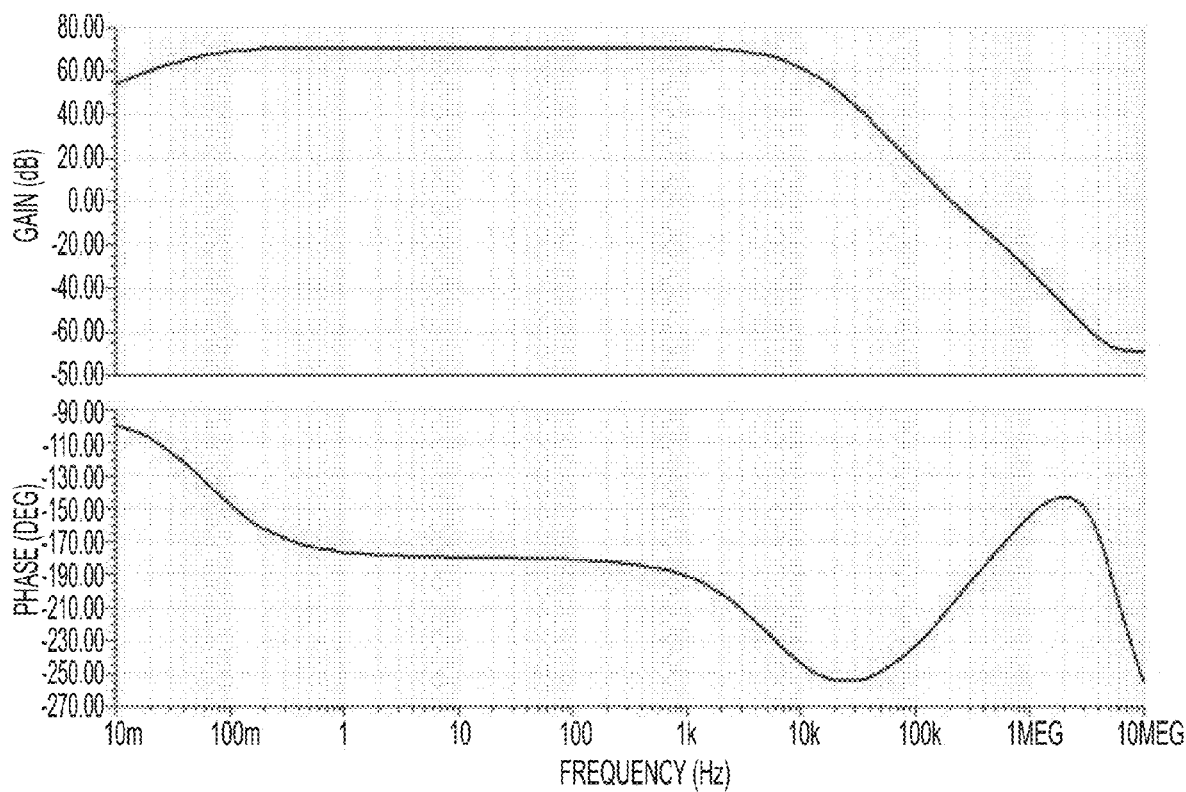
FIG. 25B shows the gain and phase response versus frequency for the circuit of FIG. 25A.
Figure 25C:
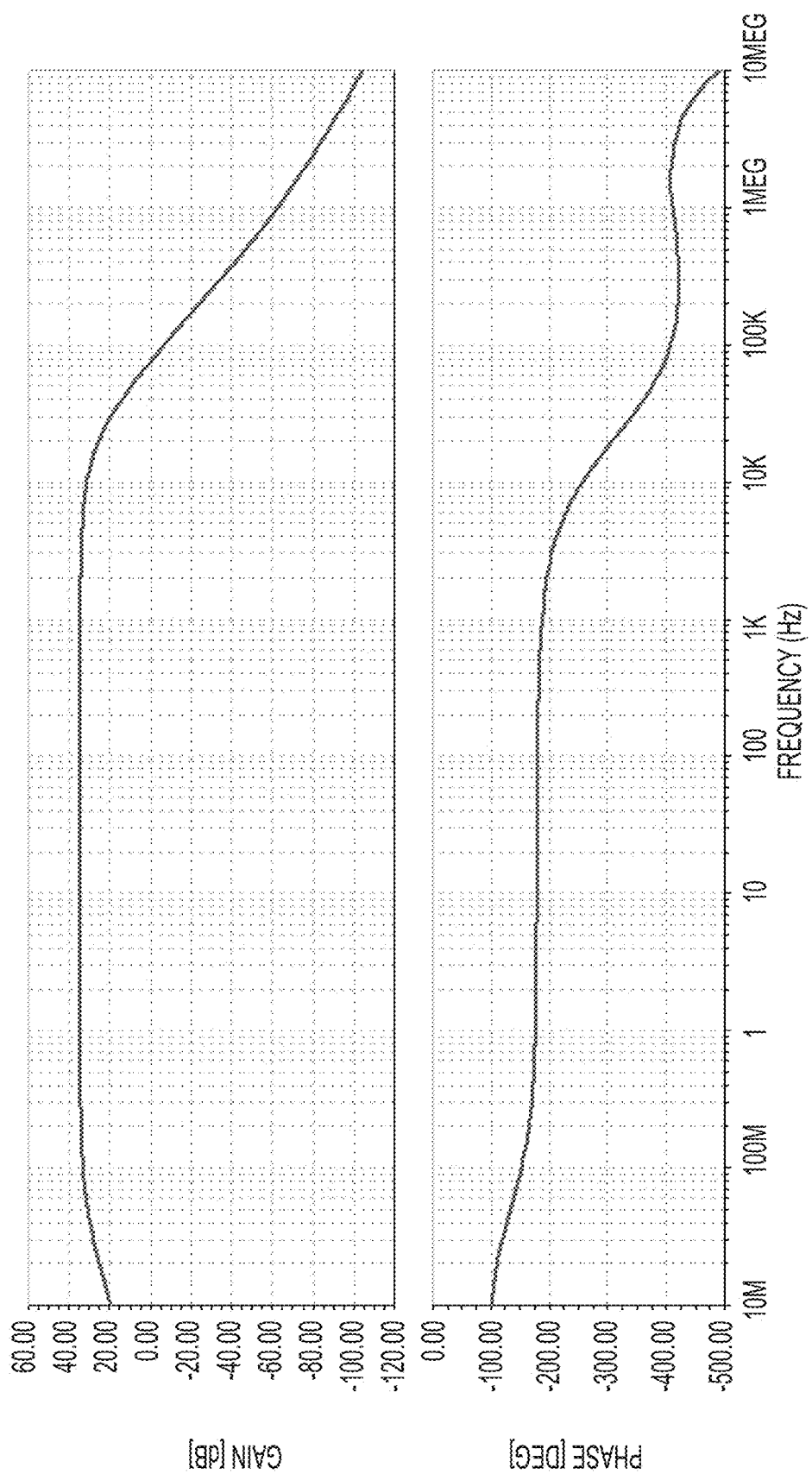
FIG. 25C illustrates transfer functions for another example signal processing circuitry.

FIG. 25A illustrates transfer functions for the example signal processing circuitry of FIG. 24. FIG. 25B illustrates the transfer function of the analog circuitry performing the first set 2410 of analog signal processing steps, using the above-described parameters. FIG. 25C illustrates the transfer function of another analog circuitry.

Following the offset 2416, the signal may pass into the second set 2420 of analog signal processing steps. As shown in FIG. 24, the first stage within the MCU may include a Programmable Gain Amplifier (PGA), which represents the third gain stage in the signal processing chain and offers the flexibility of on-the-fly adjustments of gain to optimize for ADC range. The general equation for amplification is shown in Equation 5:

$$V_{out} = V_{Ref} \pm (V_{In} - V_{Ref}) \times \text{Gain} \quad (5)$$

Figure 26:
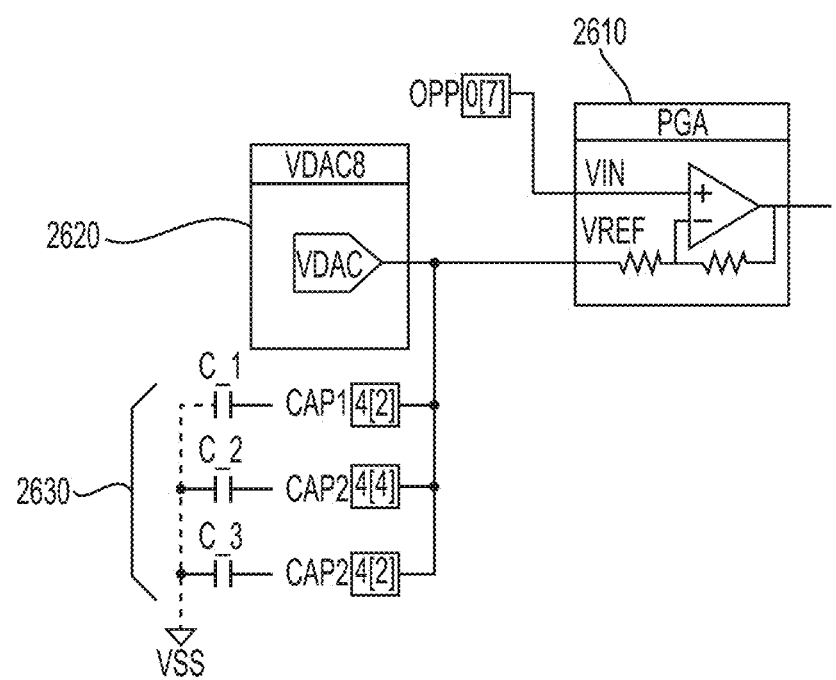
FIG. 26 is a schematic illustration of an example variation of a portion of signal processing circuitry in the signal processing chain shown in FIG. 24.

Accordingly, to amplify the dynamic signal, the offset added previously in circuitry (2416) need to only be $V_{Ref}$. As shown in the schematic of FIG. 26, a Digital-to-Analog converter (DAC) 2620 may connected to the $V_{Ref}$ pin of the PGA 2610, in order to achieve on-the-fly adjustments of the value of $V_{Ref}$. However, the DAC 2620 may add considerable noise to the amplifier beyond of what is acceptable. To address this, a set of capacitors 2630 may be added between the DAC signal to ground. Since the DAC signal is generally static, there is no concern on the dynamic behavior due to this addition—except for a short time period when voltages changed.

In addition to enabling on-the-fly adjustments of gain, the PGA may advantageously mitigate variation of the offset voltage created by the upstream circuitry. This variation is, for example, due to tolerances in electronic components and can amount to up to +/−20% variance on the offset signal (in 1616). The PGA can further be used to compensate for this offset and move the offset to half the ADC reference voltage (e.g., of 2.048 V). Trying to move the offset to exactly half of this voltage, or 1.024 V, results in the following Equation 6 to determine proper $V_{Ref}$:

$$V_{Ref} = \frac{1024 \text{ mV} - V_{In} \times \text{Gain}}{1 - \text{Gain}} \quad (6)$$

Note that Equation 6 is only valid for gain greater or equal to 2. Hence, in this example, the minimum gain to be used is 2 rather than 1. Before calculation of this new $V_{Ref}$, the true offset present on each PCB must be known, which may be determined through calibration. For example, determination of the true offset may be achieved by recording the signal for some short period of time and determining the offset value from the external circuitry via forming the mean value. This can be either done on the MCU directly or via the connected target device, and the correction send back to the MCU.

Next on the signal chain is a Track-and-Hold component (2424), which keeps the voltage constant upon a trigger signal. The voltage is ideally constant for the duration the ADC needs to sample a complete value; and is important for accurate results. The trigger is fired at the end of the previous ADC sample period, as the ADC will immediately continue with the following sample.

The Track-and-Hold voltage may be kept constant for a suitable predetermined time, such as for about 5-50 μs, before it is again released. The release allows the Track-and-Hold to follow the current voltage for another period of time (e.g., about 2 μs) before the next trigger. When sampling more than one sensor signal, Track-and-Hold components may help ensure proper time synchronization among the sensor signals, with synchrony accuracy in the range of nanoseconds.

The last component in the analog signal processing chain is the Sigma-Delta ADC (2426). In some variations, when internally running at about 3 MHz the ADC utilizes oversampling to achieve a signal of about 48-96 kHz at 16 bits in a range of about 0 V to about 2.048 V. In some variations, accuracy may be further increased by referencing the ADC ground to the circuit board ground described above.

The analog signals entering the ADC may then be sampled into the digital domain. Once analog signals are sampled into the digital domain, they may be moved to a buffer location in memory such as via fast DMA transfers (2432). The signals may be further buffered within a ring buffer, before assembled into packages (2434) and transmitted to one or more external host devices (2436). These packages may include a header and the payload. The header may have a package/frame start ID and other supplemental data that may help to keep the data in order after transmission and help detect lost data points. The payload is the sensor fusion data (e.g., vibroacoustic data, contextual data, etc.). In some variations, multi-modal data points are transmitted in each package via USB or wireless transmission (e.g., BLE, Bluetooth classic, Wi-Fi, etc.) to one or more external host devices 2404 (e.g., cloud, mobile computing device, etc.), such as for analysis. However, it should be understood that in other variations, other package sizes and/or other communication modalities may additionally or alternatively be incorporated. Additionally, or alternatively, analysis of the vibroacoustic data may be analyzed (e.g., using suitable machine learning models) locally on the sensing device before the data and/or analysis results may be similarly communicated to one or more external host devices.

1.f. Encoding Module

Software-defined biotelephony is a software-intensive approach to balance biosensing, communications and digital health computing needs against those of a variety of networks with which that user could operate. This tradeoff includes the degree of flexibility that is created a-priori (e.g. via a new protocol) versus the restricted degree of autonomy permitted by existing radios and receivers.

Encoding of audible/inaudible, seen/unseen, felt/unfelt, contact/contactless, proximal/remote captured data without loss of information such that any encoded signals will contain and transfer the same breadth, depth, quality and robust information whether be it via wireless or over wire is not possible with existing CODECS. Certain variants of the current technology's advancement of sensor module combinations and sensor data fusion also require improvements to methods and systems for data collection and data communication. The proposed technology contemplates sensing, processing, and transmitting vibroacoustic and electrical, magnetic, and electromagnetic signals having characteristic bandwidths from 0.01 Hz to over $10^{11}$ Hz (FIG. 1E), thus appropriate hardware and associated software applications commonly called CODECS (compressors/decompressors) are required for enabling the operation of the current technology.

It is generally accepted that there are two general categories of factors that affect fused encoded wide bandwidth data streams which are output by a data stream (for example audio) codec's encoder: in other words, details about the source (e.g., audio's) format and contents, and the codec and its configuration during the encoding process. For each factor that affects the encoded data stream, there is a simple rule that is nearly always true: because the fidelity of digital data stream (for example audio) is determined by the granularity and precision of the samples taken to convert it into a data stream, the more data used to represent the digital version of the audio, the more closely the sampled sound will match the source material.

Variants of the current technology deal with both issues by providing for highly efficient software based ultra-high bandwidth coding, transmission, and decoding devices, methods, and systems. Variants of the current technology provide a transmitter-receiver system and methods configured to receive and decode multi-modal signals from multi-sensor data streams. Proposed signal transmitter-receiver systems leverage "audio beacon" data streams. Signal receivers of the present disclosure provide for accurate signal decoding of a low-level signal, even in the presence of significant noise, where the software technology stack consumes very low power. Also provided are systems that include the receivers, as well as methods of using the same.

The Effect of Source Audio Format on Encoded Audio Output

There are several features that can be used to balance reproduction quality and file size. Because standard encoded radio data streams (e.g., audio, i.e., audible vibrations) inherently use fewer bits to represent each sample, the source audio format may actually have less impact on the encoded audio size than one might expect. However, a number of factors do still affect the encoded audio quality and size. Table 1 shows key source audio file format factors considered and optimized in the present technology and their accepted impact on the encoded audio:

TABLE 1

The effect of source audio format and contents on the encoded audio quality and size

| Feature | Effect on quality | Effect on size |
| --- | --- | --- |
| Channel count | The number of channels affects only the perception of directionality, not the quality. | Each channel may substantially increase the encoded audio size, depending on contents and encoder settings. |
| Noise/Hiss | Unwanted background noise or hiss tends to reduce audio quality both directly (by masking details of the foreground audio) and indirectly (by making the data stream waveform more complicated and therefore difficult to reduce in size while maintaining precision). | Hiss, static, or background noise increases the data stream complexity, which generally reduces the amount of compression possible. |
| Sample rate | The more samples available per second, the higher the resulting encoded data stream fidelity is likely to be. | Increasing the sample rate increases the encoded audio file's size. |
| Sample size | The larger the samples, the more detail each sample can contain, resulting in more accurate representation of each sample. | Depends on the codec; codecs typically have an internal sample format that may or may not be the same as the original sample size. But more source detail may make the encoded file larger; it will never make it smaller. |

The first, channel count, affects only the directionality or spatial localization of the signal. Depending on the content, the file size may be multiplied by the number of channels encoded, or, in some schemes, redundancies between the channels may be exploited to reduce the total file size without a significant degradation of the signals. Second, noise or hiss in the signal hiss tends to reduce audio quality both directly (by masking details of the foreground audio) and indirectly (by making the data stream waveform more complicated and therefore difficult to reduce in size while maintaining precision. Thus, hiss, static, or background noise increases the data stream complexity, which generally reduces the amount of compression possible. Third, the higher the sample rate, affects the quality the more samples are available per second, and the higher the resulting encoded data stream fidelity is likely to be. However, this comes at a cost of the encoded file's size, or encoded stream's bit rate.

Finally, the sample size affects the detail available in each sample, this depends on the codec; codecs typically have an internal sample format that may or may not be the same as the original sample size. However, more source detail may make the encoded file larger; it will never make it smaller.

The effects detailed above can be altered by decisions made during encoding the data stream. For example, if the encoder is configured to reduce the sample rate, the sample rate's effect on the output file will be reduced in kind.

The current technology's codecs, in certain variations, employ software-defined hardware and firmware algorithms to take source structural health and physiological health fused data streams and compress them to take substantially less space in memory or network bandwidth while not sacrificing information or data quality. In certain variations of encoder configuration, the encoder may be adjusted using parameters that choose specific algorithms, tune those algorithms, and specify how many passes to apply while encoding.

The current technology's Infrasound-to-Terahertz over wireless/IP differs from traditional audio CODECs by evolving and optimizing certain aspects for low frequency, low amplitude biometric data transmission: smart scalable switching (many more ports and easier to add just what is needed), breaking the barriers of distance, improved ratio of inputs to outputs, individual, fused and multiplexed data stream standards that extend beyond the local facility, convergence of low frequency, low amplitude biometric data and radio communications, and new options in local, edge and cloud processing.

Hardwired, circuit-based switching is basically a point-to-point technology. Wide-bandwidth data stream matrix switchers are intelligent "destination" and at "source" simultaneously. All the combinations of transmitters to receivers are resolved inside the matrix switch and it is possible match, allocate and optimally use any source at any destination according to the number of signal transmission and reception ports available on the data stream matrix switch. For example, an 8×8 matrix switch allows eight sources to be used at any of eight destinations.

Devices and systems of the current technology can perform local, edge and back-end handshake processing operations. Instead of just making any input available on any output, for example, it is possible to show any input on any—as well as many—outputs. Hence, a biometric data transmission from a broad-band biometric device, and data visualization can be a source that gets routed from a device transmitter box to a data visualization matrix switcher and then the switcher can be wired to multiple devices that can simultaneously be showing the biometric data stream in real time.

The wireless/IP (and packet-based switching) number of sources attached to the wireless/IP switch is unlimited. When physical ports run out, multiple wireless/IP switches can be connected to expand. The number of ports can be scaled to satisfy needs much more conveniently. It is possible to keep adding sources and destinations without a substantial overhaul of the data stream matrix switcher centerpiece being a major limiting factor.

The ratio of inputs to outputs can also be tailored. It is possible to have many inputs but only a few outputs, or only a few inputs but many outputs. Or you can have many of both and in widely different quantities.

In certain variations, current technology's Infrasound-to-Terahertz over wireless/IP significantly increases flexibility by overcoming limits to number of sources and destinations as well as by conquering distance limits.

In certain variations, the current technology's Infrasound-to-Terahertz over wireless/IP devices use standards-based packetization for transmission on wireless/IP networks and compatibility with wireless/IP switches, and some use proprietary packetization schemes which also work on wireless/IP networks and standard wireless/IP switches but which do not work with other products in the market.

In general, standards-based schemes provide the potential for interoperability between products from different vendors.

In certain variations, the current technology's standards-based and proprietary packetization schemas do not alone determine interoperability and also do not establish whether a product is more, or less, secure. What provides data safety and security is current variations of the Infrasound-to-Terahertz over wireless/IP encoders and decoders that are tightly coupled. One reason for this tight coupling is to provide guaranteed specifications and performance. This also allows for a very controlled out-of-the-box ease of set up and ease-of-use experience.

Encryption technologies exist for several aspects of the current technology's Infrasound-to-Terahertz over wireless/IP products, and they address multiple components of data stream system design.

The current technology's devices provide encryption on the command-and-control signaling to encoder and decoder devices. This offers security against hacking the actions of the boxes-including turning streaming on or off, or switching what source is being displayed. Another security aspect is the ability to encrypt the data streams themselves. This ensures that if the data stream is intercepted, it cannot be simply decoded and viewed.

In other embodiments, the current technology's products provide support for third-party devices using digital key exchanges or encryption. Leveraging learning from consumer examples, the overwhelming majority of AV customers are concerned with the most straightforward case-which is High-bandwidth Digital Content Protection (HDCP). The purpose of HDCP is to protect digital copyrighted content as it travels between devices. For instance, a cable or satellite receiver box, or a media player with HDMI outputs, might play content in HD or 4K that is protected content. Such content is locked and can only be viewed by HDCP-compatible products once they are properly authenticated. Similarly, the current technology's data streams have distributed ledger (e.g., blockchain) provenance, records, security and restrictions on how protected content can be extended, multiplied, altered, or viewed.

Piggybacking Data Transfer Protocols and Other CODECs to Transfer Infrasound-to-Terahertz Over Wireless IP The telephone Touch-Tone protocol is probably the most ubiquitous audible data transmission heard daily. Wherein, multi-frequency tones are used to dial numbers over the voice-frequency band. Similarly, infrasound, ultrasound and terahertz data streams can be overlaid onto audible sounds for faithful broadband data stream communications. Structural and physiological gray and standard health data collected by the current technology's sensor fusion and data fusion platform of data should are encoded onto an inaudible, near-ultrasound layer placed on top of normal, audible sounds and or onto an inaudible, near-infrasound layer placed on just below normal, audible sounds to cover broad-bandwidth data transmission. The near-infrasound and/or near-ultrasound layer overlay, turns any acoustic stethoscope, any smartphone any microphone and speaker, IoT device, etc., into a data-transfer device that then could be used for health data transfer, health insurance payments transfers, user authentication, and smart city applications such as digital locks, mass-transit turnstiles, etc.

A generic interoperable infrasound-to-Terahertz over wireless/IP platform takes advantage of the lack of a common universal protocol to connect Internet of Things and leverages the greater power, performance, intelligence, etc of smart phones, smart speakers, IoT watched and any/ everywhere digital solutions proliferating around us to perform connections.

The current technology weaves infrasound-to-Terahertz data streams into common vehicles of audible sounds, such as VOIP, streaming music, etc., public announcements. Infrasound and Ultrasound is the type of vibration/sound that the human ear does not register, but specialized equipment can pick up.

Smartphones, or any microphone, then, could be used to receive the generated audio pulses and decode the data. In turn, a smartphone speaker within proximity could send a cataloged data stream frequency tag to any receiver, such as one embedded in turning on the technology of the system 100. Indeed, any specific action could be triggered, including a purchase or communicating with a automated call center.

In certain variations, patients entering urgent care could be identified, greeted, registered and processed via targeting/ beaconing using a combination of legacy stored and real-time collected infrasound-to-Terahertz data streams using bring-your-own smart devices and in situ speakers. The infrasound-to-Terahertz over wireless/IP solution communicates even when smartphones are in Airplane Mode and data is turned off, for use in high security environments and the transportation vertical. Traditional networks, such as wireless, can overload when important information needs communicating—such as during a public safety incident. The intelligent system manages and optimizes congestion issues that might occur in a large crowd-gatherings, such as at a stadium. Additionally, leveraging "audio" smart phone/speaker beacons requires less battery-intensive than Bluetooth.

In certain other variations, the WLAN (Wireless Local Area Networks) that originated in 1985 controlled by the United States Federal Communications Commission (FCC). the unlicensed spectrum in three different regions to be used in Industry (902-928 MHz), Science (2400-2483.5 MHz) and Medicine (5725-5850 MHz), provides the ability to he Infrasound-to-Terahertz over wireless/IP solution to take advantage of the multi-vertical freedoms across a cooperative spectrum broad frequency network.

1.g. Artificial Intelligence Module

Without the right algorithms to refine data, the real value of high-resolution sensor data fusion will remain hidden. Popular approaches such as neural nets model correlation, not causal relationships, and do not support extrapolation from the data. In contrast, Developers have developed a novel Structural Machine Learning (SML) platform, which is a natural feedforward and feedback platform, where data exploration and exploitation can be achieved faster and more accurately. Automatic expression synthesis tools build generalizable and evolving models, distilling the sensor data into human-interpretable form, yielding the true value of fused data in an intelligent, agile, networked, and autonomous sensing/exploitation system.

In this respect, some variations, the system 10 includes an artificial intelligence module which is configured to use machine learning and other forms of adaptation (e.g., Bayesian probabilistic adaptation) to optimize analytical software including data-driven feedback loops, for purposes of analyzing the vibroacoustic and/or other sensor data. The training of such machine learning models for analyzing data from the sensing device may begin with human-derived prior knowledge, or "soft knowledge" artefacts. These "soft knowledge" artefacts are advantageously generally much more expressible than off-the-shelf ML models like neural nets or decision trees. Furthermore, in contrast to mainstream machine learning scenarios that have clearly delineated training and test phases, analytical software for analyzing data from the sensing device may involve learning and optimizing software inline. In other words, the notion here is to embed an "inline learning" algorithm within an artificial intelligence (AI) software system, allowing the AI system to learn adaptively as the system processes new data. Such inline (and real-time) adaptation typically leads to more performant software AI systems with respect to various functional and nonfunctional properties or metrics, at least because (i) the AI system can correct for the suboptimal biases introduced by human designers and (ii) respond swiftly to changing characteristics operating conditions (mostly to variation in data being processed).

With respect to analyzing specifically vibroacoustic data, the vibroacoustic biofield harvested from patients may be saved as audio (.wav) files. Custom cross frequency coupling methodology, in combination with averaging wavelets such as Daubechies and Haar wavelet approaches, may be used to analyze the infrasound data as static images within set time windows. The Haar wavelet is the first and simplest orthonormal wavelet basis. Since the Daubechies wavelet averages over more data points, it is smoother than the Haar wavelet and may be more suitable for some applications. Typically, the audio scenes are of complex content, including background noise mixed with rich foreground having audible and inaudible vibrations and their context. In general, both background noise and foreground sounds can be used to characterize a "diagnostic scene" for use in characterizing a subject. Other data like contextual data could be converted into a visual 2D representation and attached to the static infrasound images to create a new image. Such new image is then analyzed as a whole to increase the performance of the algorithm.

However, foreground sounds typically occur in an arbitrary order, thereby making hidden sequential patterns hard to uncover. Thus, the ability to recognize and "unmask" a surrounding diagnosis environment by isolating and identifying contextualized audible and inaudible vibration signals has potential for many diagnostic applications. One approach to accomplish this is to shift from conventional classification techniques to modern deep neural networks (DNNs), and rand convolutional neural network (CNNs). However, despite their top performance, these network variants may not be sufficiently capable of modeling sequences in certain applications. Thus, in some variations the AI system may incorporate combined deep, symbolic, hybrid recurrent and convolutional neural network R/CNNs. Furthermore, in some variations, a separate DNN may generate and propose a "crisp" (symbolic) program, where feedback from execution of such a program may be used to tune/train the above DNNs and/or CNNs in a hybrid symbolic-subsymbolic approach.

In some variations, sensitivity of the sensing platform may be increased by using biophysiologically precise simulated patient entities for machine learning algorithm training purposes. For example, such simulated entities may be uploaded and modified in a training environment using high precision clinical data (e.g., heart rate, pulse rate, breathing rate, heart rate variability, breathing rate variability, pulse delay, core temperature, upper and lower respiratory temperature gradients, etc.) collected from well-characterized clinical patients to create a large, realistic training dataset.

In certain variations, the machine learning module is configured to (i) design a Covid-19 biosignature in a training phase using variations of the sensing devices and systems described herein, and/or (ii) apply the Covid-19 biosignature using variations of the sensing devices and systems described herein.

Novel aspects of methods executed by the machine learning module comprise posing a machine learning problem (here: designing of a Covid-19 biosignature) as a task of program synthesis. To that aim, a domain-specific language (DSL) was designed to express various designs of a biosignature as programs in that language. In certain variations, inputs to the DSL comprise raw time series (detected frequency signals) as well as various types of features extracted from the series, like FFT spectrum, STFT spectrograms, MFCCs, vibe-scale features, peak locations, and more. These correspond to specific data types in the bespoke DSL. The DSL is equipped with functions (instructions) that can process inputs and variables of particular types. The DSL functions are based on domain specific knowledge. For instance, DSL functions we use now routinely include: convolution, peak finding, parameterizable low-pass and high-pass filters, arithmetic of time series, and more.

Importantly, these building blocks are defined on a much higher abstraction level than the typical vocabulary of SOTA ML techniques, where for instance deep learning models are essentially always nested compositions of dot products with nonlinearities. Secondly, they build upon the available body of knowledge that proved useful in signal processing and analysis in several past decades. Thirdly, the grammar of the DSL permits only operations that make sense in the context of signature identification, and can be used to convey experts' knowledge about the problem.

Expressing the models as programs can benefit from a wealth of theoretical and practical knowledge concerning the design and semantics of programming languages. Concerning data representation, we can rely on the formalized approach of type systems, which allow us to reason about data pieces, their relationship and their processing in a principled and sound way. To that aim, we rely on the fundamental formalism of algebraic data types, which allows systematic creation of new data types by aggregation and composition of existing types. In some variants (e.g. so-called dependent types), we can 'propagate' the properties of data through functions and so constrain their output types. Next, the actual processing of data can be conveniently phrased using recursion schemes, which provide a universal framework for aggregation and disaggregation of information for arbitrary, variable-size data structures (e.g. time series). Last but not least, the DSL is designed in a way that is compatible with the structure characteristic of a problem.

For applications of systems, methods and sensing devices of the present technology to detect Covid-19 infection in subjects (see, Example 8, for example), the structure stems from the matched case-control setup, where observations (recordings) span multiple "dimensions" related to the location of auscultation point, patient's position, age, sex, etc. These observable factoring variables can be explicitly built into the DSL. Unlike deep learning approaches, this facilitates the discrimination between correlation and cause, by filtering out of other, confounding variables. This allows the capture and exploitation of various structures on several levels, among others intra-recording (by aggregating multiple alternative feature extraction techniques), and inter-recording, by exploiting the structure endowed by the MCC setup.

The above mechanisms can "regularize" the process of program synthesis and make it more likely to find a solution (program) that is plausible for a given problem, and in particular which does not overfit to the available training data, making valid generalization more likely. This makes it possible to synthesize robust signatures, classifiers and regression models from limited numbers of training examples.

1.h. Other Features of the System

In some variations, full-spectrum vibroacoustic sensing may be selectable by enabling or disabling vibroacoustic sensing features based on a software-as-a-service subscription model. The one or more sensing devices may, for example, transition between a base or minimum functionality state, in which no vibroacoustic sensing is performed. In variations in which the sensing device is a customized piece of medical equipment such as that described below (e.g., stethoscope), the base functionality state may be a mode in which the voice coil is active via standard air tubes, akin to the traditional acoustic stethoscope. Functionality may then be scaled to one or more intermediate functionality or maximum functionality levels. At intermediate levels, certain features may be partially enabled or provided at a degraded level, while at a maximum functionality level, all vibroacoustic sensing features are functional. Furthermore, in some variations, these functionality modes may additionally or alternatively be intentionally selected by the user as different operating modes of the sensing device (e.g., the user may disable sensing of inaudible frequencies if such signals are not of interest in a particular application). Additionally, or alternatively, in some variations, a control mechanism may be hard-wired or coded via software programming to the power control to prevent tampering.

In some variations, an internal controller may control the functions of the sensing device based on the level of service available to the user (e.g., as a subscription service). The controller also may authenticate parts of the sensing device (e.g., any disposable components such as interchangeable modules), and license data, serial numbers, and/or other data structure, which may allow the subscription to be identified. Additionally, or alternatively, the controller may store levels of service, permissions, subscriptions, and/or any other relevant data to determine the level of service at any given time. The license, serial number, clock and/or calendar data is stored in non-volatile memory so that even under conditions of loss of power, significance subscription-relevant information is not lost. The controller may be triggered by the reception of a key. The key may set the level of service, the duration of service, and/or the number of times a service may be performed, for example.

Additionally or alternatively, the key may securely link the sensing device to local and/or cloud-based health record data management solutions. A subscriber may, for example, link a permissioned computing device, such as a smart watch, cell phone, tablet, or computer, directly to the sensing device (e.g., using a keypad, a wireless technique such as NFC, and/or optical techniques such as reading an image such as a QR code) and this process may provide the key to the device. In some variations, the computing device may become a tether to the sensing device that communicates and connects the device via cables or wirelessly to the cloud, other external devices, etc. using wireless and/or wired communication modes such as those described above. In some variations, the information entered into the computing device may be combined with encrypted license data, serial numbers, and/or other data structure on the vibrometer sensing device and relayed to a cloud-based server, which may verify the information and then send the operational subscription key combining starts and end date of subscription and/or other details.

Furthermore, in some variations, subscription data may be combined with device usage data (as described above) to support and/or control device functionality in academic or professional settings, for institutional policy monitoring, and/or behavior change support in home use, etc.

1.i. Sensing Device Variations

As described above, the sensing device may incorporate various components in a modular fashion and may have any various suitable form factors.

Integrated Handheld Devices

For example, in some variations, the sensing device may include a handheld housing. As described above with reference to FIGS. 3A and 3B, and 4A and 4B in some variations the housing may be standalone and integrated into the handheld sensing device 300, 400. The sensing device 300, 400 may be used, for example, as a point-of-care device for assessing one or more bodily conditions of a subject. The sensing device 300, 400 may have a wide bandwidth capable of detecting a full spectrum of vibroacoustic signals (e.g., between about 0.01 Hz to about 160 kHz) associated with the subject. In some variations, the sensing device 300, 400 may be used as part of a telemedicine platform, for example. It should also be understood that the stackup shown in FIG. 3B, 4B is exemplary only, and components may be packaged in other suitable configurations within the housing.

Figure 27A:
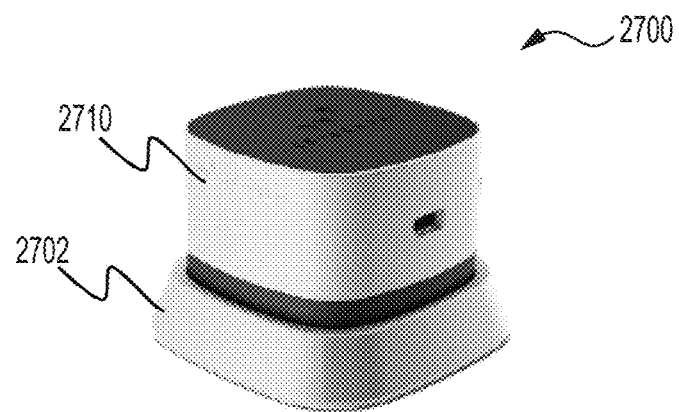
FIGS. 27A and 27B depict an assembled view and an exploded view, respectively, of an example variation of a handheld sensing device for characterizing a bodily condition of a subject.
Figure 27B:
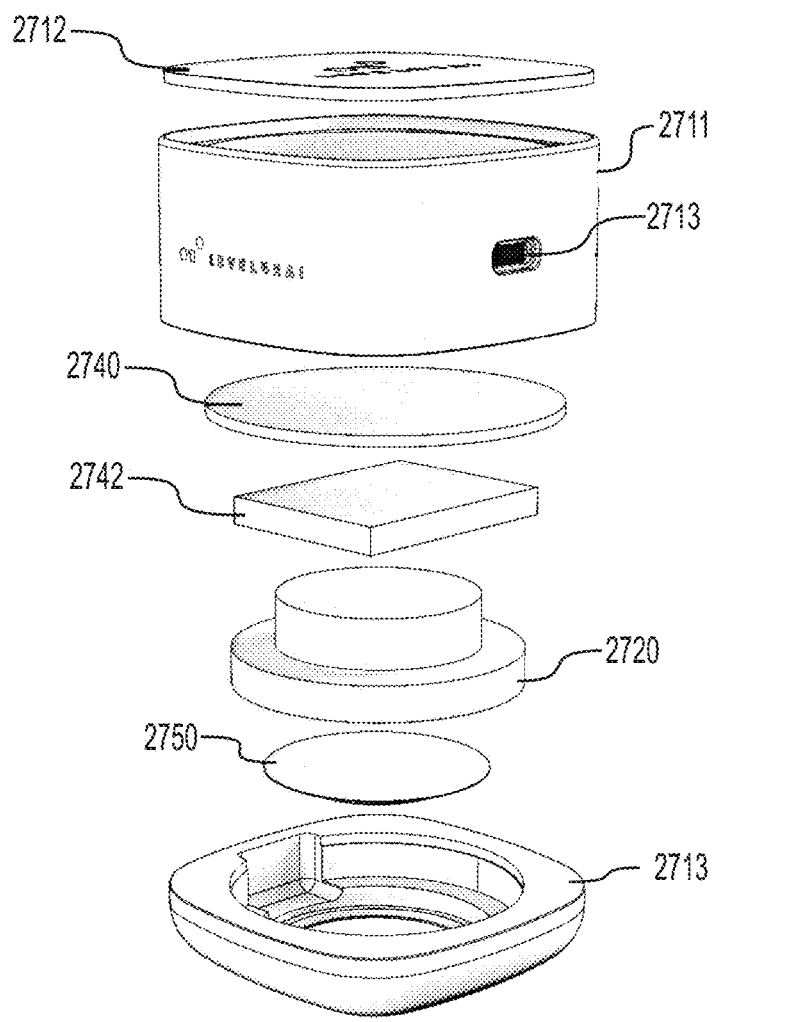

FIGS. 27A and 27B depict an exemplary variation of a sensing device 2700 including a handheld housing as part of an integrated handheld device. Like the sensing device 300, the sensing device 2700 may include a handheld housing 2710 with a base 2702, where the housing 2710 substantially surrounds one or more of the modules and other various components as described above (e.g., vibroacoustic sensor module 2720, electronics system 2740, at least one power source 2742, impedance matching diaphragm 2750). In some variations, the housing 2710 may be assembled from multiple components that couple together via one or more fasteners or through mechanical interlocking features (e.g., mating features), etc. For example, as shown in FIG. 27B, the housing 2710 may include a housing body 2711 (which may, for example, include a power port 2714) that couples to a top cover 2712 and a bottom cover 2713 so as to enclose the components of the sensing device 2700. In some variations the sensing device 2700 may further include a contextual sensor module similar to that described above. In contrast to the sensing device 300 shown in FIGS. 3B and 4B, the sensing device 2700 is more cuboidal and omits a display. The sensing device 2700 may be used, for example, as a point-of-care wideband scanner device for assessing one or more conditions of a subject, where the sensing device 2700 has wide bandwidth capable of detecting a full spectrum of vibroacoustic signals) e.g., between about 0.01 Hz to about 160 kHz) associated with the subject. Like the sensing device 300, in some variations the sensing device 2700 may be used as part of a telemedicine platform, for example. It should also be understood that the stackup shown in FIG. 27B is exemplary only, and components may be packaged in other suitable configurations within the housing.

Figure 28A:
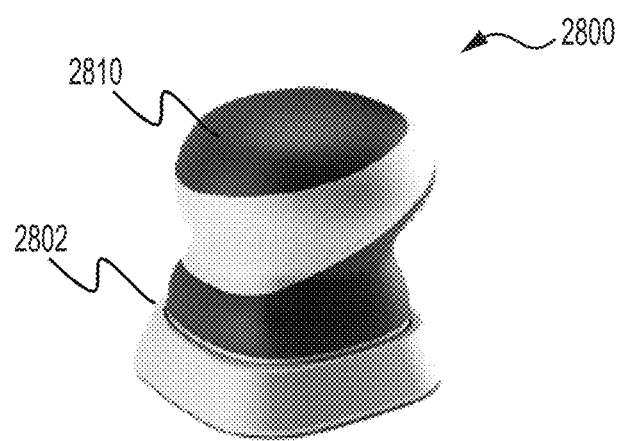
FIGS. 28A and 28B depict an assembled view and an exploded view, respectively, of an example variation of a handheld sensing device for characterizing a bodily condition of a subject.
Figure 28B:
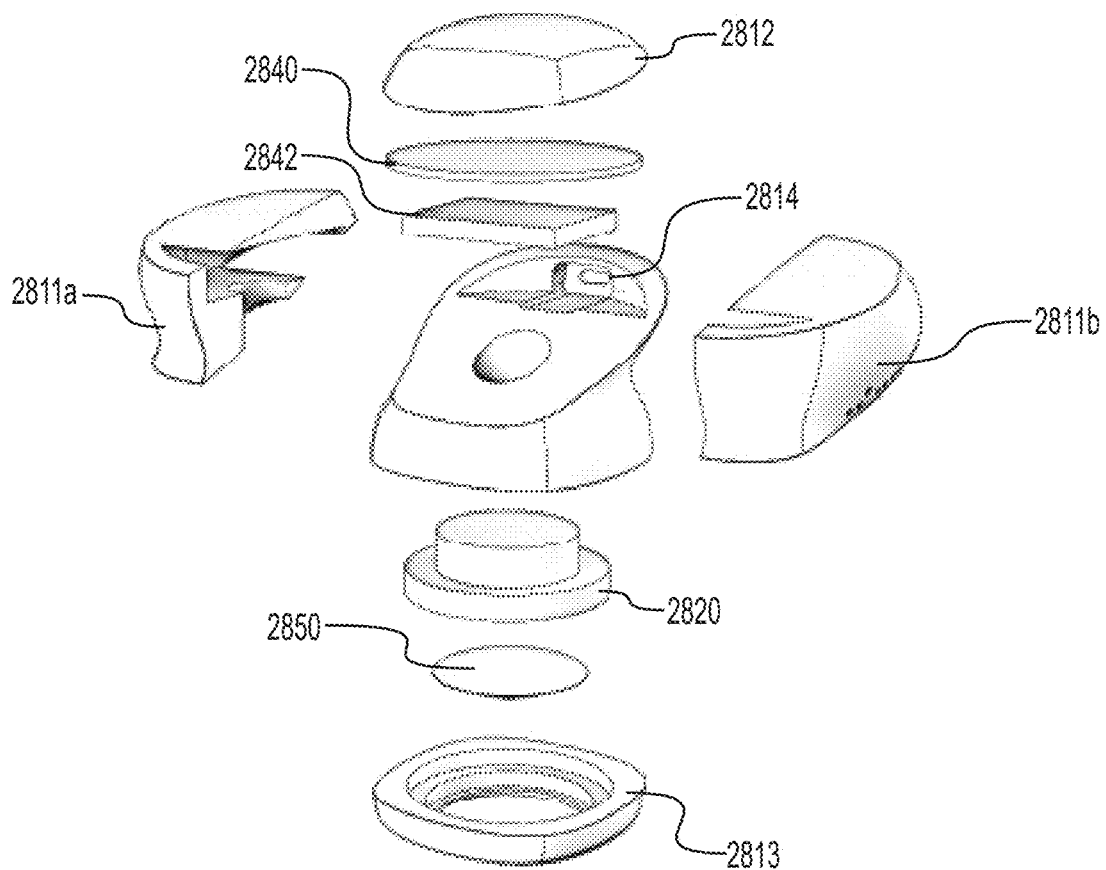

FIGS. 28A and 28B depict an exemplary variation of a sensing device 2800 including an ergonomic handheld housing as part of an integrated handheld device. The sensing device 2800 may be similar to the sensing devices 300, 400 and 2700 described above, except that the housing 2810 in the sensing device may be molded and contoured for a more ergonomic handheld grip. In some variations, the sensing device 2800 may designed to be held in a left hand, or designed to be held in a right hand, or designed to be comfortably held in either the left hand or right hand of a user. In some variations, as shown in FIG. 28B, the housing 2810 may be assembled from multiple components that couple together via one or more fasteners or through mechanical interlocking features (e.g., mating features), etc. For example, as shown in FIG. 28B, the housing may include a housing body with couplable body portions 2811a and 2811b. The housing body may further couple to a top cover 2812 and a bottom cover 2813. Furthermore, the housing 2810 may be coupled to a base 2802 and configured to substantially surround one or more of the modules and other various components as described above (e.g., vibroacoustic sensor module 2828, electronics system 2840, at least one power source 2842, impedance matching diaphragm 2850). In some variations the sensing device 2800 may further include a contextual sensor module similar to that described above. The housing 2810 may also include a power port 2814 for recharging the power source 2842, for example. It should also be understood that the stackup shown in FIG. 28B is exemplary only, and components may be packaged in other suitable configurations within the housing.

Wearable Devices

In some variations, the sensing device may include a wearable housing. The wearable housing may, for example, be coupled to an adhesive patch configured for attachment to a surface (e.g., skin) of a subject in a suitable body location (e.g., chest, stomach, etc.). As another example, the wearable housing may be coupled to a suitable garment (e.g., clothing such as a shirt or jacket, a chest strap, a belly band, arm band, etc.) for detecting vibroacoustic signals from a subject wearing the garment. Accordingly, in such variations the sensing device may enable continuous monitoring of the subject for one or more bodily conditions.

Figure 29:
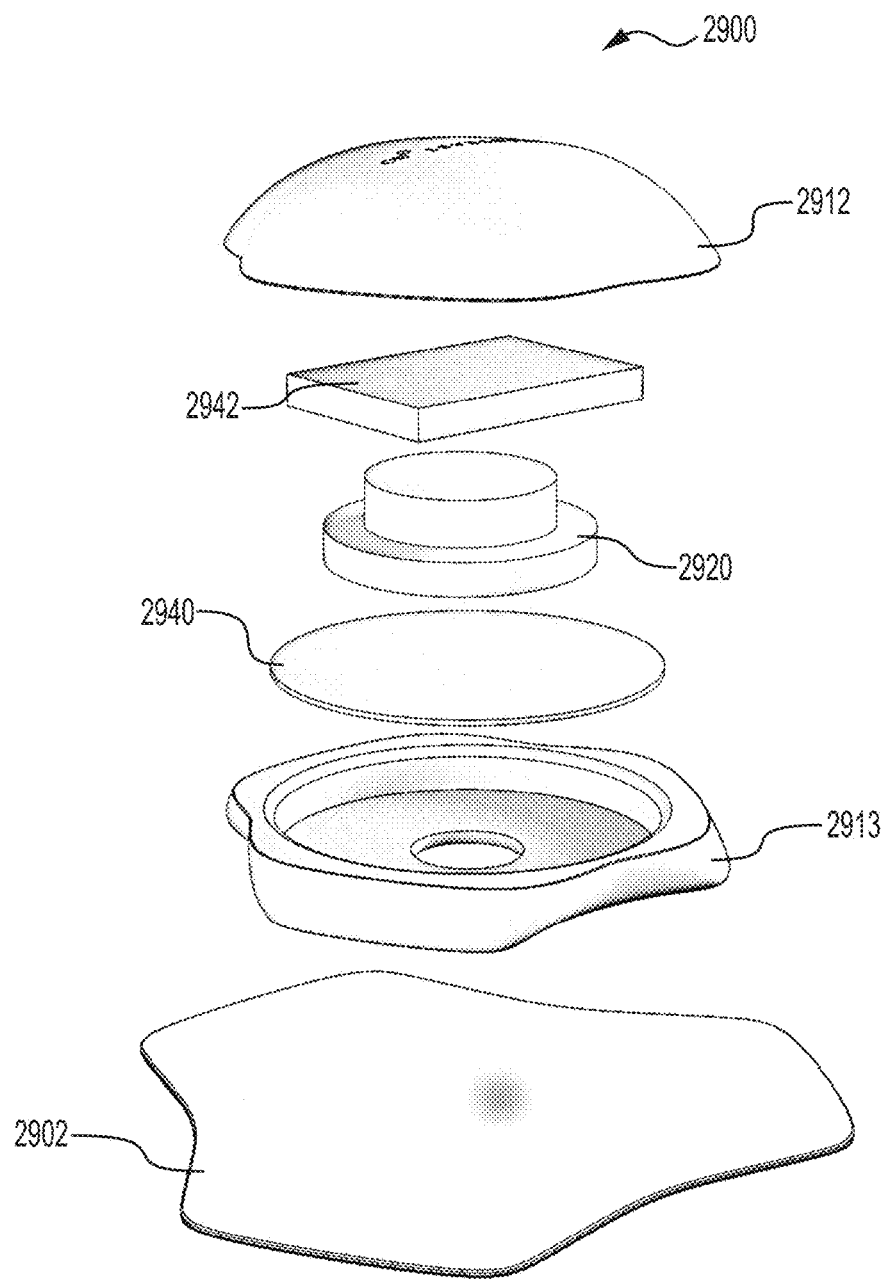
FIG. 29 is a schematic illustration of an example variation of a wearable sensing device for characterizing a bodily condition of a subject.
Figure 43:
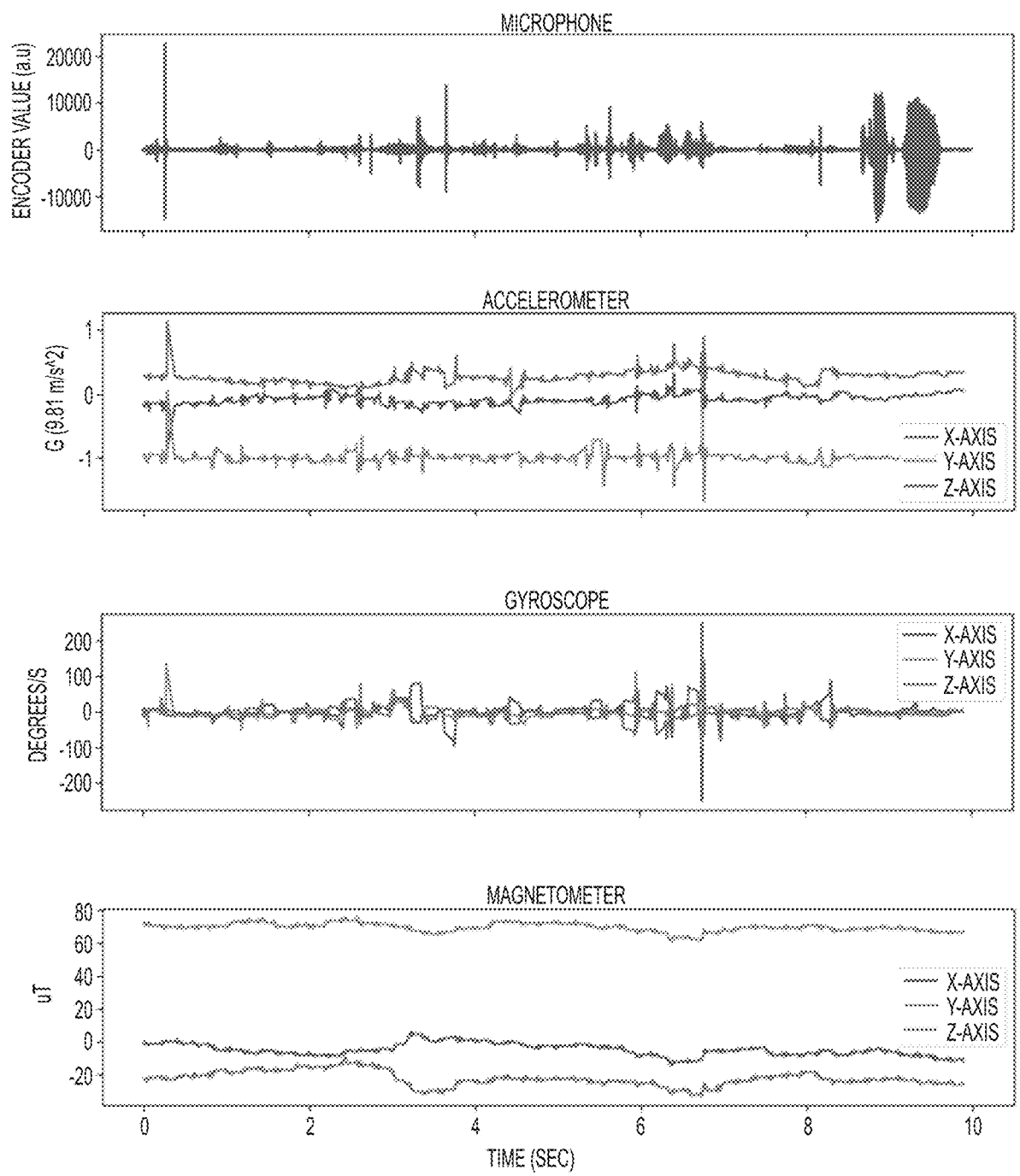
FIG. 43 depicts example signals from an example variation of a contextual sensor module of an example variation of a sensing device including a microphone and a 9-axis inertial measurement unit (including a tri-axis accelerometer, a tri-axis gyroscope, and a tri-axis magnetometer).

FIG. 29 depicts an exemplary variation of a sensing device 2900 configured as a wearable device. For example, the sensing device 2900 may include a housing coupled to an adhesive patch for attached to a user. The housing may include a top cover 2912 couplable to a bottom cover 2913 (e.g., through mechanical interlocking features, fasteners, etc.) so as to substantially surround internal components of the sensing device. Similar to that described above, the sensing device 2900 may include a vibroacoustic sensor module 2920, at least one power source 2942, and an electronics system 2940. The sensing device 2900 may have a wide bandwidth capable of detecting a full spectrum of vibroacoustic signals (e.g., between about 0.01 Hz to about 160 kHz) associated with the subject. Furthermore, in some variations the sensing device 2900 may include an impedance matching diaphragm (not shown) and/or a contextual sensor module (not shown in FIG. 29) providing additional sensor data for use in analysis. For example, in some variations, the contextual sensor module may include supplementary sensors such as a microphone and/or a 9-axis inertial measurement unit (e.g., including a tri-axis accelerometer, tri-axis gyroscope, and tri-axis magnetometer). FIG. 43 illustrates example data from such an example variation of a contextual sensor module. In the arrangement shown in FIG. 29, a continuous opening from a surface of the user to the vibroacoustic sensor module 2920 may be provided by aligned openings in an attachment backing 2902, the lower cover 2913, and/or the electronics system 2940. For example, the attachment backing 2902 may include an adhesive patch. It should also be understood that the stackup shown in FIG. 29 is exemplary only, and components may be packaged in other suitable configurations within the housing.

In some variations, a sensing device similar to sensing device 2900 may be coupled to a garment, so as to detect and measure vibroacoustic data and/or other sensors when the garment is worn by the subject. For example, the attachment backing 2902 may include an adhesive patch may attached to an outer or inner surface of a garment. As another example, the sensing device may be attached to the garment by securing the housing (e.g., lower cover 2913) to the attachment backing 2902 placed on an opposite surface of the garment, such that a layer of the garment may be sandwiched between the backing and the housing. For example, the attachment backing 2902 may be placed adjacent an inner surface of the garment, the housing may be placed on an outer surface of the garment, and the attachment backing and housing may be coupled together via one or more fasteners (e.g., adhesive, mechanical fasteners, magnets, etc.), and/or interlocking parts (e.g., threads, snap fit mating features, latches, etc.). As yet another example, the housing of the sensing device 2900 may be sewn to the garment.

Specialized Equipment

The sensing device and/or other parts of the system 100 may be incorporated into other suitable medical diagnostic equipment, such as a stethoscope. For example, a stethoscope including a sensing device may be used by a clinician to examine a subject and collect data including audible and inaudible vibroacoustic signals from the heart, lungs, gut, etc.

Stethoscope

Figure 30:
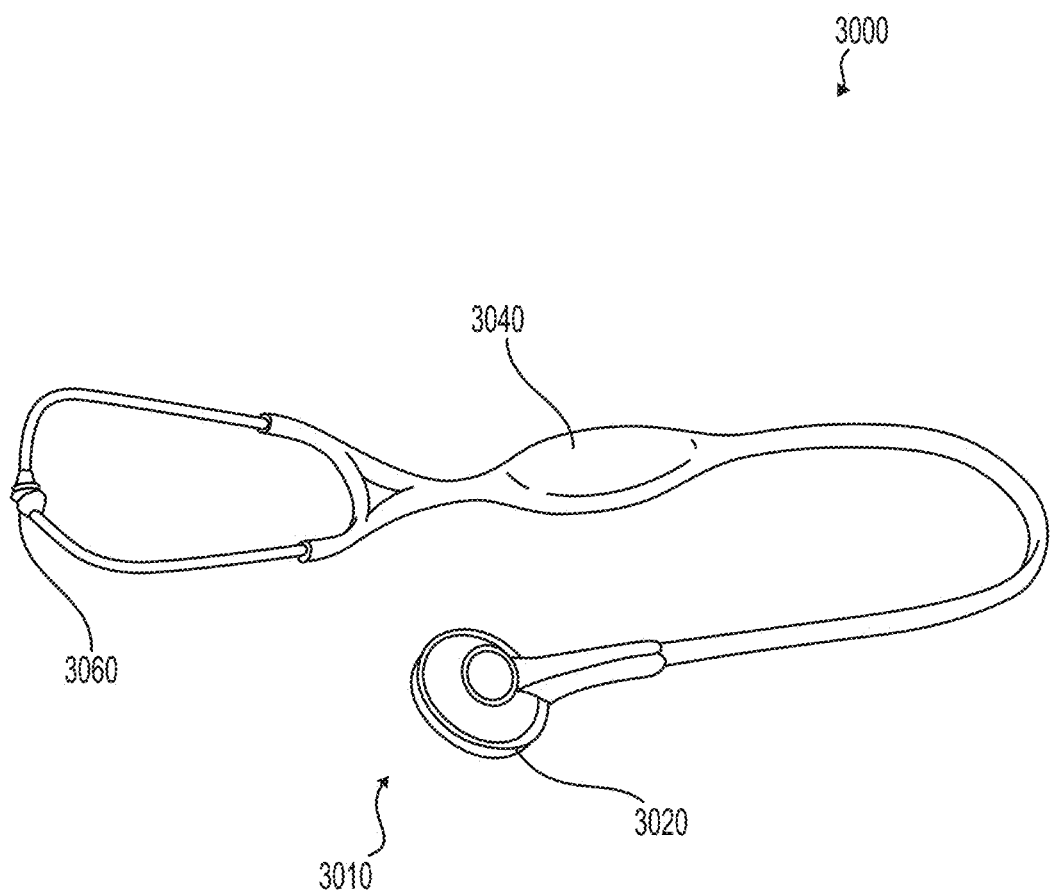
FIG. 30 is a schematic illustration of an example variation of a stethoscope sensing device for characterizing a bodily condition of a subject.

For example, as shown in FIG. 30, a stethoscope device 3000 may include a sensing device including a handheld housing 3010 (e.g., chestpiece) having a vibroacoustic sensor module 3020. The vibroacoustic sensor module 3020 may be similar to any of the variations of vibroacoustic sensor modules described above. For example, as described above, the vibroacoustic sensor module 3020 may include at least one deflecting structure (e.g., one or more flexure arms, a membrane, spider etc.) and one or more suitable sensors configured to interface with the deflecting structure to detect and measure vibroacoustic signals. In some variations, the vibroacoustic sensor module comprises a voice coil. In some variations, tubing of the stethoscope leading to earpieces 3060 may be detachably coupled to the vibroacoustic sensor module 3020 (e.g., with mating connectors, magnets, etc.). In some variations, the vibroacoustic sensor module 3020 (or a suitable component thereof, such as the impedance diaphragm as described above) may be manufactured separately and be configured to replace one or more components (e.g., dome or diaphragm) of an existing stethoscope (e.g., conventional acoustic stethoscope). In this respect, the some components of the sensing device, such as the sensing device 400, may be adapted to be retrofit to a conventional stethoscope.

Vibroacoustic signals from the vibroacoustic sensor module 3020 may be communicated to an electronics system which may be located in at least one junction box 3040 along tubing of the stethoscope device 3000 or in any suitable location for processing the signals. At least vibroacoustic signals in the audible frequency range may traverse through the tubing and heard by a user via earpieces 3060. Additionally or alternatively, the junction box 3040 may include one or more connectors enabling at least one peripheral device (e.g., headphones) to be connected to the stethoscope in a wired manner, though in some variations acoustic data may be communicated wirelessly to a peripheral device via a communication module such as that described above (e.g., over WiFi, cellular network, Bluetooth, etc.). The junction box may also include one or more connection ports such that speakers, headphones and/or air tubes may be connected to the vibrometer sensing device. Furthermore, in variations in which the electronics system includes a communication module with one or more antennas for wireless transmission, the antenna(s) may be included within the tubing to allow for optimization toward range and/or data rates. In some variations, the antenna(s) may be separated a suitable distance from other electronics to as to reduce interference and lead to improved transmission quality.

In certain variations, the sensing device may function as a stethoscope by coupling it with a smartphone or other device.

Panels

Figure 31A:
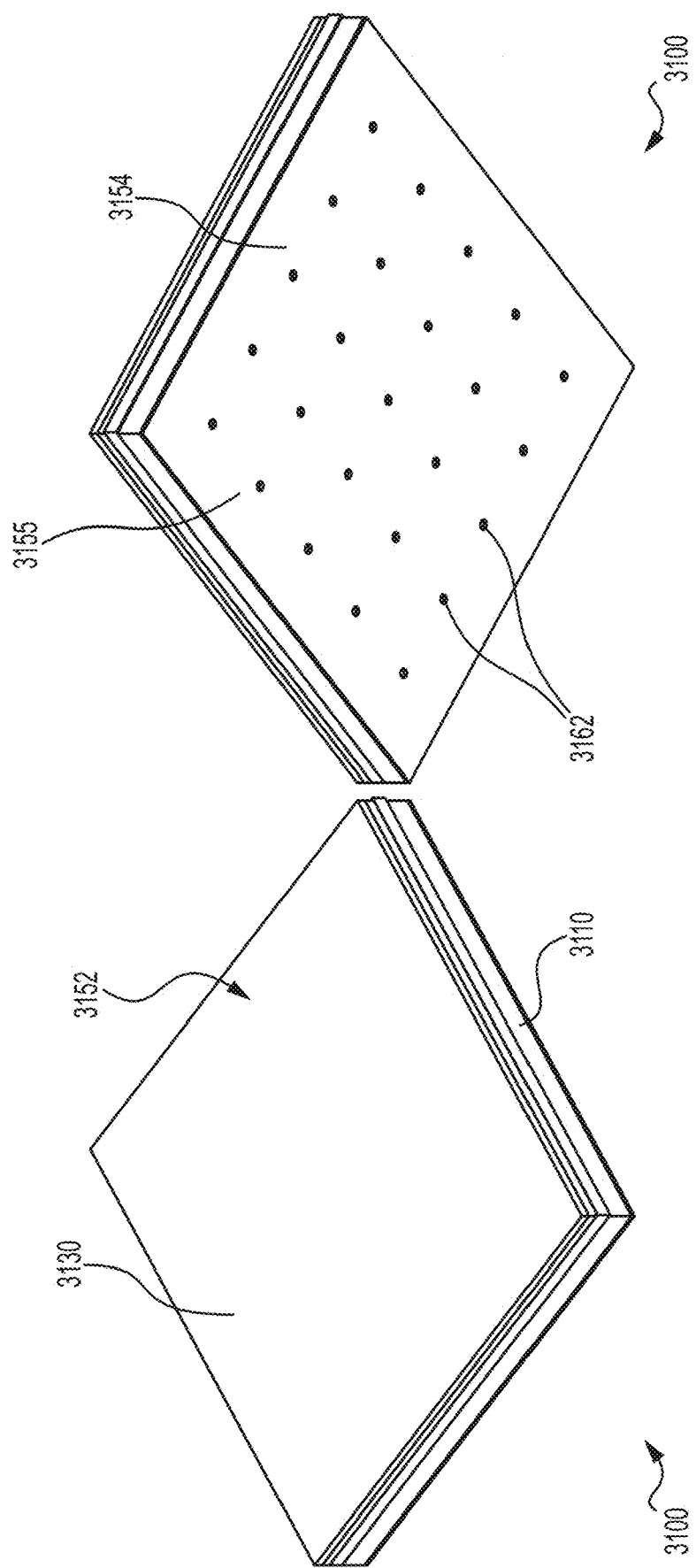
FIG. 31A depicts front and perspective views of an example variation of a sensing device embodied as a panel.
Figure 31B:
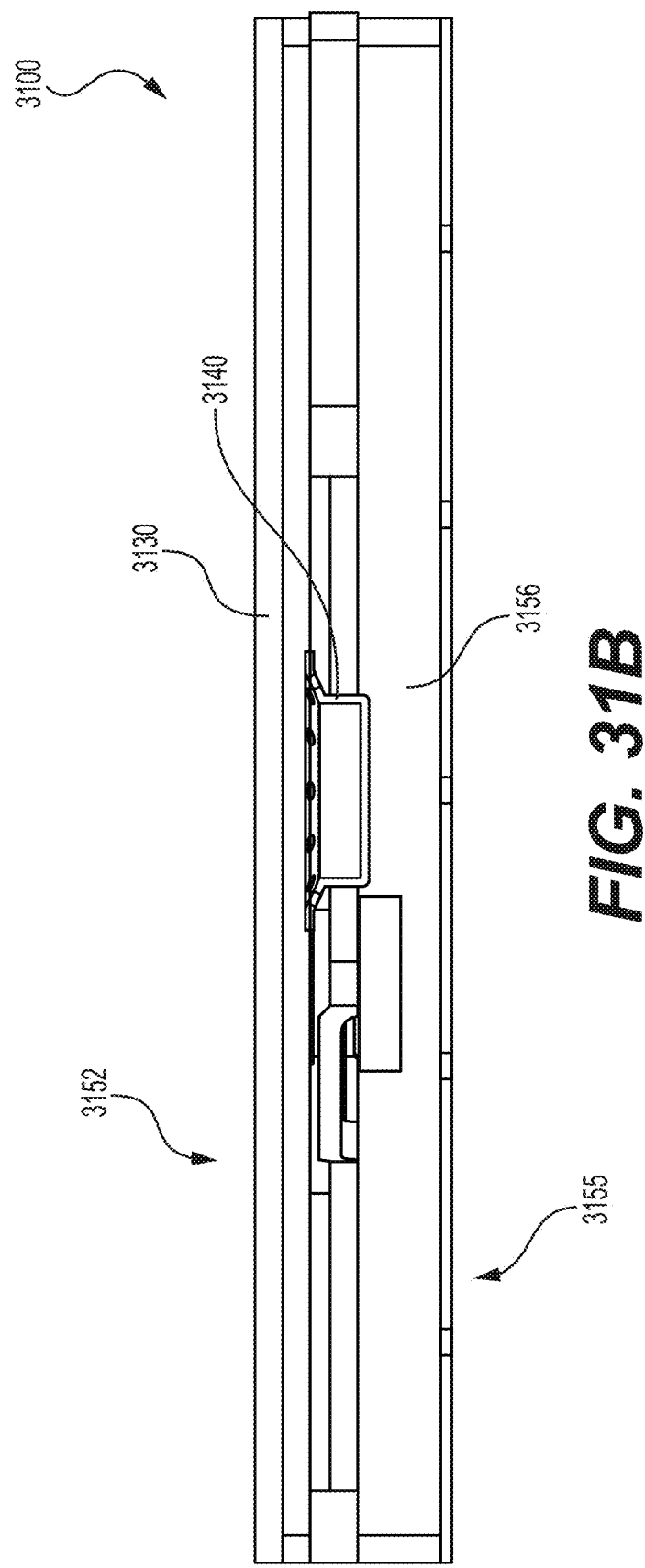
FIG. 31B is a cross-section of the sensing device of FIG. 31A.
Figure 31C:
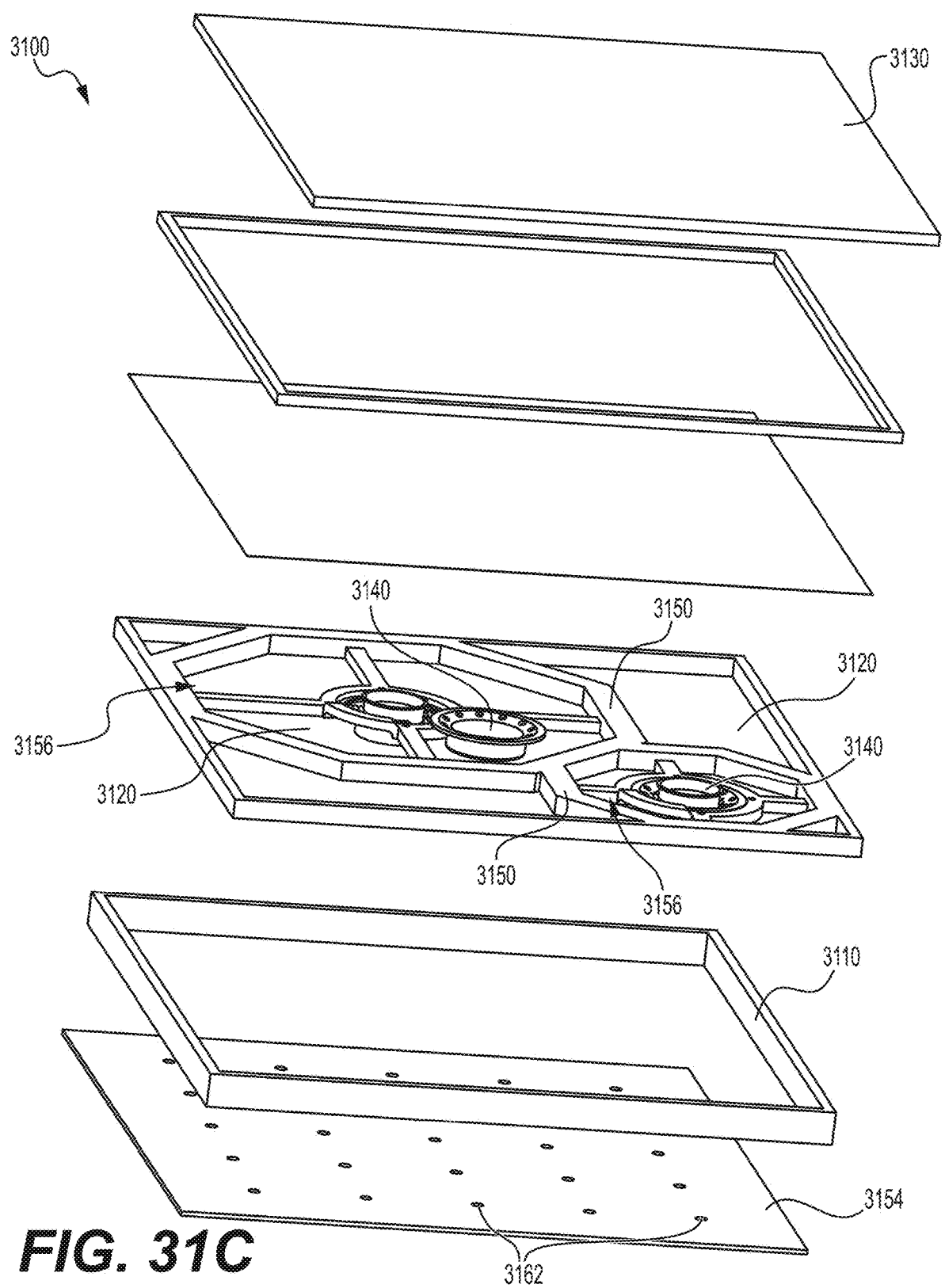
FIG. 31C depicts an exploded view of the sensing device of FIG. 31A.

Referring to FIGS. 31A-31C, in certain variations, there is provided a sensing device 3100 having a panel-like form (hereinafter referred to as "panel 3100" or "panel unit 3100"). The panel 3100 may be mountable to a support surface such as a wall, a ceiling, a doorway, etc., or be free standing. The panel 3100 may be installed in rooms, corridors, vehicles, entryways, checkpoints, doorways, vehicles, and other areas to detect sensor signals from subjects for diagnosing certain bodily conditions of the subjects. The sensing device 3100 can operate 1 cm, 5 cm, 10 cm, 25 cm, 50 cm, 100 cm, 150 cm, 200 cm, 250 cm, or 300 cm away from the subject or a clothing of the subject. The panel 3100 may be camouflaged as not to be apparent to the subject. A thickness of the panel unit 3100 may be less than 1 mm, 2 mm, 3 mm, 4 mm, 5 mm, 7.5 mm, 10 mm, 15 mm, 20 mm, 25 mm, 30 mm, 40 mm, 50 mm, or 75 mm thick.

The panel 3100 comprises a frame 3110 defining an aperture 3120, and a membrane 3130 extending at least partially across the aperture 3120 and supported by the frame 3110. A vibroacoustic sensor assembly 3140 is coupled to the frame 3110 such as by support members 3150 and configured to convert vibrations of the diaphragm 3130, such as to an analog or digital signal.

Vibroacoustic Sensor Assembly of the Panel

In certain variations, the vibroacoustic sensor assembly 3140 may be based on a voice coil type transducer, such as the vibroacoustic transducer 1600 described in relation to FIG. 16 and FIG. 17. In this respect, the vibroacoustic sensor assembly 3140 may include a conductive coil with a stationary magnet setup connected to the frame 3110. The vibroacoustic transducer may be attached to the frame 3110 by the support members 3150. The vibroacoustic transducer may be attached centrally, or asymmetrically in relationship to the frame 3110, selection of which will be described below.

In certain other variations, the vibroacoustic sensor assembly 3140 may be any type of sensor-read out element, or combinations of sensor-read out elements, such as but not limited to:

Voice coil with extremely compliant or entirely absent spider for sensitive membrane bending pickup. A compliant spider can further be shaped as a flexure to increase compliance and reduce out of plane movements. In case of an entirely absent spider the previously added spring constant of the spider is removed from the moving system. Hence, either the voice coil or magnet is integrated in the bending membrane; whichever is of lower inertia due to mass and hence less restrictive in membrane movement.

Electric Potential sensors (EPS) can pick up subtle movement of nearby objects due to the disturbance of static electric fields they cause. An EPS close to the membrane is hence able to sense the motion of the vibrating membrane. In contrast to the voice coil, such a system might not add any mass or additional spring constant to the system and hence keeps the original compliance of the membrane.

Capacitive pickup similar to capacitive microphones is a direct alternative approach to the EPS pickup, however with the need of a layer on top of the membrane with the ability to create a charge. A fixed metal plate is provided behind the membrane in close proximity to complete the two components of a capacitor with the air gap in between acting as the dielectric. The metal plate could have any size from very small to the entire size of the membrane. Further, the layer on top of the membrane can either be a conductive material that is polarized through an applied voltage (commonly known as Phantom Voltage) or could be an electret material that offers a quasi-permanent electric charge or dipole polarisation. In either case, the added layer adds mass to the vibrating membrane and hence inertia.

Magnetic field disturbance sensors are voice coil sensors, but without integration of any voice coil component within the membrane. The magnetic field of the sensor is routed through a ferroelectric layer on the membrane. Membrane vibrations modulate the magnetic field that hence induces a current in the voice coil winding resulting in a signal.

Light source (such as laser) and photodetector positioned behind the membrane. The light source is positioned to direct an energy beam to the membrane and a photodetector is positioned to detect the energy beam reflected from the membrane and to measure a change in angle of the reflected energy beam (reflected of membrane movement). The reflection angle may depend on local bending of membrane, which in turn vibrates with incoming pressure waves. The photodetector may comprise a photodiode array from which the reflection angle is determined by the specific photodiode in the array which captures the majority of the reflected signal intensity.

Strain sensor(s) can be positioned directly on the membrane surface at strategic locations to detect movement of the membrane, e.g. layers of PVDF.

Acoustic Echo Dopplers target a high frequency acoustic signal to the backside of the membrane, which is reflected into a detector. Membrane vibrations are frequency modulated into the Doppler carrier frequency, and demodulation results in a membrane vibration pickup. Acoustic Doppler could either operate in Pulsed Wave or Continuous Wave mode.

Light Tome of Flight (TOF) sensing using a light source emitting pulses and a sensor measuring the time to arrive of the reflected signal.

Laser Doppler interferometers or self-mixing interferometers utilize the doppler effect and interference. In contrast to the Acoustic Echo Doppler this light based approach results in higher SNR and amplitude resolution. Instead of using laser light, a setup could contain a Time-of-Flight radar, radar doppler or any other commonly known radar sensing technology such as Ultra-Wideband-Radar (UWB)

In addition to laser and radar, the vibration pickup could be based on any frequency of electromagnetic waves and combined with the same fundamental methodologies such as ToF and Doppler effect.

Positioning of the Vibroacoustic Sensor Assembly Relative to the Membrane

The vibroacoustic sensor assembly 3140 or other sensor read-out element can be positioned at any appropriate position with respect to edges of the membrane 3130. In certain variants, as illustrated, the vibroacoustic transducer is positioned centrally with respect to the edges of the membrane 3130. However, in other variants, the vibroacoustic transducer does not necessarily need to be in the center of the membrane 3130. Particularly if considering the membrane 3130 could be excited at higher eigenmodes there is a benefit of placing the vibroacoustic transducer off-center in any appropriate position. For example, if the voice coil transducer is placed in the center and a higher eigenmode has a node at the center, there will be no displacement at the center and no signal measured, where in reality the membrane is indeed vibrating.

For example, consider the membrane 3130 having a plurality of eigenmodes based on its geometry which will create nodes (points at which there is no displacement) on the membrane 3130. For example, if the membrane 3130 has four eigenmodes with a 2×2 configuration, there will be a node at the center of the membrane 3130. This is also the case when the membrane 3130 has two eigenmodes which also create a node (no displacement) at a central portion of the membrane 3130. In these cases, and other eigenmode situations not described, a centrally positioned vibroacoustic transducer 3140 is not optimally positioned for detecting vibrations in the membrane 3130. Accordingly, a positioning of the transducer relative to the membrane 3130 can be selected by considering the eigenmodes of the membrane 3130. In variants of the panel 3100 in which the vibroacoustic sensor assembly 3140 includes an EPIC electric potential sensor and/or a capacitive sensor, the electrodes of such sensors can be sized to cover the size of the membrane, which can minimize the localized effects of eigenmodes such as no bending/displacement of the membrane at the node. In certain other variants, the vibroacoustic sensor assembly 3140 may be configured to not sense beyond the first membrane resonance caused by the first eigenmode, which may also minimize or make redundant an effect of eigenmodes.

Frame of the Panel

The frame 3110 may be of any suitable size or shape, the dimensions and configuration of which are selected based on the desired use and the desired frequency range of detection. The frame 3110 may be constructed from any suitable material such as plastic, wood, metal, composite, glass, ceramic, or any other suitable material that can withstand the tension of the attached membrane 3130 and/or support the attached membrane 3130. Although illustrated as rectangular, the frame 3110 can be circular, oval, trapezoidal, regular polygonal, or non-regular polygonal. In certain variants, the frame 3110 is subdivided to define more than one aperture for coupling with separate membranes 3130.

Membrane of the Panel

The membrane 3130 is attached to a first side 3152 of the panel, a back cover 3153 may be provided on a second side 3155 of the panel 3100, thereby defining a cavity 3156 between the membrane 3130 and the cover 3153. The membrane 3130 is configured to vibrate at frequencies relating to a desired detection frequency range, such as the vibroacoustic range of the subject. One or more of the parameters of the material, weight, size and tension of the membrane 3130, as well as the shape or size of the cavity 3156 behind the membrane 3130, may be tailored to achieve the desired frequency range.

Larger membranes 3130 with low stiffnesses tend to pick up low frequencies well, whereas stiffer membranes pick up higher frequencies but attenuate lower ones. The weight of the membrane 3130 itself or anything connected to the membrane in general causes inertia during vibrations, which oppose and attenuate incoming vibroacoustic signals (and might cause increased reflection of the acoustic wave). A voice coil transducer connected to the membrane 3130 also means that the spider component represents an additional spring in the system; which adds to the membrane stiffness and decreases the compliance of the sensor pickup. The attached voice coil portion may also add inertia to the membrane.

For example, more compliant membranes give good signal-to-noise ratio favoring low frequencies (e.g. 0-100 Hz only). Similarly, larger membranes favor lower frequencies as well. Smaller membranes 3130 can detect high bandwidth or higher frequencies. Thicker membranes 3130 can detect high bandwidth, higher frequencies due to generally higher membrane bending stiffness. Thinner membranes 3130 can detect lower frequencies as they tend to be more compliant if all other parameters equal. Higher tension membranes can detect high bandwidth, less deflection which may lead to lower sensor amplitudes and hence signal-to-noise ratio. Lower tension membranes 3130 can detect lower bandwidth as more compliant, high deflection caused by same incoming acoustic wave (good signal-to-noise ratio).

Generally, a tradeoff is required between different values of the bending stiffness and hence ability to pick up low amplitude waves. Low bending stiffness results in a compliant membrane able to pick up waves of very low amplitudes (e.g. when <20 Hz). However, the resonance frequency and subsequent roll-off of a very compliant membrane is very low and hence obstructing the ability to pick up higher frequencies, particularly above some threshold frequencies, e.g. >100 Hz. High bending stiffness in contrast results in higher resonance modes of the membrane giving the ability to pick up higher frequencies at the expense of small amplitude lower frequencies.

In certain variants, as an alternative to finding a trade-off for an overall frequency range, the panel 3100 can be divided into smaller sub-panels 3156 (FIG. 31C), each sub-panel 3156 having the same or differing membrane 3130 stiffnesses and a respective transducer, for a particular optimum frequency range. In addition, the sub-panels 3156 can be of different sizes, e.g. the membrane 3130 for <20 Hz pickup may be larger in surface area than the membrane 3130 for detecting >100 Hz. It will be appreciated that panels 3100 without sub-panels as well as panels 3100 with sub-panels 3156 are within the scope of the present technology, according to certain variations.

In this manner, by using sub-panels 3156, a broader overall frequency range may be detected. In certain variations, the sub-panels may be separate from one another. In other variations, the configuration of the sub-panels illustrated in FIG. 31C may differ from the configuration as illustrated, in a manner known by persons skilled in the art. In certain variations, the panel 3100 may be considered to comprise multiple transducers operating on the same or different modes of operation. The multiple transducers may be arranged as an array.

In certain variations, the membrane 3130 is a compliant material such as a thermoplastic or thermoset elastomer. In other variations, the membrane 3130 may comprise metal, inorganic material such as silica, alumina or mica, textile, fiberglass, Kevlar™, cellulose, carbon fiber or combinations and composites thereof. In certain variations, the membrane 3130 is provided with a protective layer which may comprise an acoustically transparent layer, such as foam, positioned on an outer facing side of the membrane 3130 at a distance of about 1 mm to about 100 mm.

The membrane 3130 may be attached to the frame 3110 in any manner, such as by adhesive. A profile of the membrane 3130 when attached to the frame 3110 may be planar, convex or concave. If the membrane 3130 is under tension, it may be attached to the frame 3110 in a manner to apply a homogenous tension or different tensions along different orthogonal axes. The membrane 3130 may be a stretched sheet. The membrane 3130 may, in certain variations, be self-supporting or under compression instead of under tension. A damping material may be provided to dampen movement of the membrane.

With respect to the cavity 3156, certain variants of the panel 3100 provide differing extents of sealing of the cavity 3156 by the back cover 3154. For example, in certain variants, the back cover 3154 may be omitted. In this case, pressure on either side of the membrane 3130 can equalize quickly. However, a membrane 3130 can generally only bend/vibrate if there is a difference in pressure between the two sides. Since particularly at low frequencies the air has plenty of time to continuously equalize the pressure on the sides of the membrane 3130 upon the incoming pressure wave it is impossible to measure such low signals. It is then also obvious that static pressure cannot be measured with an open back setup.

In certain other variants, in which the back cover 3154 is included on the panel 3110, the back cover 3154 may function to seal the cavity 3156 to different extents. At one extreme, the back cover 3154 may comprise a solid piece which seals the cavity 3156. This can be considered like a pressure sensor which measures static pressure against the inside reference pressure. It measures down to DC (static pressure), but the static pressure opposes membrane 3130 movement to AC signals particularly the higher the input vibration amplitude. In addition, a completely sealed cavity causes the membrane 3130 to bend outwards or inwards when outside pressure is not equal to inside pressure, e.g. changing altitude. Result may be low Signal-to-Noise Ratio (SNR) at dynamic (AC) measurements at higher frequencies and larger amplitudes, depending on the volume of the cavity.

In certain other variants, the back cover 3154 includes openings 3162 for permitting airflow therethrough to the cavity 3156. The size, count and location of these openings 3162 can be optimized according to the desired frequency detection range and acceptable signal-to-noise ratios, and can be also seen as a cavity impedance optimization with the cavity volume itself. For low frequency detection (less than 20 Hz), the low frequency pressure waves give plenty of time for creating an equilibrium on either side of the membrane 3130. So the configuration of the openings 3162 need to take into account a tradeoff between letting air in/out (depending on positive or negative pressure waves) from inside the cavity 3156 to reduce pressure, and delaying the equilibrium process long enough to catch very low frequency pressure waves. Hence, the pressure on either side of the membrane 3130 will equalize at some time constant and vibrations at frequencies corresponding to a time period below that equilibrium time constant can be measured. In certain variants, dimensions of the panel are about 7 inches (width), about 9.75 inches (height), and about 0.5 inches (depth). Experimental data obtained with this variant sensing device is presented in Example 9.

The openings 3162 can have any shape (round, square, rectangular) and size and count. The openings can be of structure instead of simple opening, such as tubes of various diameter and lengths like commonly present in acoustic subwoofers. Structures as opening can be anything that allows flow of air between the cavity and outside environment, son not only limited to tubes. In an example embodiment the back cover 3154 could have a single small tube to equalize for inside DC pressure in a low frequency optimized panel with a large cavity.

In certain other variants, the cavity 3156 inside the panel 3100 can be divided into two lateral sections. The divider between the two cavities is perforated based on design needs to allow for air exchange between the two cavities. In one variation the cavity close to the membrane 3130 is a smaller one and the cavity towards the back is the bigger one, serving as an air 'reservoir'. The overall unit is sealed off from the environment entirely, or sealed with a small hole or tube to allow pressure equalization with the environment in case of slow and nearly DC type of pressure changes due to e.g. altitude change. The dual cavity setup is particularly important if a capacitive or Electric Potential sensing method is used. For example, in the capacitive sensing approach the conductive plate behind the membrane 3130 needed to form the capacitor may be of similar size as the membrane to maximize sensitivity. As this plate should be close to the membrane to maximize capacitance between membrane and plate the cavity formed is small, causing air pressure to rise under a vibrating membrane when a plate without any perforation is used. Hence, perforation in the plate connects the small cavity to the bigger back cavity for reduced pressure.

In summary, the vibroacoustic detection range of the sensing device 3100 when embodied as the panel 3100 can be considered as a function of various parameters relating to: the membrane 3130 (e.g. stiffness, material, surface area, etc.), sensor element reading the vibration (e.g. voice coil, capacitive, optical, acoustic (echo doppler), radar, etc.), pressure equalization based, for example, on size of cavity 3156 and the openings 3162 of the back cover 3154.

Front Cover of the Panel

Figure 31D:
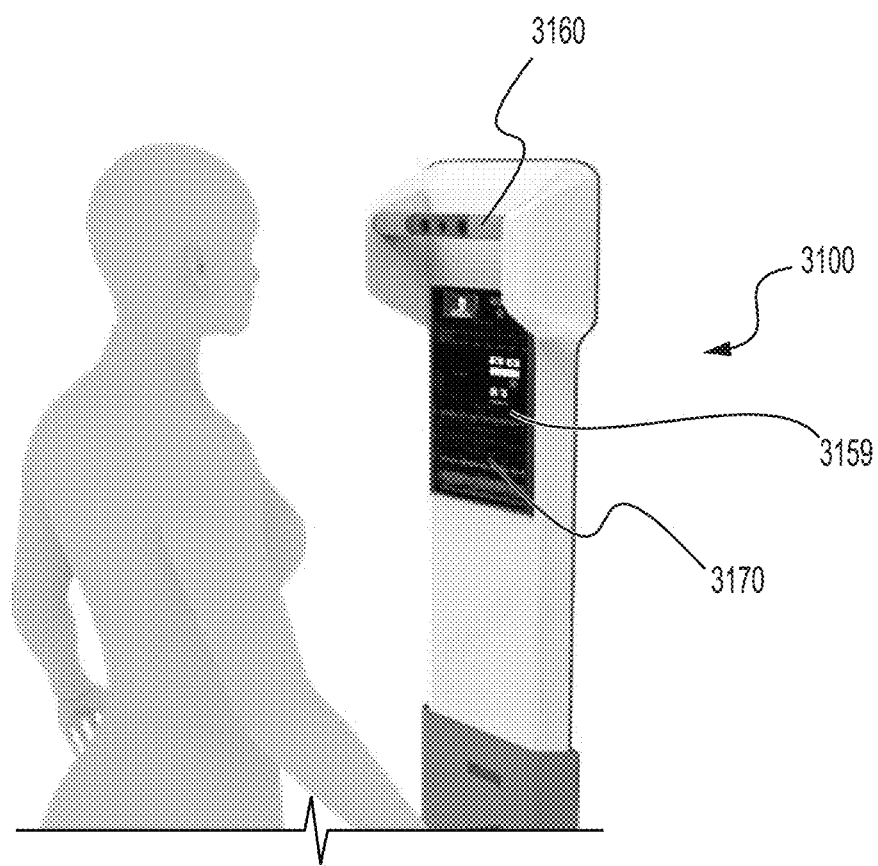
FIG. 31D depicts a front perspective view of another example variation of a sensing device embodied as a panel.
Figure 31E:
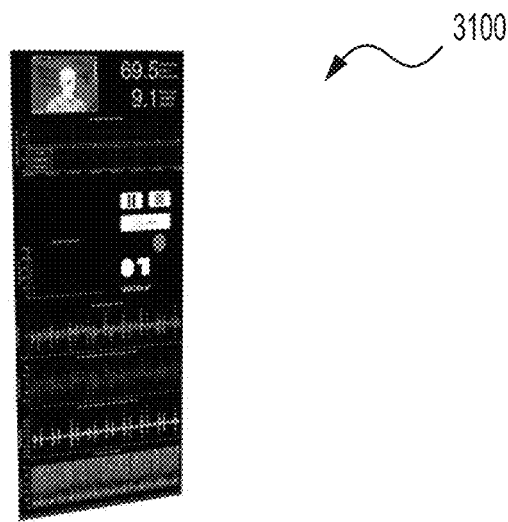
FIG. 31E depicts a close-up of a portion of the sensing device of FIG. 31D.

Other variants of the sensing device 3100 having a panel-like form are illustrated in FIG. 31D and FIG. 31E. A front cover 3159 is provided at the first side 3152 of the panel 3100. The front cover 3159 may be more rigid than the membrane 3130. The front cover 3159 may provide environmental and mechanical protection of the membrane 3130. The front cover 3159 may have any type of surface finish or configuration. For example, in certain variants, the front cover 3159 is highly reflective like a mirror. In certain variants, the front cover 3159 may include an output display unit 3170. The output display unit 3170 may include any manner of markings and indicators such as one or more of: the likelihood of the subject having a given bodily condition (e.g. displayed as a red or green light or other indicator), at least a portion of the data obtained by the sensors (e.g. physiological data of the subject such as ECG readings, environmental data). In certain variants, the front cover 3159 may be at least partially a mirror and at least partially an output display such as the output display unit 3170. The front cover 3159 may be configured to extend substantially vertically when supported on a support surface such as the wall or the floor. The front cover 3159 may be perforated to permit sound pressure come through without much attenuation, with the perforation down to micrometer size.

Additional Sensor Modules

The panel unit 3100 may incorporate one or more other sensor assemblies based on non-contact detection of signals associated with the subject or the environment, such as, without limitation, one or more of the echo doppler sensor module, the kinetic sensor module, temperature sensor module, VOC sensor module, machine vision sensor module, contextual sensor module, etc. The sensor modules of the panel unit 3100 may be configured to monitor or detect, for example, Covid-19 infection in the subject by detecting signals related to respiratory function; body temperature; gastrointestinal tract function; bladder motility; water/fluid retention (edema) in legs; peripheral vascular disease, etc.

Base Unit

Figure 32A:
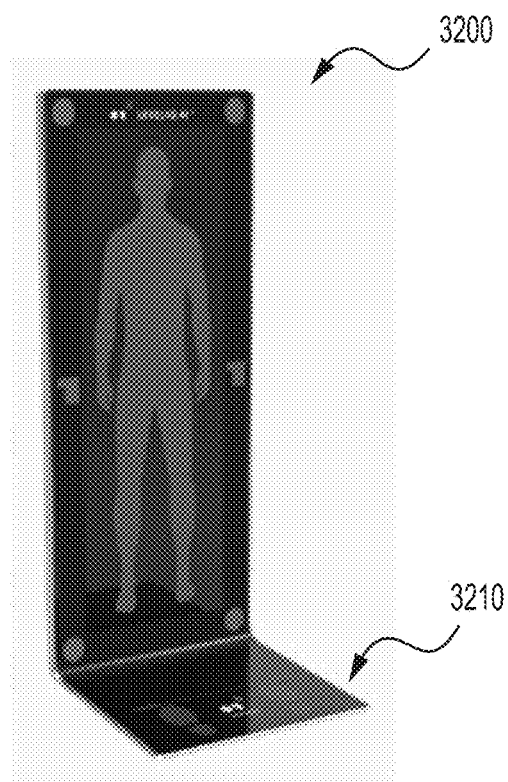
FIG. 32A depicts a perspective view of an example variation of a sensing device embodied as a panel and including a base unit.
Figure 32B:
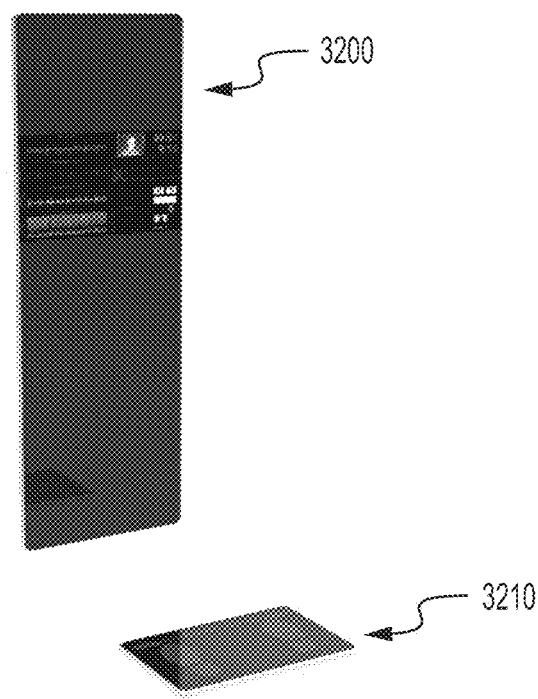
FIG. 32B depicts an example variation of the sensing device of FIG. 32A.

Turning now to FIGS. 32A and B, in addition to a panel-like sensing device 3200 (also referred to as "panel unit 3200") which can correspond to the panel unit 3100, there is provided a base unit 3210 incorporating one or more sensor modules. The one or more sensor modules may be any one or more of the sensor modules as described herein such as the vibroacoustic sensor module, the bioelectric sensor module, the capacitive sensor module, etc. The panel-like sensing device 3200 and the base unit 3210 may be an integrated single unit (FIG. 32A), or may comprise separate units spaced from one another (FIG. 32B). The panel unit 3200 and the base unit 3210 may be positioned orthogonally with respect to each other. Advantageously, this orientation may enable the sensor modules associated with the panel unit 3200 and the base unit 3210 to detect physiological parameters along different planes of the subject's body, providing an ability to obtain complementary data sets for the bodily condition determination.

The base unit 3210 may be adapted to support a body part of the subject, such as a foot, a leg, an arm, a back, a chest, a head, etc. It will be appreciated that in these cases, the system 100 provides both a contactless signal detection (from the panel unit 3210) and a contact-based signal detection (from the base unit 3210), whether direct skin contact or indirect contact through clothing and/or footwear.

The base unit 3210 may comprise a platform arranged to be supported on a support surface such as the ground in use and having an upper surface 3220 for the subject to stand on. Markings may be provided on the upper surface 3220 to indicate where the subject is to place its feet. As seen in the figures, the base unit 3210 may be relatively flat or have a stepped structure. The one or more sensor assemblies contained in the base unit 3210 may be arranged to obtain data from the subject while the subject is wearing footwear such as shoes or socks. In certain variations, the base unit includes a bio-electric sensor assembly. Other sensor assemblies may include those that detect vascularization, heat, weight, etc. The base unit 3210 may also be arranged to emit one or more signals to the subject. For example, the base unit 3210 may be arranged to vibrate in order to detect a physiological response of the subject to the vibration. The base unit 3210 may include a BCG sensor module.

In certain variations, the sensing device 3200 comprises the panel unit 3100 embodied with the configuration of FIG. 32A or FIG. 32B and optionally including the base unit 3210. The panel unit 3100 includes a vibroacoustic sensor module, an echo doppler sensor (continuous wave), optionally a heat sensor module (e.g. including a thermopile with an accuracy of mKelvin to 1 Kelvin, and optionally a black body reference to calibrate the temperature readings based on environmental temperature); a 3-D machine vision camera; optionally one or more environmental sensors (e.g. one or more of: ambient temperature, GPS, barometric pressure, altitude, ambient noise, light, etc.); optionally a MEMS microphone. The panel unit and the sensor modules are configured such that the panel unit can be positioned substantially vertically so that the subject can stand in front of it. The inclusion of an Echo doppler sensor module with the voice coil sensor module can improve a signal to noise ratio of the detected vibroacoustic signal.

The base unit 3210 includes a marker on an outer surface indicating where the subject should stand. In certain variations, the subject is invited to stand with his/her chest facing the upright unit 3325. The marker may be an image of feet. Optionally, the base unit 3310 may also include the capacitive sensor module (for example to measure galvanic skin response), and optionally a BCG sensor module.

In certain variants, an adjustment mechanism is provided within the panel unit to adjust a position of one or both of the Echo Doppler sensor module and the vibroacoustic sensor module to optimise a height of the sensor modules for optimal or adequate signal detection. In certain variants, the adjustment mechanism permits an up-down position adjustment. In certain variants, the adjustment mechanism may also permit a side-to-side position adjustment. The adjustment mechanism may comprise a linear motion system (not shown). Additional sensor modules (such a 3D camera) may be included to detect a height of the subject, and automatically adjust the height of one or both of the Echo Doppler sensor module and the vibroacoustic sensor module. The system 10 may be configured to obtain data from the 3D camera (machine vision sensor module) to detect a height of an eye of the subject, and to estimate a height of the torso of the subject. If one or both of the Echo Doppler sensor module and the vibroacoustic sensor module are not aligned with the torso height of the subject, the system 10 may be configured to adjust the height of one or both of the Echo Doppler sensor module and the vibroacoustic sensor module using the linear motion system. Optionally, the sensing device may be provided with a heat sensor module for detecting a temperature of the subject, in communication with the 3D camera for detecting a location of a tear duct of the subject. A light, such as in the form of a ring, may be provided to illuminate the subject. Illuminating the tear duct of the subject can facilitate locating the tear duct and measuring the temperature thereof. In certain variants, the heat sensor module may be configured to move to target the located tear duct. In other variants, the system 10 may be configured to receive data regarding the chest height of the subject, or otherwise a desired height of the Echo Doppler sensor module and/or the vibroacoustic sensor module, and to cause the adjustment mechanism to move the Echo Doppler sensor module and/or the vibroacoustic sensor module in response. Adequate signal detection from the subject can be obtained in about 5 seconds to about 15 seconds, and in some variations, 10 seconds.

Gateways/Kiosk/Walkthrough

Figure 33A:
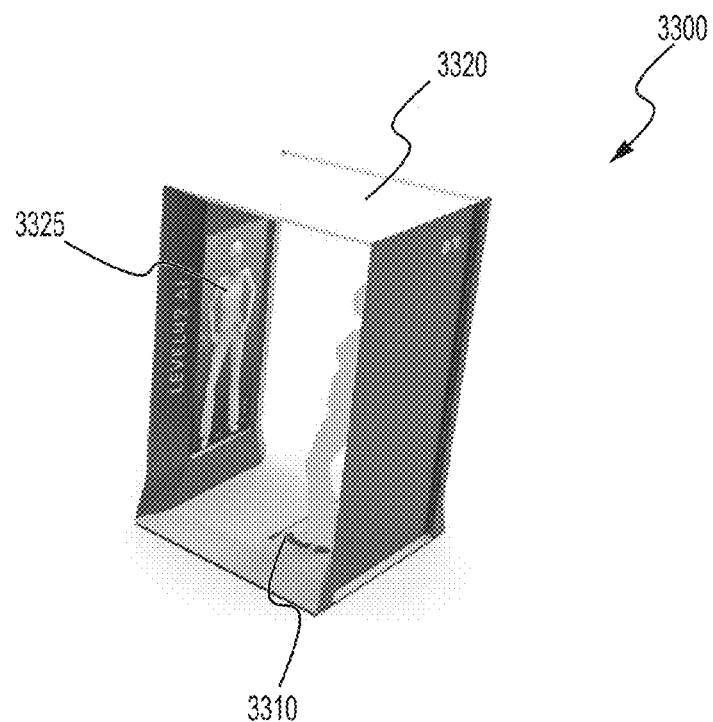
FIG. 33A depicts an example variation of a sensing device embodied as a gateway.
Figure 33B:
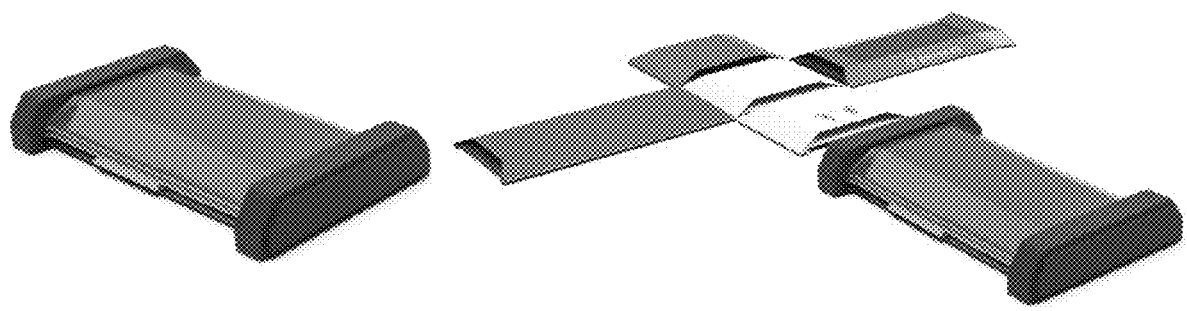
FIG. 33B depicts partially folded and fully folded example views of the sensing device of FIG. 33A.
Figure 33C:
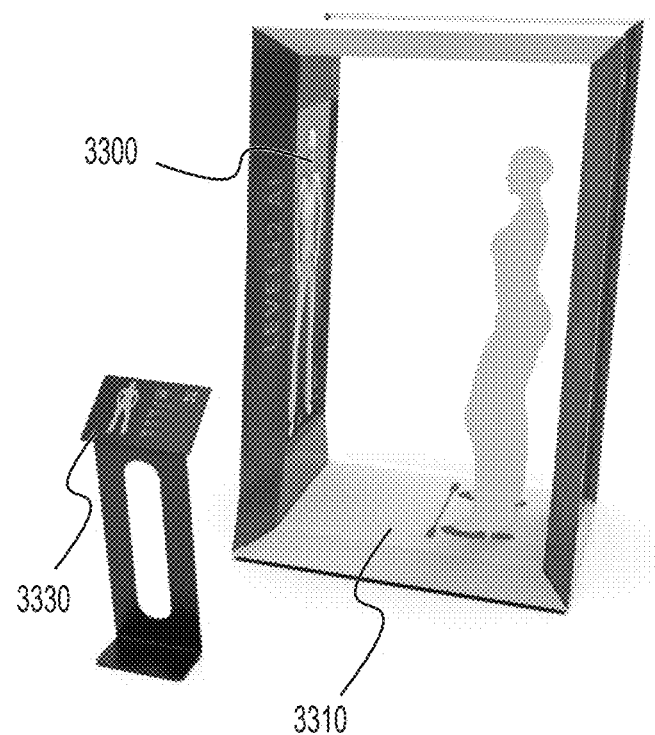
FIG. 33C depicts the sensing device of FIG. 33A and including an output display unit.
Figure 33D:
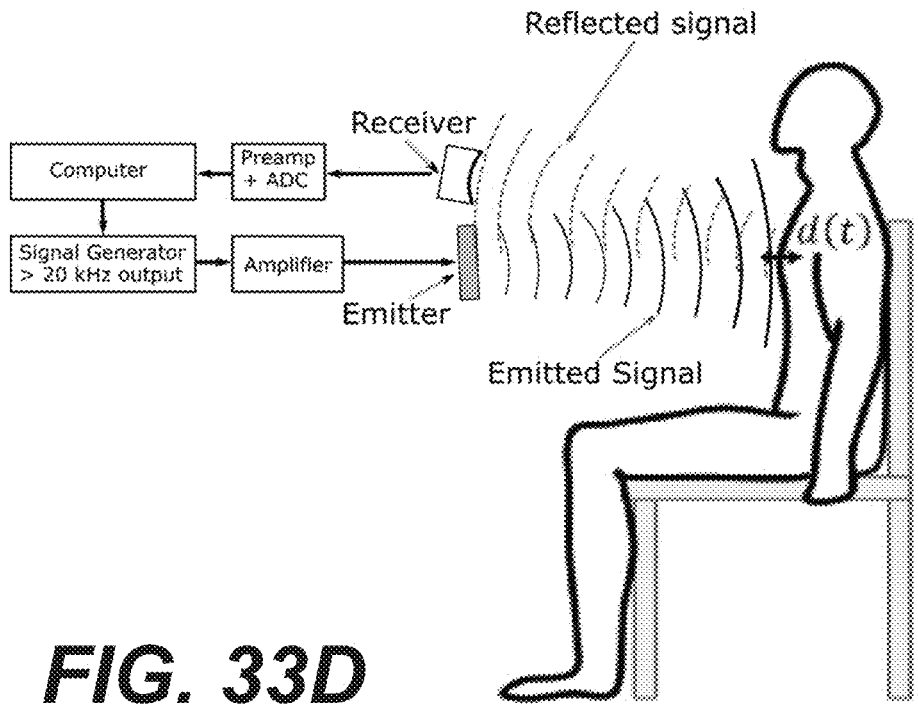
FIG. 33D-G are schematics of emitted and received signals in example variations of sensing devices including an Echo Doppler sensor module, in which the sensing device includes a single emitter and receiver (FIG. 33D); two emitters and a single receiver (FIG. 33E); two receivers and a single emitter (FIG. 33F); two receivers and two emitters (FIG. 33G).
Figure 33E:
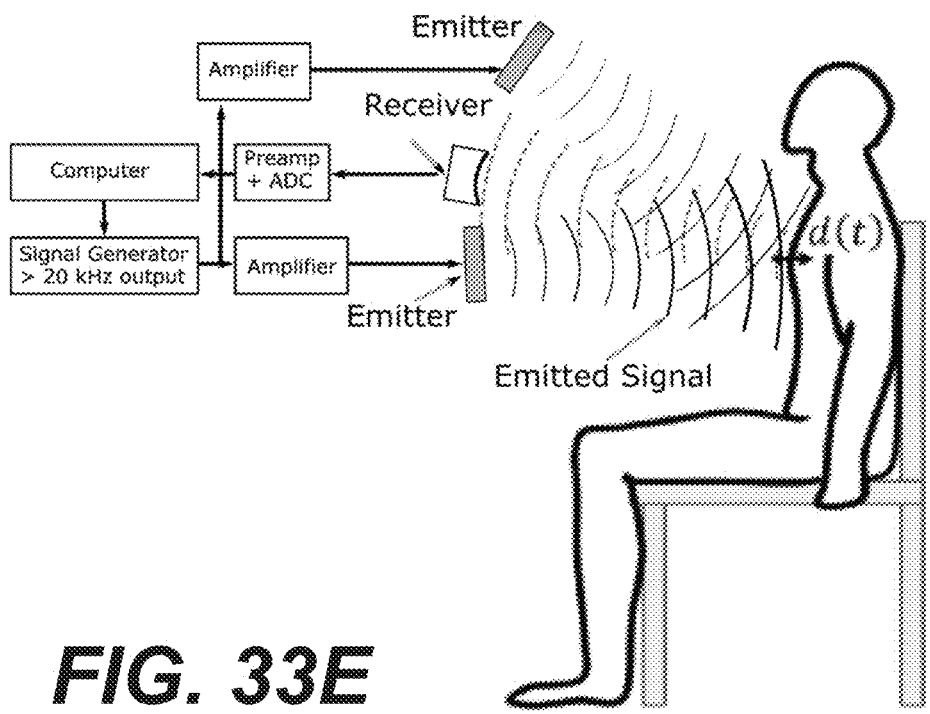
Figure 33F:
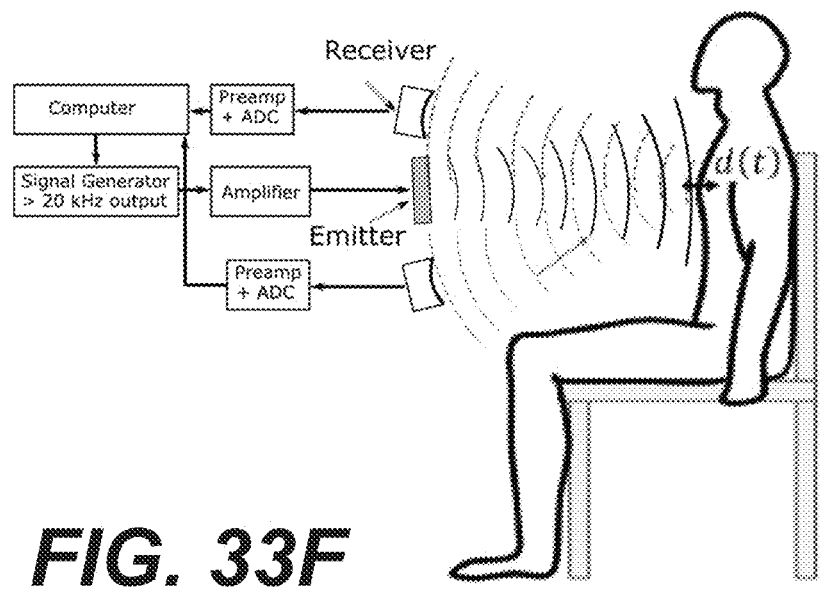

A yet further variation of the form-factor of the sensing device is illustrated in FIG. 33A-C, in which there is provided a sensing device 3300, such as the sensing device 3100 or 3200, incorporated within a gateway configuration. This is also referred to as a "kiosk" configuration. The gateway configuration may comprise a base unit 3310 such as the base unit 3210, a top unit 3320, and an upright unit 3325. Other support structures may be provided. The sensing device 3300 is configured for non-contact measurement of vibroacoustic data of the subject proximate the sensing device 3300, as well as other sensor data. The top unit 3320 may be arranged to be positioned proximate the subject's head, such as above the head. The top unit 3320 may include sensors such as those associated with EEG. The top unit 3320 may have an adjustable height from the floor or from the base unit 3310 to accommodate subject's with different height.

In certain variations, the upright unit 3325 is configured to house one or more sensor modules, such as one or more of: a vibroacoustic sensor module based, for example, based on the voice coil transducer 1600 of FIG. 16; a continuous Echo Doppler sensor module (alternatively can also be pulsed wave); a heat sensor module with an accuracy of mKelvin to 1 Kelvin (such as a thermopile heat sensor module), and optionally a black body reference to calibrate the temperature readings based on environmental temperature; a MEMS microphone (optional); environmental sensors (optionally one or more of: ambient temperature, GPS, barometric pressure, altitude, ambient noise, light, etc.); 3-D machine vision depth camera; and optionally a capacitive sensor module, such as a charge plate, to measure galvanic skin response. This can be embodied as the base unit for the subject to stand on.

Figure 33G:
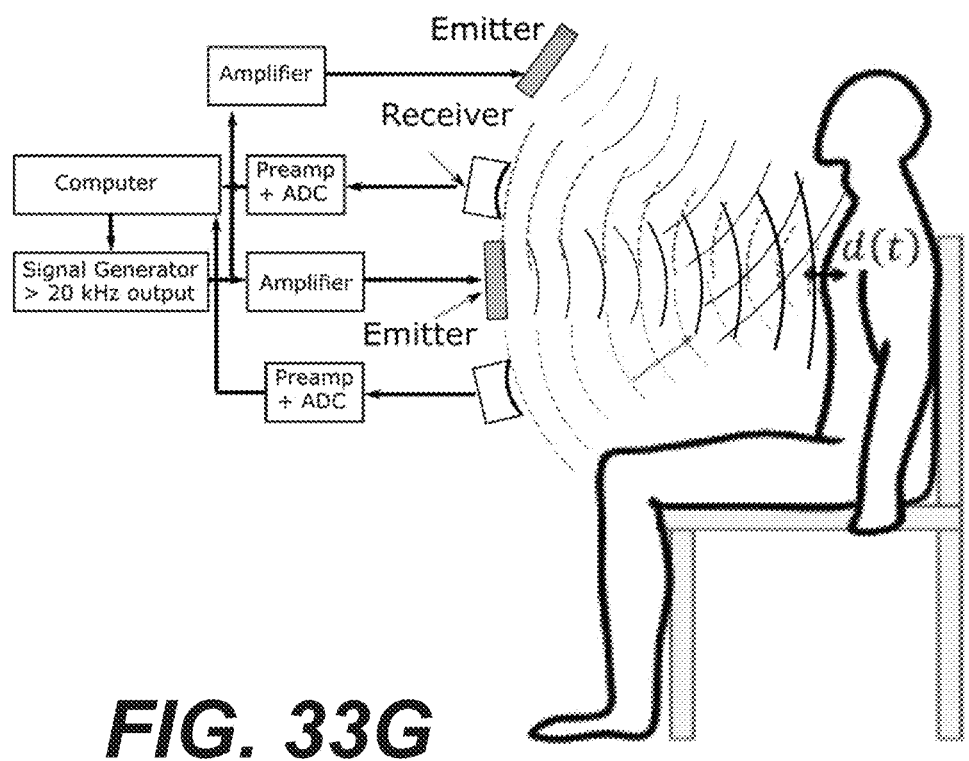

In the case of variants including the echo doppler sensor module, the echo doppler sensor module may comprise any combination of emitter and receiver components, such as one emitter and one receiver (FIG. 33D), two emitters and one receiver (FIG. 33E), one emitter and two receivers (FIG. 33F), two emitters and two receivers (FIG. 33G). In variants with dual emitters, an interference pattern that concentrates on the plane spanned by the chest of a person may be achieved and reflection of an amplified signal from that area. Surrounding walls, on the other hand, may reflect an unamplified signal to increase a signal-to-noise ratio. In variants with dual receivers, a dual receiver may allow to add a directional preference to the incoming signal such that the signal from the person's chest is amplified over incoming signals from the surrounding area, similar to directional microphone arrays. The echo doppler sensor modules can be functioning as any one of CWD, PWD or just Time-Of-Flight. FIGS. 33D-33G demonstrate the signal directionality when the echo doppler sensor module is positioned in a substantially vertical unit, such as the panel unit component of the gateway.

In certain variants, the signal-to-noise ratio may be adjusted by optimizing the ultrasound carrier frequency. There is a range of feasible ultrasound frequencies with frequency dependent attenuation characteristics. Overall, the attenuation of ultrasound waves is exponential over distance, but also exponential at increasing frequencies. By choosing a higher ultrasound carrier frequency, the attenuation of reflected signals of a wall further away than the subject will be exponentially higher than at a lower frequency. As reflected signals are undesired and considered noise, the reduced impact improves the signal-to-noise-ratio of the desired signal which is reflected off the subject.

For example, when a subject is sitting 50 cm away from the Echo Doppler sensor module, there is a total ultrasonic signal path of 1 m (twice the distance). A wall behind the subject is 2 m away from the Echo Doppler sensor module with a total signal path of 4 m.

Figure 33H:
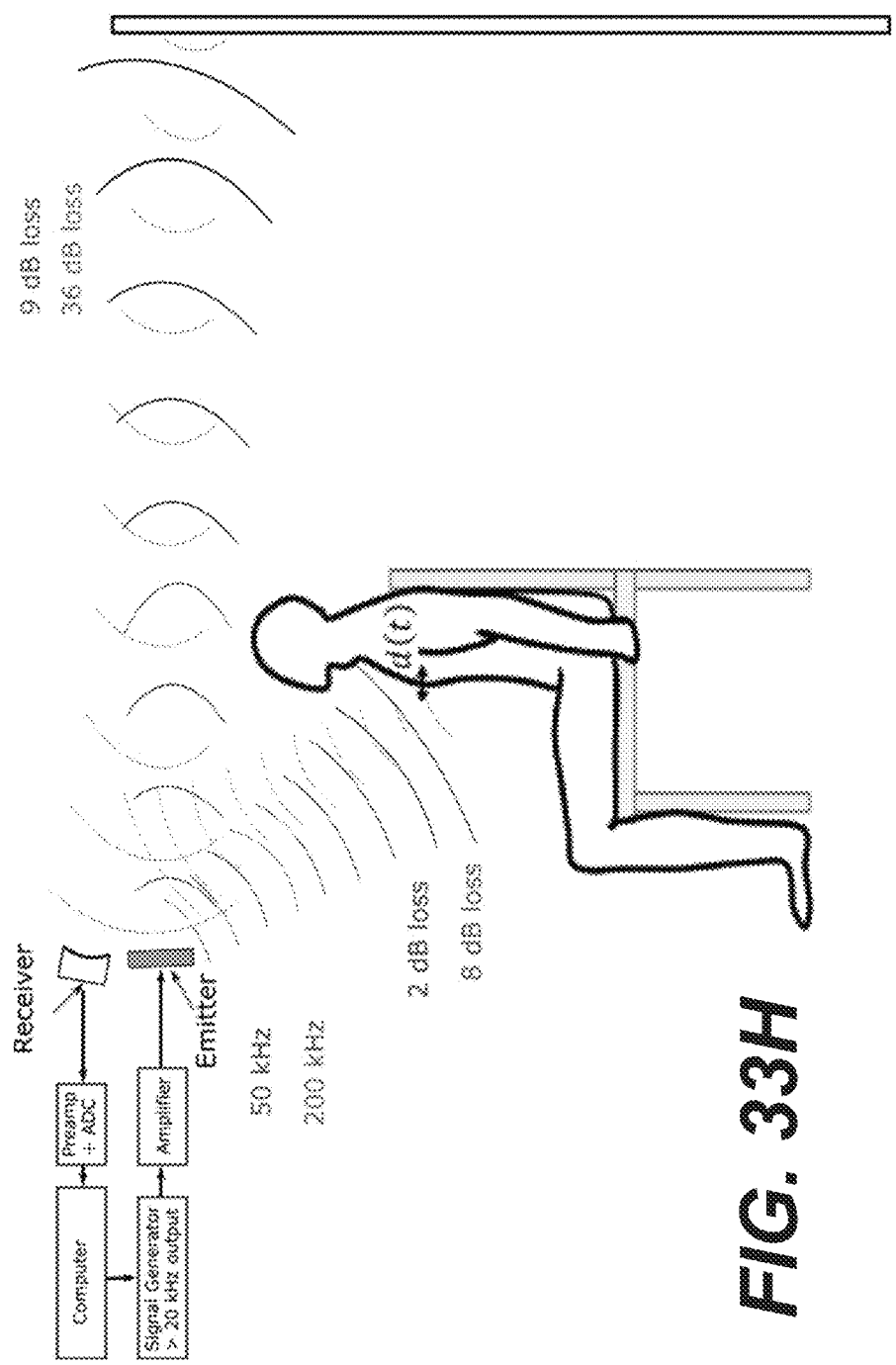
FIG. 33H depicts the sensing device variation of FIG. 33D and including example losses.

Referring to FIG. 33H, a 50 kHz carrier signal attenuates at about 2 dB/m at room temperature. This results in about 2 dB attenuation for the signal reflected of the subject, and about 8 dB attenuation for the signal reflected off the wall. Hence, when the signals combine again in the ultrasound receiver the difference between the two is 6 dB, meaning the wall reflected signal is 50% of the amplitude (or 25% of the power) of the subject's signal, which is a very significant disturbance on the signal.

In contrast, when choosing a 200 kHz carrier the attenuation is about 9 dB/m at room temperature, resulting in about 9 dB attenuation for the signal reflected of the subject, and about 36 dB attenuation for the signal reflected off the wall. The difference between the two once combined is 27 dB, meaning the wall reflected signal is 4.5% of the amplitude (or 0.2% of the power) of the subject's signal. Since the subject's signal is attenuated by 9 dB, which corresponds to about 30% of the original amplitude—or 10% of original power—either the transmitter signal could be further amplified, or amplification added after receiving the signal. However, since amplification is a linear operation on the entire signal the improved signal-to-noise ratio due to exponential loss remains.

By way of background, the emitted ultrasound signal (Carrier signal) can be defined as:

$$s_e(t) = A_c \cos(\omega_c t),$$

with $A_c$ the carrier magnitude, $\omega_c$ the carrier angular frequency based on $\omega_c = 2\pi f_c$ and $s_e$ the emitted signal. The emitter signal is frequency modulated by the chest vibrations and the received signal including Doppler shift results in:

$$s_r(t) = A_c \cos\left(\omega_c t + \frac{2}{c}\omega_c d(t)\right),$$

where c is the velocity of sound in the medium used, such as about 345 m/s in air at room temperature, and d(t) the displacement of the skin on the body location targeted. Demodulation of the received signal by the ultrasound carrier $s_e(t)$ results in the demodulated signal:

$$s_d(t) = A_c \frac{2\omega_c}{c} d(t).$$

Solving for the chest displacement hence leads to:

$$d(t) = \frac{c}{2A_c \omega_c} s_d(t).$$

Sensor Module Positioning

In certain variants, the Echo Doppler sensor module and the vibroacoustic sensor module are both included in the upright unit of the gateway sensing device 3300 or the sensing device 3200 or the sensing device 3100. Both sensor modules are positioned at approximately chest height of an average subject. In certain variants, an adjustment mechanism is provided within the upright unit to adjust a position of one or both of the Echo Doppler sensor module and the vibroacoustic sensor module. In certain variants, the adjustment mechanism permits an up-down position adjustment. In certain variants, the adjustment mechanism may also permit a side-to-side position adjustment. The adjustment mechanism may comprise a linear motion system (not shown). Additional sensor modules (such a 3D camera) may be included to detect a height of the subject, and automatically adjust the height of one or both of the Echo Doppler sensor module and the vibroacoustic sensor module. The system 10 may be configured to obtain data from the 3D camera to detect a height of an eye of the subject, and to estimate a height of the torso of the subject. If one or both of the Echo Doppler sensor module and the vibroacoustic sensor module are not aligned with the torso height of the subject, the system 10 may be configured to adjust the height of one or both of the Echo Doppler sensor module and the vibroacoustic sensor module using the linear motion system. In other variants, the system 10 may be configured to receive data regarding the chest height of the subject, or otherwise a desired height of the Echo Doppler sensor module and/or the vibroacoustic sensor module, and to cause the adjustment mechanism to move the Echo Doppler sensor module and/or the vibroacoustic sensor module in response.

In certain variants, the receiver and emitter of the echo doppler sensor module each have specific signal characteristics depending on angle. In certain variants, the echo doppler can function within a range of about to +90 to −90 degrees. In some other variants, the echo doppler can function within a range of about 360 degrees. In other variants, the echo doppler sensor module is configured to function within a range of about +−45 degrees to both focus the signal energy on a smaller volume as well as reduce reflections all around.

In certain variants, the echo doppler sensor module comprises a receiver component such as an ultrasound microphone, such as avisoft-bioacoustics, CM16/CMPA, or a MEMS microphone such as invensense ics-41352/. In certain variants, the echo doppler sensor module comprises an emitter component, such as Prowave 400EP250, or Prowave 400st-R160.

Modularity

In variants of the gateway-like form factor of the sensing device, the units of the gateway (upright, top and base units) may be configured as modular allowing for components to be flat-packed or otherwise compacted for ease of mobility and transportation in between uses (FIGS. 33A-C). To this end, the one or more parts of the gateway set up may reflect a tessellation pattern that naturally allows for the efficient folding and unfolding of the components.

One such folding pattern, known as the Miura-ori, which is a periodic way to tile a plane using a simplest mountain-valley fold in origami, is used as a basis of the tesselated pattern of the gateway components. A folded Miura can be packed into a flat, compact shape and unfolded in one continuous motion, making it ideal for packing rigid structures like solar panels. It also occurs in nature in a variety of situations, such as in insect wings and certain leaves. One or more of the panel unit, base unit and top unit may implement the tessellation pattern.

In certain variations, one or more accessories may be provided, such as beacons or transducing patches, which can be fitted to the subject, and be in communication with the processor. A beacon is a device which is attached to a part of the subject's body that facilitates the sensing of a particular state, such as a state of motion or pose. Over the last decades, state-of-the-art techniques and algorithms have been developed for cooperative and uncooperative pose determination by electro-optical (EO) sensors. EO sensors have a low power consumption and can be used to estimate all pose parameters. Consequently, such sensors are the preferred instruments for this application. In general, EO sensor systems can be classified as passive systems, systems consisting of single (monocular) or multiple (stereo) cameras, and active light detection and ranging (LIDAR) systems. Among these systems, monocular vision systems have the lowest hardware complexity and cost and can be used for remote monitoring. A stereo vision system uses more than one camera, enabling it to acquire three-dimensional (3D)

information about the target. However, monocular and stereo vision systems suffer from the same handicaps as all vision systems-sensitivity to illumination conditions and difficulty segmenting objects from complex backgrounds. In contrast, LIDAR is robust to differences in illumination and can obtain both position and intensity data in 3D; however, a LIDAR system consumes more energy and exhibits poorer real-time performance due to its enormous computational burden and high complexity. Thus, after weighing the pros and cons of the various methods, many research institutions and scholars have chosen to focus on pose determination based on monocular vision.

A typical pose determination method usually relies on artificial beacons that are accurately mounted on the target. One proximity operation sensor (PXS) consists of a camera and an array of light-emitting diodes (LEDs) on the chaser and a set of passive markers on the target. The LEDs emit pulsed visible light within a cone of 30° to illuminate the markers. Simultaneously, the camera captures images that contain the markers. Then, the data processing unit calculates the relative pose using a complex image processing algorithm. The experimental results represent the advanced performance of the present method, i.e., the measurement frequency of the PXS is 2 Hz, with centimeter-scale accuracy in the relative position and one-tenth-of-a-degree-scale accuracy in the relative attitude. Similar to the PXS, the advanced video guidance sensor (AVGS) designed by the Marshall Space Flight Center and the visual based system (VBS) designed by the Technical University of Denmark both require artificial beacons, which are either passive markers (reflectors) or active markers (LEDs).

Bluetooth Low-Energy (BLE) beacons-based indoor positioning is a promising method for indoor positioning, especially in applications of position-based services (PbS). It has low deployment cost and it is suitable for a wide range of mobile devices. Existing BLE beacon-based positioning methods can be categorized as range-based methods and fingerprinting-based methods. For range-based methods, the positions of the beacons should be known before positioning. For fingerprinting-based methods, a pre-requisite is the reference fingerprinting map (RFM). Many existing methods focus on how to perform the positioning assuming the beacon positions or RFM are known. However, in practical applications, determining the beacon positions or RFM in the indoor environment is normally a difficult task. This paper proposed an efficient and graph optimization-based way for estimating the beacon positions and the RFM, which combines the range-based method and the fingerprinting-based method. The method exists without need for any dedicated surveying instruments. A user equipped with a BLE-enabled mobile device walks in the region collecting inertial readings and BLE received signal strength indication (RSSI) readings. The inertial measurements are processed through the pedestrian dead reckoning (PDR) method to generate the constraints at adjacent poses. In addition, the BLE fingerprints are adopted to generate constraints between poses (with similar fingerprints) and the RSSIs are adopted to generate distance constraints between the poses and the beacon positions (according to a pre-defined path-loss model). The constraints are then adopted to form a cost function with a least square structure. By minimizing the cost function, the optimal user poses at different times and the beacon positions are estimated. In addition, the RFM can be generated through the pose estimations. Experiments are carried out, which validates that the proposed method for estimating the pre-requisites (including beacon positions and the RFM). These estimated pre-requisites are of sufficient quality for both range-based and fingerprinting-based positioning.

The beacon can be arranged to reflect vibroacoustics directly back to a receiver/transmitter source with minimal dispersion. For example, a vibroacoustic retroreflector (sometimes called a retroflector or cataphote) device or surface that reflects vibroacoustic radiation back to its source with minimum scattering. This works by optimizing a specific angle of incidence relative to distance (unlike a planar mirror, which does this only if the mirror is exactly perpendicular to the wave front, having a zero angle of incidence). Being directed, the retroflector's reflection could be higher/lower energy brighter than that of a diffuse reflector. Reflector design is based on light reflectors e.g., corner reflectors, and cat's eye reflectors.

In certain variations, an output display unit 3330 is provided which is separate to the panel unit and the base unit, but communicatively coupled thereto. The output display unit 3330 may be embodied as a standalone screen or in a mobile device such as a smartphone or tablet. The output display unit 3330 may be arranged to cause display of a virtual representation of the subject, in the form of an avatar for example. Depending on the context, the avatar may be a simple outline of a human figure or a detailed photo-realistic image. The avatar may be used to present data, such as the location of detected objects on the subject's body to security personnel, or to provide cues or instructions to the subject as to what pose to present, or what motions to perform. This feature may be used to enhance the performance of the system by eliminating blind spots, or to provide guidance for the performance of exercises or physical therapy movements.

The computing system/processor may be incorporated, at least in part, within one or a combination of the base unit, the panel unit and the output system. The computing system may be incorporated, at least in part, in a server.

A barrier (not shown), associated with one or more of the panel unit and the base unit, may also be provided, for delimiting the progress of the subject. On determination of the subject not having a given bodily condition, the computing system can cause the opening of the barrier to allow the subject to physically away.

In addition, there may be further provided a transductive patch that may be applied to a body surface and comprise have conductive electrodes on the inner surface that are connected via a thin inductive pattern that is present on the patch and/or capacitive elements. Thus, when the subject is proximate one or more of the panel unit, base unit and/or top unit, an alternating electromagnetic field may be used to induce a potential in the thin inductive pattern that is conducted to the skin electrodes creating an LRC circuit, whose electrical response properties may be remotely monitored. The patches may be made of paper/plastic laminates, using conductive ink or other printed circuit technologies. The patch could serve a second purpose of identifying persons that have already been successfully screened.

In this manner, a whole host of measurements may be made remotely that otherwise would require intimate contact and the opportunity to spread infection. Moreover, by allowing subjects to apply the patches themselves, issues of modesty are resolved when the ideal measurement surface is in the groin or chest area. In other variants, if the transductive patches or beacons are relatively expensive, a reusable version which attaches with a reusable, or replaceable adhesive system may be used. The device would be given out before the subject enters the apparatus, and removed after use, sanitized and prepared for re-use, such as is done with 3-d glasses in movie theatres.

Considerations During Design of Different Form Factors and Choice of Sensors

It will be appreciated that in choosing a form factor and the one or more sensors, consideration must be given to the behavior of acoustic field at certain distances from the subject: Near Field; Far Field; Free Field, and Diffuse Field acoustics. Depending on how far away an observer/sensor is from a vibration/sound emitting object, the vibration/acoustic energy produced by the vibration/sound source will behave quite differently.

Far Field

The acoustic far field is defined as beginning at a distance of two wavelengths away from the sound source, and extends outward to infinity. As wavelength is a function of frequency, the start of the far field is also a function of frequency. In the far field, the source is far enough away to essentially appear as a point in the distance, with no discernable dimension or size. At this distance, the spherical shape of the sound waves grow to a large enough radius that one can reasonably approximate the wave front as a plane-wave, with no curvature. At this distance, sound pressure level is governed by the inverse square law, and a single microphone sound recording will give reliable & predictable results. For each doubling of distance away from the source, the sound pressure will drop 6 dB in the far field. In many acoustic standards, measurements are often specified at a distance of at least one meter from the sound emitting object to ensure that the measurement is taken in the far field for the most critical frequencies.

Near Field

When close to a sound emitting object, the sound waves behave in a much more complex fashion, and there is no fixed relationship between pressure and distance. Very close to the source, the sound energy circulates back and forth with the vibrating surface of the source, never escaping or propagating away. These are sometimes called "evanescent" waves. As we move out away from the source, some of the sound field continues to circulate, and some propagates away from the object.

This transition from circulating to propagating continues in an unpredictable fashion until we reach the threshold distance of two wavelengths, where the sound field strictly propagates (the far field.) This mix of circulating and propagating waves means that there is no fixed relationship between distance and sound pressure in the near field, and making measurements with a single microphone can be troublesome and unrepeatable. Acoustic arrays featuring many microphones must therefore be used close to a source to accurately capture sound energy in the near field.

Free Field Versus Diffuse Field

When sound radiates from an object, it can reach an observer directly by traveling in a straight line, or indirectly via reflections. Reflected sound waves can bounce off surfaces such as walls, the floor, ceiling, as well as other objects in the area. Often when we experience sound, we are receiving both direct and reflected sound waves. Under carefully controlled circumstances, however, we can experience the extreme ends of this continuum: 1) an acoustic field where zero reflections are present, and only the direct sound is observed, and 2) the opposite acoustic field, where zero direct sound is observed, and only reflected sound is present. The names given to these two extreme acoustic environments are free field and diffuse field respectively. In an acoustic free field there are no reflections; sound waves reach an observer directly from a sound emitting object. The sound wave passes the observer exactly once, and never returns. Two common examples of acoustic free fields are: (i) the sound source is far enough away that it appears as a single point source, far in the distance. Visualize an airplane flying high overhead on a clear day. (ii) An anechoic chamber is a special facility constructed to approximate an acoustic free field by using materials to absorb sound waves before they can be reflected.

2. Methods for Characterizing a Bodily Condition

Figure 34:
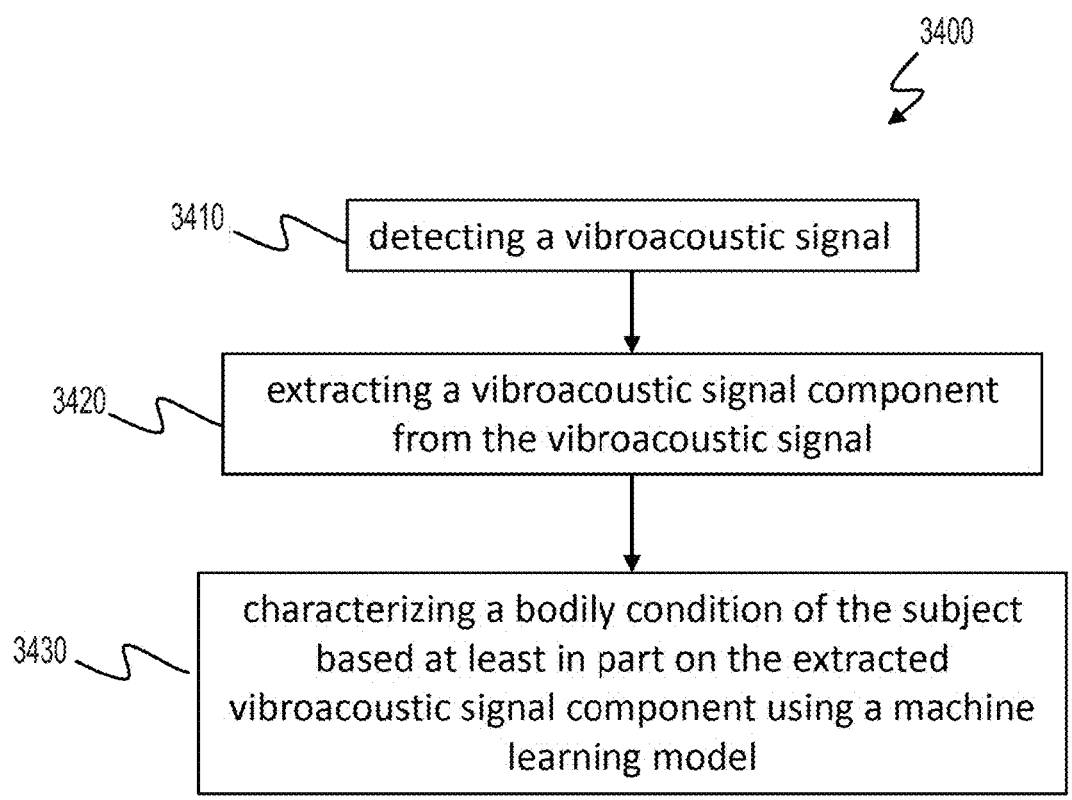
FIG. 34 depicts a flowchart summarizing an example variation of a method for characterizing a bodily condition of a subject.

As shown in FIG. 34, in some variations, a method 3400 for characterizing a bodily condition may include detecting a vibroacoustic signal with a vibroacoustic sensor module 3410 (or vibroacoustic sensor module 420, 1600), extracting a vibroacoustic signal component from the vibroacoustic signal 3420, and characterizing a bodily condition of the subject 3430 based at least in part on the extracted vibroacoustic signal component using a machine learning model. In some variations, the method 3400 may comprise obtaining vibroacoustic data from a vibroacoustic sensor, and characterizing a bodily condition of the subject based at least in part on the vibroacoustic data using a machine learning model. In some variations, instead of, or in addition to the vibroacoustic data, the method 3400 may comprise obtaining data from any sensor module described herein such as an optical sensor, a bioelectric sensor, a capacitive sensor, a thermal sensor, etc. The method may, at least in part, be executed by a processor of a computer system. In certain variations, the bodily condition is COVID-19, and the method comprises detecting a vibroacoustic signal within a frequency range of: about 0.01 Hz to at least about 160 kHz.

The data may be obtained as a live stream. Alternatively, the obtained data may be sampled from a total volume of detected data by the one or more sensors. The data may be captured as catenated raw amplitude sequences or as combined short-time Fourier transform spectra. The data from the sensors may be captured from the subject in less than 15 seconds per subject, and preferably in less than 10 seconds per subject.

The method 3400 may comprise an optional prior step of causing the one or more sensor modules to start capturing the data based on a trigger. The trigger may be manual (e.g. initiated by a user of the system) or automatic and based on a predetermined trigger parameter. The trigger parameter may be associated with a proximity of the subject to the system 10, or a contact of a body part of the subject with the device (such as when the feet of the subject contact the base unit), or on detection of a predetermined physiological parameter such as an elevated body temperature.

The processing of the data to determine a presence or absence of the bodily condition may take less than 15 seconds per subject, such as about 14 seconds, about 13 seconds, about 12 seconds, about 11 seconds, about 10 seconds, about 9 seconds, about 8 seconds, about 7 seconds, about 6 seconds, about 5 seconds, or less than 5 seconds. In certain variations, the vibroacoustic signal detected by the system spans between 3 and 5 heart beats of the subject.

Optionally, the method may comprise causing an output of the determination of the bodily condition to, for example, the output device 3330 described herein. The output may take any form such as an audio output (e.g. a beep), a visual output (e.g. a flashing light), a haptic output (e.g. a buzz), a mechanical output (e.g. barriers being opened or closed). In certain variations, the output may be an alert such as a green light indicating absence of the target condition or a red light indicating presence of the target condition. In other variations, the output may comprise causing the physical retention of the subject through control of a physical restraint member such as a barrier.

One or more of the sensor data, the determination and the output may be stored, such as in a database of the computing system. The stored data may be fed to a training MLA.

The method 3400 may comprise causing the one or more sensor modules to stop obtaining data based on a manual or automatic trigger. The automatic trigger may comprise a predetermined threshold such as a time interval or the like.

The processing the data or training the MLA comprises associating a given target condition with symptoms of the given target condition. The symptoms may include one or more symptoms related to the subject's throat, chest, constitution, gut, nasal system, eyes, and vascularization. These symptoms may include, but are not limited to a sore, painful, swollen, or scratchy throat, loss of taste, or difficulty in swallowing. The chest associated symptoms are trouble breathing, congestion, tightness, dry cough, hacking cough, wet cough, loose cough, mucous, phlegm or fibrosis. The constitutional symptoms may be dyspnea, muscle spasms, pyremia, body aches, fatigue, malaise, general discomfort, fever, or chills. The gut associated symptoms may be loss of appetite, altered gut motility, stomachache, emesis, nausea, or diarrhea. The nasal symptoms may be rhinorrhea, redness of the nasal openings or congestion. The ocular symptoms may be glassy eyes and conjunctival injection. The vascularization symptoms may include clotting, bruising, etc. For example, sore throat, dry cough, shortness of breath, muscle spasm, chills, fever, gut discomfort, brain fog and diarrhea are key indicators of a possible coronaviridae (e.g. COVID-19) infection.

These and other indicative symptoms that can be detected in a non-invasive, contactless manner by variants of the present technology are typically due to changes in tracheal and lung thickness, respiratory depression, local and systemic fluid accumulation (edema), oxygen desaturation, hypercapnia, trauma, scarring, tissue irritation, fibrotic changes, hypoventilation and hypertension. Variants of the present technology can be used to detect early and subtle changes in lung and upper respiratory airway audible and inaudible wheezes, crackles, and egophony—often caused by lung consolidation, diffuse alveolar damage, vascular injury, and/or fibrosis, with or without ECG.

Other physiological states or levels of metabolites or environmental toxins that can be detected by the method 3400 include mechanical trauma and injury, elevated interleukin (IL) 6 and polymorphonuclear inflammatory cells and mediators, lymphoid hypertrophy and prominence of adenoidal and tonsillar tissue, kinins, histamine, leukotrienes, prostaglandin D2, and TAME-esterase, ACE inhibitor increase in pro-inflammatory pharyngeal irritation, oropharyngeal mucositis, and the direct effect of ozone on respiratory tract cell membranes and fluid, lipid ozonation product activation of specific lipases that trigger the release of endogenous mediators of inflammation such as prostaglandin E, IL8, thromboxane B2 and calcitonin gene-related peptide.

In some variations, the method 3400 may be performed with any of the systems or sensing devices described herein, which may have any suitable variation of a vibroacoustic sensor module and/or other sensor modules. The sensing device may have any form factor such as a hand-held, stethoscope, panel, mirror, kiosk, gateway. The method may, for example, utilize a vibroacoustic sensor module with a plurality of MEMS or other suitable sensors (e.g., accelerometer, pressure sensor, microphone, voice coil transducer, piezoelectric transducer, etc.). In certain variations, data from a vibroacoustic sensor module based on a voice coil transducer is combined with data from an echo doppler sensor module. Such sensors may, in some variations, interface with one or more deflecting structures (e.g., flexure arms, membrane, etc.) as described above. In other variations, the method 3400 may use the sensing device 400 including the vibroacoustic sensor module 420.

In some variations, the extracted vibroacoustic signal component may include a biological vibroacoustic signal component, and the bodily condition characterized may include a health condition based on the biological vibroacoustic signal component. In this respect, the method may comprise extracting the biological vibroacoustic signal component. In certain variations, extracting the biological vibroacoustic signal component comprises passing the vibroacoustic signal through a first stage amplifier and a first stage low pass filter, and a second stage amplifier and a second stage low pass filter. The first stage low pass filter and the second stage low pass filter may form a second order low pass filter with anti-aliasing, wherein the second order low pass filter has a cutoff frequency of about 15 kHz to about 20 kHz. In certain variations, the vibroacoustic signal is also passed through a third stage amplifier comprising a programmable gain amplifier configured to dynamically amplify at least a portion of the vibroacoustic signal. In certain variations, the extracting the biological vibroacoustic signal component comprises digitizing the amplified portion of the vibroacoustic signal and providing at least a portion of the digitized vibroacoustic signal as a digitized biological vibroacoustic signal component.

For example, the method 3400 may assist healthcare professionals in collecting and intelligent analysis of audible and inaudible signals associated with cardiac, lung, gut and other internal organ functions, for rapid and accurate diagnostics such as that relating to cardiopulmonary, respiratory, and/or gastrointestinal function. In certain variations, the method 3400 may assist in the diagnosis of a viral infection, such as that of a coronaviridae or SARS virus. In certain variations, the method 3400 may assist in monitoring efficacy of a certain treatment, such as during a clinical trial.

The method 3400 may include collecting data generated by the body passively without imparting any energy (e.g., current or voltage) to the body. For example, the sensing device may be placed on the skin (e.g., at designated auscultation points, similar to a stethoscope), on the body over clothing at designated auscultation points, or pointed at the body (e.g., at designated auscultation points) to passively harvest signals generated by the body. Auscultation points may include one or more of the subject's neck, chest, back and torso. As described in further detail herein, the sensing device may collect and process audible and inaudible signals passively harvested from the body. The signals and/or analysis thereof may be communicated to an external device (e.g., mobile computing device) in a wired or wireless manner. In some variations, transmitted data may be encrypted before being saved to personalized folders for secure storage and subsequent playback in a mobile application executed by a mobile computing device. The application may provide the ability to save collected data within designated Electronic Medical Records (EMR)/Electronic Health Record (EHR) systems, share patient recordings, and annotate notes on recorded audio, etc.

The sensing devices, sensor modules, systems, and methods of the current technology may be useful in detecting conditions in living organisms including but not limited to: respiratory illnesses and diseases such as coronaviridae (e.g.

COVID-19, SARS, Digestive illnesses and diseases, Cancer, Neurological illnesses and diseases, Psychiatric illnesses and diseases, Cardiac illnesses and diseases, circulatory illnesses and diseases, lymphatic illnesses and diseases, kidney illnesses and diseases, liver illnesses and diseases, lung illnesses and diseases, Osteopathic illnesses and diseases, Orthopedic illnesses and diseases, sleep related illnesses and diseases, metabolic diseases, disorders, and states, movement disorders, viral, bacterial, fungal, parasitic, protozoal, and prion infections, substance use disorders, behavioral disorders, musculoskeletal illnesses and diseases, blood illnesses and diseases, disfunction of internal organs, genital illnesses and diseases, emotional disturbances, disorders or states, alertness, fatigue, anxiety, depression, delirium, disorientation, ataxia, insomnia, eating disorders, obesity, body composition, and such.

In some variations, the method 3400 for characterizing a bodily condition may include detecting vibroacoustic signals with active skin motion amplification methods in sensor module. The vibroacoustic signal component from the vibroacoustic signal may be extracted using active and energy imparting technologies including accelerometer-based vibrometer, common-path interferometric imaging, ultrasonic vibrometry, and/or other energy imparting technologies examples. Examples of active and/or energy imparting methods may assist healthcare professionals in collecting and intelligent analysis of skin surface vibrometry signals associated with the physical human body to assess health. For example, cough transmission through the body to the skin surface, oral, and nasal cavities may signal many things by its length, intensity, tone, frequency, etc.

In some variations, an acoustic vibrometry active sensing module may be added as an interoperable subsystem for measuring low frequency, low amplitude mechanical, vibroacoustic and skin surface mechanical motion amplification properties of a subject including using an a wide bandwidth acoustic transducer to apply wide bandwidth vibration pulses to skin surface (face, neck, chest, gut, bladder, uterus, or whole body, etc.). The applied vibration pulses may occur in an on-off time sequence in order to impart a harmonic motion at a prescribed frequency to the subject, and when the vibration pulses are off, the same (or other) transducer may be used to apply acoustic detection pulses to a motion detection point and to receive echo signals in order to sense the harmonic motion on the subject at the motion detection point. From the harmonic signal information, a harmonic signal may be detected and a characteristic such as amplitude or phase of the detected harmonic signal may be measured. The skin motion mechanical property may be calculated using the measured characteristic using, for example, a wave speed dispersion method.

In an exemplary variation, an acoustic vibrometry active sensing module may be added as an interoperable subsystem for measuring low frequency, low amplitude mechanical, mechano-acoustic and skin surface mechanical motion amplification properties of a subject including using a multi-frequency ultrasonic wave generator generating at least first and second ultrasonic waves. The multi-frequency ultrasonic wave generator may be arranged such that in operation, at least the first and second ultrasonic waves mix in a prescribed mixing zone to produce a difference-frequency acoustic wave. Parametric and multi-transducer variations have been tested. A receiver sensor may detect the difference-frequency acoustic wave and produce corresponding voltage-time or electromagnetic signals. The voltage-time/electromagnetic signals may be processed by a system processor and resulting signals may be indicative of skin or surface motion. In some variations, the ultrasonic waves may be focused to a small prescribed mixing zone.

In an exemplary variation, an ultra-wideband vibrometry active sensing module may be added as an interoperable subsystem for measuring low frequency, low amplitude mechanical, mechano-acoustic and skin surface mechanical motion amplification properties of a subject including using an ultra-wideband monitoring system and antenna. The subsystem for physiologic signal monitoring and amplification may include a signal generation/monitoring station and at least one sensor in communication with the monitoring station. The sensor may include an antenna system and an ultra-wideband radar system coupled to the antenna system. The ultra-wideband subsystem may be configured to extract from the signal information about physical or structural mechano/vibroacoustic data in a sensing volume corresponding to the antenna system volume.

Signal processing and communications may be shared across the entire vibroacoustic sensing module and routed through a central microcontroller unit.

In an exemplary variation, an optical vibrometry active sensing module may be added as an interoperable subsystem for measuring low frequency, low amplitude mechanical, mechano-acoustic and skin surface mechanical motion amplification properties and subsequent classification. In one example, an active optical source may generate and direct coherent light toward the subject. An optical imaging system may collect light reflected or transmitted from the physical subject including a scattered component and a specular component that is predominantly undiffracted by the sample. A variable phase controlling system may be used to adjust the relative phase of the scattered component and the specular component so as to change the way they interfere at the image plane.

The resultant signal may be compared to a reference signal for the same location on the sample location and the difference may be translated into a distance to the image plane. The process may be rapidly repeated in high frequency to map the time-dependent movement of the focus point on the image plane. This data may then used to calculate an amplitude and phase between data sampling points, which can be used for motion amplification, detection, and classification. This method may detect much smaller defects related to the wavelength, amplitude and operational light frequency.

In certain variations, the signal processing system further comprises a second analog subsystem comprising a programmable gain amplifier configured to dynamically amplify at least the selected portion of the vibroacoustic signal, and an analog-to-digital converter providing a digitized biological vibroacoustic signal component.

EXAMPLES

Example 1: Vibroacoustic Data Acquired Using an Accelerometer-Based Vibrometer

Figure 35A:
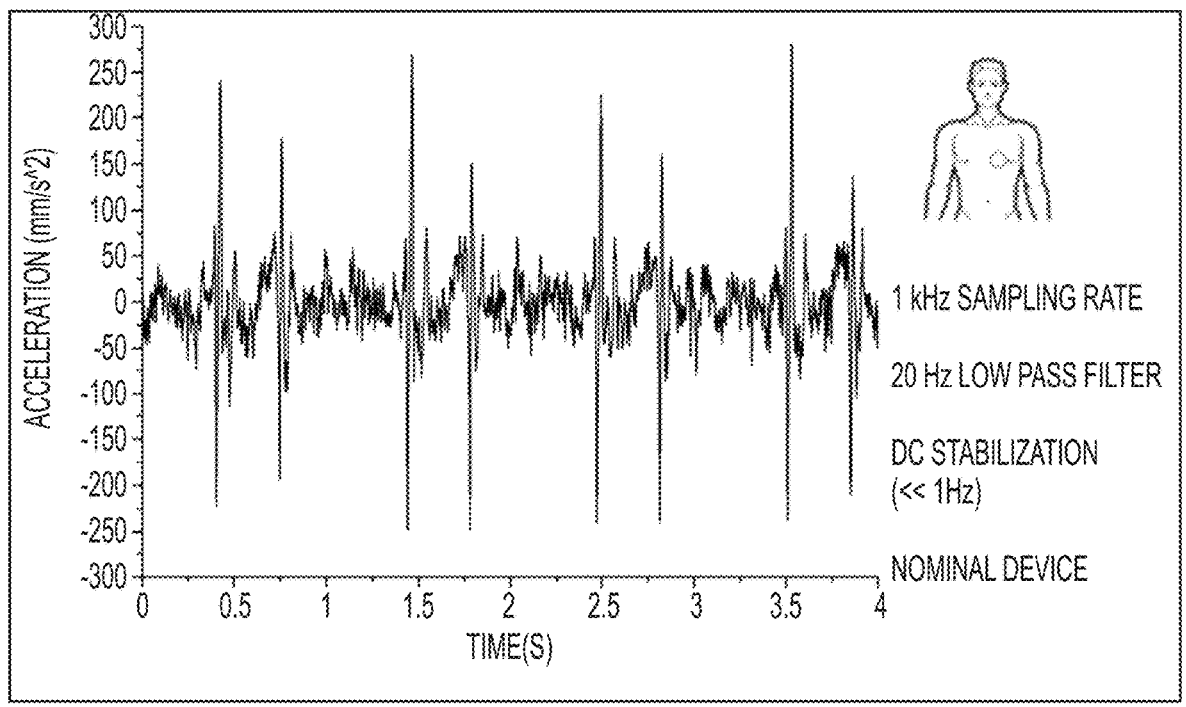
FIGS. 35A and 35B depict exemplary sensor data using an accelerometer-based example variation of a vibrometer sensor module of the present technology.
Figure 35B:
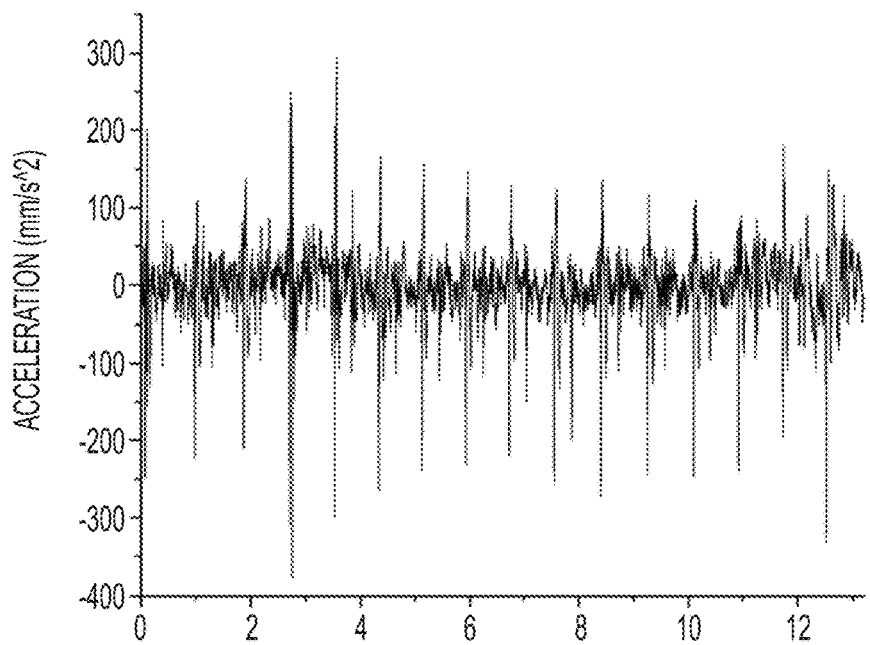

A sensing device was built as shown and described above with respect to FIGS. 5A-5I, and included a vibrometer sensing module having two flexure arms coupled to a central hub interfacing with an accelerometer. The sensing device was placed over a chest auscultation point on a subject, and was used to measure a vibroacoustic signal. The vibroacoustic signal was then conditioned in a signal processing chain as described above with respect to FIG. 24, to extract a biological vibroacoustic signal component from the measured vibroacoustic signal. FIGS. 35A and 35B depict the resulting extracted biological vibroacoustic signal over the measurement period.

Example 2: Combined Accelerometer, MEMS Microphone, High Fidelity Barometric Pressure Sensor and Voice-Coil Technology The combination of accelerometer, MEMS microphone, high fidelity barometric pressure sensor and voice-coil technology was arranged to detect vibroacoustic signals from infrasound to high ultrasound (0.1 Hz to 160 kHz). Implemented software-defined hardware was arranged in various form-factors to passively and discreetly, for example: detect and target drone/loitering munitions defense, detect buried/implanted ordinance (e.g., body cavity bomb detection), monitor structural health and track efficiency of concrete and steel structures, as well as rotating machines and equipment from turbines to generators, see through walls to search for and enable rescue of people in collapsed structures, detect footsteps and vehicular/animal traffic, etc. at sensitive borders, and/or the like. The combination of directional vibroacoustic and mechano-acoustic sensor modalities provide a unique set of low frequency, low amplitude vibrations and fluctuating shear-wave fields heterogenous degrees-of-freedom on which to optimize over.

Figure 44:
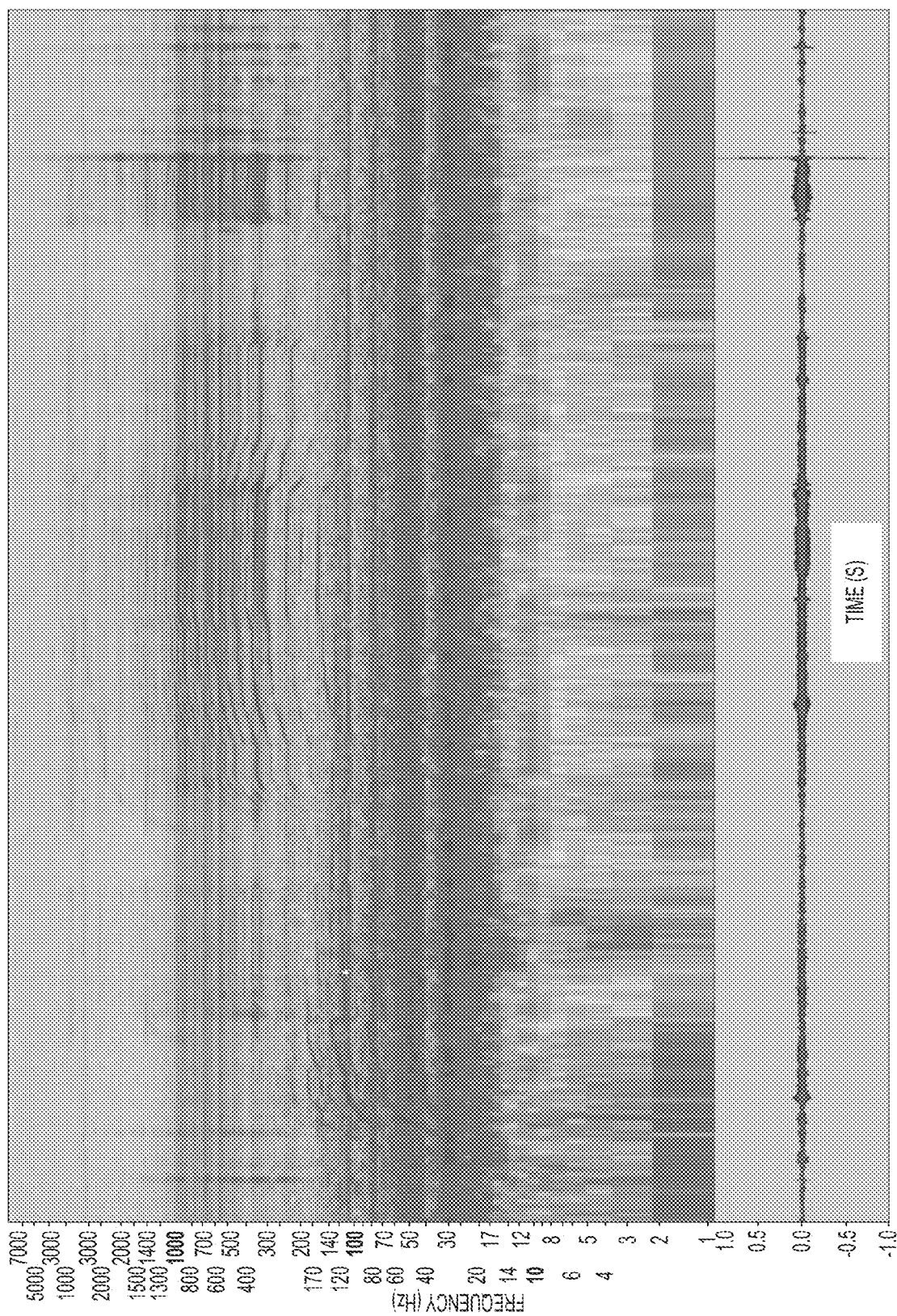
FIG. 44 depicts example vibroacoustic test data gathered for a consumer drone.

FIG. 44 depicts example vibroacoustic test data gathered for a consumer drone with interchangeable fixed wing and variable wing speed. The vibroacoustic data shown in FIG. 44 illustrates signal richness for algorithm-driven reliable drone detection, tracking, and classification. Accordingly, these test results demonstrate that ability to capture data from which information associated with a consumer drone may be derived (e.g., drone characteristics such as fixed-wing or multi-rotor, size, shape, payload, speed, etc.).

Example 3: Vibroacoustic Data Acquired Using a Voice Coil-Based Vibrometer

Figure 37A:
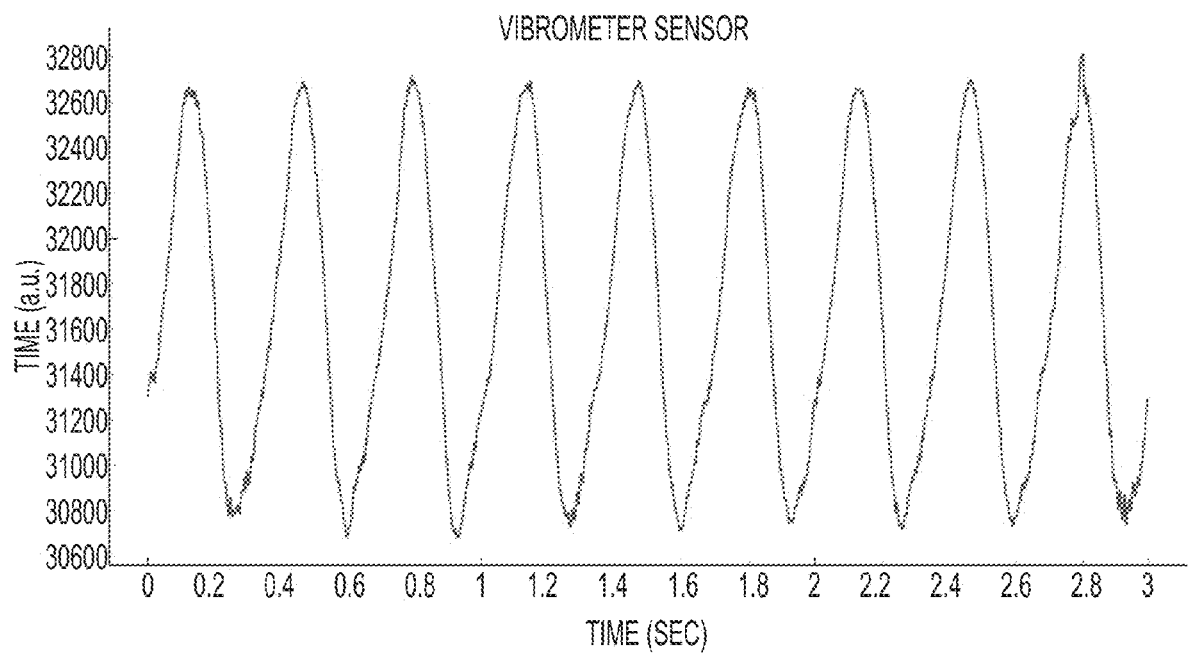
FIGS. 37A and 37B depict vibrometer data taken in the 3 Hz time domain and frequency domain, respectively, captured after applying signals using an example variation of a sensing device of an example variation of a system of the present technology to a human manikin phantom.
Figure 37B:
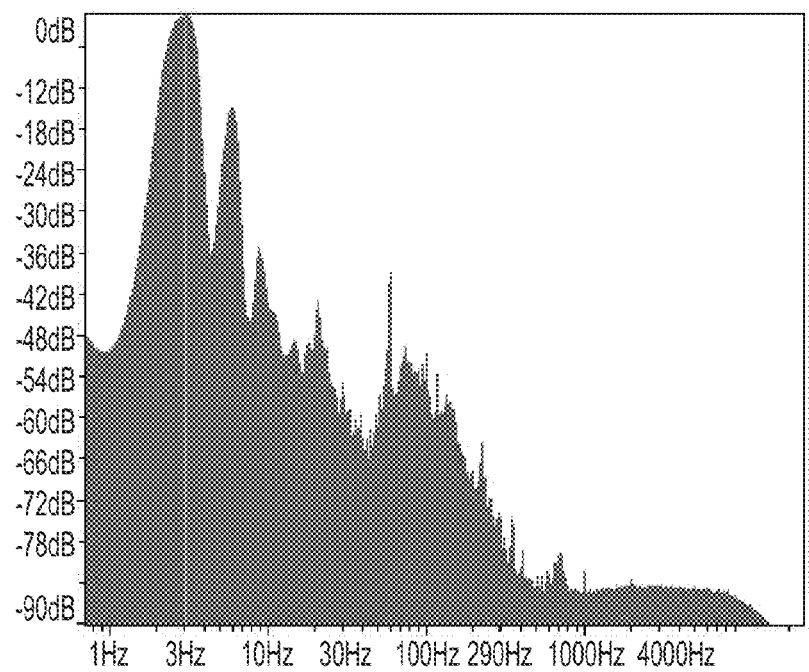
Figure 37C:
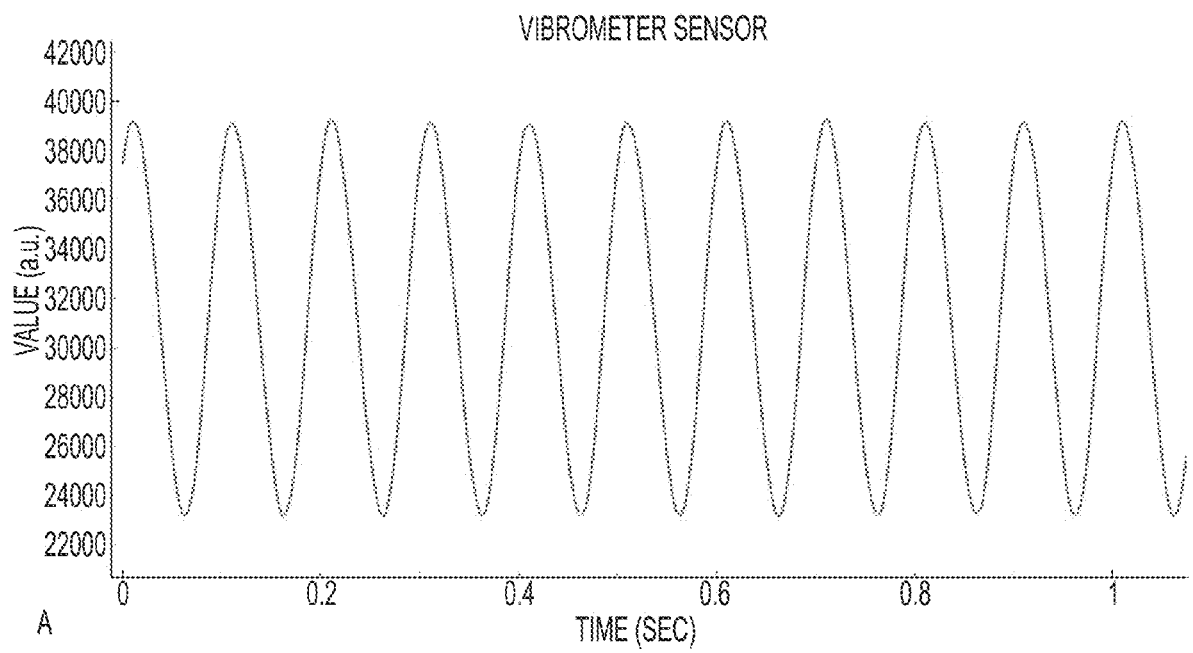
FIGS. 37C and 37D depict example vibrometer data taken in the 10 Hz time domain and frequency domain, respectively, captured after applying signals using an example variation of a sensing device of an example variation of a system of the present technology to a human manikin phantom.
Figure 37D:
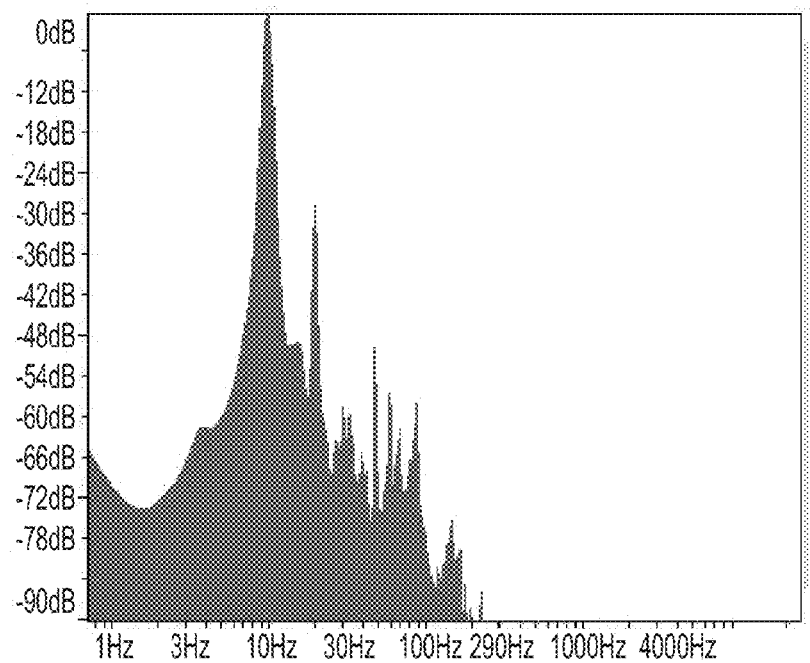
Figure 38A:
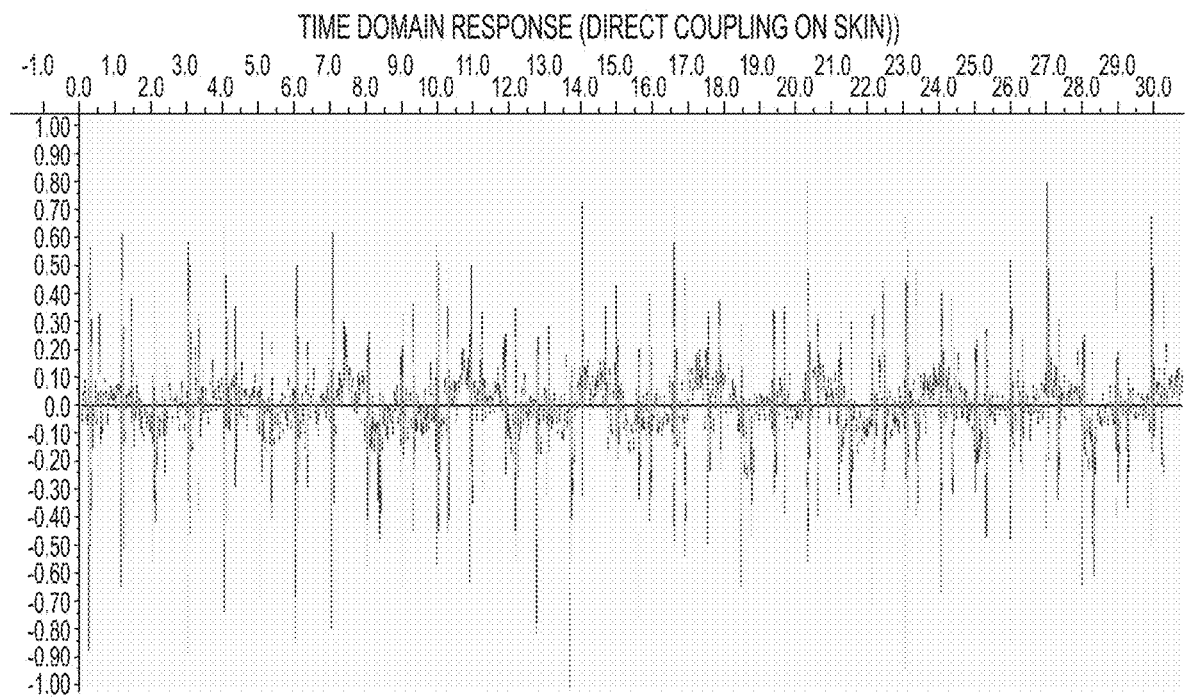
FIGS. 38A and 38B, FIGS. 39A and 39B, and FIGS. 40A and 40B depict example vibrometer data captured after applying signals to human skin using an example variation of a sensing device of an example variation of a system of the present technology through direct coupling (FIGS. 38A and 38B), through a T-shirt (FIGS. 39A and 39B), and through a wool sweater (FIGS. 40A and 40B).
Figure 38B:
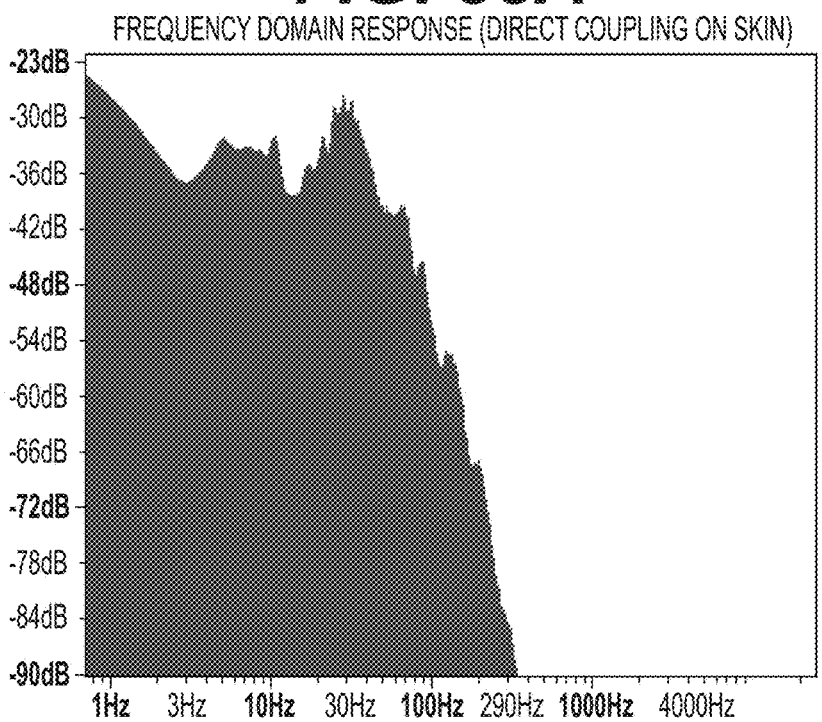
Figure 39A:
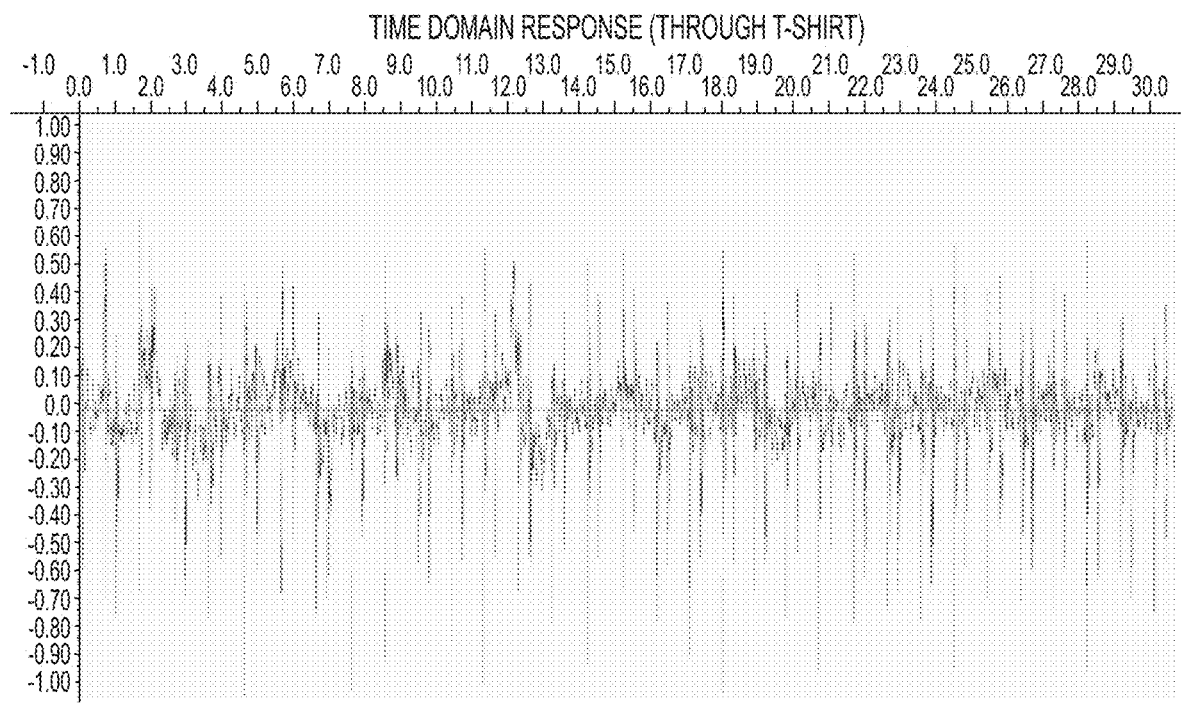
Figure 39B:
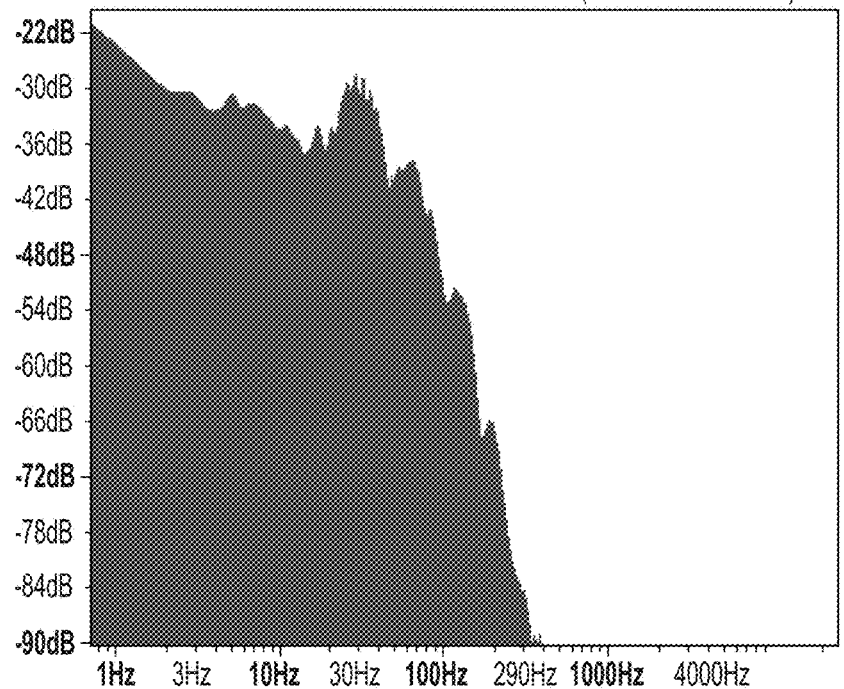
Figure 40A:
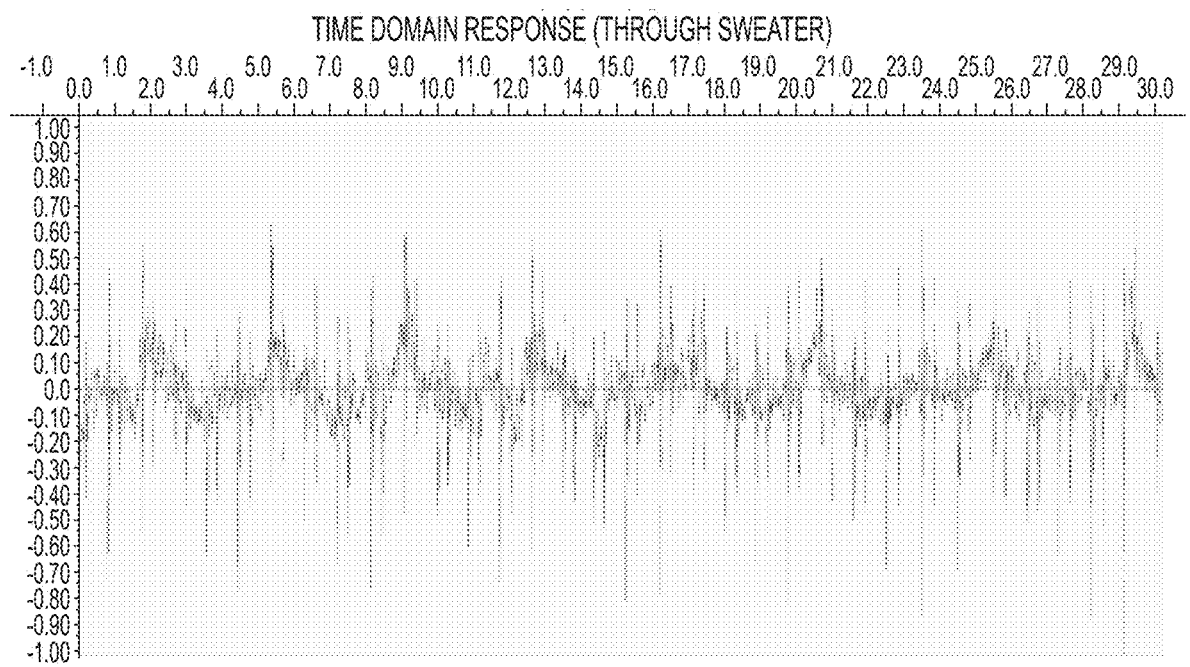
Figure 40B:
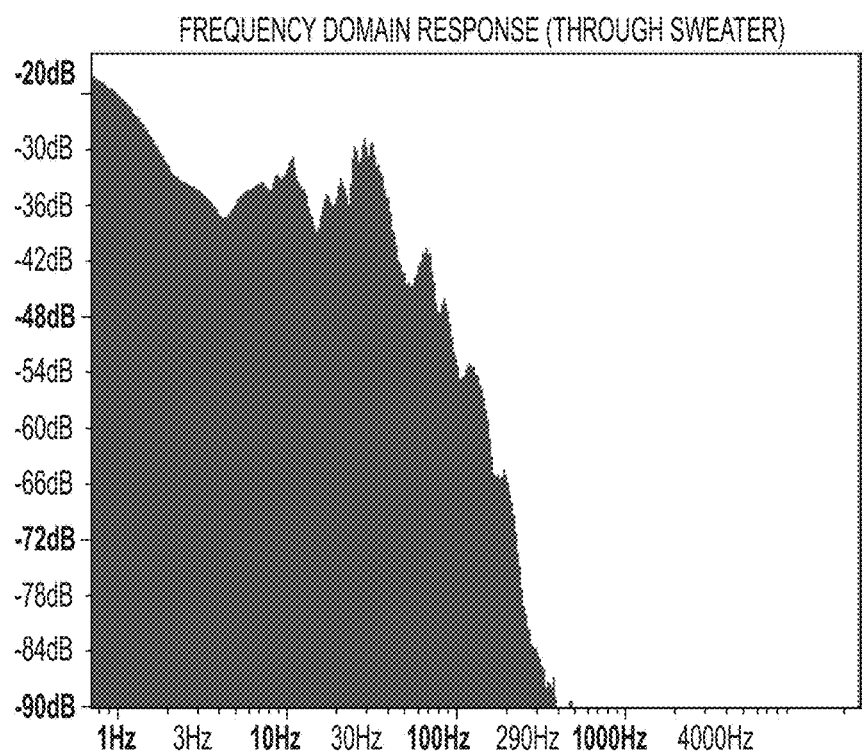
Figure 41A:
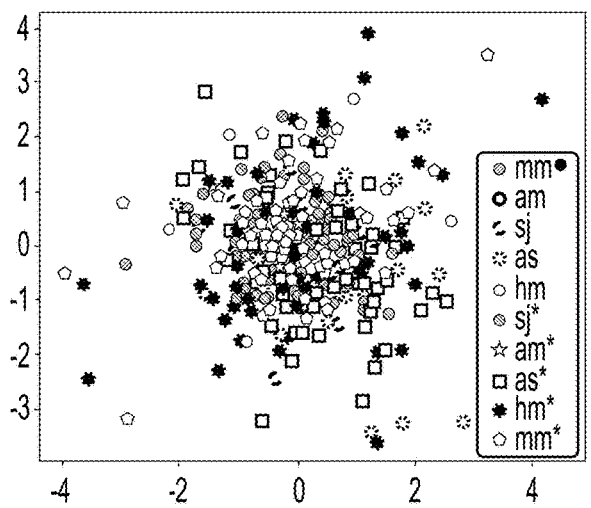
FIGS. 41A-41E depict program output for example programs for classification tasks on example vibrometer data.
Figure 41B:
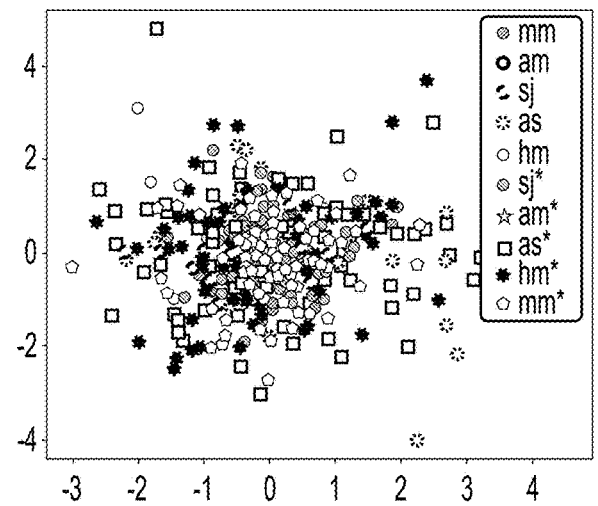
Figure 41C:
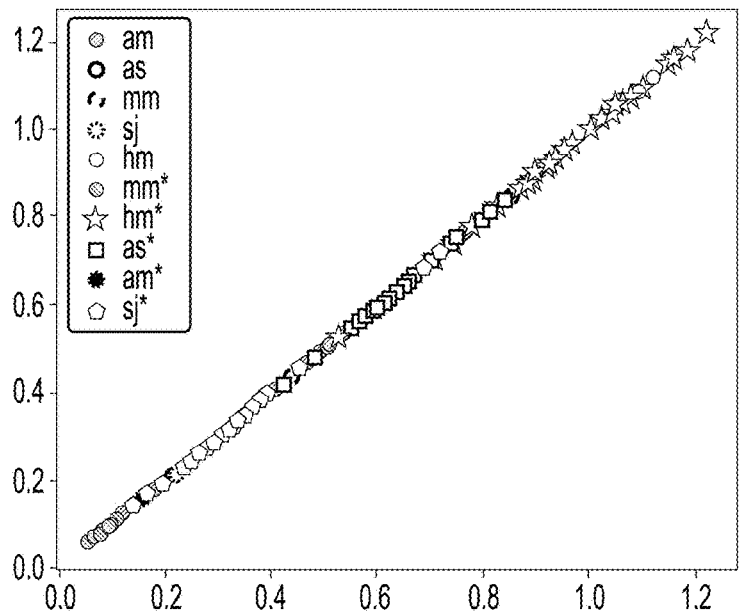
Figure 41D:
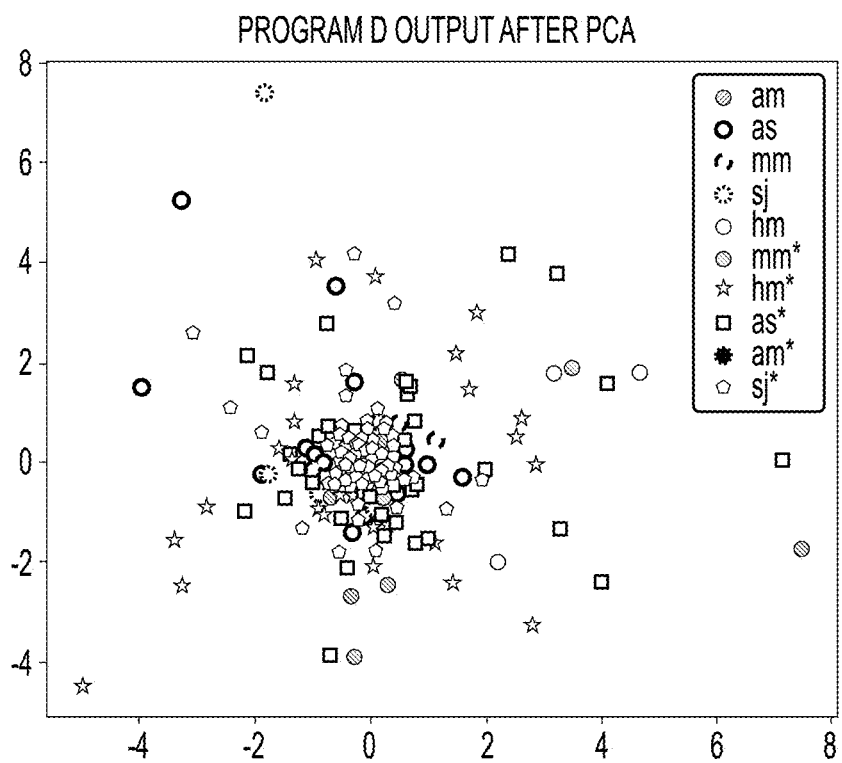
Figure 41E:
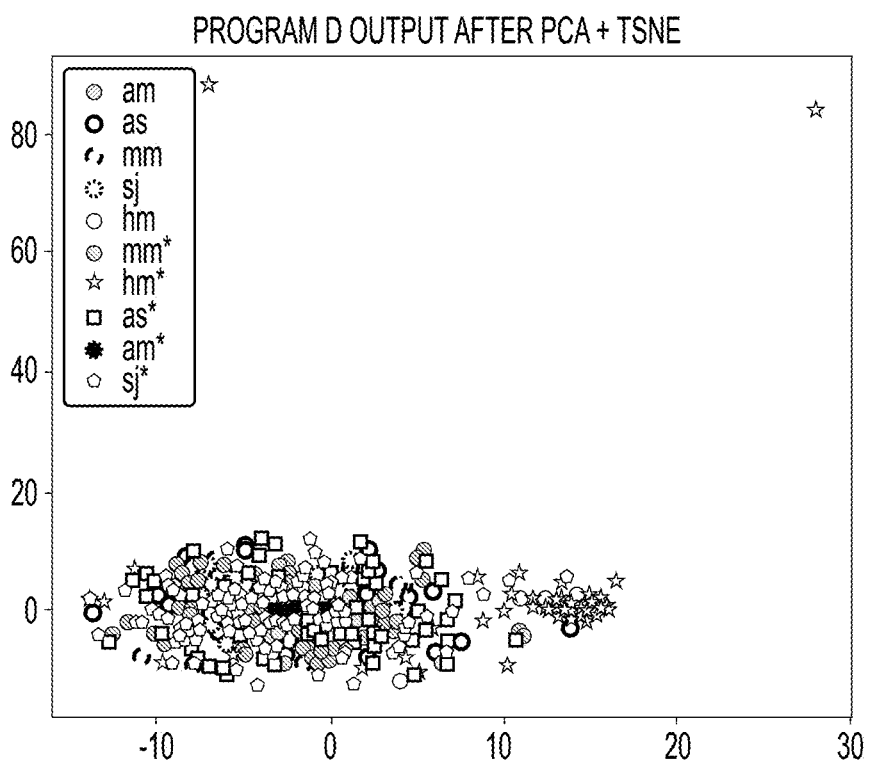

Data was collected using exemplar variations in laboratory (using a human manikin phantom) and exploratory clinical tests. Specifically, as shown in FIGS. 37A-37D, signals were applied to the phantom and captured with the vibroacoustic system described above, more particularly the sensing device 400 described in FIG. 4H. FIGS. 37A and 37B illustrate a 3 Hz time domain and its frequency domain signal, respectively. FIGS. 37C and 37D illustrate a 10 Hz time domain and its frequency domain signal, respectively. The study confirmed that the phantom transmits signals accurately, well into the infrasound frequency range, and that signals are captured properly with the illustrative vibroacoustic system.

Illustrative vibroacoustic system performance testing was performed using human manikins, and in clinical pilot studies to compare skin coupling vs. over clothes of different types (e.g., thicknesses). One test consideration compared performance consistency of the illustrative vibroacoustic system on skin versus both thin and heavy clothing on the manikin and live human being. Data was collected from the same live human participant recovered from direct coupling on skin (FIGS. 38A-38B), through a T-shirt (FIGS. 39A-39B), and a thick wool sweater (FIGS. 30A-30B). As shown in FIGS. 38A-38B, 39A-39B, and 40A-40B, correct capture of vibroacoustic signals by the vibroacoustic system was achieved on skin and through a variety of clothing with minimal or no deterioration.

Example 4: Modeling and Classification of Fatigue States Using Novel Vibroacoustic Data Vibroacoustic data from a test subject was acquired using a variant of a sensing device according to the present technology (the sensing device 400 of FIG. 4 including the ECG sensor module) and used to assess a segmentation algorithm and train and test a model for predicting fatigue states based on vibroacoustic data.

Clinical Data Collection

Vibroacoustic data was collected in a cold pressor test by having subjects immerse the non-dominant hand into an ice water bucket for one minute, and measuring changes in heart rate. These changes relate to vascular response and pulse excitability. Data was collected from healthy male participants aged 36 to 49 during rest and a cold ice water dip exercise aimed to simulate pain. Prior to the data collection session, all participants were encouraged to follow their normal daily routine including sleep, meals and hydration. Data was recorded around the intersections of the 2nd to 3rd intercostal spaces and the left midclavicular line. This position was chosen based on its proximity to the heart.

Data Classification

Many machine learning algorithms require large amounts of data before they begin to give useful results. The larger the architecture, the more data is needed to produce viable results. To augment training data for the ML/AI toolbox, vibroacoustic and mechano-acoustic data of aircraft takeoffs and landings at SFO International Airport and tracking traffic at neighborhood bridges in Alameda, Santa Clara, and San Mateo, Calif. counties was collected continuously. SFO and bridge sensor systems were trained to real time flight, weather, emissions and air quality databases available at https://flightaware.com/, https://511.org/open-data/traffic and https://www.arb.ca.gov/agmis2/metselect.php, respectively.

Rest versus pain clinical vibroacoustic data classification was initially approached following music genre classification approaches. However, commercial music search algorithms are only concerned with music genres as a flat classification problem. The idea of using the hierarchy for browsing and retrieval has been explored in a limited number of existing tools for organizing music collections. End-user systems based on the use of multiple hierarchies to organize music collections incorporate user feed-back in order to re-organize the pre-existing class hierarchy as the users see fit. The latter approach of user-defined creation of taxonomy creates new (meta-) classes on the fly on top of a pre-established taxonomy. In principle, the vibroacoustic signal hierarchical classification algorithm permits the creation of new classes, which is related to clustering.

Therefore, in contextualized vibroacoustic hierarchical clustering, we are interested in both hierarchical classification (a type of supervised learning) and hierarchical clustering (a type of unsupervised learning) in order to resolve atomistic and ecological fallacies. By combining hierarchical classification and hierarchical clustering, individuation or identification (of the atom) is extreme classification and identification/individuation, segmentation, clustering, and hierarchical classification fall along a "IS-A" continuum as asymmetric, anti-reflexive, and transitive. The "IS-A" relation is asymmetric (e.g. all dogs are animals, but not all animals are dogs) and transitive (e.g., all pines are evergreens, and all evergreens are trees; therefore, all pines are trees).

A notion of contextualized vibroacoustic data hierarchical classification is to use machine learning (ML) and other forms of adaptation to optimize software. Compared to mainstream ML, the difference is to start with pre-established taxonomy and software artefacts (possibly very imperfect software artefacts) produced by 'domain experts.' Secondly, the software artefacts are in general much more expressible than off-shelf ML models like neural nets or decision trees. Thirdly, contrary to typical ML scenarios with clearly delineated training and test phases, learning and optimization is performed 'inline.' In other words, an 'inline learning' algorithm is embedded within a software system, allowing it to learn adaptively as the system processes new data. Such adaptation typically leads to more performant software systems (with respect to various functional and nonfunctional properties/metrics), because it (i) can correct for the suboptimal biases introduced by human designers and/or "domain experts," and (ii) responds swiftly to changing characteristics and operating conditions (mostly to variation in data being processed).

Without the right algorithms to refine data, the real value of high-resolution sensor data fusion will remain hidden. Popular approaches such as neural nets model correlation, not causal relationships, and do not support extrapolation from the data. In contrast, the proposed novel Structural Machine Learning (SML) platform, is a natural feedforward and feedback platform, where data exploration and exploitation can be achieved faster and more accurately.

Optimization is one of the core components of machine learning. The essence of most machine learning algorithms is to build an optimization model and learn the parameters in the objective function from the given data. Variational inference is a useful approximation method which aims to approximate the posterior distributions in adaptive machine learning. Structural Machine Learning (SML) were fitted to the full bandwidth, high pass (HP)-filtered, and low pass (LP)-filtered contextualized vibroacoustic data segments.

Four exemplary program expressions (Programs A-D) for data classifications are shown below.

Program A:
   autocorrelate(min_filter(moving_avg(x, MovingAverageWindow0), WindowSize1)) Constants A:
   {'MovingAverageWindow0': MovingAverageWindow(data=3), 'WindowSize1': WindowSize(data=381)}

Program B:
   concat(lowpass_buffer(max_filter(exponential_moving_avg(x, MovingAverageWindow0), WindowSize0), CutoffRatio0,SamplingRate0, FilterOrder0), autocorrelate(min_filter(x, WindowSize1)))
   Constants B: {'MovingAverageWindow0': MovingAverageWindow(data 7), 'CutoffRatio0': CutoffRatio (data=0.99999), 'WindowSize0': WindowSize (data=220), 'WindowSize1': WindowSize(data=262), 'FilterOrder0': FilterOrder(data=1), 'SamplingRate0': SamplingRate(data=1000.0)}

Program C:
   time_width(mul_vecs(exponential_moving_avg(x, MovingAverageWindow0), x)) Constants C:
   {'MovingAverageWindow0': MovingAverageWindow (data=3)}

Program D:
   concat(highpass_buffer(x, CutoffRatio1, SamplingRate0, FilterOrder1), dot_product(min_filter(min_filter(x, WindowSize1), WindowSize1), min_filter(moving_avg(x, MovingAverageWindow1), WindowSize1)))
   Constants D: {'MovingAverageWindow1': MovingAverageWindow(data=3), 'CutoffRatio1': CutoffRatio (data=0.99999), 'WindowSize1': WindowSize (data=169), 'FilterOrder1': FilterOrder(data=1), 'SamplingRate0': SamplingRate(data=1000.0)}"

Score (fitness) is multidimensional generalization of ANOVA F-statistic. It increases with between group variance and decreases with increasing within group variance. Table 3 shows scores for the exemplary Programs A-D.

TABLE 3

Scores for the Exemplary Programs A-D

| | Score (log(F)) | |
|---|---|---|
| Program | Train | Test |
| A | 6.15 | 4.36 |
| B | 5.99 | 4.36 |
| C | 5.50 | 4.06 |
| D | 6.13 | 4.47 |

Program output visualization shows that some kind of clustering is achieved. The goal is to look for tight, homogenous groups of points that lie far from each other. Subjects and data from training/test sets are represented by different colors. A ' * ' means that group of points come from the test set. FIGS. 31A-31E illustrate outputs of programs on identification task.

Two additional exemplary program expression (Programs E and F) for data classifications are shown below.

Program E:
   lowpass_buffer(moving_avg(min_filter(min_filter(min_filter(x, WindowSize0), WindowSize1), WindowSize0), MovingAverageWindow0), CutoffRatio0, SamplingRate0, FilterOrder0)
   Constants E: {'MovingAverageWindow0': MovingAverageWindow(data=125), 'CutoffRatio0': CutoffRatio (data 0.99999), 'WindowSize0': WindowSize (data=11), 'WindowSize1': WindowSize(data 33), 'FilterOrder0': FilterOrder(data 1), 'SamplingRate0': SamplingRate(data 1000)}

Program F:
   lowpass_buffer(mul_vecs(moving_avg(div_vecs(exponential_moving_avg(x, MovingAverageWindow0), median_filter(x, WindowSize0)), MovingAverageWindow0), exponential_moving_avg(moving_avg(min_filter(x, WindowSize0), MovingAverageWindow0), MovingAverageWindow0)), CutoffRatio1, SamplingRate0, FilterOrder1)
   Constants F: {'MovingAverageWindow0': MovingAverageWindow(data=106), 'CutoffRatio1': CutoffRatio (data 0.99999), 'WindowSize0': WindowSize (data=54), 'FilterOrder1': FilterOrder(data=1), 'SamplingRate0': SamplingRate(data=1000)}

Table 4 illustrates results of a segmentation task where score is mean AUC of segmentation of a given pattern on all data samples, for Programs E and F.

TABLE 4

Segmentation task for Programs E and F

| | Score (mean AUC) | |
|---|---|---|
| Program | Test S1 | Test S2 |
| E | 0.97 | 0.81 |
| F | 0.91 | 0.95 |

Figure 42A:
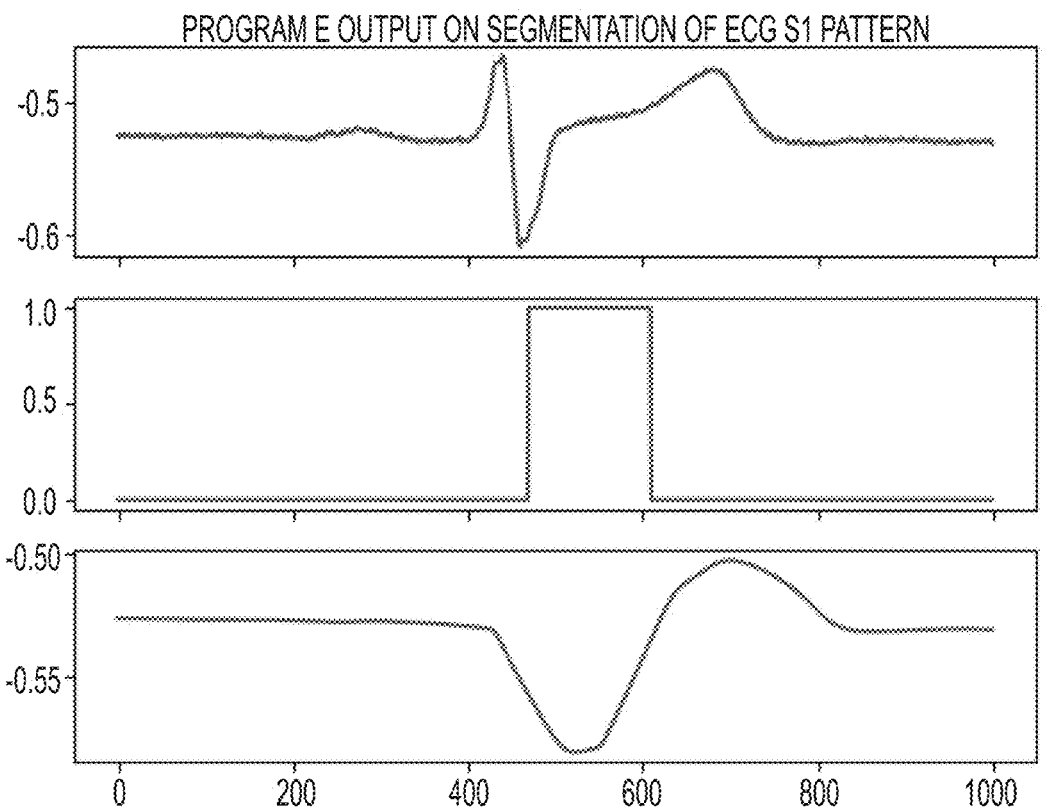
FIGS. 42A and 42B depict program output on segmentation tasks on example vibrometer data.
Figure 42B:
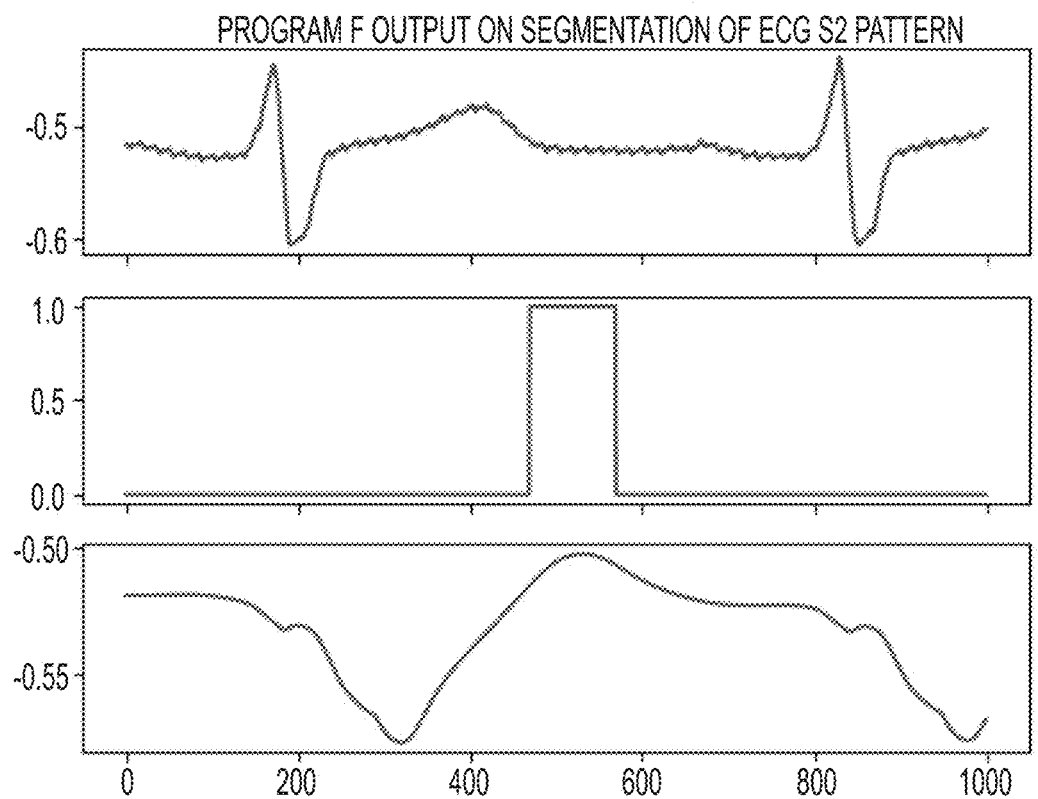

Output visualization of Programs E and F is shown in FIGS. 42A and 42B. Each program output visualization consists of 3 plots: the top plot is the input ECG signal, the middle plot is the Springer Segmentation output, and the bottom plot is the program outputs given the input ECG. The goal is to maximize AUC, so we look for separation in output value whenever a pattern (S1/S2) is met. FIGS. 32A and 32B illustrate outputs of programs on segmentation task.

Example 5: Classification Examples Using Vibrometer Data

Vibroacoustic data from a test subject was acquired using a sensing device according to a variant of the present technology, such as the sensing device of FIG. 4, and used to assess a segmentation algorithm and train and test a model for predicting fatigue states based on vibroacoustic data. The sensing device included the ECG sensor module which was used to determine the heart beat of the subject, and to use the heart beat to segment the detected vibroacoustic data.

Clinical Data Collection

Multiple episode data was collected from a single individual over monitoring before and after five workout sessions over a 7-month period, while in two different functional states: "at rest" and "stressed," achieved by aerobic exercise. Exertion was self-reported as "high" during the aerobic activity, which included running distances between 3 and 5 miles on each of five workout sessions. "At rest" data were collected prior to the workout. "Stressed/Fatigued" data were collected approximately 20 minutes following aerobic activity cessation during the recovery phase. Data was recorded around the intersections of the 2nd to 3rd intercostal spaces and the left midclavicular line. This position was chosen based on its proximity to the heart.

TABLE 5

Exercise activity included in analysis

| Date | Time (workout start) | Duration |
|---|---|---|
| May 31, 2019 | 4:30 PM | 3.5 miles |
| Jun. 4, 2019 | 6:50 AM | 2.9 miles |
| Jun. 7, 2019 | 5:50 AM | 3.0 miles |
| Jun. 11, 2019 | 5:40 AM | 3.0 miles |
| Jan. 3, 2020 | 4:30 PM | 5.0 miles |

The data from the first four data collection dates shown in Table 5 was chosen to serve as the training data, while the data from January 2020 was selected as the test data. This was done intentionally, because the last data collection session was approximately seven months after the others, and anticipated as helpful to illustrate some measure of vibrometer data stationarity over time.

Signal Processing

Vibrometer data was decimated from a 48 kHz sampling frequency to a 1 kHz sampling frequency using an 8th order Chebyshev type I anti-aliasing filter, after which the data was split into three datasets: (i) full bandwidth (no additional filtering), (ii) HP-filtered (6th order high-pass Butterworth filter with critical frequency of 20 Hz), and (iii) LP-filtered (6th order high-pass Butterworth filter with critical frequency of 20 Hz). Some overlap in the three datasets existed due to the non-ideal frequency cutoffs for the filters (higher filter orders would help alleviate this issue).

Vibrometer Data Segmentation

Fixed-duration heart sounds, rather than the full vibrometer records or individual heart cycles, were chosen as inputs to the classifiers. One reason for this is that the fatigued state has a higher heart rate (HR) and lower heart rate variability (HRV) than the non-fatigued state. The higher HR would have resulted in different length heart cycle input data for the models, which would have been quite easy to classify. If the full heart cycles were resampled to homogenize the data lengths, the intra-sample time spacing, and therefore the absolute measures of frequencies, would be lost. Another reason for using fixed-duration heart sounds as inputs to the classifiers is that the relative location of the S2 sound is affected by HR, providing another feature that would make the classification almost trivial. Additionally, S1 and S2 heart sounds can be extracted with assumed uniform durations using the Springer Segmentation Algorithm. For this analysis, the first heart sound S1 was chosen, with a fixed duration of 100 milliseconds.

Classification Models

Figure 36A:
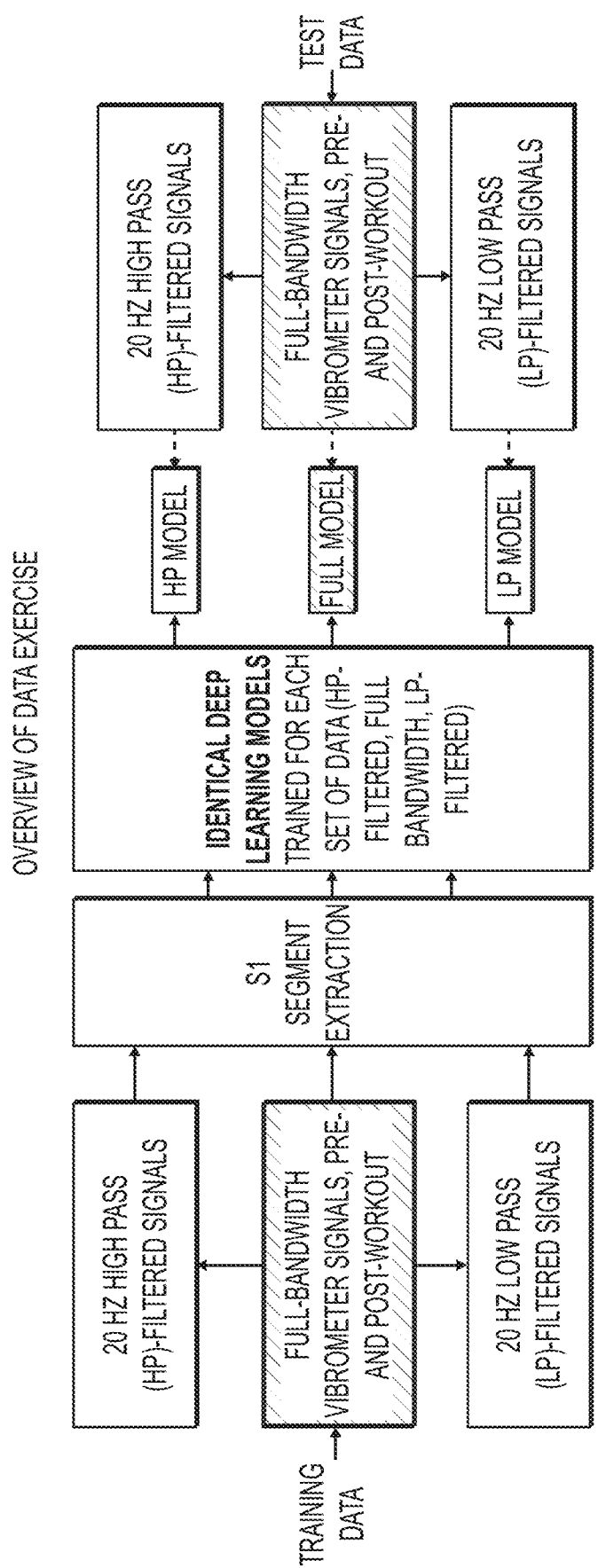
FIG. 36A is a summary of development of classification models in an example of training and testing a machine learning model for classification of fatigue and non-fatigue states in a subject in example variations of a system of the present technology.

Three "deep learning" models with identical structures were fitted to the full bandwidth, HP-filtered, and LP-filtered S1 data segments. The identical model structure chosen was a neural network composed of two convolutional layers followed by a dense layer. To help avoid overfitting, dropout layers were also included. The full bandwidth, HP-filtered, and LP-filtered models were then tested with full bandwidth, HP-filtered, and LP-filtered S1 segments from the test data, respectively (FIG. 36A).

Metrics were calculated from the test data and include loss (binary cross-entropy), accuracy, sensitivity, specificity, false positive rate, true positive rate, and AUC. Since model fitting using the chosen tools is stochastic, the model fitting and metric calculations were repeated 30 times. All data processing and modeling were done using Python and Keras/Tensorflow.

Results: Vibrometer Data Segmentation

Figure 36B:
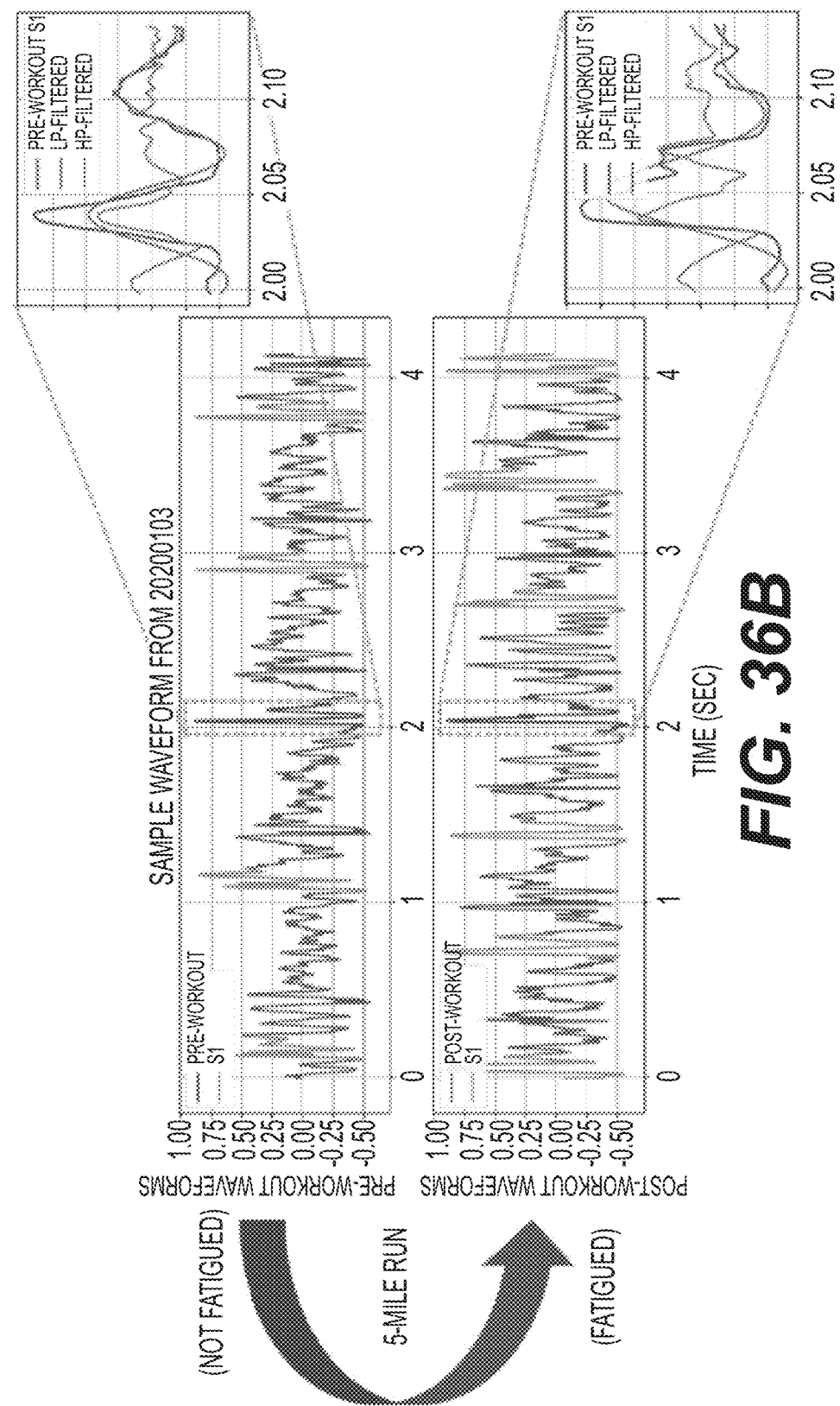
FIG. 36B depicts sample heart sound data extracted as segments from a vibrometer waveform using an example variation of a sensing device of an example variation of a system.

FIG. 36B shows an example of extracted S1 heart sounds (including filtering) from a vibrometer waveform. Visual inspection suggested that the segmentation algorithm performed as expected. Table 6 shows the number of S1 segments extracted from each pre/post-workout session. As expected, the number of S1 segments is quite small, which is the reason for the simple model structure chosen in this analysis.

TABLE 6

Number of S1 segments extracted from data records

| Date | S1 segments, not fatigued/pre-workout (n) | S1 segments, fatigued/post-workout (n) |
|---|---|---|
| May 31, 2019 | 73 | 97 |
| Jun. 4, 2019 | 124 | 175 |
| Jun. 7, 2019 | 122 | 145 |
| Jun. 11, 2019 | 125 | 138 |
| Jan. 3, 2020 | 125 | 180 |

The total number of S1 segments pre/post-workout were randomly balanced for both the training and test sets and fixed for all subsequent model training/testing. There were a total of 444 pairs (pre- and post-workout S1 segments, 888 total) of training data and 125 pairs (pre- and post-workout S1 segments, 250 total) of test data.

Results: Model Performance

Mean metrics from the 30 model fits are shown in Table 7, which shows high performance of the models trained with data containing low frequencies.

TABLE 7

Mean metrics from 30 model fits calculated from test data set. It is assumed that "positive" = post-workout in these calculations.

|  | HP model | Full bandwidth model | LP model |
|---|---|---|---|
| Accuracy | 0.503 | 0.706 | 0.823 |
| Sensitivity | 0.951 | 0.978 | 0.943 |
| Specificity | 0.055 | 0.434 | 0.703 |
| AUC | 0.705 | 0.934 | 0.941 |

Figure 36C:
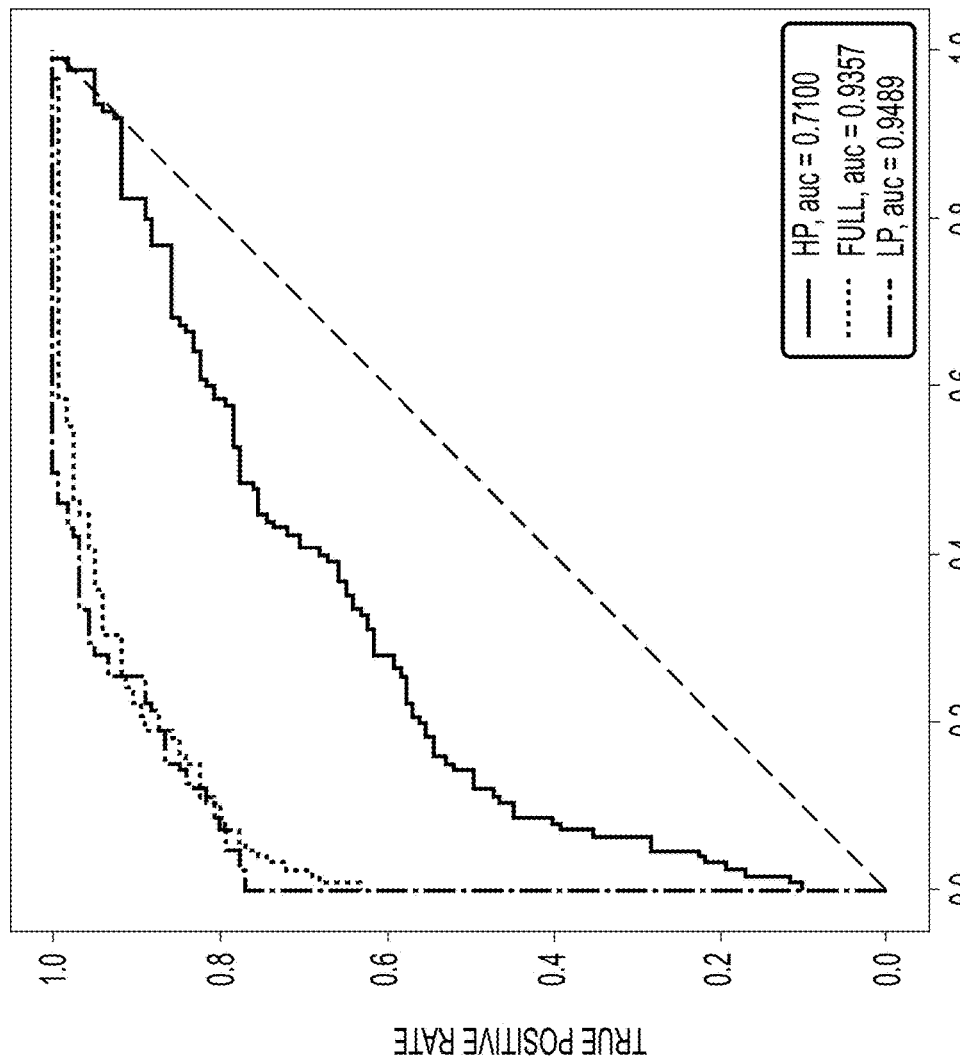
FIG. 36C depicts a Receiver Operator Curve (ROC) for a classification model fit closest to a mean area under the ROC values of data obtained using an example variation of a sensing device of an example variation of a system of the present technology.

Similarly, graphical representations of model performance also show the value of low frequencies. For example, the ROC curve for the model fit closest (in the 2-norm sense) to the mean AUC is shown in FIG. 36C.

These results suggest that, for a given and fixed model structure, novel low frequency vibrometer data may generate more robust model predictions than higher frequency acoustic data. This is supported by both the models based on full-bandwidth and LP-filtered data outperforming the model based on HP-filtered data in most metrics listed in Table 7.

Example 6—Design of Voice Coil Sensor Module

Developers goal was to develop a novel voice coil-based sensor module for human/animal physical monitoring. Among the optimization parameters were:
- magnet size, shape and material for strong and uniform magnetic field;
- coil material, length, number of windings and number of layers for maximum length while minimizing resistance and weight;
- lightweight support structure e.g. flexure-based structure, or flexible diaphragm holding windings;
- overall dimensions constrained because of the need to incorporate the sensor module into lightweight small wearable device or handheld device.

Performance of candidate transducer designs was evaluated based on three output variables: force responsivity, receiving sensitivity, and frequency-response efficiency.

Force Responsivity

The actuating abilities of the transducers were evaluated by measuring the force exerted by the transducers as a function of frequency. A Dynamic Signal Analyzer (DSA) was used to step through source frequencies in the range of 0.01 to 160,000 Hz and to calculate a frequency response spectrum of the signal from the force transducer measured for each source frequency.

Receiving Sensitivity

The DSA was used to step through a range of source frequencies and to calculate a frequency response spectrum of the receive signal from the test transducer, measured at each source frequency.

Reciprocal Concrete Transmission Efficiency

To verify that it is indeed possible to collect and transmit infrasound through to ultrasound mechano-acoustic waves passively harvested from the human body using these test voice coil transducers, measurements were made from patients and on a physiologic manikin. Two identical transducers were used for this experiment: one for transmission and one for reception. The reciprocity in the transmissions was investigated by repeating each measurement with reversed transducer configuration, so that the transducer that previously transmitted acted as receiver and vice versa.

The DSA source was used, via the power amplifier, to apply a sinusoidal signal with stepped frequency to the transducer that acted as a transmitter. The output of the power amplifier was fed into Ch. 1 of the DSA for reference. The output from the receiving transducer was fed into the DSA (Ch. 2). By dividing Ch. 2 with Ch. 1 the voltage transfer function was established. By then dividing by the transducer complex impedance the transmission efficiency was determined.

TABLE 8

Voice coil parameter ranges in certain variants of the present technology.

| Parameter | Present technology | Conventional voice coil |
|---|---|---|
| Impedance | 150 ohms ± 2% | 4 ohms |
| DC Resistance (Re) | 150 ohms ± 2% | 4.3 ohms |
| Voice Coil Inductance (Le) | 7.5 mH at 1 kHz/ 2.5 mH at 10 kHz | 0.27 mH at 1 kHz/ 0.12 mH at 10 kHz |
| Coil Resonant Frequency (Fs) | 80-170 Hz | 224 Hz |
| Total Q (Qts) Inverse of damping | 0.25 to 0.65 (depending on exciter)/100 mg to 100 g depending on no. windings) | 0.78 |
| Moving Mass (Mms) | 100 mg to 100 g (depends on number of windings) For test exciters specifically 1.15 g | 1.61 g |
| Mechanical Compliance of Suspension (Cms) (inverse of suspension) | 04 to 3.2 mm/N | 0.338 mm/N |
| BL Product (BL) | 18.5 N/Amp (same as Tm) | 3.63 Tm |
| Voice Coil Diameter | 25 mm | 25 mm |
| RMS Power Handling | 2 W | 24 watts |
| Wire Diameter | 0.05 mm | 0.15 (including insulation) |
| Number of windings | 208 | 46 |
| Number of Layers | 4 | 2 |

TABLE 8-continued

Voice coil parameter ranges in certain variants of the present technology.

|  | Present technology | Conventional voice coil |
|---|---|---|
| Magnet Size | 24 mm × 3.5 mm | 24 mm × 3.5 mm |
| Overall Outside Diameter | 50.5 mm (5 × 5 × 0.1 to 50 × 50 × 10) | 50.5 |
| Overall Depth | 20.5 mm | 20.5 |
| Wright Parameters |  |  |
| K(r) | 26-27 | 0.275 |
| X(r) | 0.175-0.185 | 0.286 |
| K(i) | 0.00709-0.01118 | 0.00045 |
| X(i) | 0.827-0.866 | 0.843 |

By way of background, and to support the above described experimental approach, the following was considered. An electrodynamic sensoriactuator is a reversible voice coil transducer which has capability to provide input vibrational energy to a host mechanical structure. It can be regarded as a two-port system, including electromechanical coupling through two pairs of dual variables: the voltage e and current i for the electrical side, and the transverse force $F_s$ and velocity $v_s$ for the mechanical side.

Using phasors to represent the complex amplitude (magnitude and phase) of sinusoidal functions of time, the characteristic equations of the sensoriactuator when attached to a host mechanical structure can be written as:

$$Bli = \underline{Z}_{ma}\underline{v}_a - \underline{Z}_{ms}\underline{v}_s \qquad (7)$$

$$\underline{e} = \underline{Z}_e i - \underline{\varepsilon} \qquad (8)$$

where $\sqrt{v}_a$ is the velocity of the moving mass, $\underline{v}_s$ is the transverse velocity at the base of the actuator, $\underline{e}$ is the input voltage applied to the electrical terminals, i is the current circulating in the coil, $\underline{Z}_{ma} = j\omega M_a + R_a + K_a/j\omega$ is the mechanical impedance of the inertial exciter, $\underline{Z}_e = R_e + j\omega L_e$ is the blocked electrical impedance of the transducer, and $\underline{Z}_{ms} = R_a + K_a/j\omega$ is the impedance of the spring-dashpot mounting system. Equations 7-8) contain terms of electrodynamic coupling; $\underline{F}_{mag} = Bli$ is the force caused by the interaction of the magnetic field and the moving free charges (current), and $\underline{\varepsilon} = Bl(\underline{v}_a - \underline{v}_s)$ is the back electromotive force (voltage) induced within the voice coil during motion. It is also assumed that all the forces acting on the actuator are small enough so that the displacements remain proportional to applied forces (small-signal assumptions).

The input impedance of the sensoriactuator is the complex ratio of the voltage to the current in the electrical circuit of the transducer. It determines the electrical impedance (in Ω) "seen" by any equipment such as electronic drive source, electrical network, etc., connected across its input terminals. When attached to a pure mass, the closed form expression of the input impedance of the sensoriactuator can be obtained by combining Eq. (7) and (8), as $$Zin = \frac{e}{i} = Z_e + \frac{(Bl)^2}{Z_{ma}} \qquad (9)$$

As can be seen in Eq. (9), $\underline{Z}_{in}$ contains all the electromechanical effects that are operating, including all resistances and reactances of the actuator impedance. As discussed in the following, measuring the input impedance of the actuator enables certain key parameters such as the dc resistance and natural frequency to be evaluated.

Substituting now Eq. (7) in Eq. (8), the transverse velocity at the base of the actuator be expressed as:

$$\gamma = \frac{Zma}{jwMaBl}(e\_Zei) + \frac{Bl}{jwMa}i \qquad (10)$$

Equation (10) clearly shows that the transverse velocity of the structure where the actuator is located can be estimated from the driving current and the voltage sensed at its input terminals.

Example 7—Preliminary Detection of COVID-19 Infection

Figure 45:
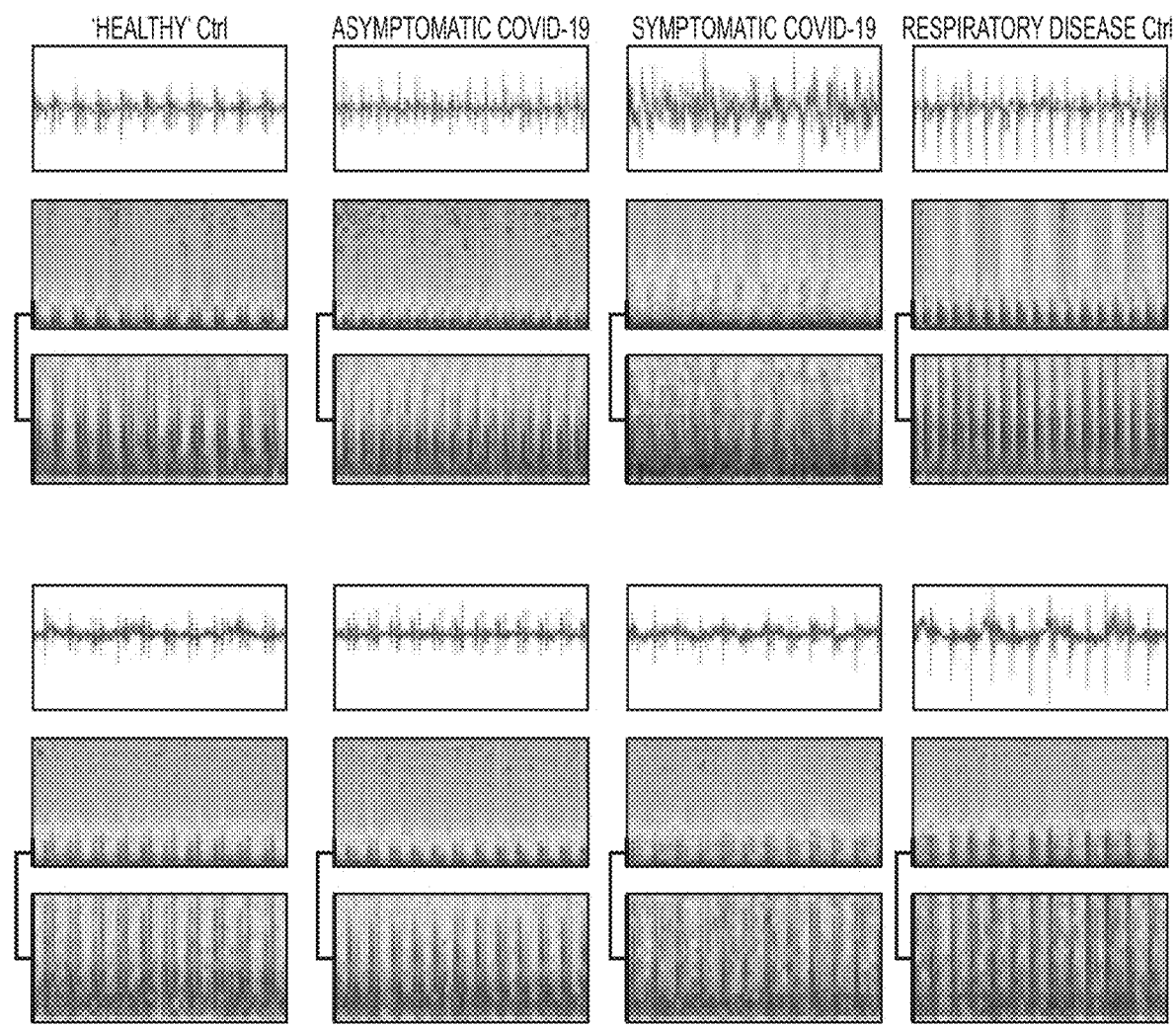
FIG. 45 depicts example vibroacoustic test data collected by a sensing device of the present technology from control subjects (control), asymptomatic subjects with a covid-19 infection, symptomatic subjects with a covid-19 infection, and subjects with another respiratory disease (control).

As seen in FIG. 45, in a preliminary study, Developers identified that subjects with certain target conditions have a biosignature distinguishable from those of healthy subjects. For example, Developers have demonstrated that vibroacoustic biosignatures can be used to determine infection with Covid-19. Differences were observed in the vibroacoustic biosignatures of Covid-19 symptomatic and asymptomatic subjects compared to those of healthy control subjects. These findings can be reasonably extrapolated to other respiratory conditions, as well as other viral and bacterial conditions and the like. The vibroacoustic signal detection was performed using the sensing device 400 as described with respect to FIG. 4.

Example 8—Clinical Trial for COVID-19 Infection

Detection of COVID-19 infection in subjects remains challenging, particularly using non-invasive and fast techniques. As previously mentioned, current COVID-19 screening approaches are either simple and fast but lack accuracy (e.g., temperature checks), or are accurate but neither simple nor fast (e.g., antibody screening). The gold standard for COVID-19 diagnosis is real-time reverse-transcriptase polymerase chain reaction (RT-qPCR), however, many counties and states have limited RT-PCR testing to individuals with overt symptoms, and there are often significant delays between testing and result reporting—providing opportunity for unknown infectious spread. In addition to the 'classic' COVID-19 illness, COVID-19-associated multisystem inflammatory syndrome in children (MIS-C) has recently emerged as a complicated and potentially fatal outcome resulting in school and workplace closures. While COVID-19 is primarily characterized by acutely compromised lung and respiratory function with symptoms peaking 7-10 days following infection, MIS-C affects multiple organ systems 2-4 weeks post-illness, and can include gastrointestinal distress, kidney injury, neurologic symptoms, and impaired heart function. With features that often resemble toxic shock syndrome, MIS-C can occur in children without prior symptoms of COVID-19 and can have a variable clinical presentation depending on affected organ systems. These attributes make MIS-C difficult to predict, and challenging to diagnose. Convenient and reliable screening approaches to identify those with likely infection is critical to limiting outbreaks, while understanding development of worsening illness is essential for triage and mortality reduction.

In the present Pilot study, the study participants include 15 patients with confirmed COVID-19 with pulmonary symptoms ("case patients") matched with 15 hospitalized control inpatients without COVID-19 with non-pulmonary diagnoses or symptoms ("control patients"). Study participant matching attempted to make sure that the control group is sufficiently similar to the cases group, with respects to variables such as age, sex, BMI, smoking status, etc. The methodology adopted in this Pilot Study data analysis addresses the deficiencies of modern classification techniques by exposing the structure of case-control matching to the data analysis methods. The approach in this Example models not only the 'horizontal' classification into cases and controls, but also the "vertical" transformations related to the matching variables (age, sex, BMI, etc.), and so acquires additional knowledge about the problem, which in turn lowers the risk of overfitting and facilitates learning from small samples.

Signal detection using variants of the present system, such as the sending device 400, was performed on the Case subjects and the Control Subjects. Readings were taken from each subject when the subject was in different body positions (neutral sit, neutral upright stand, supine, left lateral decubitus position (LLDP). Whilst in each position, readings were taken whilst the subjects were performing different activities (handgrip and cough, and vocalizations that reveal pulmonary consolidation). Each set of readings was taken by positioning the sensing device 400 on nine different auscultation positions on the subject (9-step staircase ladder procedure starting at the right carotid). The so obtained data was segmented into 10, 5, 3 heart cycles, and further split by frequency range (<20 Hz (infrasound), 20-20,000 Hz (audible sound), and >20,000 Hz (ultrasound)) to expand the paired data structure and facilitate classification/clustering/individuation. The sensing device 400 was positioned over clothing. The sensing device 400 was also arranged to collect additional sensor data such as IMU data, contextual data, heart beat.

The sensor data for this study illustrates the use of high-dimensional data where the number of variables is close to or moderately higher than the number of subjects. The approach also helps with low-dimensional data with appropriate variable selection. Since the framework seamlessly incorporates variable selection with fitting the prediction model for the matched design, variable selections can be evaluated, ignoring and considering the matched design to quantify impact on the prediction model performance. As a matter of fact, the approach goes beyond traditional feature selection and ventures into feature construction, autonomously synthesizing 'derivative descriptors' from the available variables.

Figure 46:
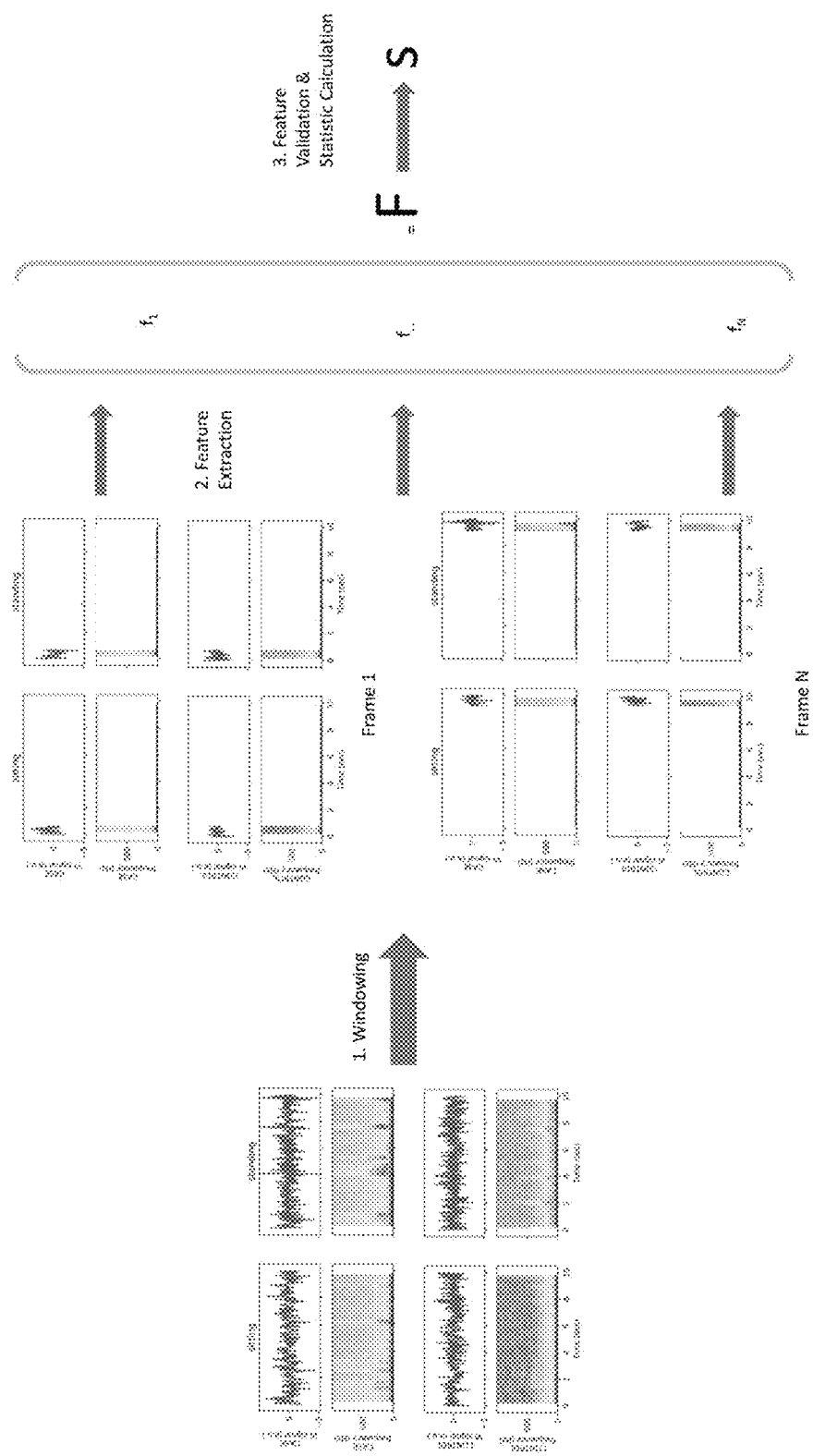
FIG. 46 depicts an example workflow of processing detected data including windowing and feature extraction.

With reference to FIG. 46, in terms of sensor data/signal processing, the vibroacoustic signal was first divided into $_n$-term segments (windows) and then, for each segment, the t-term processing stage was carried out. The n-term segment was p ms long with q ms overlap between adjacent frames (the frame rate is r frames per second), where p, q and r are optimized as part of the algorithm development. At a next step, the feature sequence, F, which was been extracted from a n-term segment, was used for computing feature statistics, (e.g. volume/loudness, bandwidth, pitch, silence/pauses, and single frequency sound markers, global and frame-based time-domain features, spectral features, energy features, harmonic features, and perceptual features). The features underlying the COVID-19 biosignature has V bits, computed from W subbands covering $Y_L$-$Y_H$ Hz cross-frequency couplets in bark-scale. In the end, each n-term segment is represented by a set of statistics which correspond to the respective t-term feature sequences. During n-term processing, it was assumed that the n-term segments exhibit homogenous behavior with respect to audio type and it therefore makes sense to proceed with the extraction of statistics on a segment basis. In practice, the duration of n-term windows provides the minimum time required to make a reliable diagnosis.

Once the t-term feature sequences were generated, feature matrix is obtained, with vectors that contain the features and vectors that contain the resulting feature statistics. If, for example, 23 feature sequences have been computed on a t-term basis and two n-term statistics are drawn per feature (e.g. the mean value and the standard deviation of the feature), then, the output of the n-term function is a 46-dimensional matrix.

In some cases, the n-term feature extraction process was employed in multi time-scales and/or multi-frequency bands, in order to capture salient features of the broad-band vibroacoustic signal. For example, in the context of COVID-19 classification of cases vs. controls it was sometimes desirable to extract a single feature vector as the representative of the class. In such cases, $t_{short}$-term features were first extracted as described above and at an intermediary step, $t_{longer}$-term statistics were computed on a $t_{longer}$-term segment basis. At a final stage, the $t_{all}$-term statistics were long-term averaged, in order to provide a single vector representation of the biosignature signal.

The general framework for the COVID-19 biosignature was as follows—a) sensor data was first segmented into n-term frames, and b) global and frame-based time-domain features, spectral features, energy features, harmonic features, and perceptual features were extracted for each frame. Then, these features were c) mapped into and class biosignature that is a compact representation. This process is repeated ad nauseum to increase sensitivity and specificity across classification/clustering/individuation.

Mel-frequency cepstral coefficients (MFCC) or cepstral coefficients (CC) are widely used for speech recognition and speaker recognition applications. While both of these provide a smoothed representation of the original spectrum of an audio signal, MFCC further considers the non-linear property of the human hearing system with respect to different frequencies. Given the success of MFCC in the speech domain, it is also every popular in other audio signal processing, for example, audio/music classification, audio content segmentation, speaker segmentation, language identification, etc. For audio-based video copy detection, MFCC, equalized MFCC (the mean of cepstral features in each audio is subtracted to generate zero mean features), and Gaussianized MFCC (non-linear transformation is applied to the cepstrum such that the features have a Gaussian distribution) were adopted in. MFCC has 13 dimensions, and when the first order temporal derivative of MFCC is considered, the total feature dimension becomes 26. The difference between any two MFCC feature vectors can be measured by their Euclidean Distance. Other acoustic features that can be used for audio content identification include Fourier Coefficients, Linear Predictive Coding (LPC) coefficients, Modulated Complex Lapped Transform (MCLT), etc.

The method of determining the COVID-19 biosignature featured the following steps:
1. Pull frames in the file (p ms frames shifted by q ms each time)
2. For each frame: Extract the data, do optional dithering, pre-emphasis and dc offset removal, and multiply it by a windowing function (e.g. Hamming)
3. Determine frame energy and perform stateless frame by frame energy max-normalization. [The spectrogram, computed for the input audio by short-time Fourier transform, represents the vibroacoustic energy at certain (time, frequency) coordinate. Peaks, the time-frequency points whose energy is the local maximum in a region centered around the point, are selected to construct a constellation map. For an anchor point in the constellation map, a target zone is constructed in the constellation map based on its time and frequency. The anchor point and any point in the target zone form a pair, and their frequencies and time difference are used to create a ø-bit unsigned integer (biosignature). Once identified the bisosignatures and accompanying covariates are bootstrap recycled to quantify reproducibility, even in the presence of noise and compression]
4. Perform FFT and compute the power spectrum. [Alternatively, short-time Fourier transform (STFT), and then converted into D bands in vibe-scale. Spectral salient points can then be selected, which are the local spectral peaks in time and/or frequency domains. The average energy values of all regions are computed and a fixed length binary descriptor is constructed by comparing the energy of a selected pair of regions. This local binary descriptor is used as vibroacoustic biosignature for indexing and retrieval]
5. Compute the energy in each vibe bin; these are e.g. $\varsigma$ triangular overlapping bins whose centers are equally spaced in the vibe-frequency domain
6. Compute the log of the energies and take the cosine transform, keeping as many coefficients as specified
7. Perform cepstral liftering and piecewise linear mapping of the interval $[Y_L$ low-freq, $Y_H$ high-freq] to $[Y_L$ low-freq, $Y_H$ high-freq].
8. Perform domain adaptive feature extraction using domain specific languages for biosignature identification.

The lower and upper cutoff of the frequency range covered by the triangular vibe bins are controlled by the options $Y_L$-low-freq and $Y_H$-high-freq.

Low resolution images were created from the sensor data. Self-Organizing Maps (SOMs) provide a useful approach to vibroacoustic data feature visualization. They are capable of generating 2D quantized (discretized) representations of an initial vibroacoustic data feature space. SOMs are neural networks trained in an unsupervised mode in order to produce the desired data organizing map. An important difference among SOMs and typical neural networks is that each node (neuron) of a SOM has a specific position in a defined topology of nodes. In other words, SOMs implement a projection of the initial high-dimensional feature space to a lower-dimensional grid of nodes (neurons). Compact fingerprints were created from the sensor data (audio spectrogram), which is treated as an image. The image could be extended to include other data, if it makes sense at this location. Specifically, a spectrogram was computed for the input vibroacoustic signal, and was decomposed using the multi-resolution Haar wavelets. To reduce the effect of noise, only the top Haar wavelets according to their magnitudes were kept. Instead of keeping the actual values of the wavelet coefficients, their signs were used to save memory usage. Then Min Hash technique was applied on this binary vector multiple times (β times) to create a set of p integers as the audio fingerprint. Basically, the Min Hash method permutes the binary vector positions in a pseudorandom order, and measures the first position that 1 occurs. The β dimension fingerprint can be further compressed with the Locality Sensitive Hashing (LSH) to reduce the number of comparisons in retrieval stage.

Example data extracts of the collected vibroacoustic sensor data from the Subject and Control cases are illustrated in FIGS. 47-51. The data extracts were extracted by: (1) using position flags to extract a middle 25 sees of VI data for each {body position}×{auscultation point}; (2) within this 25 sec segment, the 10 sec segment that has the smallest max(VI)–min(VI) value was found (this was to avoid segments where the device is moved against clothing, etc. to avoid disturbances); and (the 10 see VI segment was normalized by subtracting its mean and dividing by its standard deviation.

Figure 47:
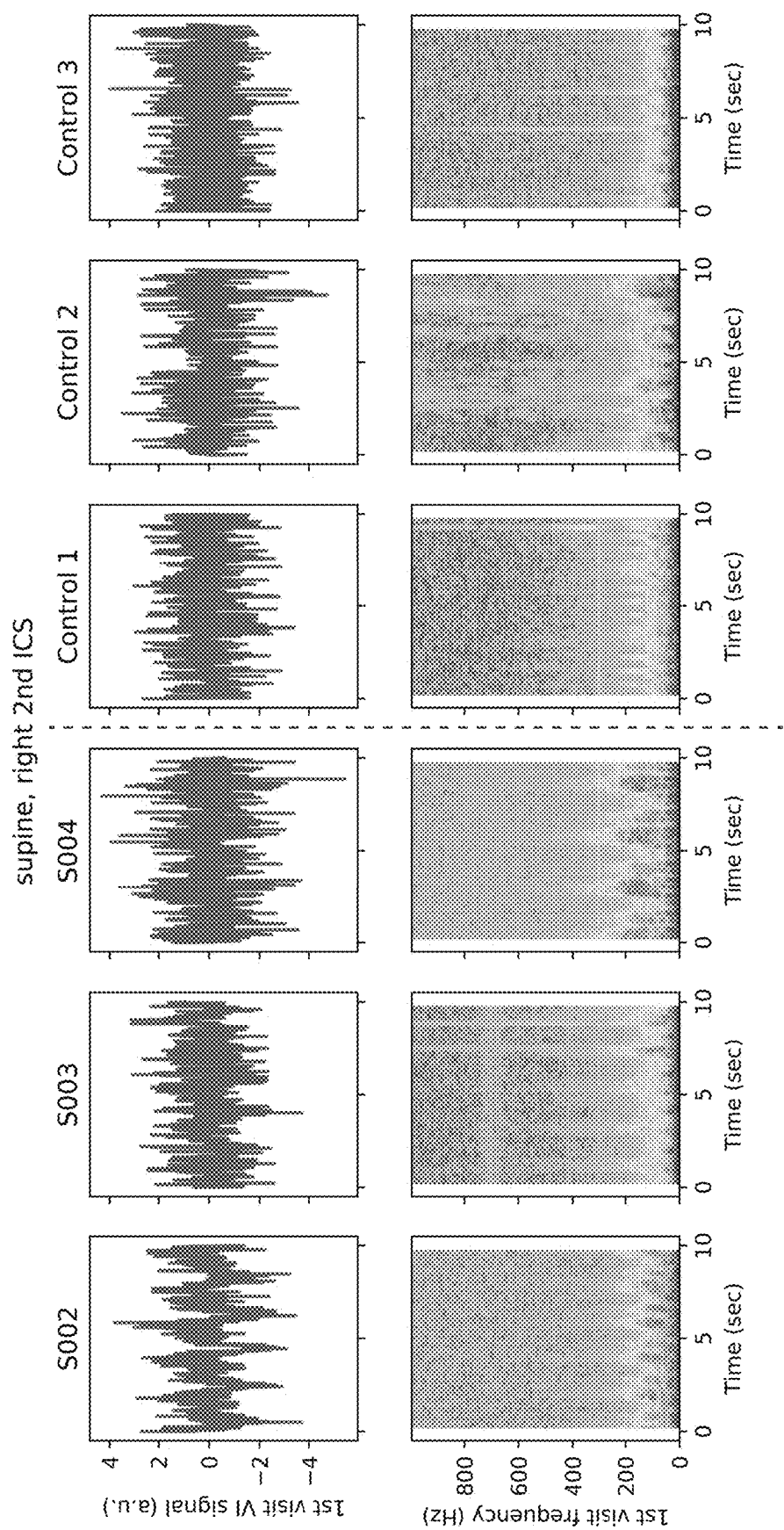
FIG. 47 depicts example vibroacoustic test data collected by a sensing device of the present technology from control subjects (control 1, control 2, control 3), and subjects with a covid-19 infection (S002, S003, S004) in which the vibroacoustic test data was collected while the subjects were in the supine position, and the data was collected from the right $2^{nd}$ ICS of the subjects' body.

In FIG. 47, sensor data extracts (vibroacoustic only) of three Subject Cases and three Control Cases are shown, in which the data was collected while the subjects were in the supine position, and the data was collected from the right $2^{nd}$ ICS of the subjects' body.

Figure 48:
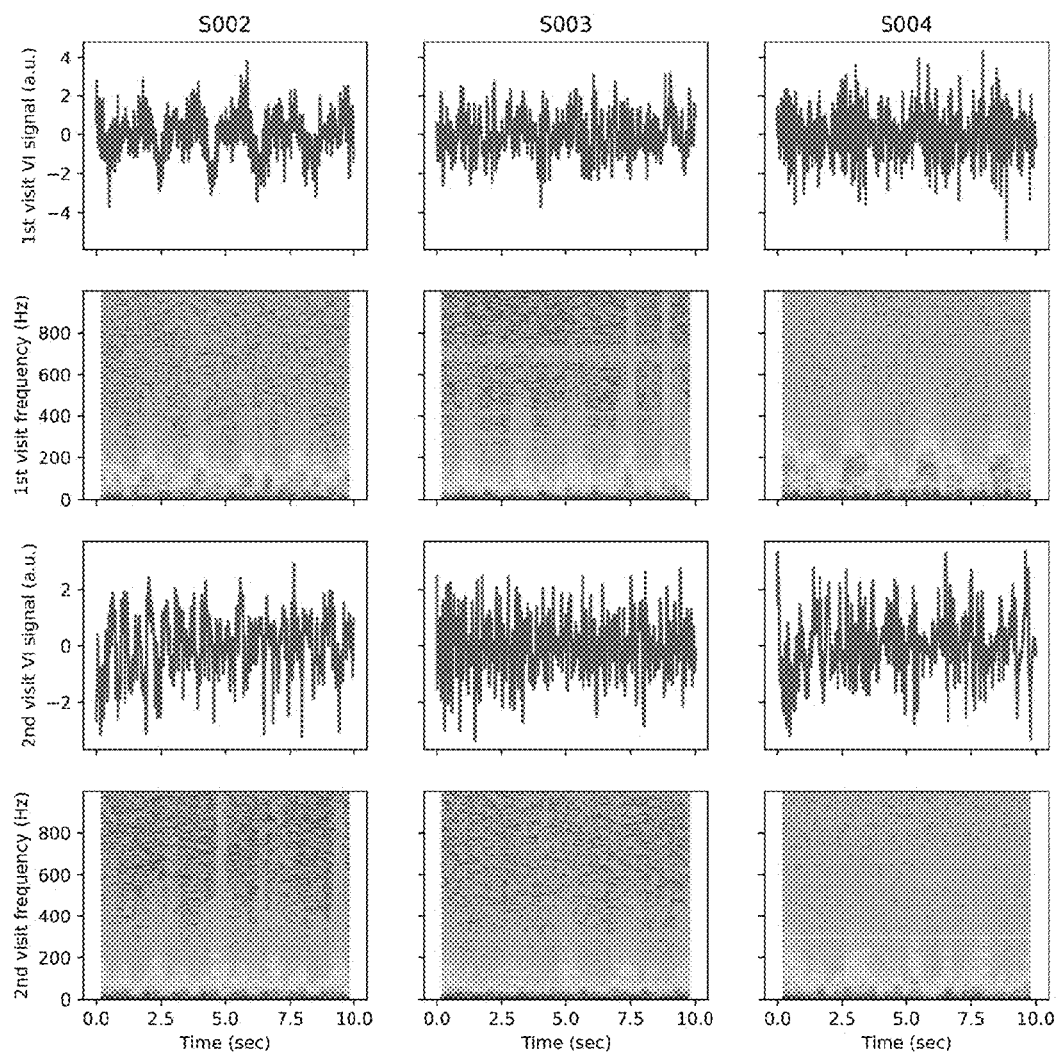
FIG. 48 depicts example vibroacoustic test data collected by a sensing device of the present technology from subjects with a covid-19 infection (S002, S003, S004), in a first visit and a second visit, in which the vibroacoustic test data was collected while the subjects were in the supine position, and the data was collected from the right $2^{nd}$ ICS of the subjects' body.

FIG. 48 shows sensor data extracts from three Subject cases (S002, S003, S004), in a first visit and a second visit, in which the vibroacoustic test data was collected while the subjects were in the supine position, and the data was collected from the right $2^{nd}$ ICS of the subjects' body.

Figure 49:
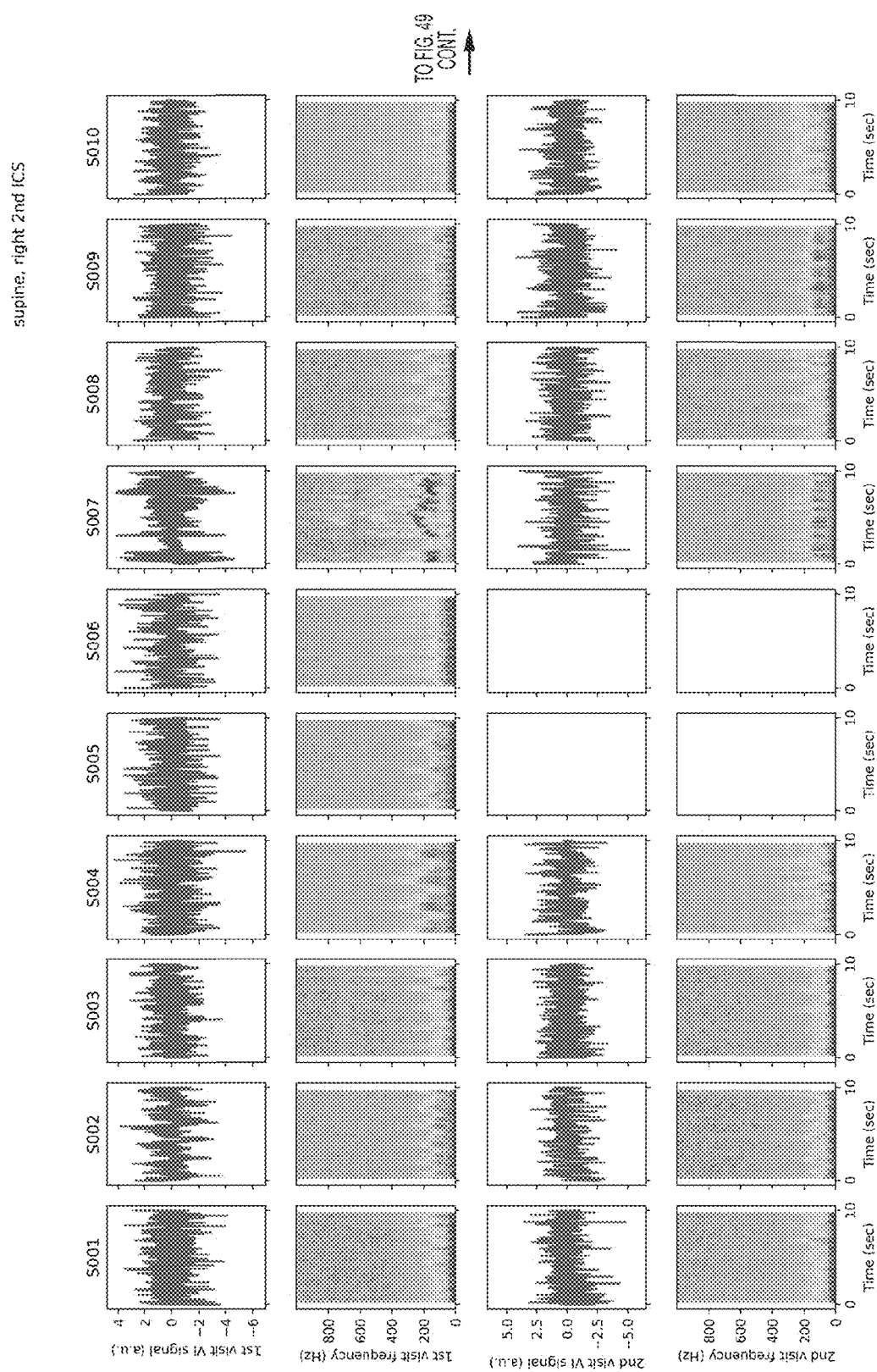
FIG. 49 depicts example vibroacoustic test data collected by a sensing device of the present technology from control subjects (control 1, control 2, control 3), and subjects with a covid-19 infection (S001-S0015) in which the vibroacoustic test data was collected while the subjects were in the supine position, and the data was collected from the right $2^{nd}$ ICS of the subjects' body.
Figure 49:
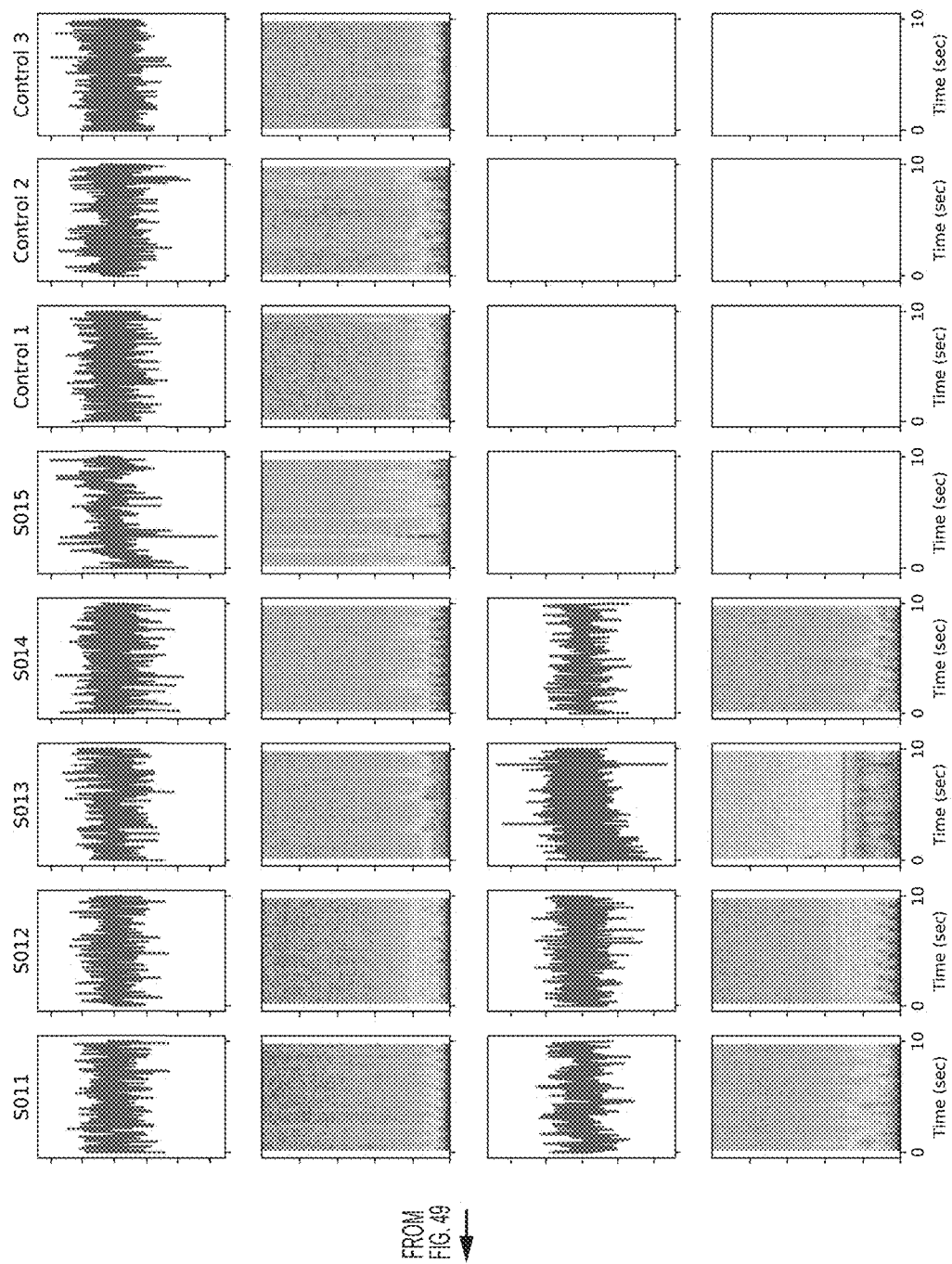

FIG. 49 shows sensor data extracts (vibroacoustic only) of fifteen Subject Cases and three Control Cases taken while the patients were in the supine position and from a $2^{nd}$ ICS location on their bodies. The blank rectangles indicate when the subjects were not able to assume the given position.

Figure 50:
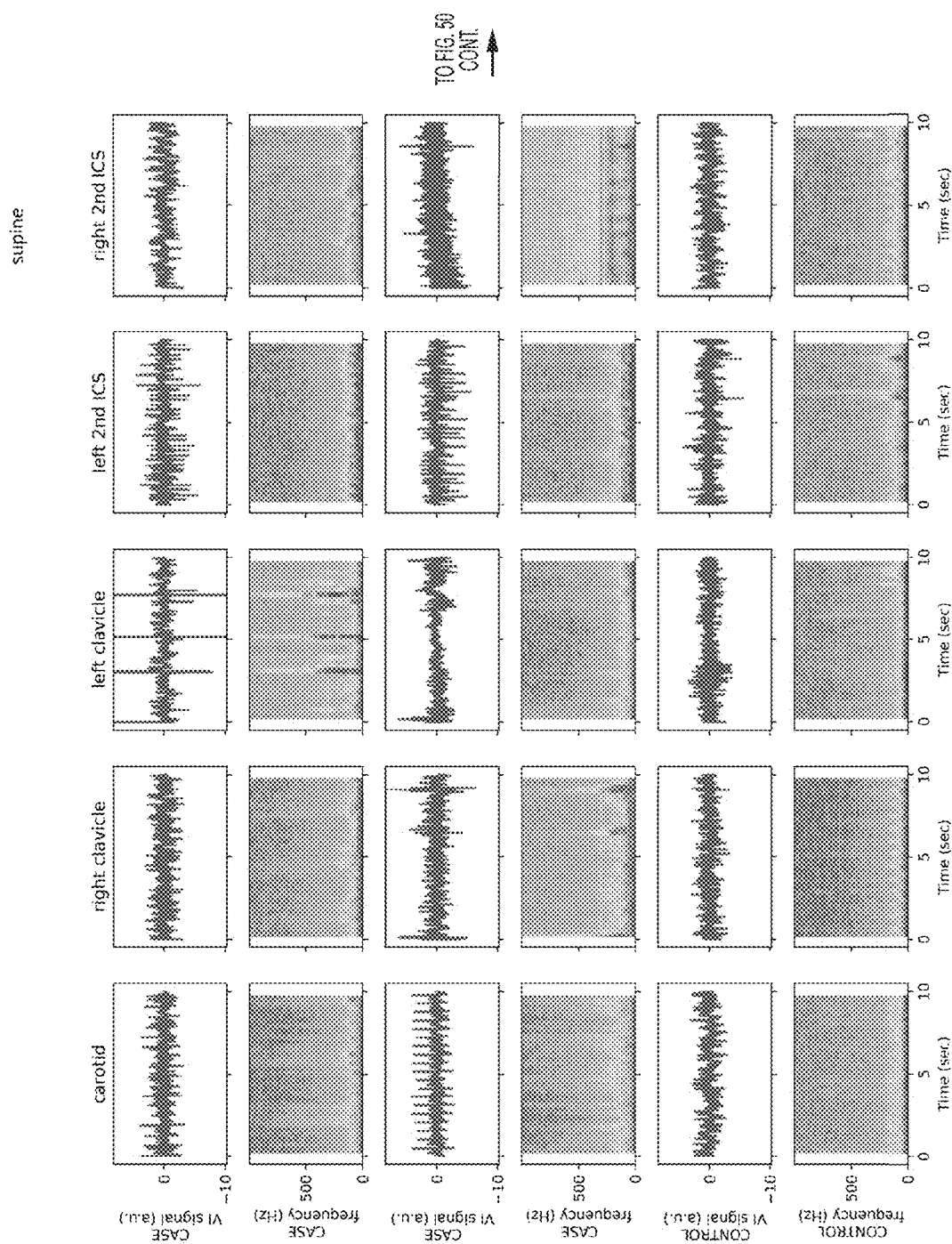
FIG. 50 depicts example vibroacoustic test data collected by a sensing device of the present technology from control subjects, and subjects with a covid-19 infection in which the vibroacoustic test data was collected while the patients were in the supine position, and from different locations on their bodies (carotid, right clavicle, left clavicle, left $2^{nd}$ a ICS, right $2^{nd}$ ICS, right $4^{th}$ ICS, left $4^{th}$ ICS, left $6^{th}$ ICS, right $6^{th}$ ICS).
Figure 50:
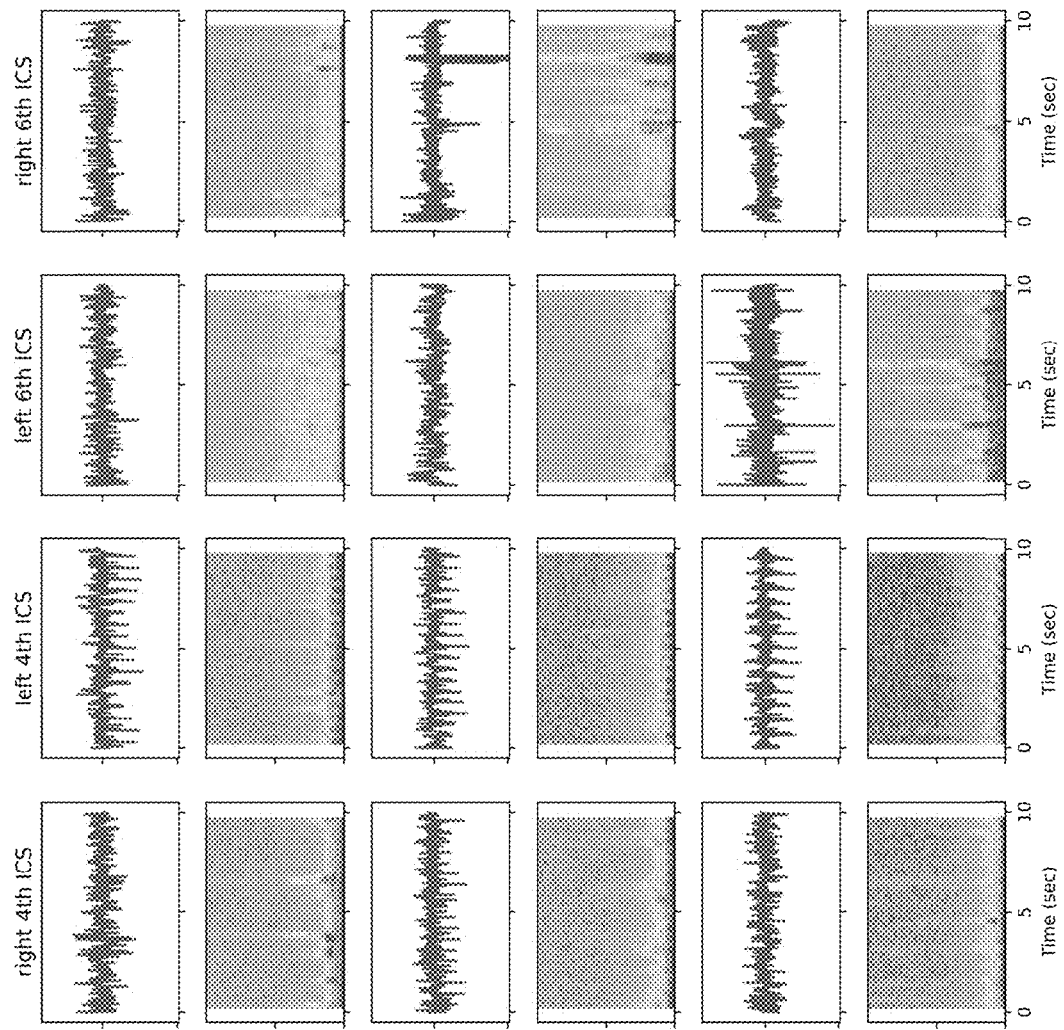

FIG. 50 shows sensor data extracts (vibroacoustic only) of two Subject Cases and three Control Cases taken while the patients were in the supine position, and from different locations on their bodies (carotid, right clavicle, left clavicle, left $2^{nd}$ ICS, right $2^{nd}$ ICS, right $4^{th}$ ICS, left $4^{th}$ ICS, left $6^{th}$ ICS, right $6^{th}$ ICS).

Figure 51:
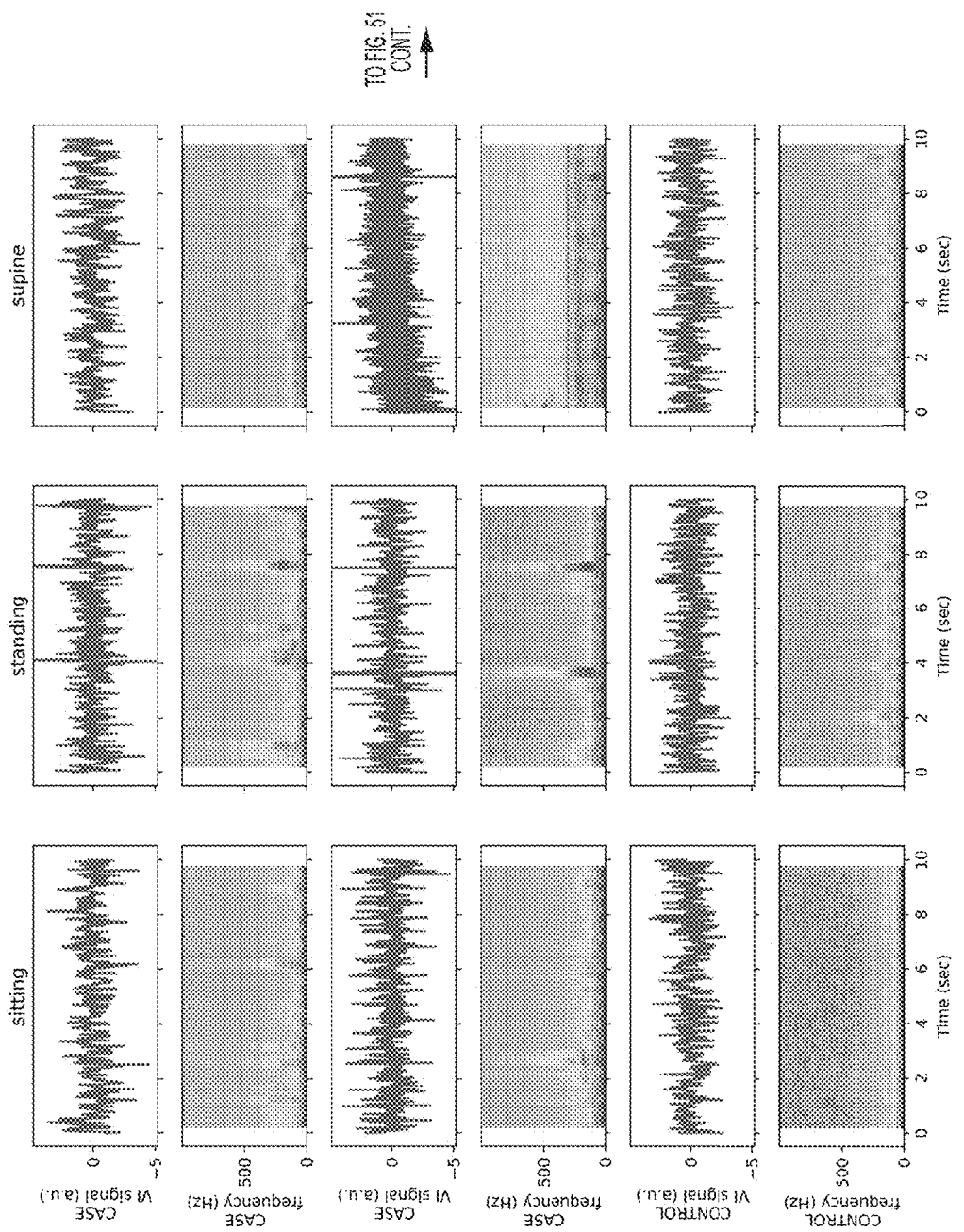
Figure 51:
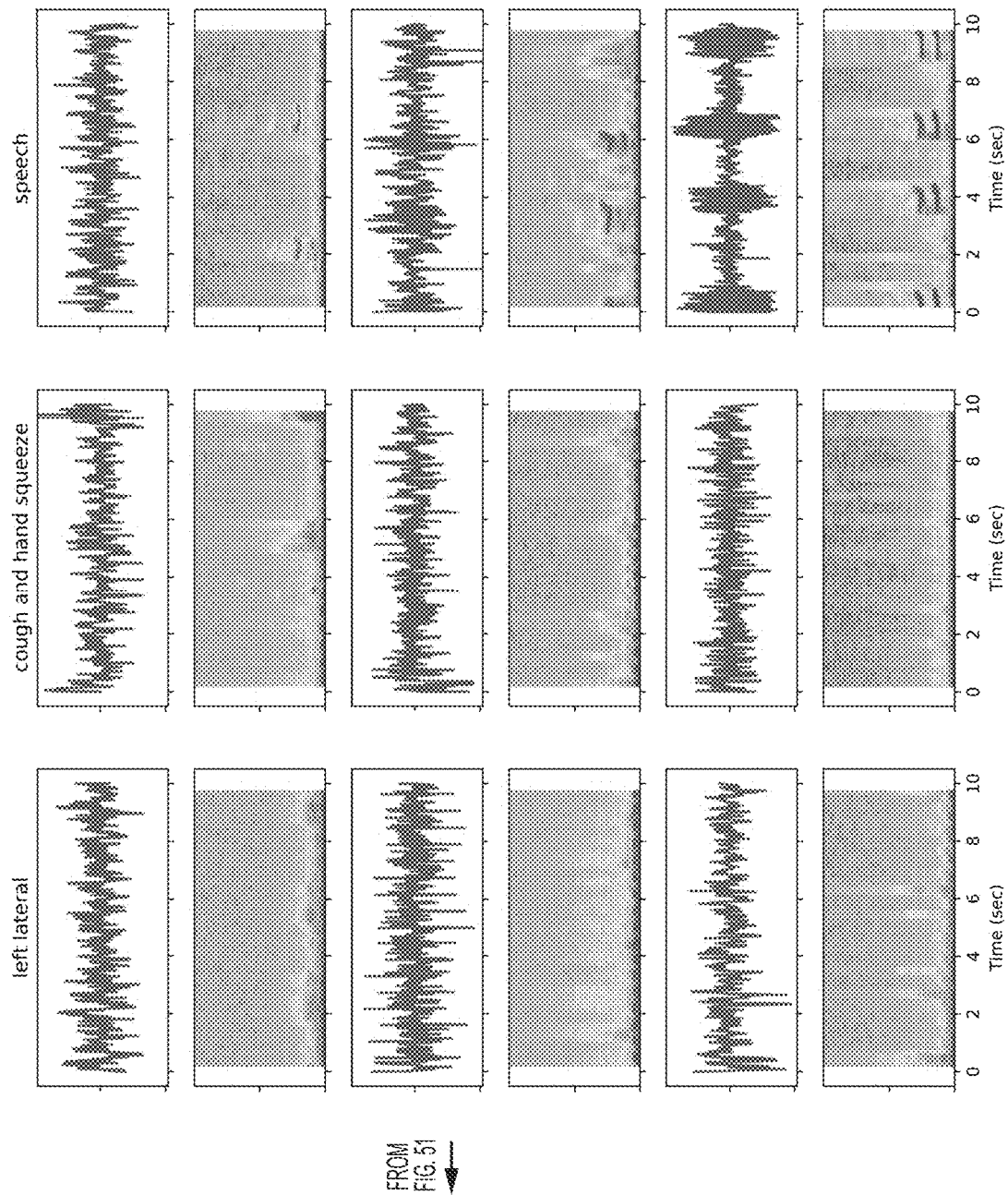

FIG. 51 shows sensor data extracts (vibroacoustic only) of two Subject Cases and three Control Cases taken while the patients were in different positions and performing different actions (sitting, standing, supine, left lateral, cough and hand squeeze, speech) with the sensing device position on the right $2^{nd}$ a ICS location on their bodies.

These plots show some clear differences associated with respiration based on the detected vibroacoustic sensor data. For the COVID-19 patients, one can see frequency envelopes in the spectrograms associated with breathing (breathing can be assumed by either looking at the timescales of these envelopes or by looking at the low-frequency baseline changes in the VI plots). These envelopes are not present to the same extent in the controls. Respiratory vibrational changes consistent with those observed in the plots above are expected with COVID-19. During inhalation, inflammatory and other immune responses that constrict the airways in the upper respiratory system are expected to elicit more turbulent airflow entering the lungs. The increased turbulence will be associated with higher-frequency respiratory sounds. Additionally, in COVID-19 patients with fluid accumulation and inflammation in the lungs, higher-frequency sounds (e.g., rales or pleural friction rub) will be present.

Interestingly, for the COVID-19 patients with a second visit (FIG. 48), the envelopes seem to get smaller on the second visit in the sense that the higher frequencies are diminished. Assuming that "higher frequencies⇔pathological" and the patients are recovering while in the hospital, this highlights the need for diagnosing early disease.

Biosignature of COVID-19 was developed using variations of the machine learning module of the present technology. As well as the vibroacoustic data, data from phonocardiograms augmented with sociodemographic, medical history, and current health characteristics was also used. Data from healthy unexposed participants and participants who were exposed but did not develop infection was also included.

Biosignature development comprised bootstrapping the within-pair comparisons by splitting the MCC study data by—a) body position (neutral sit, neutral upright stand, supine, left lateral decubitus position (LLDP), handgrip and cough, and vocalizations that reveal pulmonary consolidation), b) device location on the body in the 9-step staircase ladder procedure starting at the right carotid, c) segmentation into 10, 5, 3 heart cycles, and d) further splitting data into <20 Hz (infrasound), 20-20,000 Hz (audible sound), and >20,000 Hz (ultrasound) to expand the paired data structure and facilitate classification/clustering/individuation.

Independent data sets were used for each of the training, validation, and testing phases. Concerning the construction of specific ML models, a portfolio of methods were applied ranging from statistics and conventional machine learning through to novel evolutionary models. The latter allows posing the task of feature construction from wide-spectrum vibroacoustics as a program synthesis task. The unique advantage of this approach is the ability to provide the search algorithm with additional expert guidance, by supplying it with a formal grammar and symbolically expressed cardiopulmonary, digital signal processing and sound engineering domain-specific language that encapsulates the relevant domain knowledge. This not only makes the resulting features transparent (which are expressed, among others, as algebraic expressions and/or, if/then rules), but also eases learning from small data, both in 'n-sense' (low number of available samples/examples) and 't-sense' (relatively short duration of recordings).

The hybrid numeric-symbolic representation of the present technology allows to reason formally about the synthesized descriptors and provide formal guarantees about their outcomes. The language was designed so that it embraces the semantics of the functional health data phenotypes. The domain-specific knowledge incorporated into this approach ensures that learned relationships are causally meaningful, thereby greatly aiding in both the predictive capability of the resulting models and their human interpretability. These approaches build generalizable models by combining principled Bayesian inference with a learning algorithm that respects relational dependencies in the data. This is in stark contrast to mainstream machine learning, where training usually requires large volumes of data (or otherwise the models tend to overfit) and the models are completely opaque (there is little or no insight in the inner workings of the model, and consequently limited capability to explain the decisions being made).

As well as splitting the MCC study into non-overlapping training and validation datasets, a nested case-control design was also looked at that includes bootstrapped cases and selects matched/alternate controls for a case among in the full continually expanding cohort (risk-set matched case-control design). This design is expected to produce a similar result to the training and validation sequential analysis. As additional data from planned studies is accumulated, the MCC study will be used as the training data set without losing statistical power in the development and the rest of the cohort as the validation data set. When predicting uncommon clinical events, limiting false positive prediction (1-specificity) is often more of interest than limiting false negative prediction. Then, since all cases are included in the case-control cohort, only partial validation will be available based on the fraction of true negative prediction (specificity). In the nested case-control cohort, variable selection is conducted and fit a prediction model on those selected variables. Then, the selection is validated by comparing the specificity of the fitted prediction model in the case-control subjects (internal) to that in the subjects who were not selected as controls within the cohort (external).

Example 9—Remote Sensing

An example variation of a sensing device of the present technology in a panel-form, such as the sensing device illustrated and described in FIG. 31, was evaluated. The sensing device had a sealed cavity. A subject was positioned at varying distances from the diaphragm of the panel and including different barriers between the subject and the diaphragm in terms of apparel (wearing a sweater, without a sweater).

Figure 52B:
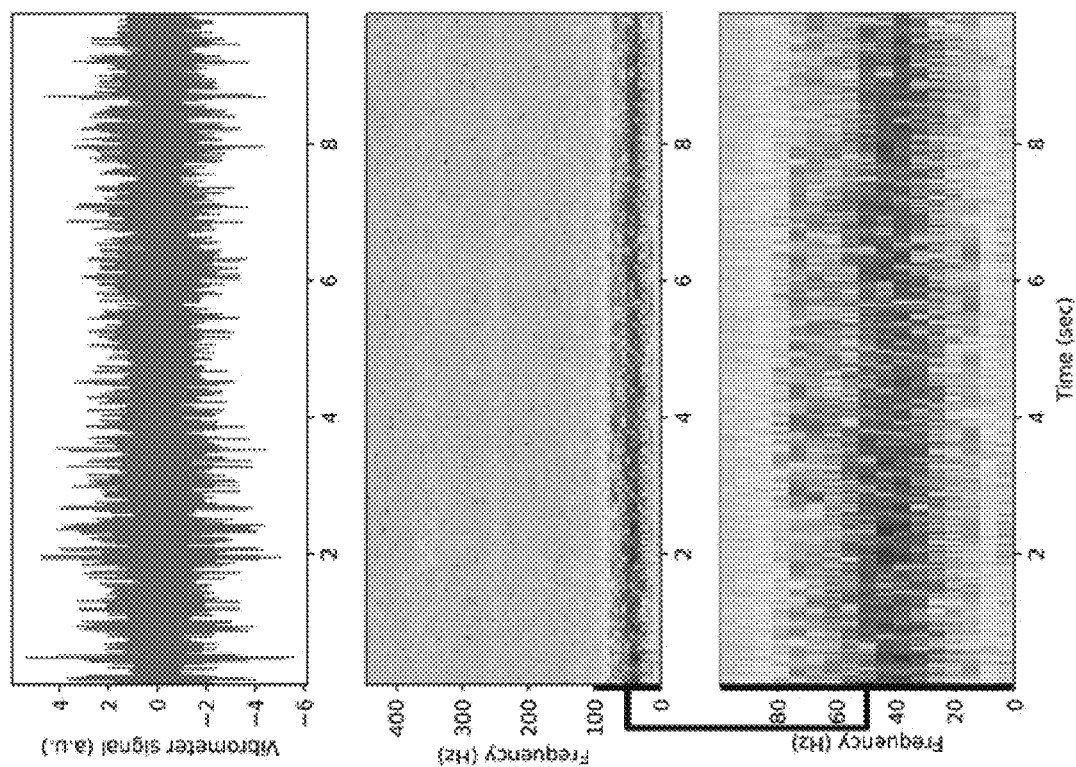
FIGS. 52A-52D show vibroacoustic test data collected by a sensing device of the present technology, FIG. 52A, when a subject without a clothing barrier is positioned 12 cm from a diaphragm of the sensing device, FIG. 52B, when a subject without a clothing barrier is positioned 100 cm from a diaphragm of the sensing device 100 cm away, FIG. 52C, when a subject wearing a sweater is positioned 12 cm from a diaphragm of the sensing device, and FIG. 52D, when a subject wearing a sweater is positioned 100 cm from a diaphragm of the sensing device 100 cm.
Figure 52A:
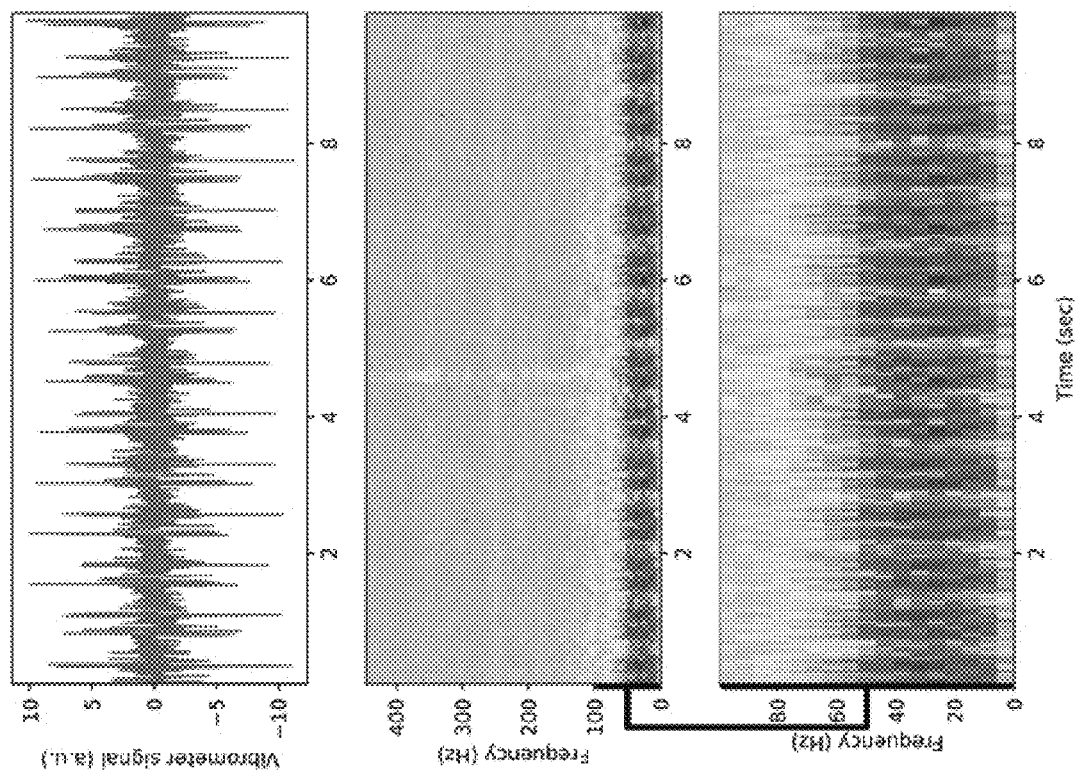
Figure 52C:
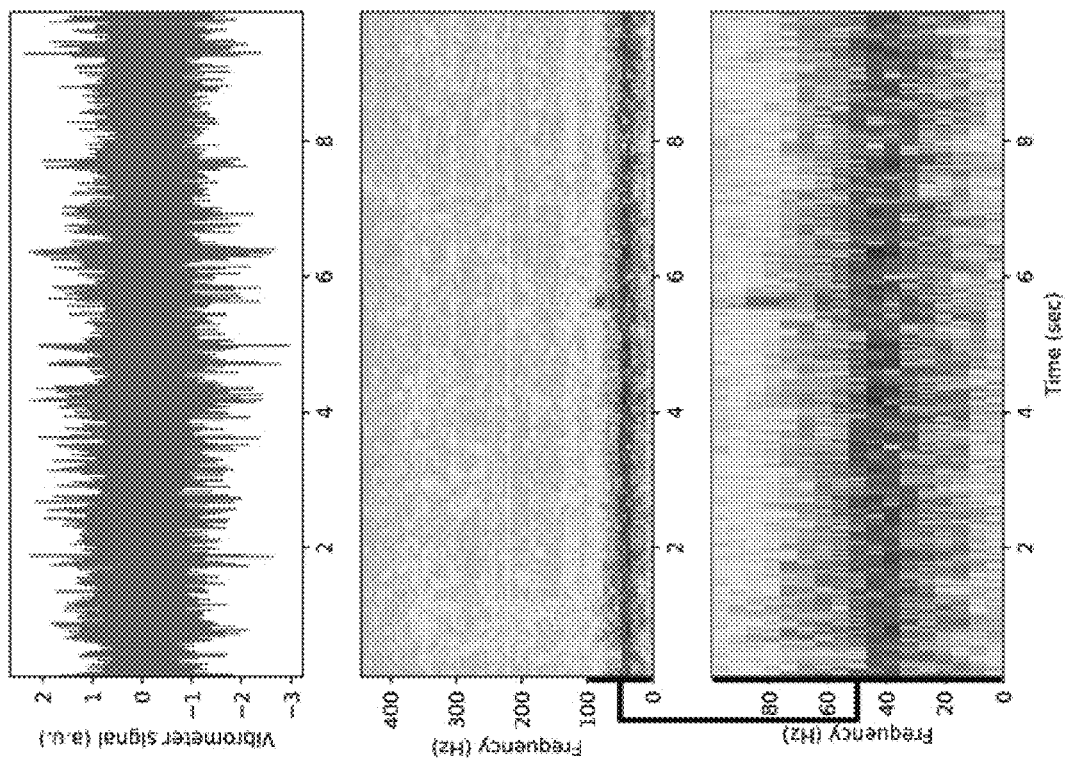
Figure 52D:
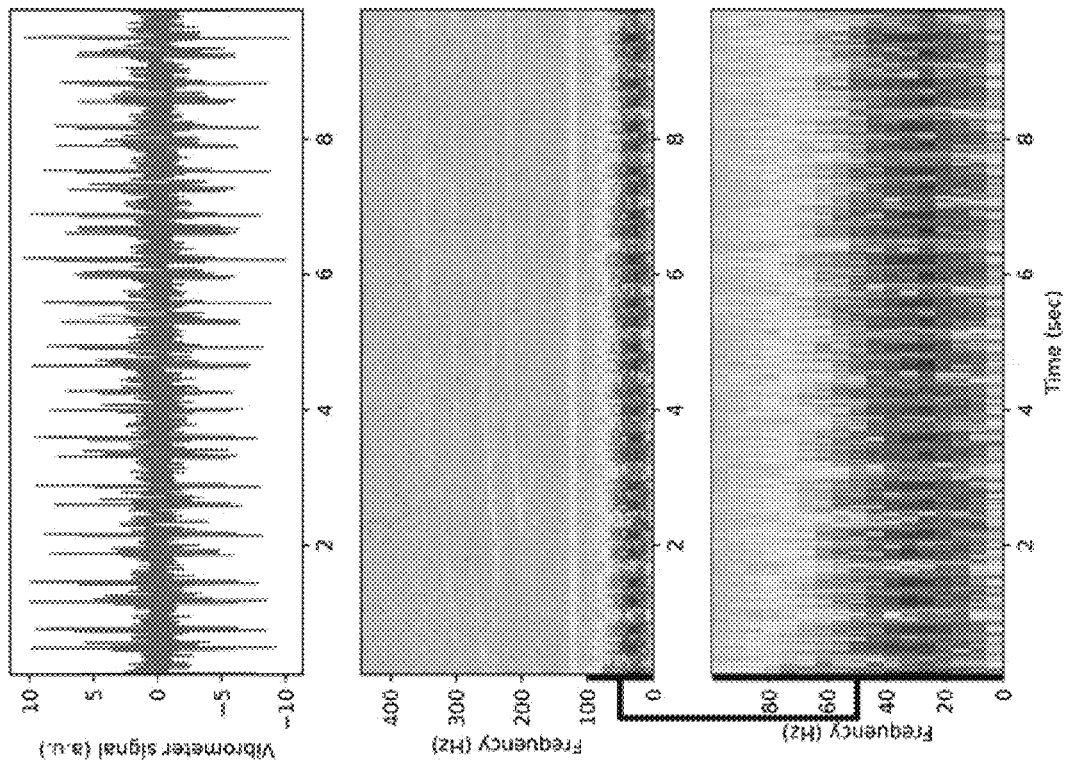

FIG. 52 shows vibroacoustic test data collected by the sensing device when the subject without a clothing barrier is positioned 12 cm from the diaphragm of the sensing device (FIG. 52A), the subject without a clothing barrier is positioned 100 cm from the diaphragm of the sensing device 100 cm away (FIG. 52B), the subject wearing a sweater is positioned 12 cm from the diaphragm of the sensing device (FIG. 52C), and the subject wearing a sweater is positioned 100 cm from the diaphragm of the sensing device (FIG. 52D).

It is clear from the figures that systems and sensing devices of the present technology can detect body vibrations remotely through air gaps of various distances. Due to attenuation inherently present in the propagating sound signals the amplitude is reduced at greater distances, as most evident in the time domain signals. However, as evident from the frequency spectra, signals are still being captured at the larger distance and can be extracted. In addition, the important lower frequencies are less attenuated due to near field conditions, which allows sensing them from even greater distances. As can also be seen, the presence of clothing has little effect on the signal quality.

Figure 53A:
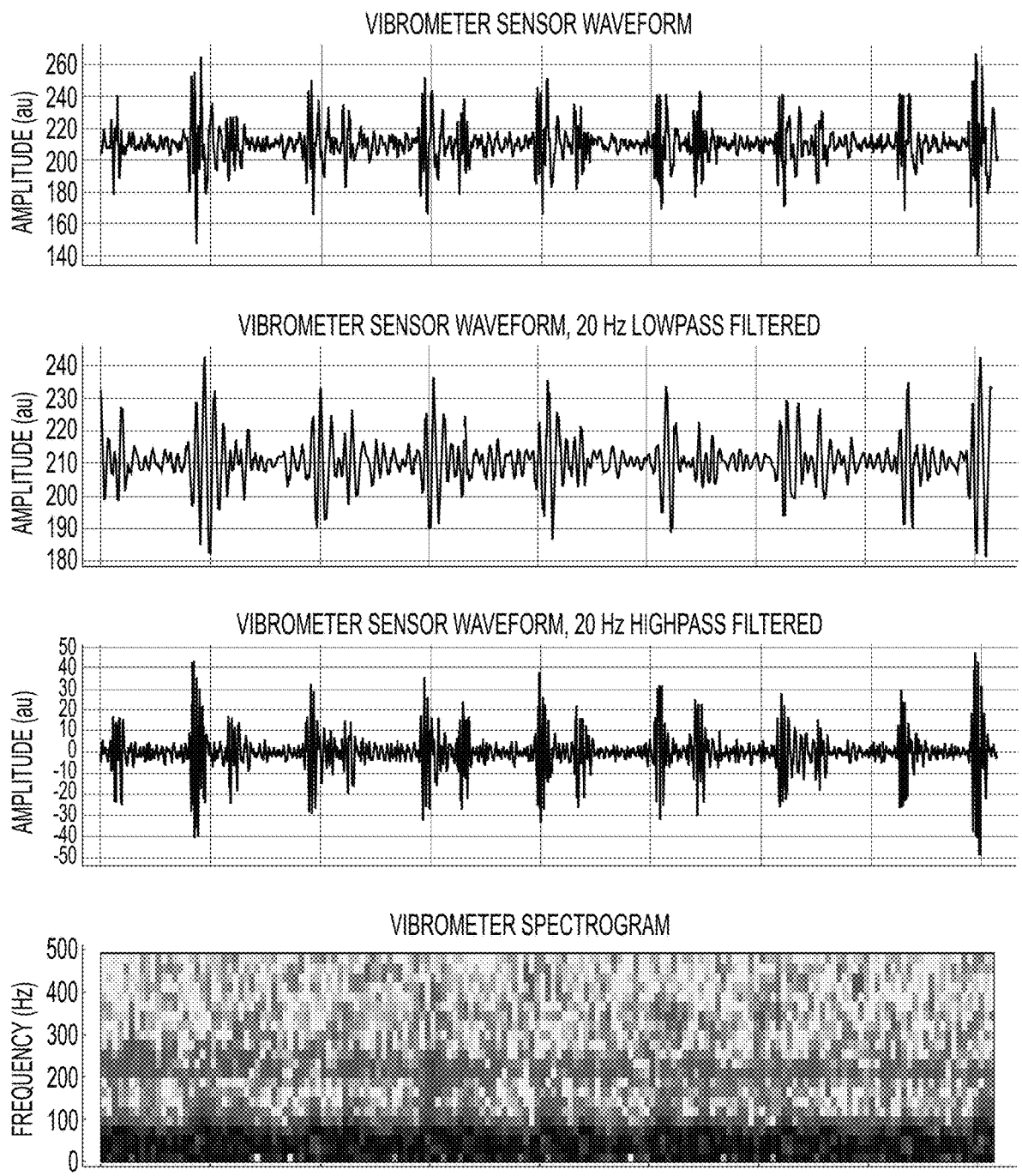
FIGS. 53A-53C show vibroacoustic test data collected by a sensing device of the present technology, FIG. 53A, when a subject wearing a sweater is positioned 10 cm from a diaphragm of the sensing device and is facing the diaphragm, FIG. 53B, when the subject wearing a sweater is positioned 10 cm from a diaphragm of the sensing device and is facing away from the diaphragm, and FIG. 53C, when the subject wearing a sweater is positioned 100 cm from a diaphragm of the sensing device and is facing the diaphragm.
Figure 53B:
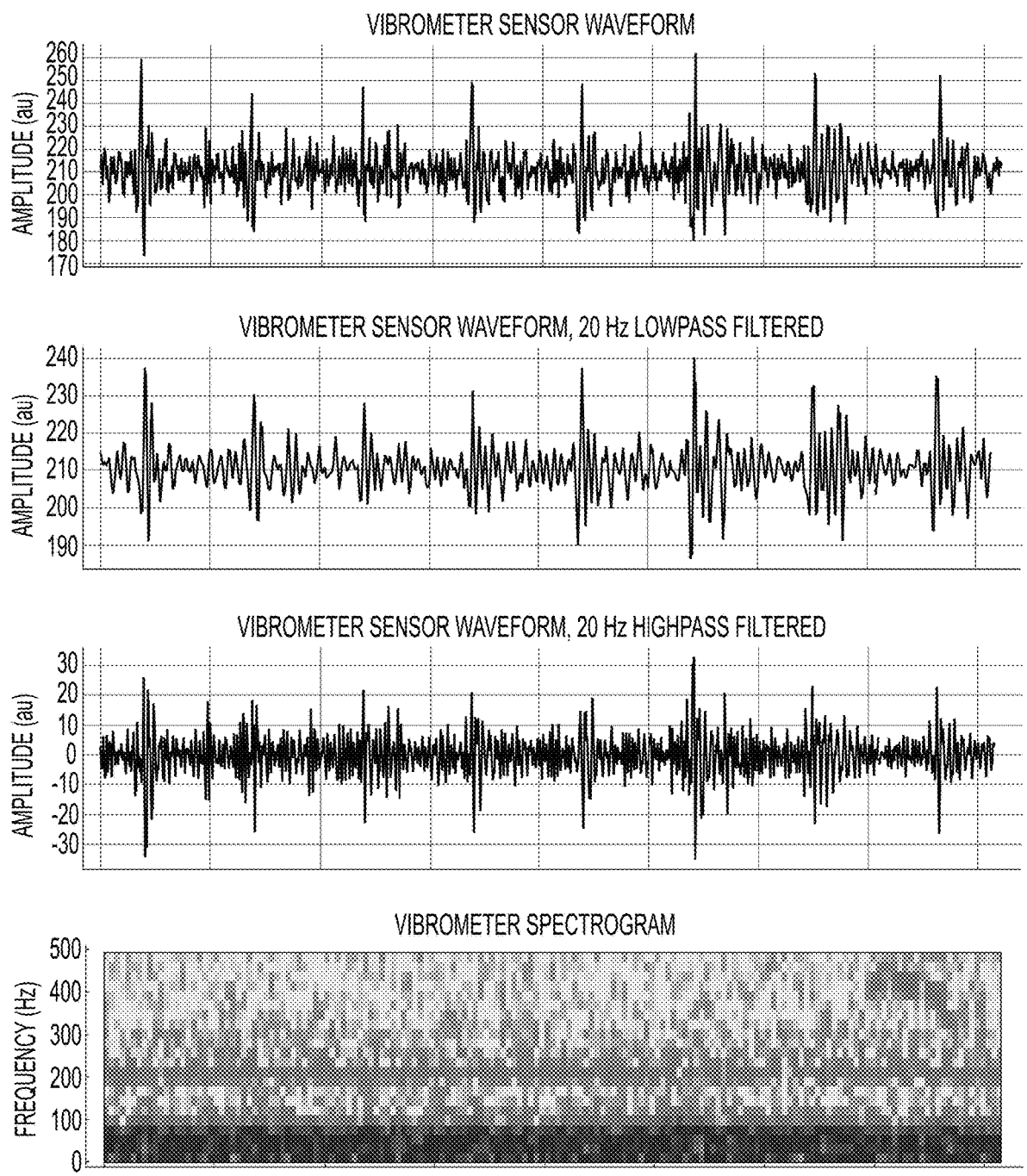
Figure 53C:
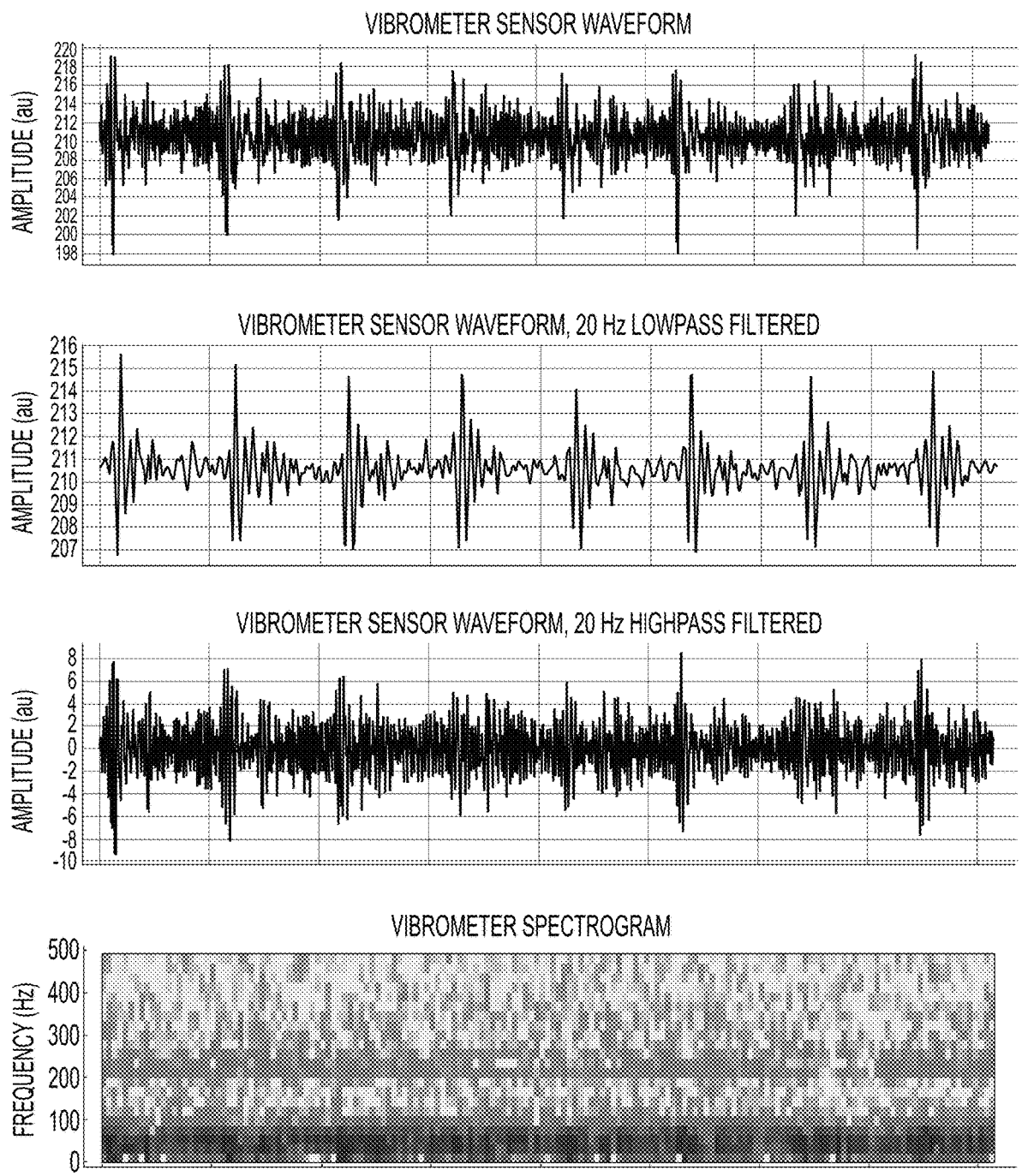

FIG. 53 shows vibroacoustic test data collected by the sensing device when the subject wearing a sweater is positioned 10 cm from a diaphragm of the sensing device and is facing the diaphragm (FIG. 53A), the subject wearing a sweater is positioned 10 cm from a diaphragm of the sensing device and is facing away from the diaphragm (FIG. 53B), and the subject wearing a sweater is positioned 100 cm from a diaphragm of the sensing device and is facing the diaphragm. These signals are presented as time domain signals, and separated into relevant frequency bandwidths. The top cyan colored signal is the combined captured signal, the green signal the infrasound component in the captured signal (<20 Hz), the yellow signal is the audible component (>20 Hz) and the bottom is a spectrogram. It is evident that infrasound and audible spectrum are captured with good signal to noise ratio. Although frequencies in the audible spectrum are attenuated compared to a distance of 10 cm, the infrasound components are still captured well.

It is reasonably expected that when openings are provided on the back cover, the effect on frequency detected would be affected (i.e. shifted to higher frequencies). Optimization of the sensing device can therefore be performed through a combination of analytical and finite element analysis (FEM) of different extents of sealing of the cavity and based on a desired frequency detection range in a high dimensional parameter space.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A sensing system for detecting a vibroacoustic signal from a subject, the sensing system comprising:
   a sensing device comprising:
     a vibroacoustic sensor module for detecting vibroacoustic signals having a bandwidth ranging from 0.01 Hz to 160 kHz, the vibroacoustic sensor module comprising:
       a voice coil component comprising a coil holder supporting wire windings;
       a magnet component comprising a magnet supported by a frame, the magnet having a magnet gap configured to receive at least a portion of the voice coil component in a spaced and moveable manner;
       a connector connecting the voice coil component to the magnet component, the connector being compliant and permitting relative movement of the voice coil component and the magnet component;
       a diaphragm configured to induce a movement of the voice coil component in the magnet gap responsive to incident acoustic waves, wherein the diaphragm is attached to the voice coil component, wherein the diaphragm is dome-shaped, wherein at least a portion of the voice coil component is positioned outside of the magnet gap, wherein pressure applied to the diaphragm causes the at least the portion of the voice coil to enter the magnet gap, and wherein the wire windings are spaced from the diaphragm; and
       an Inertial Measurement Unit (IMU) mounted to the diaphragm;
     a housing for retaining the vibroacoustic sensor module, wherein the sensing device is a hand-held device, the housing having a handle end and a sensor end, the sensor end having a sensor end surface with an opening defined therethrough, the vibroacoustic sensor module positioned such that at least a portion of the diaphragm of the vibroacoustic sensor module extends across the opening; and
     an outer cover which is attached to the housing at the sensor end and extends over the opening to cover the diaphragm; and
   a computing device comprising at least one processor and memory storing executable instructions that, when executed by the at least one processor, cause the computing device to:
     receive, from the sensing device, vibroacoustic signal data corresponding to the subject and collected by the vibroacoustic sensor and the IMU; and
     output, based on the vibroacoustic signal data and using a trained machine learning model, an indication of the presence or absence of a COVID-19 infection in the subject.

2. The sensing system of claim 1, wherein the vibroacoustic signal data comprises:
   a first vibroacoustic signal component which originates from the subject, and
   a second vibroacoustic signal component which does not originate from the subject, and wherein the instructions, when executed by the at least one processor, cause the computing device to extract the first vibroacoustic signal component from the vibroacoustic signal data; and to determine the presence or absence of the COVID-19 infection in the subject based on the first vibroacoustic signal component and the trained machine learning model.

3. The sensing system of claim 2, wherein the instructions, when executed by the at least one processor, cause the computing device to extract biological vibroacoustic signals from the first vibroacoustic signal component, the vibroacoustic signal data having been detected through remote contact with the subject, through clothed contact with the subject, or through direct skin contact with the subject.

4. The sensing system of claim 1, the sensing device further comprising one or both of:
   (a) an electronics component, housed in the housing, and connected to the voice coil component configured to convert an induced current in the windings from the acoustic waves to the detected vibroacoustic signals; and
   (b) a power source, housed in the housing, connected to one or both of the electronics component and the voice coil component; and
   (c) a wireless communication module configured to communicate the detected vibroacoustic signal or an extracted first vibroacoustic signal component to the computing device.

5. The sensing system of claim 1, the sensing device further comprising a bioelectric sensor module for detecting electrical signals from the subject, the bioelectric sensor module comprising, at the sensor end of the housing, at least one capacitive electrode, and at least one driven right leg (DRL) electrode for providing a feedback circuit of the at least one capacitive electrode.

6. The sensing system of claim 1, wherein the voice coil component has an impedance of 5 Ohm to 170 Ohm.

7. The sensing system of claim 1, wherein the connector comprises a deflecting structure extending radially from the voice coil component and including apertures formed therein.

8. The sensing system of claim 1, wherein the connector comprises at least two flexure arms extending radially from the voice coil component, the at least two flexure arms being spaced from one another to define at least one aperture therebetween.

9. The sensing system of claim 1, wherein a mechanical compliance of the connector is in a range of 0.1 mm/N to 5.0 mm/N.

10. The sensing system of claim 1, wherein the diaphragm can travel up to 4 millimeters, and wherein the voice coil component has an overall depth equal to or less than 20.5 millimeters.

11. The sensing system of claim 1, wherein the trained machine learning model was trained to detect a biosignature of COVID-19 infection, and wherein the biosignature is defined in a domain-specific language (DSL) that defines the biosignature based on time series data and features extracted from the time series data.

12. The sensing system of claim 1, wherein the instructions, when executed by the at least one processor, cause the computing device to:
    segment the vibroacoustic signal data into a plurality of segments; and
    determine, based on a subset of the plurality of segments, the presence or absence of a COVID-19 infection in the subject.

13. The sensing system of claim 1, wherein the instructions, when executed by the at least one processor, cause the computing device to:
    apply a first stage amplifier and a first stage low pass filter to the vibroacoustic signal data; and
    apply a second stage amplifier and a second stage low pass filter to the vibroacoustic signal data, wherein the first stage low pass filter and the second stage low pass filter form a second order low pass filter with anti-aliasing.

14. The sensing system of claim 13, wherein the second order low pass filter has a cutoff frequency of 15 kHz to 20 kHz.

15. The sensing system of claim 1, wherein a ratio of voice coil inductance to moving mass of the vibroacoustic sensor module is at least 6.52 mH per gram at 1 kHz.

16. The sensing system of claim 1, wherein a ratio of mechanical compliance of suspension to moving mass of the vibroacoustic sensor module is at least 0.348 mm/N per gram.

17. The sensing system of claim 1, wherein a ratio of BL product to moving mass of the vibroacoustic sensor module is at least 16 N/Amp per gram.

18. The sensing system of claim 1, wherein the trained machine learning model forms part of a Structural Machine Learning (SML) platform for determining the presence or absence of the COVID-19 infection in the subject based on the vibroacoustic signal data.

19. The sensing system of claim 1, wherein the instructions, when executed by the at least one processor, cause the computing device to:
    decompose the vibroacoustic signal data into a plurality of wavelets;
    remove one or more wavelets having a magnitude below a predefined threshold magnitude from the plurality of wavelets; and
    determine, based on the plurality of wavelets, the presence or absence of a COVID-19 infection in the subject.

* * * * *